(12) United States Patent
MacDonald et al.

(10) Patent No.: US 8,410,054 B2
(45) Date of Patent: Apr. 2, 2013

(54) METHODS FOR TREATING PAIN BY INHIBITION OF THE SCN9A CHANNEL

(75) Inventors: Marcia L. MacDonald, Vancouver (CA); Mark E. Samuels, Vancouver (CA); Robin Sherrington, North Vancouver (CA); Yigal P. Goldberg, Vancouver (CA)

(73) Assignee: Xenon Pharmaceuticals Inc., Burnaby, B.C. (CA)

( * ) Notice: Subject to any disclaimer, the term of this patent is extended or adjusted under 35 U.S.C. 154(b) by 0 days.

(21) Appl. No.: 12/590,935

(22) Filed: Nov. 17, 2009

(65) Prior Publication Data

US 2010/0076058 A1  Mar. 25, 2010

Related U.S. Application Data

(62) Division of application No. 10/369,909, filed on Feb. 19, 2003, now Pat. No. 7,659,082.

(60) Provisional application No. 60/357,964, filed on Feb. 19, 2002, provisional application No. 60/429,836, filed on Nov. 26, 2002.

(51) Int. Cl.
*A61K 38/00* (2006.01)
*A61K 38/16* (2006.01)

(52) U.S. Cl. .................... 514/18.3; 514/21.3

(58) Field of Classification Search .............. None
See application file for complete search history.

(56) References Cited

U.S. PATENT DOCUMENTS

| 5,225,326 | A | 7/1993 | Bresser et al. |
| 5,356,777 | A | 10/1994 | Hoffman et al. |
| 5,474,796 | A | 12/1995 | Brennan |
| 6,110,672 | A | 8/2000 | Mandel et al. |
| 7,195,879 | B2 | 3/2007 | Dubin et al. |

FOREIGN PATENT DOCUMENTS

| EP | 0 789 575 | 9/2008 |
| WO | WO 96/14077 | 5/1996 |
| WO | WO 03/087769 | 10/2003 |
| WO | WO 2007/109324 | 9/2007 |

OTHER PUBLICATIONS

Drenth and Waxman, J. Clinical Investigation, vol. 117, pp. 3603-3609 (Dec. 2007).
Cox et al., "An SCN9A Channelopathy Causes Congenital Inability to Experience Pain," Nature, vol. 44, pp. 894-898 (2006).
Cronin et al., "Binding of the Anticonvulsant Drug Lamotrigine . . . " J. Biol. Chem., vol. 278, pp. 10675-10682 (2003).
Kaye et al., PNAS, vol. 87, pp. 6922-6926 (1990).
Klugbauer et al., GenBank No. NP_002968 (Oct. 31, 2000).
Krafte et al., "Sodium channels and nociception: recent concepts and therapeutic opportunities," Curr. Opin. Pharm., vol. 8, pp. 50-56 (2008).
McNulty et al., "State-dependent Mibefradil Block of Na+ Channels," Mol. Pharm., vol. 66, pp. 1652-1661 (2004).
Rudinger et al., Peptide Hormones, Parsons, University Park Press, Baltimore, p. 1-7 (1976).
Sangameswaran et al., J. Biol. Chem. vol. 272, pp. 14805-14809 (1997).
Skolnick et al., Trends in Biotech, vol. 18, pp. 34-39 (2000).
Middleton et al., Two Tarantula Peptides Inhibit Activation of Multiple Sodium Channels, Biochemistry, vol. 41, pp. 14734-14747 (2002).
Rosker et al., The TTX metabolite 4,9-anhydro-TTX is a highly specific blocker of the Nav1.6 voltage-dependent sodium channel, Am J Physiol Cell Physiol, vol. 293, pp. C783-C789 (2007).
Safo et al., Distinction among Neuronal Subtypes of Voltage-Activated Sodium Channels by m-Conotoxin PIIIA,The Journal of Neuroscience, vol. 20(1), pp. 76-80 (2000).
Schmalhofer et al., ProTx-II, a Selective Inhibitor of NaV1.7 Sodium Channels, Blocks Action Potential Propagation in Nociceptors, Mol Pharmacol, vol. 74, pp. 1476-1484 (2008).
Smith et al. Molecular Interactions of the Gating Modifier Toxin ProTx-II with Nav1.5, J. Biol. Chem., vol. 282, pp. 12687-12697 (2007).
Klugbauer et al., EMBO Journal, vol. 14, pp. 1084-1090 (1995).

*Primary Examiner* — Christine J Saoud
*Assistant Examiner* — Jon M Lockard
(74) *Attorney, Agent, or Firm* — Elliot M. Olstein; Alan J. Grant

(57) ABSTRACT

The present invention relates to the discovery that mutations in SCN9A are causative of Congenital Indifference to Pain (CIP) in humans. The invention also relates to methods of utilizing the SCN9A gene and expression products thereof for the screening and identification of therapeutic agents, including small organic compounds, which are selective for SCN9A, and are useful in the treatment of pain and other disorders. The invention also relates to methods of using these compounds to treat or otherwise ameliorate such disorders.

10 Claims, 10 Drawing Sheets

Figure 4a
c.5067G>A, p.W1689X

```
Normal  5041 ttccaaattacaacctctgctggatggattgctagcacctattcttaacagtaag 5100
        1681  F  Q  I  T  T  S  A  G  W  D  G  L  L  A  P  I  L  N  S  K   1700

CIP     5041 ttccaaattacaacctctgctggtgaGATGGATTGCTAGCACCTATTCTTAACAGTAAG 5100
        1681  F  Q  I  T  T  S  A  G  *                                    1688
```

Figure 4b
c.984C>A, p.Y328X

```
Normal  961 tcagtcagtgtccagagggtacacctgtgtgaaattggcagaaaccctgattatggc 1020
        321  S  G  Q  C  P  E  G  Y  T  C  V  K  I  G  R  N  P  D  Y  G    340

CIP     961 tcagtcagtgtccagagggtaACCTGTGTGAAAATTGGCAGAAACCCTGATTATGGC 1020
        321  S  G  Q  C  P  E  G  *                                        327
```

Figure 4c
c.2488C>T, p.R830X

```
Normal  2461 tcagttctgcgatcattcagactgctccgagtcttcaagttggcaaaatcctggccaaca 2520
        821   S  V  L  R  S  F  R  L  L  R  V  F  K  L  A  K  S  W  P  T   8400

CIP     2461 tcagttctgcgatcattcagactgctctgaGTCTTCAAGTTGGCAAAATCCTGGCCAACA 2520
        821   S  V  L  R  S  F  R  L  L  *                                 829
                                          Exon14 | Exon 15
```

SCN9A gene

SCN9A mRNA
Neonatal isoform generated from alternative splicing

SCN9A mRNA
Adult isoform generated from alternative splicing

Figure 6

```
                  ---|----------|----------|----------|----------|----------|----------|----------|----------|----------|
human SCN9A  A    597 atatgtgacagagttgtggacctggcaatgtcttcagcattgagaacattcagagttctccgacattgaaaacaattcagtcattgaaactattcttcgaagctttgagagctttcgaaacattcagagtt      688
              200  Y V T E P V D L G N V S A L R T F R V L R A L K T I S V I P G                                                                    229
human SCN9A  N    597 gtattaacagaattgtggacctggcaatgttcagctcttcagcgttgagaacattcagagttctccgactcttgaaaacaattcagtcattgaaactattcttctgtaatccag                  688
              200  . . . L . . . . . . . . N . . . . . . . . . . . . . . . . . . . . . . . . . . . .                                                      229
rabbit SCN9A A    597 atatgtgacggagttgtggacctggcaatgtcctcagcgtctgagaacattcagagttctccgactcttgaaaacaattcagtcattcag                                         688
              200  . . . . V . . . . . D . . . . . . . . . . . . . . . . . . . . . . . . . . .                                                            229
rabbit SCN9A N    597 gtattaacagaattgtataaacctaggcaatgttcagctcttcagcgttgagaacattcagagttctccgacttcttgaaaacaattcagtcattgaaactattcttctgtaatccag              688
              200  . . . L . . . . . . . . N . . . . . . . . . . . . . . . . . . . . . . . . . . . .                                                      229
human SCN2A2 A    606 atatgtgacagagttctgtggacctggcaatgtcttcagctcttcagcgttgagaacattcagagtcttcgactttcagagcattgaaaacattcagtcattccag                         697
              203  . . . . V . . . . . D . . . . . . . . . . . . . . . . . . . . . . . . . . .                                                            233
human SCN2A2 N    606 gtatgtaacagaattgtaaacctaggcaatgtttcagctcttcagcgttgagagactttcagagtcttcgagtttcagagcattgaaaacaatatcagtcattccag                      697
              203  . . . . V . . . . . N . . . . . . . . . . . . . . . . . . . . . . . . . . . .                                                          233
rat SCN2A1   A    606 atatgtgacagagttctgtggacctggcaatgtcttcagctcttcagcgctcgagacgttcagagttcttcgactttcagagtcttgaaaacattcagtcattcag                         697
              203  . . . . V . . . . . D . . . . . . . . . . . . . . . . . . . . . . . . . . .                                                            233
rat SCN2A1   N    606 gtatgtaacagaattgtaaacctaggcaatgtttcagctcttcagcgttgagagtcttcgactctcttcgagagtcttgaaactattcttctgtaattccag                            697
              203  . . . . V . . . . . N . . . . . . . . . . . . . . . . . . . . . . . . . . . .                                                          233
human SCN3A  A    602 atatgtgacagagttgtggacctgggcaatgtctcacgttctccgcaatcgagagtcttcgagagcacgagacacctgaaaacaattcagtcattcag                                720
              202  . . . . V . . . . . D . . . . . . . . . . . . . . . . . . . . . . . . . . .                                                            232
human SCN3A  N    603 gtatgtaacagaattgtaagcctaggcaatgttcagccctcgaactttcgagagtcttcgagagtcctcgagagtcttgagagctctgagaaactattcttctgtaattccag                 694
              202  . . . . V . . . . . S . . . . . . . . . . . . . . . . . . . . . . . . . . . . .                                                        232
rat SCN3A    A    603 atatgtgacagagtttgtggacctggcaatgtctcagcgttctgagaacgttcagagtcttcgagcattgagagcagctctgaaaacaatatcagtcattccag                          694
              202  . . . . V . . . . . D . . . . . . . . . . . . . . . . . . . . . . . . . . .                                                            232
rat SCN3A    N    603 gtatgtaacagaattgtaagcctaggcaatgttcagccctcgacctttcgacctttcgcagctcttcagagtcttgcgagctctgaaaactattcttctgtaattccag                    694
              202  . . . . V . . . . . S . . . . . . . . . . . . . . . . . . . . . . . . . . . . .                                                        232
```

Figure 9

| | | |
|---|---|---|
| human_SCN9A | 597 | VTIDKATSDDS |
| rat_SCN9A | 596 | VTIDKATSDDS |
| mouse_SCN9A | 596 | VTIDKATSDDS |
| rabbit_SCN9A | 595 | VTIDKATSDDS |
| human_SCN1A | 617 | VTIDKPATDDN |
| rat_SCN1A | 617 | VTIDKPATDDN |
| human_SCN8A | 610 | VKIDKAATDDS |
| rat_SCN8A | 610 | VKIDKAATD-S |
| mouse_SCN8A | 610 | VKIDKAATD-S |

METHODS FOR TREATING PAIN BY INHIBITION OF THE SCN9A CHANNEL

This application is a divisional of U.S. application Ser. No. 10/369,909, filed 19 Feb. 2003 now U.S. Pat. No. 7,659,082, which claims priority of U.S. Provisional Application No. 60/357,964, filed 19 Feb. 2002, and 60/429,836, filed 26 Nov. 2002, the disclosures of all of which are hereby incorporated by reference in their entirety.

FIELD OF THE INVENTION

The present invention relates to the discovery that mutations in SCN9A are causative of Congenital Indifference to Pain in humans. The invention also relates to methods of utilizing the SCN9A gene and expression products thereof for the screening and identification of therapeutic agents, including small organic compounds, which are selective only for SCN9A, and are useful in the treatment of pain. The invention also relates to methods of using these compounds to treat or otherwise ameliorate pain.

BACKGROUND OF THE INVENTION

This invention is concerned with a hereditary pain disorder known as "Congenital Indifference To Pain" (also referred to herein "C-I-P"). It is an extremely rare but interesting medical condition. It is an autosomal recessive disorder that interferes with the normal perception of pain (see, Landrieu, P. S. G., and Allaire, C. Ann. Neurology, 27 (5):574-58 (1990) and Comings D E and Amromin G D, 1974. Neurology. September; 24(9):838-48.)

The description of the condition is fascinating. Patients are essentially completely indifferent to sensations that would cause pain in most individuals; yet at the same time they are quite able to distinguish between other sensations, such as thermal (hot/cold) and tactile (sharp/dull) sensations. Tendon reflex and vibration recognition is normal. Patients do not perceive inflammatory pain or dental pain even though there is a normal flare response to intradermal histidine injection, indicating that the peripheral arc reflex is intact. (Landrieu et al, 1990) A general description of C-I-P can be found at Online Mendelian Inheritance in Man (OMIM) reference *243000.

It is highly intriguing that the genetic mutation that underlies this disorder has such a specific and selective medical consequence. The inventors recognize that identification of the mutant gene which is associated with the disorder will provide a therapeutic target against which novel therapeutic agents can act. The inventors recognize that therapeutic agents which are highly selective for this therapeutic target, if they can be designed to mimic the effect of the mutation, have the potential to induce the same kind of analgesia, in the general population, as experienced by C-I-P patients.

It thus serves to examine in detail the physiological consequences of C-I-P. One C-I-P patient (3 years old, female) had no pain sensation but had normal thermal and tactile sensation and deep sensation. She appeared normal physically, although having tissue damage presumably resulting from the disorder, such as a shorter tongue, lack of some fingertips and multiple scars on fingers due to old burns. She learned to walk at 18 months (somewhat delayed). (Guillermo A. and A. Grinspan, "Congenital indifference to pain, a propos of a case with antecedents of consanguinity". Rev Neurol (Paris), 1970. 123(6): 434-5). In a follow up examination at age 34, patient appeared normal. Intelligence was normal. A broken bone not identified by the patient had resulted in an orthopedic deformity. Patient had a dental prosthesis. Sweating was normal. Tendon reflex and vibration recognition was normal. Position sense was normal. Patient was able to discriminate between "hot and cold" and between "sharp and dull" but discrimination between "touch" and "pinprick" was attenuated. Her maternal grandfather and her paternal grandmother were first cousins who had a common cousin who was apparently indifferent to pain. This consanguinity is in support of autosomal recessive inheritance.

Sweating, blood pressure and other autonomic responses are quite normal. No histological abnormalities are present in the peripheral nerves. (see Comings et al (1974) and Hirsch E, Moye D, Dimon J H 3rd. South Med J, 88(8):851-857 (1995)).

Still, to date, no genes or genetic loci responsible for C-I-P have been reported. Karyotype analysis of one C-I-P patient appeared normal. (Amguerra-Escobio, 2001, unpublished observations). One of the confusing aspects that has prevented identification of genes in the past is that there are other patients who have other hereditary pain disorders which have not been properly distinguished from autosomal recessive C-I-P. This makes it significantly harder to identify the common underlying genetic cause of the disorder.

For example, there are autosomal dominant and sporadic cases of congenital indifference to pain. The inventors believe that many of these cases have a different genetic basis than autosomal recessive C-I-P. Reports of these cases may be found at Becak et al, Acta Genet. Statist. Med. 14:133-142 (1964); Comings et al (1974); Landrieu et al, 1990).

Further, there is a very different from of the disease known as Hereditary Sensory and Autonomic Neuropathy (HSAN). HSAN is the classic "insensitivity" to pain. It has been classified into types I-V (Reilly, M. M. 1998. J. Neurol 245(1):6-13). Each of these conditions is linked to an inherited neuropathy of sensory nerves. Some of these conditions have been linked to genes or genetic loci, however, none of these are believed to correspond to the genetic basis underlying C-I-P.

It should be recognized that "insensitivity" and "indifference" are often used interchangeably in the art, but that they should be properly distinguished for better understanding of the pathology of the disorder. The term "insensitivity" refers to situations in which sensory pathways are altered leading to lack of painful sensation while "indifference" refers to situations wherein the sensory pathway appears normal but there is a lack of reaction to a painful stimulus. The key distinction between these groupings is that the former are inherited neuropathies in which neuropathy is the primary part of the disease and the sensory pathway is the sole or primary part of the neuropathy, whereas in the latter, the sensory pathway appears, at a microscopic and macroscopic level, to be intact and normal. (Comings et al 1974)

Because this invention is directed towards genes, proteins and other tools which are targets for analgesic agents, an additional area of relevant background relates to existing analgesic agents and their therapeutic targets, where known.

Therapeutic agents for treatment of pain fall into two main classes—the NSAIDs (non-steroidal anti-inflammatory drugs) and the opioids. NSAIDs treat pain in a way similar to the mechanism of aspirin, the most well-known and oldest member of the class. Common NSAIDs include acetaminophen, ibuprofen and naproxen. These drugs mainly inhibit the body's ability to synthesize prostaglandins. The common mechanism of action for all NSAIDs is the inhibition of the enzyme cyclooxygenase (COX). A major commercial success has been achieved with specific inhibitors of COX-2, such as Celebrex™ from Pharmacia/Pfizer, and Vioxx™ from Merck & Co. The recently launched Bextra™ from Pharmacia/Pfizer, which is highly selective for inhibition of COX-2 over COX-1, is also expected to become commercial success.

Opioids act through the opioid receptor family. These drugs include the weak opioids such as codeine and Tylenol 3, and strong opioids such as morphine and methadone. Some are long acting, others are of short duration. Opioid analgesics have a tendency to addiction and dependency, and so are not ideal for long-term or chronic pain management.

Outside of the NSAIDs and opioids, there are a number of other suggested analgesic agents in clinical trials (i.e. not yet approved for marketing) which are believed to have alternative targets. Some clinical trials are attempting to establish that central neuropathic pain may respond to ion channel blockers such as blockers of calcium, sodium and/or NMDA (N-methyl-D-aspartate) channels. For example, in development are low affinity NMDA channel blocking agents for the treatment of neuropathic pain. The literature provides substantial pre-clinical electrophysiological evidence in support of the use of NMDA antagonists in the treatment of neuropathic pain. Such agents also may find use in the control of pain after tolerance to opioid analgesia occurs, particularly in cancer patients.

In accordance with the present invention, the identification of the hereditary basis for Congenital Indifference To Pain will be a key step for developing novel therapeutic agents because it has the potential to be a novel therapeutic target. This therapeutic target can be used to identify and discover more effective analgesics. Discovery of the target will also provide new methods and compositions for diagnosis of C-I-P and for distinguishing between types of inherited pain disorders.

BRIEF SUMMARY OF THE INVENTION

The present invention relates to the discovery that the human gene SCN9A (also known as $Na_v 1.7$) when mutated, results in congenital indifference to pain.

In one aspect, the invention relates to the nucleic acid sequence for SCN9A, including the genomic sequence, mRNA or cDNA, polymorphic, allelic, isoforms (adult, neo-natal, etc.) and mutant forms thereof, and nucleic acid constructs of the gene, including vectors, plasmids and recombinant cells and transgenic organisms containing SCN9A (or knock-outs thereof). Such nucleic acid sequences are set forth in SEQ. ID Nos. 1, 3, 5, 7, 9, 11, 13, 14, 15, 17, 19.

In another aspect, the invention relates to the gene product of SCN9A, including the polypeptide, protein, and amino acid sequence, and the polymorphic, allelic, isoforms (adult, neo-natal, etc.) and mutant forms thereof, and recombinant cells and transgenic organisms wherein this polypeptide is expressed. Such amino acid sequences are set forth in SEQ. ID Nos. 2, 4, 6, 8, 10, 12, 16, 18, 20.

In one aspect of the present invention, the SCN9A gene or protein is incorporated into a screening assay whereby compounds (potential therapeutic agents) are tested to determine if they modulate SCN9A gene expression or SCN9A protein activity, thereby identifying potential therapeutic agents.

Thus, in one aspect the present invention relates to a method for identifying an agent that modulates the activity of a polynucleotide whose expression contributes to pain sensation or whose non-expression contributes to lack of pain sensation, comprising:
  a) contacting under physiological conditions a chemical agent with a polynucleotide corresponding to a promoter of the SCN9A gene, preferably having the sequence of SEQ. ID NO. 14, under conditions promoting such contacting; and
  b) detecting a change in the expression of said polynucleotide as a result of said contacting;
  thereby identifying an agent that modulates said polynucleotide activity.

Such modulation is preferably a decrease in expression. In preferred embodiments, such expression is measured by measuring the amount of an expression product encoded by said polynucleotide, most preferably an RNA or a polypeptide. In a preferred embodiment the promoter sequence is operably linked to a reporter gene, and the assay measures relative expression of the reporter gene or its gene product.

In preferred embodiments, the polynucleotide whose expression is to be measured or monitored is present in an intact cell, preferably a mammalian cell, most preferably a neuronal cell, and may include a recombinant cell. In preferred embodiments, such an intact cell is a cell that has been engineered to comprise said polynucleotide, such as by genetic engineering, most preferably wherein the cell does not express the subject gene or polynucleotide absent having been engineered to do so.

In another aspect, the present invention relates to a method for identifying an agent that modulates the activity of a polypeptide encoded by a polynucleotide as disclosed herein, comprising:
  a) contacting under physiological conditions a chemical agent with a polypeptide encoded by a polynucleotide corresponding to a SCN9A gene, preferably having the sequence of SEQ. ID NO. 1, 3, 5, 15, 17, 19; and
  b) detecting a change in the activity of said polypeptide as a result of said contacting;
  thereby identifying an agent that modulates said polypeptide activity.

In a preferred embodiment, the observed change in activity in step (b) is a decrease in activity, most preferably wherein said change in activity is the result of binding to or interacting with said polypeptide by said chemical agent of step (b), especially where the polypeptide is an ion channel, and the ion channel is selectively blocked by said binding. In a further preferred embodiment, the polypeptide is a sodium channel, and said blocking is voltage dependent.

In additional preferred embodiments, the polypeptide is part of a lipid bilayer, such as an intact cell, preferably a mammalian cell, such as a neuronal cell, most preferably a recombinant cell. In one such embodiment, a cell that has been engineered to comprise said polypeptide, including by genetic engineering, especially where the cell does not possess the polypeptide absent said engineering.

In one preferred embodiment of such method, the polypeptide is a polypeptide that reacts with an antibody that is specific for a polypeptide having the amino acid sequence of SEQ ID NO: 2, 4, 6, 16, 18, or 20. In another preferred embodiment, the polypeptide has an amino acid sequence at least 95% identical to, more preferably at least 98% identical to, the sequence of SEQ ID NO: 2, 4, 6, 16, 18, or 20. Alternatively, in the polypeptide the difference in the amino acid sequence from SEQ ID Nos. 2, 4, 6, 16, 18, or 20 is due only to conservative amino acid substitutions. In an especially preferred embodiment, the polypeptide has the amino acid sequence of SEQ ID NO: 2, 4, 6, 16, 18, or 20.

In a further aspect, the present invention relates to a method for identifying an analgesic agent, comprising:
  a) administering to an animal an agent found to have activity using a method as disclosed herein, and
  b) detecting in said animal a decrease in response to a pain stimulus due to said administering,
  thereby identifying an analgesic agent.

Preferably, the animal is a mammal, such as a human being. In specific embodiments, the pain stimulus is a heat stimulus and reaction or sensitivity to hot and/or cold may be measured. In another embodiment, an electrical stimulus may be used. In all cases, the stimulus may be represented as a sharp or dull sensation.

In a preferred embodiment of the invention, the compound identified which modulates SCN9A gene expression or SCN9A polypeptide activity is selective for SCN9A as opposed to other sodium channel alpha subunits (i.e. SCN1A to SCN8A, SCN10A to SCN12A). Such selectivity of modulation is preferably at least 10%, 50%, 100%, 10 times, 20 times, 100 times, 1000 times, 10,000 times or higher for SCN9A over any other sodium channel alpha subunit. Alternatively, a compound which is selective for SCN9A may not demonstrate an absolute preference for SCN9A, but the compound may show a preference for modulating SCN9A compared to any other sodium channel which preference is greater than any other known compound.

In a further aspect, the present invention relates to a method for treating a condition in an animal afflicted with a source of chronic pain comprising administering to said animal an effective amount of an analgesic agent first identified by an assay method of the invention. Preferably, said animal is a human patient, such as a patient afflicted with a chronic ailment, such as cancer or chronic back pain.

In a further aspect, the compounds identified by the assays disclosed herein, and the methods of treating patients with such compounds, are applied to alternative or additional indications beyond analgesia, including for anesthesia, treating epilepsy, stroke and any other disorder treatable by modulating sodium channel activity.

In another aspect, the present invention relates to a method for producing a product comprising identifying an agent according to the process of the invention wherein said product is the data collected with respect to said agent as a result of said process and wherein said data is sufficient to convey the chemical structure and/or properties of said agent.

In another aspect, the present invention relates to diagnostic and pharmacogenomic compositions, kits and methods which identify the presence or absence in a patient of one or more mutations in a polynucleotide or a polypeptide corresponding to SEQ ID Nos. 1-6 and 13-20, including those specific mutations identified at SEQ ID Nos 7-12.

BRIEF DESCRIPTION OF THE DRAWINGS

FIG. 4*a*. Nucleotide sequence of the 5067G>A SCN9A mutation in CIP patient CIP-10-503 (SEQ ID NO: 23). The patient is homozygous for a G>A substitution at nt 5067 (numbered relative to the initiator methionine in Genbank record NM_002977). This corresponds to a change to a stop codon at tryptophan 1689. The wild-type amino acid sequence from an unaffected patient is shown on top (SEQ ID NO: 22) and the wild-type nucleotide sequence as SEQ ID NO: 21. The amino acid sequence for the mutant is given as SEQ ID NO: 24. FIG. 4*b*. Nucleotide sequence of the 984C>A SCN9A mutation in CIP patient CIP-14-A005 (SEQ ID NO: 27). The patient is homozygous for a C>A substitution at nt 984. This corresponds to a change to a stop codon at tyrosine 328. The wild-type amino acid sequence from an unaffected patient is shown on top (SEQ ID NO: 26) with the wild-type nucleotide sequence above it (SEQ ID NO: 25). The mutant amino acid sequence is SEQ ID NO: 28. FIG. 4*c*. Nucleotide sequence of the 2488C>T SCN9A mutation in CIP patient CIP-08-11:01 (SEQ ID NO: 31). The patient is homozygous for a C>T substitution at nt 2488. This corresponds to a change to a stop codon at arginine 830. The wild-type sequence from an unaffected patient is shown on top (SEQ ID NO: 30) with the wild-type nucleotide sequence above it (SEQ ID NO: 29). The mutant amino acid sequence is SEQ ID NO: 32.

FIG. 6. Comparison of the alternatively spliced exons of other sodium channels with the two variants of human SCN9A. The cDNA sequence and the predicted amino acid sequence of the alternatively spliced exon 5 of the A and N isoforms of the human (SEQ ID NO: 33 and 35, respectively) and rabbit (SEQ ID NO: 36 and 37, respectively) SCN9A, human (SEQ ID NO: 42 and 43, respectively) and rat (SEQ ID NO: 44 and 45, respectively) SCN3A, human SCN2A2 (SEQ ID NO: 38 and 39, respectively), and rat (SEQ ID NO: 40 and 41, respectively) SCN2A1 are shown. Isoform-specific differences in the amino acid sequence are indicated below the nucleotide sequence (SEQ ID NO: 34 is the human SCN9A isoform A).

FIG. 9. Evolutionary conservation of the additional amino acids of Exon 11 B in other members of the sodium channel gene family (SCN9A, SCN1A, SCN8A). Here, the alignment shows human SCN9A (SEQ ID NO: 114), rat SCN9A (SEQ ID NO: 115), mouse SCN9A (SEQ ID NO: 116), rabbit SCN9A (SEQ ID NO: 117), human SCN1A (SEQ ID NO: 118), rat SCN1A (SEQ ID NO: 119), human SCN8A (SEQ ID NO: 120), rat SCN8A (SEQ ID NO: 121) and mouse SCN8A (SEQ ID NO: 122).

DETAILED DESCRIPTION OF THE INVENTION

Figure 1:
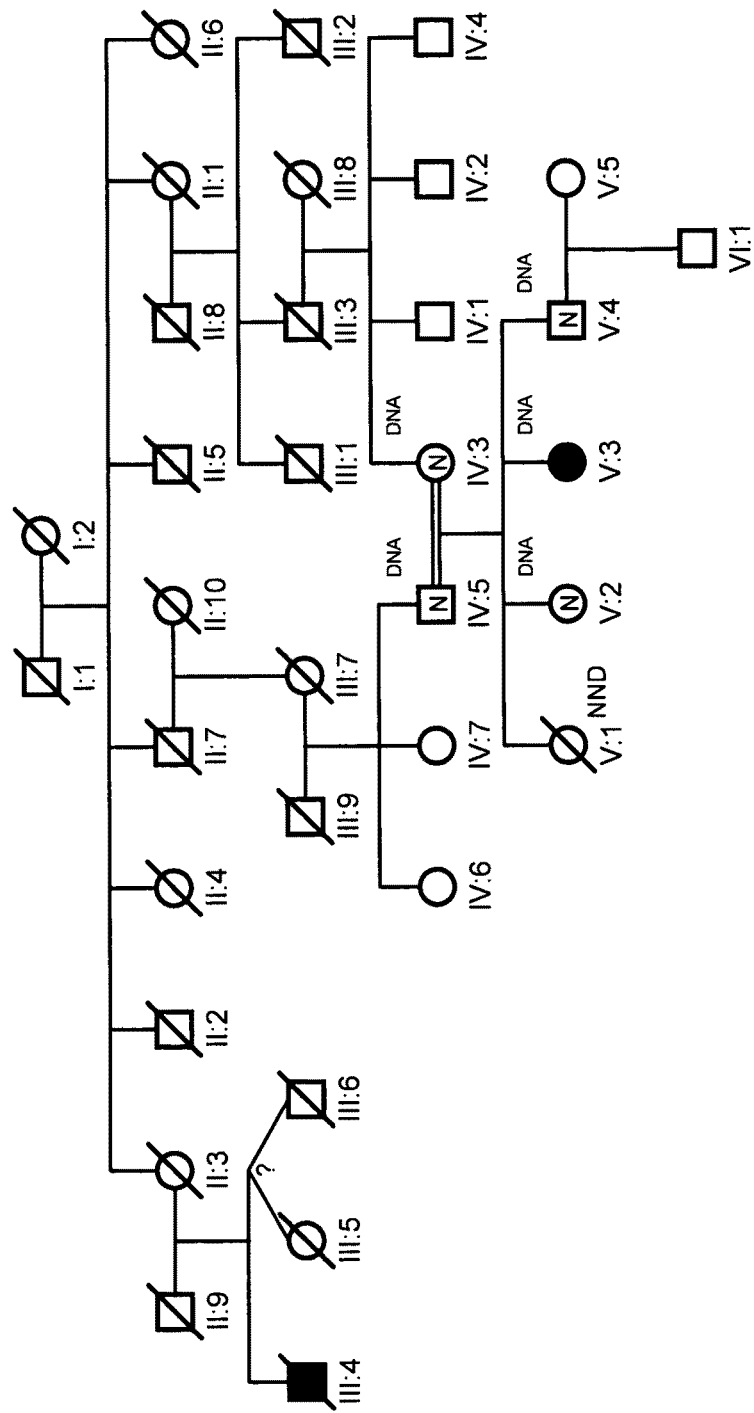
FIG. 1 shows the pedigree for a family designated CIP-10 showing family relationships and haplotypes. Squares and circles represent males and females, respectively. Filled symbols indicate individuals with CIP. Symbols with an "N" indicate individuals diagnosed as normal, and clear symbols with a question mark indicate individuals who have not been diagnosed

The present invention provides a novel therapeutic target related to pain response and methods of using this target to identify useful analgesic agents, as well as methods for treating pain in human patients.

Description of SCN9A

In one aspect, the present invention identifies a gene and its corresponding protein related to pain indifference, one such embodiment being the SCN9A gene. The SCN9A gene and protein may be known to those skilled in the art under a variety of names, including voltage-gated sodium channel type IX alpha polypeptide, neuroendocrine sodium channel, peripheral sodium channel 1, Schwann cell sodium channel, NENA, NE-Na, hNE-Na, hNE, PN1, hPN1, NaS, Nas, Na$_v$1.7, hNav1.7, and Na(v)1.7. Preliminary versions of the cDNA and amino acid sequences are found at GenBank Accession No. NM_002977.1 or XM_011955; The gene is described further at OMIM (On-line Mendelian Inheritance in Man) reference *603415.

The correct wild type nucleic acid sequence of the two isoforms of SCN9A (herein called "neo-natal" and "adult") is herein provided for the first time. The neo-natal SCN9A nucleic acid sequence is shown in SEQ ID NO: 1 with the correct neo-natal wild type amino acid sequence set forth at SEQ ID NO: 2. Table 1 identifies where the correct wild type sequence of neo-natal SCN9A set forth in SEQ ID NO: 1 diverges from the previously available public sequences of neo-natal SCN9A. The distinction between neo-natal and adult forms is a tentative description based on alternate Exon 5 (i.e. Exon 5N (for neo-natal) and Exon 5A (for adult)) further described, below. A nucleic acid sequence encoding a predicted adult splice variant of SCN9A employing exon 5A is found in SEQ ID NO: 3. The corresponding amino acid sequence of the predicted splice variant of SCN9A employing exon 5A is found in SEQ ID NO: 4. A nucleic acid sequence employing an alternate splice donor site at the end of Exon 11, herein called Exon 11B, is set forth at SEQ ID No. 5. The corresponding amino acid sequence of the predicted splice variant of SCN9A employing Exon 11B is found at SEQ ID No. 6.

The sequences listed in Table 1, shown below, represent SEQ ID NO: 46 to 111, respectively.

TABLE 1

| Sequence variations (numbered relative to initiator methionine) | Exon/Intron | Variation in relation to a cDNA sequence | Variation in relation to a protein sequence | | |
|---|---|---|---|---|---|
| Differences between all samples or genomic sequence and Genbank entry NM_002977.1 | 26 | 6182_6185delGATT | not applicable | Public sequence:<br>Correct sequence: | AAAAGTGATTGATTCAGTTTTTTG<br>AAAAGTGATTCAGTTTTTTG |
| Mutations | 8 | 984C > A | Y328X | More common:<br>Less common: | CAGAGGGGTACACCTGTGTGA<br>CAGAGGGGTAAACCTGTGTGA |
|  | 15 | 2488C > T | R830X | More common:<br>Less common: | CTTTTAGCTCCGAGTCTTCAA<br>CTTTTAGCTCTGAGTCTTCAA |
|  | 26 | 5067G > A | W1689X | More common:<br>Less common: | CTGCTGGCTGGGATGGATTGC<br>CTGCTGGCTGAGATGGATTGC |
| Polymorphisms | 1 | 174A > G | not applicable | More common:<br>Less common: | CTGGCAAACAACTGCCCTTCA<br>CTGGCAAACAGCTGCCCTTCA |
|  | 3 | 444G > A | not applicable | More common:<br>Less common: | TGAATAACCCGCCGGACTGGA<br>TGAATAACCCACCGGACTGGA |
|  | 9 | 1119C > T | not applicable | More common:<br>Less common: | CGCTGCGTGCCGCTGGCAAAA<br>CGCTGCGTGCTGCTGGCAAAA |
|  | 9 | 1266G > A | not applicable | More common:<br>Less common: | AAGAATTAGAGTTTCAACAGA<br>AAGAATTAGAATTTCAACAGA |
|  | 9 | 1287A > T | not applicable | More common:<br>Less common: | TGTTAGACCGACTTAAAAAAG<br>TGTTAGACCGTCTTAAAAAAG |
|  | 18 | 3448C > T | R1150W | More common:<br>Less common: | GTTGTGTACGGAGGTTCTC<br>GTTGTGTATGGAGGTTCTC |
|  | 26 | 4779G > T | not applicable | More common:<br>Less common: | CGTATTTTGTGTCCCCTACCC<br>CGTATTTTGTTTCCCCTACCC |
|  | Intron 2 | 377 + 93_94delTGInsGA | not applicable | More common:<br>Less common: | TTTGCACCTTTGAAGACTCTGG<br>TTTGCACCTTGAAAGACTCTGG |

TABLE 1-continued

| Sequence variations (numbered relative to initiator methionine) Exon/Intron | Variation in relation to a cDNA sequence | Variation in relation to a protein sequence | | |
|---|---|---|---|---|
| Intron 2 | 378 − 90A > T | not applicable | More common:<br>Less common: | ATTTTTTTCTAAGGAAAAGTT<br>ATTTTTTTCTTAGGAAAAGTT |
| Intron 3 | 478 − 219T > C | not applicable | More common:<br>Less common: | ATATTCTTAGTTATTTCAAGT<br>ATATTCTTAGCTATTTCAAGT |
| Intron 4 | 596 + 25T > C | not applicable | More common:<br>Less common: | CTTTTTGAAATGGCAAATTTA<br>CTTTTTGAAACGGCAAATTTA |
| Intron 4 | 596 + 591T > G | not applicable | More common:<br>Less common: | TCAGAAAAATTGATTTTTACA<br>TCAGAAAAATGGATTTTTACA |
| Intron 6 | 902 − 118T > C | not applicable | More common:<br>Less common: | GGATGCATATTGCCTGGGACC<br>GGATGCATATCGCCTGGGACC |
| Intron 8 | 1107 + 41A > G | not applicable | More common:<br>Less common: | TTTGAATGGCATATGTACCTG<br>TTTGAATGGCGTATGTACCTG |
| Intron 8 | 1107 + 48T > C | not applicable | More common:<br>Less common: | GGCATATGTATCTGGTGTATG<br>GGCATATGTACCTGGTGTATG |
| Intron 9 | 1314 + 76C > T | not applicable | More common:<br>Less common: | GCGGTATATGCTTGGCCTTCT<br>GCGGTATATGTTTGGCCTTCT |
| Intron 9 | 1314 + 199C > T | not applicable | More common:<br>Less common: | CCCATAATCACCTCACTGCAT<br>CCCATAATCATCTCACTGCAT |
| Intron 10 | 1603 − 388T > C | not applicable | More common:<br>Less common: | TTTGTGAAGCTTGGGGATTGA<br>TTTGTGAAGCCTGGGGATTGA |
| Intron 11 | c.1942 − 2_3insT | not applicable | More common:<br>Less common: | ATTTTTTTTTAGGGCACGACC<br>ATTTTTTTTTTAGGGCACGACC |
| Intron 12 | 2072 − 14T > C | not applicable | More common:<br>Less common: | ATGTTCTCTGTTTTTTCTCC<br>ATGTTCTCTGCTTTTTCTCC |
| Intron 19 | 3769 − 70T > C | not applicable | More common:<br>Less common: | TAGTGAGTTTTAGAATTGACT<br>TAGTGAGTTTCAGAATTGACT |
| Intron 19 | 3769 − 4A > G | not applicable | More common:<br>Less common: | TGTTATTTTTATAGGTTTCTT<br>TGTTATTTTTGTAGGTTTCTT |
| Intron 21 | 4173 + 58_59delAA | not applicable | More common:<br>Less common: | CGAAGGATATAAGTTATTCTTT<br>CGAAGGATATGTTATTCTTT |
| Intron 21 | 4173 + 77C > A | not applicable | More common:<br>Less common: | TTTAAATAGTCTATTAATTAT<br>TTTAAATAGTATATTAATTAT |
| Intron 21 | 4174 − 146insA | not applicable | More common:<br>Less common: | TTTAAAAAATCTTTACATT<br>TTTAAAAAAATCTTTACATT |
| Intron 21 | 4174 − 196A > G | not applicable | More common:<br>Less common: | ATAATTAACTAGGACTAAGAT<br>ATAATTAACTGGGACTAAGAT |
| Intron 23 | 4365 + 99A > G | not applicable | More common:<br>Less common: | TTCATGATTAATTTATTAGA<br>TTCATGATTAGTTTATTAGA |
| Intron 23 | 4366 − 13_14insGTTT | not applicable | More common:<br>Less common: | TTTTTTGTTTCTTTACCTTG<br>TTTTTTGTTTGTTTCTTTACCTTG |
| Intron 25 | 4741 + 16A > T | not applicable | More common:<br>Less common: | AATATTTATTATTCAGATTTT<br>AATATTTATTTTTCAGATTTT |

The present invention further provides at SEQ ID No. 7, a first mutation in the gene encoding this protein found in a first family (CIP-10) at G5067A (herein shown in the 5N/11 isoform, although 5A and 11B isoforms are also expected at different developmental stages). The mutation results in a truncation described as W1689X (SEQ ID NO: 8). The present invention also provides a second mutation in the gene encoding SCN9A which is responsible for congenital indifference to pain in a different family (CIP-14). The nucleic acid sequence of this second mutation, C984A, is set out in SEQ ID NO: 9 (herein shown in the 5N/11 isoform) and the corresponding mutant protein, Y328X, is described in SEQ ID NO: 10. The present invention also provides a third mutation in the gene encoding SCN9A which is responsible for congenital indifference to pain in a third family (CIP-08). The nucleic acid sequence of this second mutation, C2488T, is set out in SEQ ID NO: 11 (herein shown in the 5N/11 isoform) and the corresponding mutant protein, R830X, is described in SEQ ID NO: 12.

This invention also provides human BAC clone RP11-437H3 (AC108146) which carries the complete human genomic fragment bearing the SCN9A gene. This BAC may be obtained commercially from well known sources. A short part of this BAC bearing the nucleotide sequence from the 3' end of exon 4 to the 5' end of exon 6, including exon 5A and exon 5N, is set forth at SEQ ID No. 13. The promoter region of SCN9A, including both genomic sequence and the 5'UTR of SCN9A is set forth at SEQ ID No. 14.

This invention also provides SCN9A from mouse (*M. musculus*) and various isoforms in Table 2 below.

TABLE 2

Isoforms of Mouse SCN9A disclosed

| SEQ ID No. | Mouse SCN9A isoform |
|---|---|
| 15 | Mouse 11B nt |
| 16 | Mouse 11B a.a. |
| 17 | Mouse 5A nt |
| 18 | Mouse 5A a.a. |
| 19 | Mouse 5N nt |
| 20 | Mouse 5N a.a. |

Thus the invention thus discloses several novel isoforms and mutants of human and mouse SCN9A.

In aspects of the invention relating to the use of SCN9A, such as in screening assays, or for the development of antibodies, etc., etc., the inventors recognize that those skilled in the art may prefer to use forms of SCN9A corresponding to the sequences disclosed herein, although not necessarily the same. For example, screening assays may utilize SCN9A from a different organism, preferably a vertebrate, and most preferably from a mammalian species. The shared technical features of these forms of SCN9A, are that, when expressed, they have sodium channel activity, and that they share functional similarity with SCN9A, such as may be determined by those skilled in the art. Thus the invention encompasses the use of, for example, sheep, dog or horse SCN9A, for the same purposes as set out more specifically herein for human or mouse SCN9A.

As used herein, the term "correspond" means that the gene has the indicated nucleotide sequence or that it encodes the same RNA as would be encoded by the indicated sequence, including splice variants thereof.

Because of the processing that may take place in transforming the initial RNA transcript into the final mRNA, the sequences disclosed herein may represent less than the full genomic sequence. They may also represent sequences derived from alternate splicing of exons, ribosomal and/or transfer RNAs. Consequently, the genes present in the cell (and representing the genomic sequences) and the sequences disclosed herein, which are mostly cDNA sequences, may be identical or may be such that the cDNAs contain less than the full genomic sequence. Such genes and cDNA sequences are still considered corresponding sequences because they both encode similar RNA sequences. Thus, by way of non-limiting example only, a gene that encodes an RNA transcript, which is then processed into a shorter mRNA, is deemed to encode both such RNAs and therefore encodes an RNA complementary to (using the usual Watson-Crick complementarity rules), or that would otherwise be encoded by, a cDNA (for example, a sequence as disclosed herein). (Those skilled in the art understand that the word "encode" and its derivatives mean, in this field "can be transcribed into".) Thus, the sequences disclosed herein correspond to genes contained in the cells and are used to determine relative levels of expression because they represent the same sequences or are complementary to RNAs encoded by these genes. Such genes also include different alleles and splice variants that may occur in the cells used in the processes of the invention.

Thus, the polynucleotides, such as the genes disclosed herein, for use in the screening assays of the invention "correspond to" the polynucleotide encoding SCN9A mRNA (processed or unprocessed, including naturally occurring splice variants and alleles) at least 60%, preferably at least 70%, even more preferably at least 80%, or even at least 85%, most preferably at least 90%, or even at least 95%, or most especially at least 98%, with the especially preferred embodiment of identical to, and especially having the sequence of, an RNA that would be encoded by, or be complementary to, such as by hybridization under reasonably stringent conditions, with a SCN9A polynucleotide (SEQ ID NO: 1). In addition, sequences encoding the same polypeptides and proteins as any of these sequences, regardless of the percent identity of such sequences, are also specifically contemplated by any of the methods of the present invention that rely on any or all of said sequences, regardless of how they are otherwise described or limited. Thus, any such sequences are available for use in carrying out any of the methods disclosed according to the invention. Such sequences also include any open reading frames, as defined herein, present within an SCN9A polynucleotide.

As used herein, the term "percent identity" or "percent identical," when referring to a sequence, means that a sequence is compared to a claimed or described sequence after alignment of the sequence to be compared (the "Compared Sequence") with the described or claimed sequence (the "Reference Sequence"). The Percent Identity is then determined according to the following formula:

$$\text{Percent Identity}=100[1-(C/R)]$$

wherein C is the number of differences between the Reference Sequence and the Compared Sequence over the length of alignment between the Reference Sequence and the Compared Sequence wherein (i) each base or amino acid in the Reference Sequence that does not have a corresponding aligned base or amino acid in the Compared Sequence and (ii) each gap in the Reference Sequence and (iii) each aligned base or amino acid in the Reference Sequence that is different from an aligned base or amino acid in the Compared Sequence, constitutes a difference; and R is the number of bases or amino acids in the Reference Sequence over the length of the alignment with the Compared Sequence with any gap created in the Reference Sequence also being counted as a base or amino acid.

If an alignment exists between the Compared Sequence and the Reference Sequence for which the percent identity as calculated above is about equal to or greater than a specified minimum Percent Identity then the Compared Sequence has the specified minimum percent identity to the Reference Sequence even though alignments may exist in which the hereinabove calculated Percent Identity is less than the specified Percent Identity.

As used herein, the terms "portion," "segment," and "fragment," when used in relation to polypeptides, refer to a continuous sequence of nucleotide residues, sequence forms a subset of a larger sequence. Such terms include the products produced by treatment of said polynucleotides with any of the common endonucleases, or any stretch of polynucleotides that could be synthetically synthesized. These may include exonic and intronic sequences of the corresponding genes.

Identification of SCN9A Modulating Agents

The present invention readily affords different means for identification of SCN9A modulating agents which are useful as therapeutic agents. One such protocol involves the screening of chemical agents for ability to modulate the activity of SCN9A thereby identifying an SCN9A modulating agent. SCN9A modulating agents so identified are then tested in a variety of in vivo models so as to determine if they alleviate pain, especially chronic pain or other disorders. In a preferred embodiment the agent modulates the activity of SCN9A downwards.

Thus, in one aspect the present invention relates to a method for identifying an agent that modulates the activity of a polynucleotide whose expression contributes to pain sensation or whose non-expression contributes to lack of pain sensation, comprising:

a) contacting under physiological conditions a chemical agent with a polynucleotide corresponding to a promoter of the SCN9A gene, preferably having the sequence of SEQ. ID NO. 14, under conditions promoting such contacting; and b) detecting a change in the expression of said polynucleotide as a result of said contacting;

thereby identifying an agent that modulates said polynucleotide activity.

Such modulation is preferably a decrease in expression. In preferred embodiments, such expression is measured by measuring the amount of an expression product encoded by said polynucleotide, most preferably an RNA or a polypeptide. In a preferred embodiment the promoter sequence is operably linked to a reporter gene, and the assay measures relative expression of the reporter gene or its gene product.

In preferred embodiments, the polynucleotide whose expression is to be measured or monitored is present in an intact cell, preferably a mammalian cell, most preferably a neuronal cell, and may include a recombinant cell. In preferred embodiments, such an intact cell is a cell that has been engineered to comprise said polynucleotide, such as by genetic engineering, most preferably wherein the cell does not express the subject gene or polynucleotide absent having been engineered to do so.

Agents that alter the activity of SCN9A or active fragments or portions of said gene, or that may modulate the activity of polypeptides encoded by SCN9A, or polypeptides that act as transcription factors to modulate the activity of such genes, or other related gene segments, such as enhancers or other regulatory genetic elements that modulate the activity of SCN9A, acting either in cis or trans fashion, are thereby identified and may prove useful in treating chronic and other types of pain. Related genes might include those with high sequence homology, perhaps at least 98%, to the sequences disclosed herein and would, preferably, have sequences identical to the sequences disclosed herein.

In another aspect, the present invention relates to a method for identifying an agent that modulates the activity of a polypeptide encoded by a polynucleotide as disclosed herein, comprising:

a) contacting under physiological conditions a chemical agent with a polypeptide encoded by a polynucleotide corresponding to a SCN9A gene, preferably having the sequence of SEQ. ID NO. 1, 3, 5, 15, 17, 19; and b) detecting a change in the activity of said polypeptide as a result of said contacting;

thereby identifying an agent that modulates said polypeptide activity.

In a preferred embodiment, the observed change in activity in step (b) is a decrease in activity, most preferably wherein said change in activity is the result of binding to or interacting with said polypeptide by said chemical agent of step (b), especially where the polypeptide is an ion channel, and the ion channel is blocked by said binding. In a further preferred embodiment, the polypeptide is a sodium channel, and said blocking is voltage dependent. A preferred therapeutic agent may be an irreversible binding agent or it may be a reversible binding agent.

In additional preferred embodiments, the polypeptide is part of a lipid bilayer, such as an intact cell, preferably a mammalian cell, such as a neuronal cell, most preferably a recombinant cell. In one such embodiment, a cell that has been engineered to comprise said polypeptide, including by genetic engineering, especially where the cell does not possess the polypeptide absent said engineering.

In another embodiment, the polypeptide is part of a cell, tissue, cell-line, immortalized cell or the like, which carries the gene and that expresses it, either naturally or upon induction. In this embodiment, the expressed gene is non-recombinant. As a non-limiting example, the PC-12 cell line derived from a transplantable rat pheochromocytoma responds reversibly to nerve growth factor (NGF) by induction of the neuronal phenotype and SCN9A expression. See Toledo-Aral J J, et al. Proc Natl Acad Sci USA. 1997 Feb. 18; 94(4):1527-32.

In one preferred embodiment of such method, the SCN9A polypeptide is a polypeptide corresponding to a polypeptide having the amino acid sequence of SEQ ID NO: 2, 4, 6, 16, 18, or 20.

Thus, the present invention specifically contemplates embodiments in which the cell is engineered by other than genetic engineering, such as where the activity of a polypeptide is to be enhanced and the cell has been engineered to contain, or have on its surface, said polypeptide but wherein the polypeptide is present due to physical insertion of the polypeptide into the membrane or cytoplasm of the cell and not through expression of a gene contained in the cell. Such engineering includes direct insertion of the polypeptide into the lipid bilayer, such as where a lipid bilayer comprising the polypeptide is fused to a membrane, such as that of an intact cell, resulting in the cell membrane comprising the polypeptide. Methods well known in the art, such as use of polyethylene glycol, viruses, and the like, are available to effect such insertions and the details of such procedures need not be further described herein.

In one preferred embodiment of such method, the polypeptide is a polypeptide that reacts with an antibody that reacts with, or is specific for, a polypeptide having an amino acid sequence at least 95% identical to, more preferably at least 98% identical to, the sequence of SEQ ID NO: 2 and where any difference in amino acid sequence is due only to conservative amino acid substitutions. In an especially preferred embodiment, the polypeptide has the amino acid sequence of SEQ ID NO: 2.

In a further aspect, the present invention relates to a method for identifying an analgesic agent, comprising:

a) administering to an animal an agent found to have activity using an assay or screening method as disclosed herein, and b) detecting in said animal a decrease in response to a pain stimulus following said administering and due thereto, thereby identifying an analgesic agent.

Preferably, the animal is a mammal, such as a human being. In specific embodiments, the pain stimulus is a heat stimulus and reaction or sensitivity to hot and/or cold may be measured. In another embodiment, an electrical stimulus may be used. In all cases, the stimulus may be represented as a sharp or dull sensation. In some cases, the animal may otherwise react normally to such stimulus so that a decrease in normal response due to the test agent is being measured whereas in other cases the animal may initially possess a heightened sensitivity to the stimulus prior to administering the test agent. In all cases, observation of an analgesic effect need not necessarily involve a reduced sensitivity or response to pain but may involve simply a reduced sensation of a particular stimulus. The analgesics identified by the methods of the invention may induce general analgesia in an animal or may have more localized analgesic or anesthetic effects.

Further embodiments of the assays useful for identifying modulators of SCN9A are set out further below in this specification.

Selectivity for SCN9A Over Other Sodium Channels

The present invention specifically contemplates the identification of chemical agents, especially small organic molecules, that inhibit the expression of an SCN9A gene or the activity of an SCN9A polypeptide, with high specificity and/or selectivity and that have limited effect on other sodium channel genes and/or expression products. The inventors recognize on the basis of their discovery that selective inhibition of SCN9A as opposed to any of the other sodium channels leads to the therapeutically desirable outcomes observed in C-I-P. Because the other sodium channels are implicated in other essential physiological processes, such as heart activity, muscle contraction, and various neurological processes, it is highly desirable to avoid modulation of these other sodium channels.

This invention thus sets forth, for the first time, a scientifically justified rationale for the pursuit and discovery of sodium channel blockers which are highly selective for SCN9A for use as analgesics and to induce other symptomatic responses observed in C-I-P. The invention herein provides a solution to the problems posed in Anger et al. (2001. J. Med. Chem. 44(2):115-137) about the lack of information concerning which sodium channel sub-type to pursue and about the significant uncertainty in the art regarding the extent of selectivity required.

Also, by identifying SCN9A as the therapeutic target of choice in humans, the invention overcomes prior art teachings which suggested, but did not prove, that SCN9A may be involved in essential bodily functions such as bladder control and temperature control. SCN9A was believed to be the primary sodium channel of unmyelinated sensory and autonomic nerve cells. This prior art work led the field to believe that SCN9A was to be avoided as a target for therapeutic modulation because such modulation would negatively effect these essential bodily functions. However, the instant invention teaches, for the first time, that in humans, modulation of SCN9A can provide a highly desirable result, namely the treatment of pain, evidently without other physiological or autonomic impacts.

Thus, in a preferred embodiment of the invention, the compound identified which modulates SCN9A gene expression or SCN9A polypeptide activity is selective for SCN9A as opposed to other sodium channel alpha subunits (i.e. SCN1A to SCN8A, SCN10A to SCN12A). Such selectivity of modulation is preferably at least 10%, 50%, 100%, 10 times, 20 times, 100 times, 1000 times, 10,000 times or higher for SCN9A over any other sodium channel alpha subunit. Alternatively, a compound which is selective for SCN9A may not demonstrate an absolute preference for SCN9A, but the compound may show a preference for modulating SCN9A compared to any other sodium channel which preference is greater than any other prior art sodium channel blocker.

In another preferred embodiment, the methods disclosed herein for identifying an agent that modulates, preferably inhibits, expression or activity of a gene or polypeptide corresponding to SCN9A comprise first identifying such agent and then testing such agent for effects on expression or activity of at least one other sodium channel gene or polypeptide, as the case may be, preferably at least two other such genes, or polypeptides, with little or no effect. A preferred compound identified herein normally demonstrates no more than 25% of the effect that any compound heretofore measured has on the other sodium channel gene and/or polypeptide, preferably no more than 10% of such activity, most preferably no more than 5% of such activity and especially exhibiting no more than 1% of such activity. In such cases, the activity may be measured as the rate at which sodium ions are transported under the actions of the polypeptide or the amount of RNA expressed by said gene, especially on a weight-to-weight basis, or the nanomole ratio of RNA products produced by transcription of the gene.

Thus, the agents contemplated by the present invention are highly selective for the SCN9A gene or protein and administration of such an agent to a human or other animal in need thereof generates a temporary condition which mimics the Congenital Indifference to Pain phenotype to the highest degree possible, or aspects thereof. For example, it mimics the effects of one or more of the mutated forms of the gene as disclosed herein. In a preferred embodiment, the agent generates indifference to pain, but does not diminish sensations which are available to patients with CIP, such as but not limited to heat/cold sensing, pressure sensing, sharp/dull sensations, and does not diminish physiological responses such as sweating, heart rate, muscle activity and the like. For example, indifference to pain without any concomitant numbness or loss of sensation would represent a useful manifestation of the results to be achieved.

It is a preferred embodiment of this invention to use the screening assays of the invention to identify potential therapeutic agents, or analogs thereof, that are selective for the SCN9A sodium channel ahead of other sodium channels, in humans and other animals. It will therefore be apparent to those skilled in the art that a series of assays for measuring differential interaction with other sodium channels would provide the tools necessary to identify selective agents for SCN9A. In this embodiment, a first screening assay employing SCN9A is used to identify compounds which inhibit SCN9A activity. A suite of secondary assays are then employed, each containing one or more different sodium channels selected from among $Na_v1.1$ (SCN1A); $Na_v1.2$ (SCN2A), $Na_v1.3$ (SCN3A), $Na_v1.4$ (SCN4A), $Na_v1.5$ (SCN5A), $Na_v1.6$ (SCN8A), $Na_v1.8$ (SCN10A), $Na_v1.9$ (SCN11A), and $Na_x$ (SCN6A, SCN7A) (for consensus nomenclature see Goldin, A L. 2001. Ann. Rev. Physiol. 63:871-894). Compounds which were found to inhibit SCN9A expression or activity, are systematically tested against the assays for the other sodium channels. Those compounds which are more selective for SCN9A over other channels than current sodium channel blocking compounds used in the art are preferred compounds.

The other sodium channels can be incorporated into screening assays according to methods disclosed herein, or as disclosed elsewhere in the art or as later discovered or invented. As such, the $Na_v1.1$, $Na_v1.2$ and $Na_v1.3$ screening assays set out in WO 01/38564 (Rouleau et al, published 31 May 2001) may be used to effectively distinguish compounds which are broadly selective for sodium channels from those that are specific and selective exclusively for SCN9A.

Some of the standard screening assays for a protein like SCN9A are set out in U.S. Pat. No. 6,110,672 (a US counterpart of WO 96/14077), incorporated herein by reference in its entirety. These assays provide for basic analysis of agents which interact with a protein like SCN9A (although the reference provides no guidance on achieving selectivity among sodium channels). The genetic and phenotypic information provided in the instant patent application now provides therapeutic agents which effectively mimic the Congenital Indifference to Pain phenotype, by selecting those compounds which are selective for SCN9A over other sodium channel family members. The invention provides a compound which, while not necessarily being selective for the peripheral nervous system over the central nervous system (as prescribed in WO 96/14077), the compound is specific for SCN9A ahead of all other sodium channels. Such a compound provides analgesic relief without side-effects such as nausea, tremor and irritability.

The benefits of the present invention and the value of selectivity for SCN9A over other sodium channels for the treatment of pain is further illustrated in Table 4 below. Table 4 sets out the known phenotypic or disease consequences of mutations in various known sodium channels in rodents and humans. As can be seen, modulation of the activity of almost all the other sodium channels results in severe and undesirable physiological consequences. For example, inhibitory mutations in human SCN1A result in a type of epilepsy. Gain of function mutations in rodent SCN2A result in behavioral disorders. Loss of function mutations in rodent SCN2A result in severe neurological disorders. SCN2A mutations in humans also result in a type of epilepsy. The list leads to the conclusion that a compound which selectively inhibits SCN9A will be a useful treatment for pain, and will not cause the undesirable consequences of modulation of the other sodium channels.

TABLE 4

| Gene | Protein | Rodent Phenotype | Human Disease or Phenotype | Reference |
|---|---|---|---|---|
| SCN1A | Na(v)1.1 | Unknown | Generalized epilepsy with febrile seizures plus type II (OMIM 604233); severe myoclonic epilepsy of infancy (OMIM 607208) | 1, 2, 3, |
| SCN2A2, SCN2A | Na(v)1.2 | Transgenic Mouse - seizures, focal motor abnormalities, behavioral arrest and stereotyped repetitive behaviors; Knock-Out Mouse - perinatal lethal with severe hypoxia and massive neuronal apoptosis in the brainstem | Generalized epilepsy with febrile seizures plus (OMIM 604233) | 4, 25 |
| SCN3A | Na(v)1.3 | Unknown | Unknown | |
| SCN4A | Na(v)1.4 | Unknown | Hyper-(and hypo-) kalemic periodic paralysis (OMIM 170500, 170400 paramyotonia congenita (OMIM 168300, 168350) | 10, 11 |
| SCN5A | Na(v)1.5 | Knock-In Mice - arrhythmias; Knock-Out mice (−/−) - intrauterine lethality with defective ventricular morphogenesis; Knock-Out mice (+/−) - arrhythmias | Long QT syndrome-3 (OMIM 603830), Brugada syndrome (601144); heart block (OMIM 113900; paroxysmal familial ventricular fibrillation (OMIM 603829) | 12, 13, 14, 15, 16, 17, 26 |
| SCN8A | Na(v)1.6 | Various spontaneous mutations result in: motor endplate disease - progressive paralysis and juvenile lethality in C57BL/6J mice; Viable adults with dystonia in C3H mice; Jolting mice - cerebellar ataxia; DMU mice - skeletal and cardiac muscle degeneration; heterozygotes unaffected | Unknown | 5, 6, 7, 8, 9 |
| SCN10A | Na(v)1.8 | Knock-out mice mechanical analgesia, reduced thermal hyperalgesia, and delayed inflammatory hyperalgesia, but normal neuropathic pain perception (heterozygotes like wild-type); Knock-down mice - reduced inflammatory hyperalgesia and neuropathic pain (note discrepancy with above) | Unknown | 18, 19, 20, 21, 22 |
| SCN12A, SCN11A | Na(v)1.9 | Knock-down in rat: No effect on nerve-injury induced behavior responses | Unknown | 23 |
| SCN6A, SCN7A | Na(x) | Knock-out: Altered salt intake | Unknown | 24 |

TABLE 4-continued

| Gene | Protein | Rodent Phenotype | Human Disease or Phenotype | Reference |
|---|---|---|---|---|
| SCN9A | Na(v)1.7 | Unknown | Congenital indifference to pain (OMIM 243000) | This work |

The emphasis noted herein on the preferred selectivity for SCN9A over other sodium channels, should also be understood to include selectivity over other ion channels and related proteins and genes. Preferred selective SCN9A modulating agents have limited or no effect on the activity of ion channels such as potassium, calcium, ion co-transporters and the like, nor does it effect the hERG channel or other physiologically relevant channels. The emphasis on sodium channel selectivity is based on the high degree of similarity among sodium channels among which selectivity is technically more challenging to achieve than with less closely related proteins/genes.

On another note, this invention also establishes that improved therapeutic agents for the treatment of pain must take advantage of the dynamic state of a sodium channel. Therapeutic agents can now be identified with entirely novel modes of action against the channel. A sodium channel cycles from the open (activated) state to the closed (inactivated) state, then to the resting (closed but capable of being activated) state, where it waits for an electrical signal to convert to the open state and allow passage of sodium ions. The transition from open to closed may be by fast inactivation or slow inactivation. Previous knowledge of the SCN9A channel did not allow for the identification of which state or transition state of the channel was preferred for therapeutic intervention. The instant invention now establishes that the Y328X or the W1689X mutation causes the desired channel behavior to generate the desirable indifference to pain in humans. An irreversible binding agent may be as suitable for use as a reversible binding agent. This invention therefore provides mutant proteins which may be used in the screening assays to assist in the identification of therapeutic agents or their analogs which mimic the truncation mutations of the invention. It also teaches a functional description about what the binding agent/blocking agent must do to achieve analgesia.

Further Assays

Stated broadly, the screening assays of the invention simplify the identification, evaluation and development of classes of compounds which are suitable for use as analgesic agents and for the reduction of adverse pain responses to disease, such as chronic disease, for example cancer. In general, these screening methods provide a ready means for selecting either natural product extracts or synthetic compounds of interest from a large population (i.e. a chemical library, for example, one produced by combinatorial means). As stated previously, an assay is first designed which measures SCN9A expression or activity. Exemplary methods useful for the identification of such compounds are detailed herein, although those skilled in the art will be aware of alternative means. In a first step, compounds are sequentially tested against the assay to determine whether they influence a measurable biological activity of the assay.

Functional assays may be based one or more of the diverse measurable biological activities of a gene or polypeptide corresponding to SCN9A. "SCN9A activity" as used herein, especially relating to screening assays, is to be interpreted broadly and contemplates all directly or indirectly measurable and identifiable biological activities of the SCN9A gene and protein. Relating to the purified SCN9A protein, SCN9A activity includes, but is not limited to, all those biological processes, interactions, binding behavior, binding-activity relationships, pKa, pD, enzyme kinetics, stability, and functional assessments of the protein. Relating to SCN9A activity in cell fractions, reconstituted cell fractions or whole cells, these activities include, but are not limited to the rate at which the SCN9A channel transports sodium, guanidine, lithium or other ions across a membrane, or the dynamics of this transport (such as voltage dependence, rate of transition between states) and all measurable consequences of these effects, including cell growth, development or behavior and other direct or indirect effects of SCN9A activity. Relating to SCN9A genes and transcription, SCN9A activity includes the rate, scale or scope of transcription of genomic DNA to generate RNA; the effect of regulatory proteins on such transcription, the effect of modulators of such regulatory proteins on such transcription; plus the stability and behavior of mRNA transcripts, post-transcription processing, mRNA amounts and turnover, and all measurements of translation of the mRNA into polypeptide sequences. Relating to SCN9A activity in organisms, this includes but is not limited biological activities which are identified by their absence or deficiency in disease processes or disorders caused by aberrant SCN9A biological activity in those organisms. Broadly speaking, SCN9A biological activity can be determined by all these and other means for analyzing biological properties of proteins and genes that are known in the art.

The invention therefore provides numerous assays which measure an activity of SCN9A and are useful for the testing of chemical compounds to identify which ones effect such activity. The invention also invites those skilled in the art to develop further SCN9A activity assays which go beyond those disclosed herein, for use in the screening compound libraries.

A typical assay uses patch-clamp techniques to study the behavior of channels. Such techniques are known to those skilled in the art, and may be developed, using current technologies, into low or medium throughput assays for evaluating compounds for their ability to modulate sodium channel behavior.

A competitive binding assay with known sodium channel toxins such as tetrodotoxin, alpha-scorpion toxins, and the like, may be suitable for identifying potential therapeutic agents with high selectivity for SCN9A.

In still another assay, uptake of radioactive isotopes into or out of a vesicle can be measured. The vesicles are separated from the extra-vesicular medium and the radioactivity in the vesicles and in the medium is quantitated and compared.

Other typical assays employ drug screening technology such as (but not limited to) radioactive, colorimetric or fluorescent based measurements. A classic colorimetric assay measures the ability of a dye to change color in response to changes in assay conditions resulting from the activity of the polypeptides. A useful instrument for the study of ion channels, including sodium channels is the ICR 8000 available from Aurora Biomed Inc. (Vancouver, BC).

Functional drug screening assays can also be based upon the ability of SCN9A polypeptides to interact with other proteins. Such interacting proteins can be identified by a variety of methods known in the art, including, for example, radioimmunoprecipitation, co-immunoprecipitation, co-purification, and yeast two-hybrid screening. Such interactions can be further assayed by means including but not limited to fluorescence polarization or scintillation proximity methods. Drug screens can also be based upon functions of the polypeptides deduced upon X-ray crystallography of the protein and comparison of their 3-D structure to that of proteins with known functions. Drug screens can be based upon a function or feature apparent upon creation of a transgenic or knockout mouse, or upon overexpression of the protein or protein fragment in mammalian cells in vitro. Moreover, expression of mammalian (e.g., human) polypeptides in yeast or C. elegans allows for screening of candidate compounds in wild-type and mutant backgrounds, as well as screens for mutations that enhance or suppress a low pain sensitivity phenotype. Modifier screens can also be performed in transgenic or knock-out mice.

Additionally, drug screening assays can also be based upon polypeptide functions deduced upon antisense interference with the gene function. Intracellular localization of SCN9A polypeptides, or effects which occur upon a change in intracellular localization of such proteins, can also be used as an assay for drug screening. Immunocytochemical methods may be used to determine the exact location of the pain-related polypeptides.

Polypeptides encoded by the polynucleotides disclosed herein can be used as an antigen to raise antibodies, including monoclonal antibodies. Such antibodies will be useful for a wide variety of purposes, including but not limited to functional studies and the development of drug screening assays and diagnostics. Monitoring the influence of agents (e.g., small organic compounds) on the expression or biological activity of the pain-related polypeptides identified according to the invention can be applied not only in basic drug screening, but also in clinical trials. For example, the effectiveness of an agent determined by a screening assay as described herein to increase or decrease gene expression, protein levels, or biological activity can be monitored in clinical trails of subjects exhibiting symptoms of chronic or persistent pain due to inadequate gene expression, protein levels, or biological activity (for example, the individuals studied herein. Alternatively, the effectiveness of an agent determined by a screening assay to modulate expression of SCN9A, as well as structurally and functionally related genes, including genes with high homology thereto, and including protein levels, or biological activity can be monitored in clinical trials of subjects exhibiting decreased altered gene expression, protein levels, or biological activity. In such clinical trials, the expression or activity of the genes or polypeptides disclosed herein and, preferably, other genes that have been implicated in, for example, congenital indifference to pain stimuli, can be used to ascertain the effectiveness of a particular analgesic drug.

As a non-limiting example, genes that are modulated in cells by treatment with an agent (e.g., compound, drug or small molecule) that modulates the activity of the SCN9A gene, or any expression products thereof, or polypeptides that modulate the activity of SCN9A (e.g., identified in a screening assay as described herein) can be identified. Preferably, such cells are recombinant cells engineered to express a polynucleotide or polypeptide as disclosed herein. Thus, such recombinant cells are prepared and RNA isolated and analyzed for the levels of expression of SCN9A after contacting said cells with agents that may have analgesic properties. The levels of gene expression can be quantified by Northern blot analysis or RT-PCR, or, alternatively, by measuring the amount of protein produced, by one of a number of methods known in the art, or by measuring the levels of biological activity of polypeptides encoded thereby or other genes. In this way, the gene expression can serve as a marker, indicative of the physiological response of the cells to the agent. Accordingly, this response state may be determined before, and at various points during, treatment of the individual with the agent.

In another aspect, the invention provides a method for computationally identifying a compound having analgesic properties. The method involves (a) determining crystal structure and preferably the active site of a SCN9A protein (i.e. through x-ray crystallography or other techniques); and (b) through computational modeling, identifying a compound which interacts with the active site, thereby identifying a compound, or its analog, as a compound which is useful for modulating the activity of such a polypeptide. Useful screening assays may also be performed in silico using available computerized databases for the identification of such compounds.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) including the steps of (i) determining that a patient exhibits discomfort due to a disease or disorder that causes some type of painful stimulus; (ii) administering an effective amount of an agent identified using one of the screening assays disclosed herein; (iii) ascertaining a reduction to pain or other stimuli following said administration and (iv) altering the administration of the agent to the subject accordingly. For example, increased administration of the agent may be desirable to decrease the expression or activity of gene or encoded polypeptide, i.e., to increase the effectiveness of the agent.

Where the patient is non-human, biopsy samples can be taken to show a decrease in gene expression, such as by measuring levels of protein, mRNA, or genomic DNA post-administration samples and comparing the level of expression or activity of said protein, mRNA, or genomic DNA in the pre-administration sample with that of the corresponding post administration sample or samples, thereby showing the effects of drug administration on one or more of the genes disclosed herein and concomitant reduction in pain response and/or sensitivity.

The gene disclosed herein as being involved in congenital indifference to pain in an animal can be used, or a fragment thereof can be used, as a tool to express a protein, where such genes encode a protein, in an appropriate cell in vitro, or can be cloned into expression vectors which can be used to produce large enough amounts of protein to use in in vitro assays for drug screening. Expression systems which may be employed include baculovirus, herpes virus, adenovirus, adeno-associated virus, bacterial systems, and eucaryotic systems such as CHO cells, HEK cells and other cells commonly available. Naked DNA and DNA-liposome complexes can also be used.

Candidate modulators may be purified (or substantially purified) molecules or may be one component of a mixture of compounds (e.g., an extract or supernatant obtained from cells). In a mixed compound assay, SCN9A activity is tested against progressively smaller subsets of the candidate compound pool (e.g., produced by standard purification techniques, e.g., HPLC or FPLC; Ausubel et al.) until a single compound or minimal compound mixture is demonstrated to modulate gene or protein activity or expression in a manner having analgesic effects.

Specific compounds which will modulate the gene expression or gene transcript levels in a cell of SCN9A include antisense nucleic acids, ribozymes and other nucleic acid compositions which specifically hybridize with SCN9A (including exons or introns of such genes, promoters, 3' tails, etc.). These specific compounds are compounds of the invention, and are useful for treating the diseases discussed previously. Design and manufacturing of such compounds are well known to those skilled in the art.

Specific compounds which modulate the activity of a SCN9A polypeptide include antibodies (polyclonal or monoclonal) which specifically bind to an epitope of said polypeptide. These specific compounds are compounds of the invention, and are useful for inducing resistance of tolerance to pain stimuli. Design and manufacturing of such compounds are well known to those skilled in the art.

Specific compounds which modulate the activity of SCN9A in the body include gene therapy vectors comprising all or a part of the SCN9A gene sequence or mutant SCN9A sequence. As is well known to those skilled in the art, gene therapy allows the delivery of the SCN9A gene in an organism to cells where it is taken up and expressed, thus changing the level or amount of SCN9A protein in such cell. These vectors thereby modulate the activity of SCN9A in the body and are useful for the therapeutic indications disclosed herein.

In accordance with the foregoing, the present invention provides the amino acid sequence of a protein, designated SCN9A, that is a known ion channel structure found in neuronal cells (SEQ ID NO: 2) and which is associated with hereditary transmission of indifference to pain. In addition, a mutation, here a truncation, has been found in this sequence derived from individuals found to have such indifference to pain. Thus, agents that mimic the phenotypic effects of this truncation, such as aberrant protein structure and decreased, or absent, function represent candidate compounds for evaluation as analgesic agents. In addition, agents that have the effect of reducing the half-life of such polypeptide in cells would also act to induce decreased sensitivity to pain and thereby achieve analgesia.

By way of non-limiting example, cells expressing a wild-type SCN9A polypeptide are transiently metabolically labeled during translation, contacted with a candidate compound, and the half-life of the polypeptide is determined using standard techniques. Compounds that decrease the half-life of the polypeptide are useful compounds in the present invention.

In other embodiments, treatment with an antagonist of the invention may be combined with other analgesics to achieve a combined, possibly even synergistic, effect.

The ability of analgesic compounds to modulate polypeptides as disclosed herein, such as SCN9A, can be determined by any number of different binding assays, including use of a solid support, either as part of a column or as a batch procedure. Such support may be composed of plastic or glass, and includes standard resins and resin beads. Such assays are also available to test the ability of polypeptides, such as SCN9A, including mutated and/or truncated forms thereof, to bind to such test compounds or to other proteins present in cells, thereby identifying modulators of SCN9A activity according to the invention.

In one such assay for which the polypeptides encoded by genes disclosed herein are useful, the polypeptide (or a polypeptide fragment thereof or an epitope-tagged form or fragment thereof) is bound to a suitable support (e.g., nitro-cellulose or an antibody or a metal agarose column in the case of, for example, a his-tagged form of said polypeptide). Binding to the support is preferably done under conditions that allow proteins associated with the polypeptide to remain associated with it. Such conditions may include use of buffers that minimize interference with protein-protein interactions. If desired, other proteins (e.g., a cell lysate) are added, and allowed time to associate with the polypeptide. The immobilized polypeptide is then washed to remove proteins or other cell constituents that may be non-specifically associated with it the polypeptide or the support. The immobilized polypeptide can then be used for multiple purposes. In a compound screening embodiment, compounds can be tested for their ability to interfere with interactions between SCN9A and other bound molecules (which are presumably SCN9A interacting proteins). Compounds which can successfully displace interacting proteins are thereby identified as SCN9A modulating agents of the invention.

In an alternative embodiment designed to identify the SCN9A interacting proteins, the immobilized polypeptide is dissociated from its support, and proteins bound to it are released (for example, by heating), or, alternatively, associated proteins are released from the polypeptide without releasing the latter polypeptide from the support. The released proteins and other cell constituents can be analyzed, for example, by SDS-PAGE gel electrophoresis, Western blotting and detection with specific antibodies, phospho-amino acid analysis, protease digestion, protein sequencing, or isoelectric focusing. Normal and mutant forms of such polypeptide can be employed in these assays to gain additional information about which part of the polypeptide a given factor is binding to. In addition, when incompletely purified polypeptide is employed, comparison of the normal and mutant forms of the protein can be used to help distinguish true binding proteins. Such an assay can be performed using a purified or semipurified protein or other molecule that is known to interact with a polypeptide encoded by a SCN9A polynucleotide.

This assay may include the following steps.

1. Harvest the encoded polypeptide and couple a suitable fluorescent label to it;

2. Label an interacting protein (or other molecule) with a second, different fluorescent label. Use dyes that will produce different quenching patterns when they are in close proximity to each other vs. when they are physically separate (i.e., dyes that quench each other when they are close together but fluoresce when they are not in close proximity);

3. Expose the interacting molecule to the immobilized polypeptide in the presence or absence of a compound being tested for its ability to interfere with an interaction between the two; and 4. Collect fluorescent readout data.

An alternative assay for such protein interaction is the Fluorescent Resonance Energy Transfer (FRET) assay. This assay can be performed as follows.

1. Provide the encoded protein or a suitable polypeptide fragment thereof and couple a suitable FRET donor (e.g., nitro-benzoxadiazole (NBD)) to it;

2. Label an interacting protein (or other molecule) with a FRET acceptor (e.g., rhodamine);

3. Expose the acceptor-labeled interacting molecule to the donor-labeled polypeptide in the presence or absence of a compound being tested for its ability to interfere with an interaction between the two; and 4. Measure fluorescence resonance energy transfer.

Quenching and FRET assays are related. Either one can be applied in a given case, depending on which pair of fluorophores is used in the assay.

One or more of the genes disclosed herein may act by altering membrane permeability, such as the permeability of membranes to ions, an example being the SCN9A gene disclosed herein. Such activity may be assayed for using vesicles, such as liposomes or intact cells, wherein such structures comprise one or more of the polypeptides of the invention, which polypeptides are expressed in such vesicle, preferably an intact cell, such as a mammalian recombinant cell, and the permeability of the membrane of the cell is determined in the presence or absence of such expression. In the same way, such permeability can then be assayed in the presence and absence of chemical agents known to modulate the activity of one or more of the genes disclosed herein. Thus, the utility of these agents in enhancing the activity of proteins known to affect such membrane transport can be readily determined. In the same way, the ability of these agents to affect the transport of other molecules, such as lipids, amino acids, and the like, across such membranes is readily determined.

In performing such assays, the test cell, such as a mammalian recombinant cell expressing SCN9A, or a polynucleotide corresponding to such gene, is loaded with a reporter molecule (such as a fluorescent ion indicator whose fluorescent properties change when it binds a particular ion) that can detect ions (to observe outward movement), or alternatively, the external medium is loaded with such a molecule (to observe inward movement). A molecule which exhibits differential properties when it is inside the vesicle compared to when it is outside the vesicle is preferred. For example, a molecule that has quenching properties when it is at high concentration but not when it is at another low concentration would be suitable. The movement of the charged molecule (either its ability to move or the kinetics of its movement) in the presence or absence of a compound being tested for its ability to affect this process can be determined.

Throughput of test compounds is an important consideration in the choice of screening assay to be used. In some strategies, where hundreds of thousands of compounds are to be tested, it is not desirable to use low throughput means. In other cases, however, low throughput is satisfactory to identify important differences between a limited number of compounds. Often it will be necessary to combine assay types to identify preferred SCN9A modulating compounds In brief, electrophysiology using patch clamp techniques is accepted as a gold standard for detailed characterization of sodium channel compound binding. There is a manual low-throughput screening (LTS) method which can compare 2-10 compounds per day; a recently developed system for automated medium-throughput screening (MTS) at 20-50 patches (i.e. compounds) per day; and a technology reportedly in development from Molecular Devices Corporation (Sunnyvale, Calif.) which permits automated high-throughput screening (HTS) at 1000-3000 patches (i.e. compounds) per day.

Binding Assays are also available, however these are of only limited functional value and information content. Designs include traditional radioactive filter based binding assays or the confocal based fluorescent system available from Evotec OAI group of companies (Hamburg, Germany), both of which are HTS.

Radioactive flux assays can also be used. In this assay, channels are stabilized in an open state with veratridine, and channel blockers are identified by their ability to prevent ion influx. The assay can use radioactive 22[Na] and 14[C] guanidinium ions as tracers. FlashPlate & Cytostar-T plates in living cells avoids separation steps and are suitable for HTS. Scintillation plate technology has also advanced this method to HTS suitability. Because of the functional aspects of the assay, the information content is reasonably good.

Yet another format measures the redistribution of membrane potential using the FLIPR system membrane potential kit (HTS) available from Molecular Dynamics (a division of Amersham Biosciences, Piscataway, N.J.). Again, in this assay channels are stabilized in an open state with veratridine, and channel blockers are identified. The assay can use radioactive 22[Na] and 14[C] guanidinium ions as tracers. This method is limited to slow membrane potential changes. Some problems may result from the fluorescent background of compounds. Test compounds may also directly influence the fluidity of the cell membrane and lead to an increase in intracellular dye concentrations. Still, because of the functional aspects of the assay, the information content is reasonably good.

Sodium dyes can be used to measure the rate or amount of sodium ion influx through a channel. This type of assay provides a very high information content regarding potential channel blockers. The assay is functional and would measure Na influx directly. CoroNa Red, SBFI and/or sodium green (Molecular Probes, Inc. Eugene Oreg.) can be used to measure Na influx; all are Na responsive dyes. They can be used in combination with the FLIPR instrument. The use of these dyes in a screen has not been previously described in the literature. Calcium dyes may also have potential in this format.

In a further embodiment, FRET based voltage sensors are used to measure the ability of a test compound to directly block Na influx. Commercially available HTS systems include the VIPR™ II FRET system (Aurora Biosciences Corporation, San Diego, Calif., a division of Vertex Pharmaceuticals, Inc.) which may be used in conjunction with FRET dyes, also available from Aurora Biosciences. This assay measures sub-second responses to voltage changes. There is no requirement for a modifier of channel function. The assay measures depolarization and hyperpolarizations, and provides ratiometric outputs for quantification. A somewhat less expensive MTS version of this assay employs the FLEXstation™ (Molecular Devices Corporation) in conjunction with FRET dyes from Aurora Biosciences.

The present invention also relates to assays that may employ transcription factors for one or more of the genes disclosed herein. The effect of a test compound on the relative ability of such transcription factor to modulate transcription of the SCN9A gene is assessed by means of such an assay. In accordance with the disclosure herein, untranslated regions and promoter regions of SCN9A are provided or readily obtained. Such genomic or untranslated regions may be included in plasmids comprising the identified gene, such as in assays to identify compounds which modulate expression thereof. In one such assay, 1-5 kilobases of upstream genomic region of SCN9A is operably linked (i.e. ligated) to a reporter gene, and incorporated into an expression plasmid. The plasmid is transfected into a cell, and the recombinant cell is exposed to test compound(s). Those compounds which increase or decrease the expression of the reporter gene are then modulators of the SCN9A gene/protein, and are considered therapeutic agents of the invention.

Those skilled in the art are familiar with typical and easily measured reporter genes, such as luciferase, chloramphenicol acetyl-transferase (CAT), and other luminescent or fluorescent assays.

Thus, in one aspect the present invention relates to a method for identifying an agent that modulates the activity of a polynucleotide whose expression contributes to pain sensation or whose non-expression contributes to lack of pain sensation, comprising:

a) contacting under physiological conditions a chemical agent with a polynucleotide corresponding to a promoter of the SCN9A gene, preferably having the sequence of SEQ. ID NO. 14, under conditions promoting such contacting; and b) detecting a change in the expression of said polynucleotide as a result of said contacting;

thereby identifying an agent that modulates said polynucleotide activity.

Medicinal Chemistry and Lead Optimization

While this invention discloses a wide variety of assays for measuring the effect of a compound on SCN9A expression or activity, it is important to note that this compound detection is merely the first step in the industrial process of identification of an approvable therapeutic agent. The library screening accomplished with the first screening assay may be low, medium or high-throughput screening. It identifies "hits" or individual compounds from the library which cause the desired modulation of SCN9A expression or activity. The hits are further evaluated at a chemical structure level, and, if possible, are organized according to shared core structures, which presumably define chemical features required to achieve the desired modulation of SCN9A. This process, sometimes called lead identification, may involve a structure-activity relationship (or SAR) analysis. Various cycles of medicinal chemistry or focussed library generation may then be employed to generate multiple analogs of such core structures in a process called lead optimization. Finally, those skilled in the art know how to identify and test those preferred analogs (optimized leads) which have improved characteristics as therapeutic agents, generally through a series of in vitro and in vivo analyses.

In general, novel agents having SCN9A modulating properties are identified from large libraries of both natural product or synthetic (or semi-synthetic) extracts or chemical libraries according to methods known in the art. Those skilled in the field or drug discovery and development will understand that the precise source of test extracts or compounds is not critical to the screening procedure(s) of the invention. Accordingly, virtually any number of chemical extracts or compounds can be screened using the exemplary methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or compound is readily modified using standard chemical, physical, or biochemical methods.

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their analgesic and/or anesthetic activities should be employed whenever possible.

When a crude extract is found to have SCN9A modulating activity, further fractionation of the positive lead extract is necessary to isolate chemical constituent responsible for the observed effect. Thus, the goal of the extraction, fractionation, and purification process is the careful characterization and identification of a chemical entity within the crude extract having potential therapeutic activities. The same assays described herein for the detection of activities in mixtures of compounds can be used to purify the active component and to test derivatives thereof. Methods of fractionation and purification of such heterogeneous extracts are known in the art.

In an alternative strategy, if a compound is identified which is known to modulate expression or activity of a polynucleotide or polypeptide corresponding to SCN9A, analogs of that compound can be developed and tested for improved selectivity, potency, binding affinity or the like against the target gene/protein. According to the invention, such analogs will also be tested against other sodium channels (such as NaV 1.1 to 1.6 and NaV 1.8 to 1.12) to identify analogs which are preferentially selective towards blocking NaV 1.7 and which do not interact with the others. Such improved analogs, which are compounds of the invention, are expected to demonstrate reduced side effects and improved analgesic effects in human patients as compared to their parent compounds.

In an alternative embodiment, an investigator may desire to initiate research with known sodium channel blockers and to develop analogs of the blocker which are more selective for SCN9A. Known sodium channel modulators that may be selectively improved to increase specificity for SCN9A include:

| Drug/clinical candidate | Company |
|---|---|
| AWD-140-190 | ASTA Medica AG |
| AWD-33-173 | ASTA Medica AG |
| BIA-2-024 | Boehringer Ingelheim |
| BIA-2-093 | Boehringer Ingelheim |
| Co-102862 | University of Saskatchewan |
| Conopeptides | Cognetix Inc |
| DCUKA | Lohocla Research Corp |
| felbamate | Carter-Wallace Inc |
| fosphenytoin | InterX Research Corp |
| GW-273293 | Glaxo Wellcome plc |
| lamotrigine | Glaxo Wellcome plc |
| OROS (phenytoin) | ALZA Corp |
| oxcarbazepine | Novartis AG |
| rufinamide | Novartis AG |
| safinamide | Pharmacia & Upjohn AB |
| topiramate | Johnson & Johnson |
| valproate semisodium | Abbott Laboratories |
| vinpocetine | Richter Gedeon VG |
| ZM-227189 | Zeneca Group plc |
| zonisamide | Dainippon Pharmaceutical Co Ltd. |

Improved analogs may also include compounds with improved stability, biodistribution, pharmacokinetics or other desirable features for therapeutic agents which are not directly related to modulation of the therapeutic target.

In a preferred embodiment, the improved analog of the invention is effectively delivered, either by physiological means or assisted means, to cells of the body expressing the SCN9A protein.

Compounds identified as having potential therapeutic value are subsequently analyzed using any standard in vitro assay or in vivo animal model for the disease indication known in the art.

Method of Treatment

In a further aspect, the present invention relates to a method for treating a condition in an animal afflicted with a source of chronic pain comprising administering to said animal an effective amount of an analgesic agent first identified by an assay method of the invention. Preferably, said animal is a human patient, such as a patient afflicted with a chronic ailment, such as a cancerous condition.

Therapeutic Use of Selective SCN9A Modulators

In a preferred embodiment, the agent generates indifference to pain, but does not diminish sensations which are available to patients with CIP, such as but not limited to hot/cold sensing, pressure sensing and sharp/dull sensations. For example, indifference to pain without any concomitant numbness or loss of sensation would represent an important use of the compounds of the invention. In an alternative embodiment, a preferred therapeutic agent is useful in humans or other animals for treating pain, inducing analgesia or anesthesia, or another disorder which is connected to the C-I-P phenotype.

Compounds first identified as useful in reducing sensitivity to pain stimuli using one or more of the assays of the invention may be administered with a pharmaceutically-acceptable diluent, carrier, or excipient, in unit dosage form. Conventional pharmaceutical practice may be employed to provide suitable formulations or compositions to administer such compositions to patients. Although oral administration is preferred, any appropriate route of administration may be employed, for example, intravenous, parenteral, subcutaneous, intramuscular, intracranial, intraorbital, ophthalmic, intraventricular, intracapsular, intraspinal, intrathecal, epidural, intracisternal, intraperitoneal, intranasal, or aerosol administration. Therapeutic formulations may be in the form of liquid solutions or suspension; for oral administration, formulations may be in the form of tablets or capsules; and for intranasal formulations, in the form of powders, nasal drops, or aerosols.

Methods well known in the art for making formulations are found in, for example, *Remington: The Science and Practice of Pharmacy*, (19th ed.) ed. A. R. Gennaro A R., 1995, Mack Publishing Company, Easton, Pa. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for agonists of the invention include ethylenevinyl acetate copolymer particles, osmotic pumps, implantable infusion systems, and liposomes. Formulations for inhalation may contain excipients, or example, lactose, or may be aqueous solutions containing, for example, polyoxyethylene-9-lauryl ether, glycocholate and deoxycholate, or may be oily solutions for administration in the form of nasal drops, or as a gel.

The methods of the invention simplify the evaluation, identification and development of active agents for the treatment and prevention of conditions of chronic or other types of pain while not necessarily treating the causative condition. Of course, both may be treated simultaneously as contemplated by the invention. For example, an analgesic agent identified by one of the screening methods disclosed herein may be administered along with an agent intended to treat a coincident conditions, such as where analgesic and antitumor agents are given together or contemporaneously.

Process of Data Transfer

The present invention also relates to a process that comprises a method for producing a product comprising identifying an agent according to one of the disclosed processes for identifying such an agent (i.e., the therapeutic agents identified according to the assay procedures disclosed herein) wherein said product is the data collected with respect to said agent as a result of said identification process, or assay, and wherein said data is sufficient to convey the chemical character and/or structure and/or properties of said agent. For example, the present invention specifically contemplates a situation whereby a user of an assay of the invention may use the assay to screen for compounds having the desired enzyme modulating activity and, having identified the compound, then conveys that information (i.e., information as to structure, dosage, etc) to another user who then utilizes the information to reproduce the agent and administer it for therapeutic or research purposes according to the invention. For example, the user of the assay (user 1) may screen a number of test compounds without knowing the structure or identity of the compounds (such as where a number of code numbers are used the first user is simply given samples labeled with said code numbers) and, after performing the screening process, using one or more assay processes of the present invention, then imparts to a second user (user 2), verbally or in writing or some equivalent fashion, sufficient information to identify the compounds having a particular modulating activity (for example, the code number with the corresponding results). This transmission of information from user 1 to user 2 is specifically contemplated by the present invention.

In one embodiment of the foregoing, the present invention relates to a method for producing test data with respect to the SCN9A polynucleotide modulating activity of a compound, comprising a) contacting a chemical agent with a polynucleotide corresponding to a SCN9A polynucleotide, or corresponding to a SCN9A promoter sequence polynucleotide and under conditions promoting expression of such polynucleotide;

b) detecting a change in the expression of said polynucleotide as a result of said contacting; and (c) producing test data with respect to the SCN9A polynucleotide modulating activity of said compound based on a change in the expression of the determined SCN9A polynucleotide modulating activity indicating such modulating activity.

Diagnostics and Pharmacogenomics

In a further embodiment, the invention relates to diagnostic and pharmacogenomic compounds, kits and methods. This aspect relates to analysis SCN9A for the diagnosis of insensitivity or indifference to pain, other pain disorder, or in the selection of a therapeutic agent for a patient (i.e. pharmacogenomics).

For example, nucleic acid analysis can be used to identify the G5067A or the C984A mutation thus confirming the diagnosis of congenital indifference to pain. Many nucleic acid diagnostic techniques are well known to those skilled in the art. Such techniques include DNA sequencing, hybridization probing, single stranded conformational analysis, PCR based techniques such as mismatch amplification, and myriad other well known methods. All such analysis can be performed on a small sample of blood, saliva, urine or other tissue provided by the patient.

Alternatively, protein based analyses such as antibody based assays (Elisa, Radioimmunoassay and the like) can be employed to identify the expression, amount or presence or absence of a mutant SCN9A protein, such as the W1689X or Y328X mutant.

Gene expression, both comparable and absolute, as well as biological activity, and mutational analysis can each serve as a diagnostic tool for pain disorders; thus determination of the amount of SCN9A mRNA can be used to diagnose the presence or absence of a mutation correlated with such pain disorder.

Pharmacogenomics deals with clinically significant hereditary variations in the response to drugs due to altered drug disposition and abnormal action in affected persons (Eichelbaum, M., Clin. Exp. Pharmacol. Physiol., 23:983-985, 1996; Linder, M. W., Clin. Chem., 43:254-266, 1997). In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). Altered drug action may occur in a patient having a polymorphism (e.g., an single nucleotide polymorphism or SNP) in promoter, intronic, or exonic sequences of SCN9A. Thus by determining the presence and prevalence of polymorphisms allow for prediction of a patient's response to a particular therapeutic agent.

This pharmacogenomic analysis can lead to the tailoring of drug treatments according to patient genotype, including prediction of side effects upon administration of therapeutic agents, particularly therapeutic agents for treating disorders disclosed in this specification. Pharmacogenomics allows for the selection of agents (e.g., drugs) for therapeutic or prophylactic treatment of an individual based on the genotype of the individual (e.g., the genotype of the individual is examined to determine the ability of the individual to respond to a particular agent).

Diagnostics employing a gene or protein corresponding to SCN9A can also be useful in selecting patients for clinical trials of a potential therapeutic agent. Patients can be stratified according to the DNA or protein sequence of SCN9A and their response to drug treatment can be evaluated. Such stratification can greatly reduce the number of patients required to establish efficacy for a potential therapeutic agent.

Sequences 1 to 20 have the following identifications:
SEQ ID NO: 1—*Homo sapiens* sodium channel, voltage-gated, type IX, alpha polypeptide (SCN9A), mRNA sequence
SEQ ID NO: 2—*Homo sapiens* sodium channel, voltage-gated, type IX, alpha polypeptide (SCN9A), protein sequence
SEQ ID NO: 3—*Homo sapiens* sodium channel, voltage-gated, type IX, alpha polypeptide (SCN9A), mRNA sequence, predicted splice variant
SEQ 4—SCN9A predicted splice variant
SEQ 5—*Homo sapiens* sodium channel, voltage-gated, type IX, alpha polypeptide (SCN9A), mRNA, alternately spliced transcript using exon 5N and alternate splice donor site for exon 11 (11B)
SEQ 6—*Homo sapiens* sodium channel, voltage-gated, type IX, alpha polypeptide (SCN9A), protein sequence, alternately spliced isoform using exon 5N and alternate splice donor site for exon 11 (11B)
SEQ 7—*Homo sapiens* sodium channel, voltage-gated, type IX, alpha polypeptide (SCN9A), mRNA sequence, CIP-10 mutant
SEQ 8—SCN9A W1689X protein sequence
SEQ 9—*Homo sapiens* sodium channel, voltage-gated, type IX, alpha polypeptide (SCN9A), mRNA sequence, CIP-14 mutant
SEQ ID NO: 10—SCN9A Y328X protein sequence
SEQ ID NO: 11—*Homo sapiens* sodium channel, voltage-gated, type IX, alpha polypeptide (SCN9A), mRNA sequence, c.2488C>T mutation in CIP-08
SEQ ID NO: 12—*Homo sapiens* sodium channel, voltage-gated, type IX, alpha polypeptide (SCN9A), protein sequence, R830X CIP-08 mutation
SEQ ID No. 13—Partial Sequence from human BAC clone RP11-437H3 (AC108146) showing genomic arrangement of Exon 5A and Exon 5N. The first exon is the 3' end of Exon 4 (residues 1-16). Next Exon is Exon 5N (residues 1479-1570). The one following is Exon 5A (residues 1686-1777). The final exon is the 5' end of Exon 6 (residues 2506-2521).
SEQ ID NO: 14—human genomic sequence containing the SCN9A promoter region ending with the ATG of the initiator methionine codon; a partial cDNA sequence appears as residues 9913-9963.
SEQ ID NO: 15—predicted mouse SCN9A 11B isoform
SEQ ID NO: 16—predicted mouse SCN9A 11B isoform
SEQ ID NO: 17—predicted mouse SCN9A 5A isoform
SEQ ID NO: 18—predicted_1 mouse SCN9A 5A isoform
SEQ ID NO: 19—predicted mouse SCN9A 5N isoform
SEQ ID NO: 20—predicted mouse SCN9A 5N isoform In carrying out the procedures of the present invention it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

The invention is described in more detail in the following non-limiting examples. It is to be understood that these methods and examples in no way limit the invention to the embodiments described herein and that other embodiments and uses will no doubt suggest themselves to those skilled in the art.

Example 1

Figure 2:
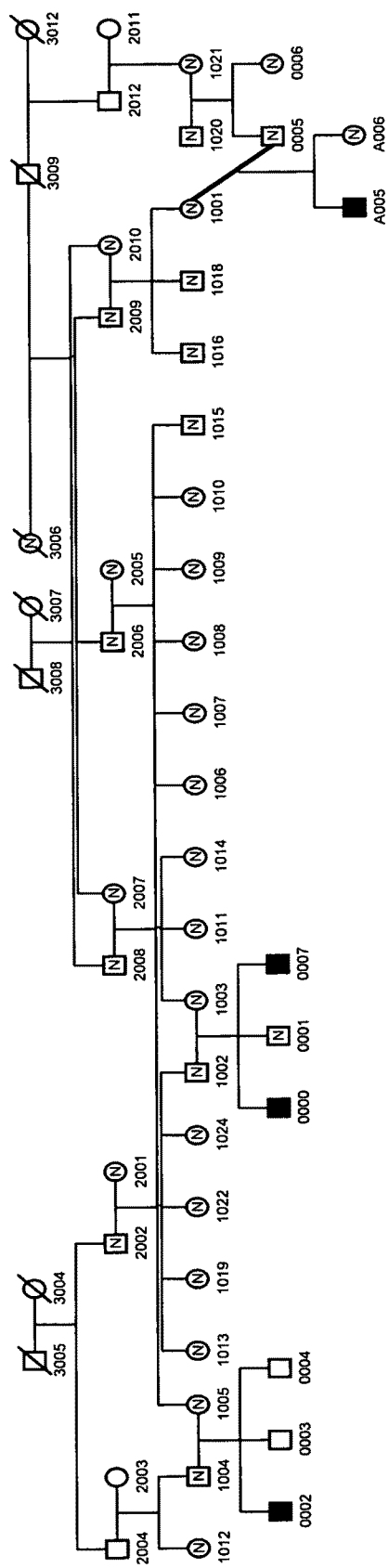
FIG. 2 shows the pedigree for a family designated CIP-14. Symbols as in FIG. 1.

Identification of the Genetic Mutation Responsible for Congenital Indifference to Pain (CIP) in Humans We collected a multigenerational family with 3 affecteds (CIP-14) FIG. 1 and a smaller family with 1 affected (CIP-10) FIG. 2 reported previously (Guillermo A. and A. Grinspan. 1970. Rev Neurol (Paris) 123(6): p. 434-5.)

31 family members from CIP-14 were genotyped at 763 autosomal markers and at 48× markers. A genome-wide two-point analysis identified 8 regions with LOD scores >1.0. A region on chromosome 2 had two consecutive markers—D2S2330-D2S335—spanning 6cM, with positive scores. A LOD score of 1.51 at zero recombination was obtained at D2S2330. Multi-point analysis of this region was consistent with linkage to CIP. The CIP-14 pedigree contains 3 affecteds, one issued from a consanguineous marriage, and two expected to share one allele identical by descent with the first case and one allele identical by descent between themselves. Because the pedigree comes from an isolated population, it can be expected that there would be linkage disequilibrium at the disease gene, and that all 3 affecteds would share alleles. However, as there was only one allele that could be assumed to be inherited identically by descent to the 3 affecteds, a scoring method was designed to assign scores to allele sharing taking that into consideration. The allele sharing algorithm identified 4 regions as having two-point LOD scores >1.0, and identified 3 additional regions that had not been excluded in two-point linkage analysis.

Haplotype construction using 12 polymorphic markers in candidate regions identified by 2-point linkage analysis and allele-sharing methods suggested that only the D2S2330-D2S335 region was consistent with linkage to CIP. All 3 affecteds shared one chromosome in common inherited from 3006/3009. Individuals 0000 and 0002 share another chromosome in common inherited from a 3004/3005. A005 has a chromosome introduced through 1020 that appears to be identical by state (and potentially identical by descent) to the one inherited from 3006/3009, which may be explained by the consanguinity of the population. The homozygous haplotypes in the 3 affecteds could represent multiple copies of a single ancestral chromosome. Recombination with the proximal marker D2S306, and the distal marker, D2S2188, is seen in 2002 and 0002/A006, respectively, provided centromeric and telomeric boundaries for the disease gene at the 2q24-31 locus.

Definition of the CIP Minimal Genomic Region

The interval between D2S306 and D2S2188 corresponds to a genetic size of ~16cM. To increase the resolution of the interval, we performed fine mapping with 32 additional markers, including several novel dinucleotide-repeat markers identified from genomic sequence. Haplotype construction using 41 polymorphic markers revealed one proximal and 5 distal recombinations. Of the 6 recombinant individuals, one was affected and 5 were carriers. The additional data narrowed the boundaries defined in 2002 and A006 to approximately 11.2 MB, between CA1AC010876 and D2S1267.

To assess whether the disease in CIP-10 maps to the 2q24-31 locus, five family members were genotyped using the 41 polymorphic markers described above. The proband was homozygous for markers between D2S2299 and D2S2177, and the genotypic data was consistent with linkage to CIP. Haplotype construction revealed a candidate interval of ~19cM defined by inferred recombination events that must have occurred in the untyped generations.

Use of genetic data from CIP-14 and CIP-10 together provided a centromeric boundary at CA1AC010876 (based a meiotic recombination in CIP14-2002) and a telomeric boundary at D2S2177 (based on the haplotype sharing data of CIP-10).

Mutation Analysis

Figure 3:
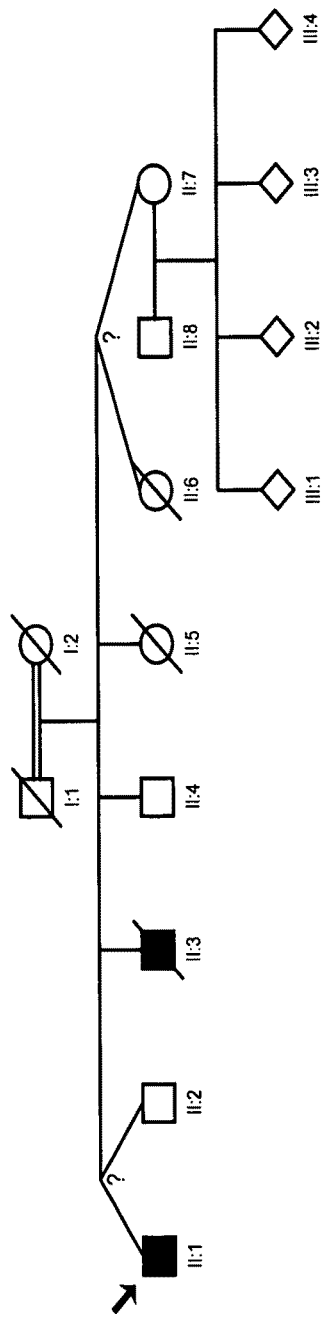
FIG. 3 shows the pedigree for a family designated CIP-08. Symbols as in FIG. 1.

We next embarked on a positional cloning effort. According to the UCSC August 2001 genomic sequence assembly, the CIP genomic region contains 26 known genes, five of which code for alpha polypeptides of voltage-gated sodium channels. We initiated sequencing of the coding regions of SCN9A and SCN3A in CIP-14-A005 and CIP-10-503, theorizing that selective expression in dorsal root ganglia and upregulation in models of neuropathic pain, respectively, made them interesting candidate genes. In CIP-10-503, we detected a homozygous nucleotide change of G>A at nt 5067 in SCN9A that resulted in a change to a stop codon at tryptophan 1689 (FIG. 4a). The stop codon results in deletion of 289 amino acids at the C-terminal of SCN9A, including the last transmembrane domain of the fourth channel domain. In CIP-14-A005 we detected a homozygous nucleotide change of 984C>A in SCN9A that resulted in a change to a stop codon at tyrosine 328 (FIG. 4b). We developed PCR-RFLP assays and showed that both mutations cosegregated perfectly with the disease and the affected haplotypes. Both mutations were absent in 142 control chromosomes from individuals of similar ancestral background. A third mutation was identified in a CIP proband descended from first cousins in another previously identified family. FIG. 3 (See Lievre J A, et al. 1968. Bull Mem Soc Med Hop Paris. 1968 Mar. 15; 119(5):447-56.) Patient CIP-08-11:1 is homozygous for a C>T substitution at nt 2488 that corresponds to a change to a stop codon at arginine 830 (FIG. 4c).

Alternative Exons 5N and 5A

Figure 5A:
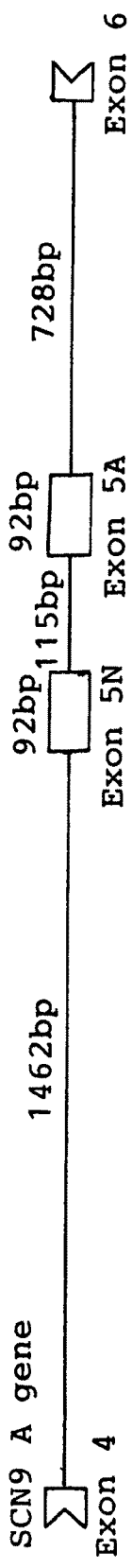
FIG. 5*a*. Genomic arrangement of alternatively spliced exon 5N and 5A of the human SCN9A gene. The neonatal (N) and adult (A) isoforms are generated by a mutually exclusive alternative splicing mechanism. The length in base pairs of the introns and exons are shown.
Figure 5B:
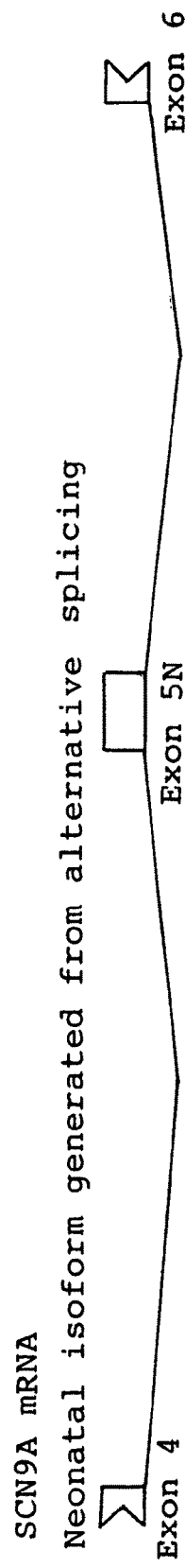
FIG. 5*b*. Formation of SCN9A 5N (neonatal) isoform generated by splicing.
Figure 5C:
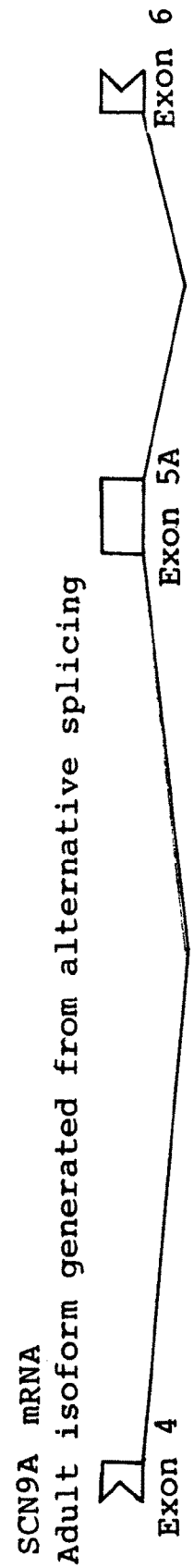
FIG. 5*c*. Formation of SCN9A 5A (adult) isoform generated by splicing. Bent lines indicated portions of the pre-mRNA which are removed to generate the mature mRNA for translation.
Figure 7:
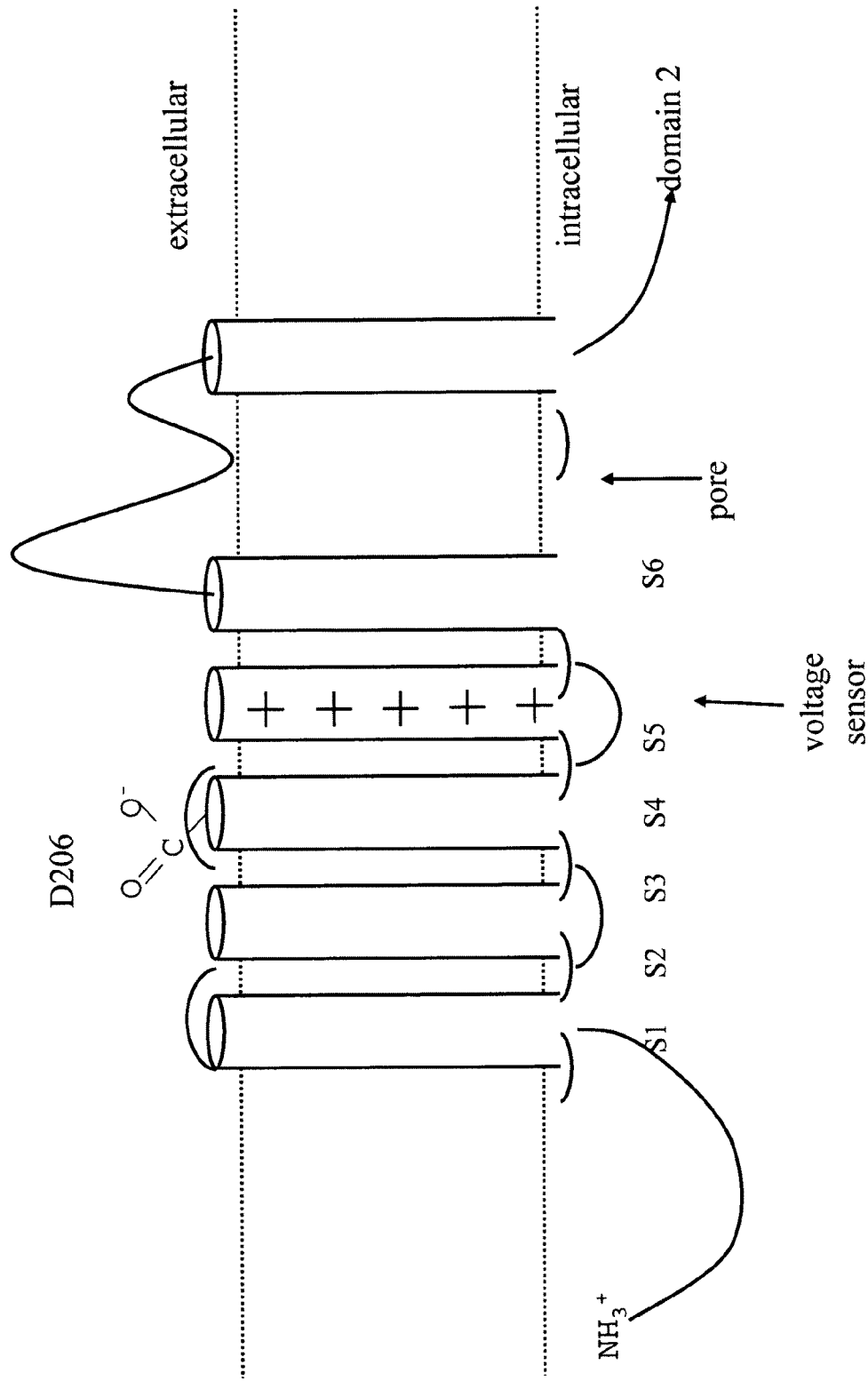
FIG. 7. The proposed transmembrane topography of the first domain of a sodium channel protein. The 30 amino acids specified by these exon 5 variants encode a short extracellular portion of the S3 transmembrane helix, the short extracellular loop between S3 and S4, and most of the S4 transmembrane helix, which is thought to be involved in sensing changes in membrane potential. The + symbols refer to the repeating basic (positively charged) residues within the S4 transmembrane segment. Amino acid 206 of SCN9A is shown as an aspartate residue (A isoforms); it would be an uncharged residue in the N isoforms (i.e. asparagine in SCN9A and SCN2A; and serine in SCN3A).

The rabbit SCN9A gene (NaS), the rat and human SCN2A and SCN3A genes, and the human SCN8A gene contain two alternatively spliced exons encoding segments S3 and S4 of channel domain I. (See Belcher S M, et al. Proc Natl Acad Sci USA. 1995 Nov. 21; 92(24):11034-8; Sarao R, et al. Nucleic Acids Res. 1991 Oct. 25; 19(20):5673-9; Gustafson T A, et al. J Biol. Chem. 1993 Sep. 5; 268(25):18648-53; Lu C M, and Brown G B. J Mol Neurosci 1998 February; 10(1):67-70; and Plummer N W, et al. Genomics. 1998 Dec. 1; 54(2):287-96.) The two exons are separated by introns of ~90-150 bp. The isoforms are believed to be developmentally regulated, and without being bound to theory, it is suggested that the upstream exon (N) is predominantly expressed during the neonatal period, while the downstream exon (A) is expressed in adult brain. To determine whether this organization is conserved in human SCN9A, we aligned the genomic sequence from BAC clone RP11-437H3 (Genbank accession #AC108146) SEQ ID No. 13, with the human and rabbit coding sequences, and found that two potential copies of exon 5 are separated by 115 bp (FIG. 5). The exons contain two predicted amino acid differences. Alternative splicing for these exons is illustrated in FIG. 5. Residue 201 in the second exon is valine rather than leucine and residue 206 (corresponding to 209 in SCN2A and 208 in SCN3A) is aspartic acid rather than asparagine. A species and channel comparison in FIG. 6 shows the conserved relationship between isoforms. Because their physical arrangement and amino acid sequence correspond to those in other sodium channel genes, they are designated exons 5N and 5A. It has been suggested that the proximity of the residue 206 in these exons and the positively charged residues of the voltage sensor in transmembrane segment IS4 (see FIG. 7) may alter the voltage dependence or permeability of the neonatal and adult channels. Plummer NW, supra.

We used PCR to amplify the region of human SCN9A described above from total RNA of adult dorsal root ganglia (DRG) to examine exon usage within intact cDNAs. Primers designed to specifically bind cDNAs containing either exon 5A or exon 5N produced fragments of the expected size and sequencing confirmed mutually exclusive use of both exons.

Alternative Splice Donor for Exon 11

Two clones containing exons 1-13 of SCN9A amplified from human DRG were sequenced. One clone contained an additional 33 nucleotides located between the sequences of exon 11 and exon 12. To identify the origin of the extra 33 bp in the novel transcript, we examined the genomic sequence of the human SCN9A gene. Two alternative splice donor sites separated by 33 bp were identified. Splicing at the downstream site generates the novel transcript that encodes a protein with 11 additional amino acids in cytoplasmic loop 1

Figure 8:
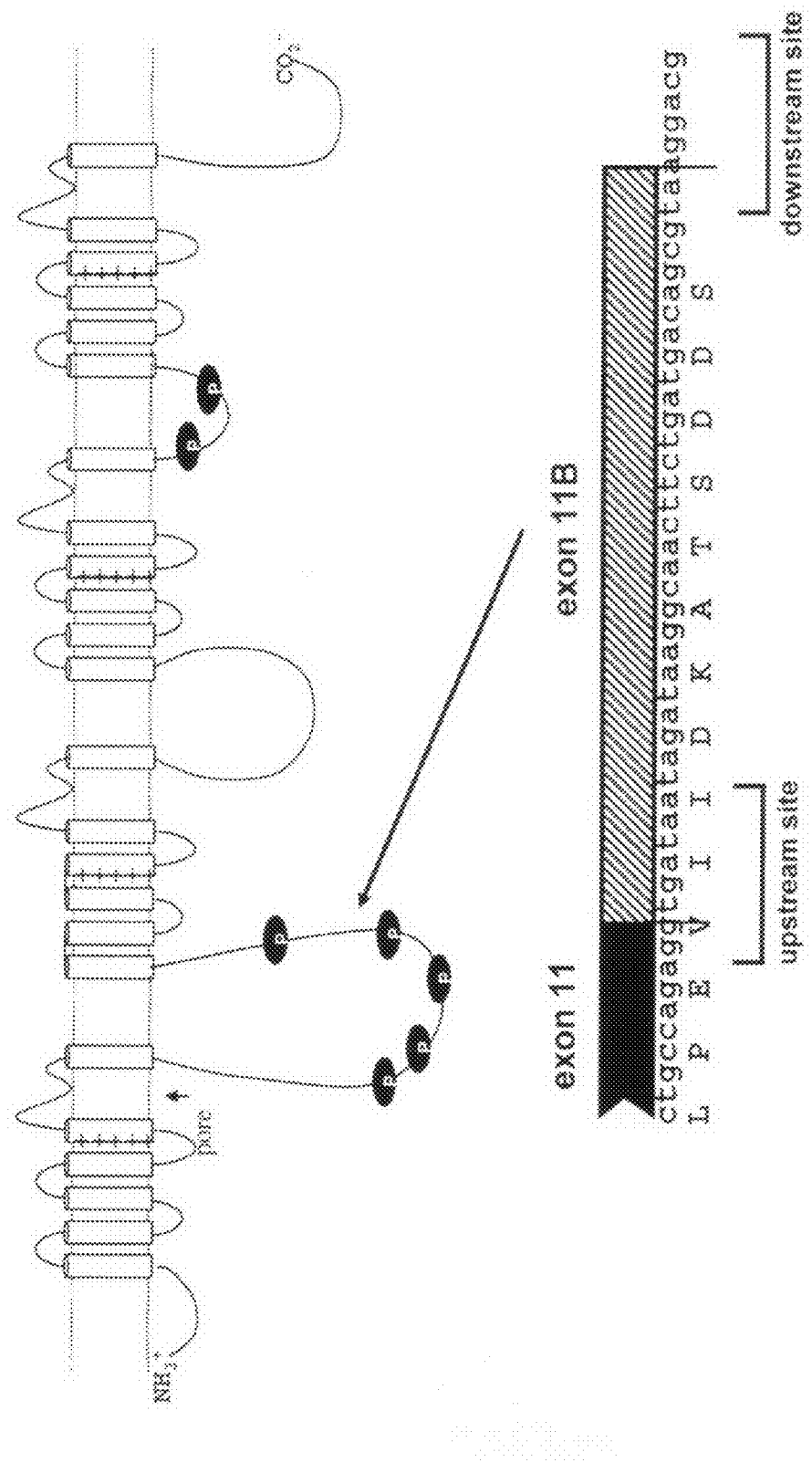
FIG. 8. Illustration of nucleotide and amino acid sequence of alternative exon 11B. Alternative splice donor sites for exon 11 found in SCN9A isoform are indicated as upstream site and downstream site. Arrow indicates the approximate position of the additional amino acids in the secondary structure of the sodium channel protein.

(FIG. 8). The sequence of the additional amino acids is conserved in rat and rabbit SCN9A and additional members of the channel gene family (FIG. 9).

Example 2

Figure 10:
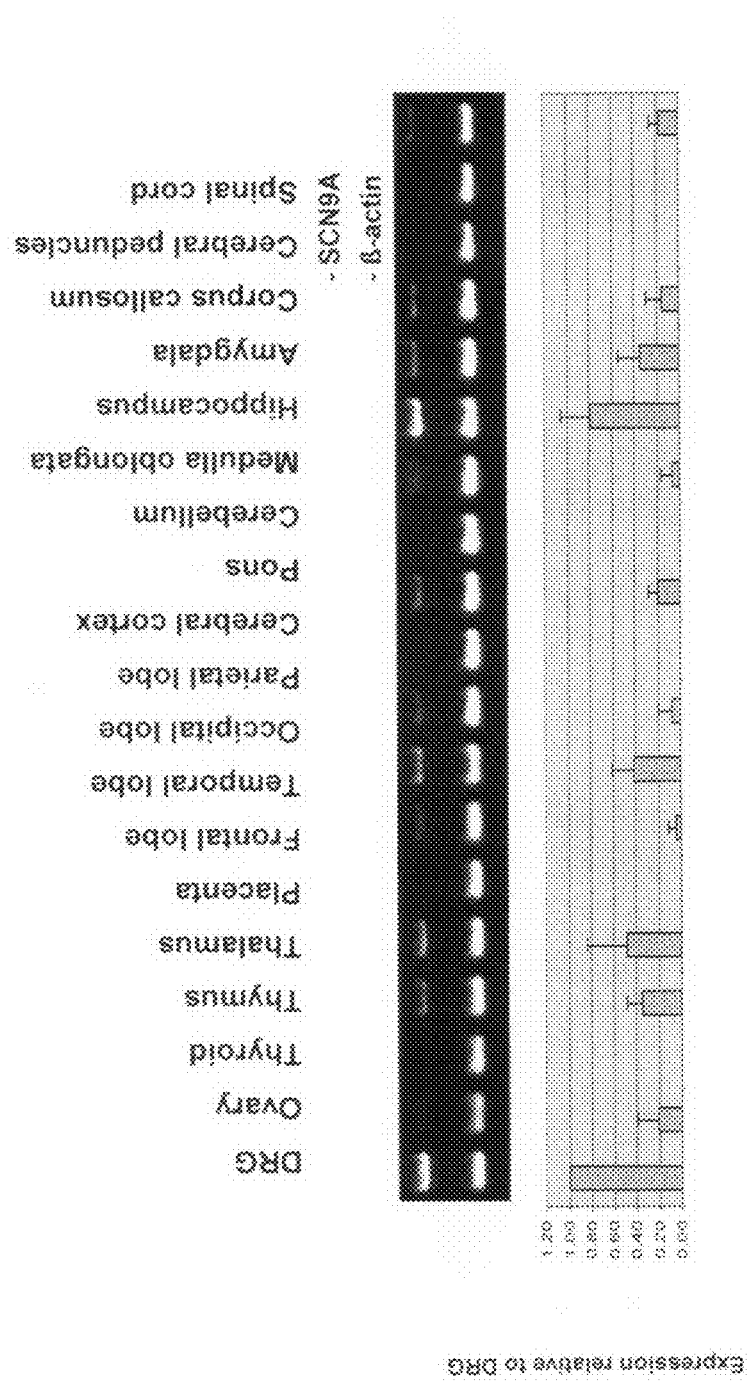
FIG. 10. Expression of SCN9A mRNA in various tissues of the central nervous system (CNS) and other organs. A representative gel is shown. To control for difference in the amounts of RNA among samples, pixel density relative to an internal β-actin standard was calculated. The graph shows the results of 3 relative quantitative RT-PCR experiments relative to a dorsal root ganglia (DRG) positive control.

RT-PCR Analysis of Relative SCN9A Expression cDNAs from a variety of human tissues were used to perform relative quantitative RT-PCR with primers and conditions that specifically amplified the SCN9A transcript (FIG. 10). Experiments to determine the tissue distribution of SCN9A were performed with three separate primer sets. Dorsal root ganglia was included as a positive control and β-actin was included as an internal standard. We found highest levels of SCN9A relative to the β-actin standard in dorsal root ganglia and medulla oblongata. Lower levels of SCN9A product were detected in the samples from temporal lobe, thymus, hippocampus, cerebral cortex, amygdala, frontal lobe, spinal cord, occipital lobe, cerebellum, thalamus, and ovary. SCN9A expression was not detected in cDNA from parietal lobe, corpus callosum, cerebral peduncles, pons, thyroid, or placenta. The sequences of the RT-PCR products amplified from dorsal root ganglia and medulla oblongata were identical to human SCN9A cDNA. Previous studies have reported low levels of SCN9A in the CNS relative to the PNS, but we have detected significant levels in the CNS, and particularly high levels in the medulla oblongata.

This expression profile teaches those skilled in the art where compounds which modulate SCN9A gene expression or SCN9A protein activity are likely to have effect. For example, expression of SCN9A in the CNS may support a role for this gene in central perception of pain, although alternative theories are suggested. It also is strongly suggestive of the other therapeutic indications for SCN9A modulating agents.

REFERENCE LIST

1. Claes, L. et al. De novo mutations in the sodium-channel gene SCN1A cause severe myoclonic epilepsy of infancy. Am. J. Hum. Genet. 68, 1327-1332 (2001).
2. Rouleau, G. et al. Loci for idiopathic generalized epilepsy, mapping to chromosome 2, mutations thereof and method using the same to assess, diagnose, prognose or treat epilepsy. PCT Patent Publication WO 01/38564 published May 31, 2001, priority date Nov. 25, 1999. Also see: Escayg, A. et al. Mutations of SCN1A, encoding a neuronal sodium channel, in two families with GEFS+2. Nat. Genet. 24, 343-345 (2000).
3. Lossin, C., Wang, D. W., Rhodes, T. H., Vanoye, C. G., & George, A. L., Jr. Molecular basis of an inherited epilepsy. Neuron 34, 877-884 (2002).
4. Planells-Cases, R. et al. Neuronal death and perinatal lethality in voltage-gated sodium channel alpha(II)-deficient mice. Biophys. J. 78, 2878-2891 (2000).
5. Burgess, D. L. et al. Mutation of a new sodium channel gene, Scn8a, in the mouse mutant 'motor endplate disease'. Nat. Genet. 10, 461-465 (1995).
6. Kohrman, D. C., Harris, J. B., & Meisler, M. H. Mutation detection in the med and medJ alleles of the sodium channel Scn8a. Unusual splicing due to a minor class AT-AC intron. J. Biol. Chem. 271, 17576-17581 (1996).
7. Kohrman, D. C., Smith, M. R., Goldin, A. L., Harris, J., & Meisler, M. H. A missense mutation in the sodium channel Scn8a is responsible for cerebellar ataxia in the mouse mutant jolting. J. Neurosci. 16, 5993-5999 (1996).
8. De Repentigny, Y. et al. Pathological and genetic analysis of the degenerating muscle (dmu) mouse: a new allele of Scn8a. Hum. Mol. Genet. 10, 1819-1827 (2001).
9. Sprunger, L. K., Escayg, A., Tallaksen-Greene, S., Albin, R. L., & Meisler, M. H. Dystonia associated with mutation of the neuronal sodium channel Scn8a and identification of the modifier locus Scnm1 on mouse chromosome 3. Hum. Mol. Genet. 8, 471-479 (1999).
10. Rojas, C. V. et al. A Met-to-Val mutation in the skeletal muscle Na+ channel alpha-subunit in hyperkalaemic periodic paralysis. Nature 354, 387-389 (1991).
11. Bendahhou, S., Cummins, T. R., Kula, R. W., Fu, Y. H., & Ptacek, L. J. Impairment of slow inactivation as a common mechanism for periodic paralysis in DIIS4-S5. Neurology 58, 1266-1272 (2002).
12. Nuyens, D. et al. Abrupt rate accelerations or premature beats cause life-threatening arrhythmias in mice with long-QT3 syndrome. Nat. Med. 7, 1021-1027 (2001).
13. Papadatos, G. A. et al. Slowed conduction and ventricular tachycardia after targeted disruption of the cardiac sodium channel gene Scn5a. Proc. Natl. Acad. Sci.U.S.A 99, 6210-6215 (2002).
14. Wang, Q. et al. SCN5A mutations associated with an inherited cardiac arrhythmia, long QT syndrome. Cell 80, 805-811 (1995).
15. Chen, Q. et al. Genetic basis and molecular mechanism for idiopathic ventricular fibrillation. Nature 392, 293-296 (1998).
16. Schott, J. J. et al. Cardiac conduction defects associate with mutations in SCN5A. Nat. Genet. 23, 20-21 (1999).
17. Bennett, P. B., Yazawa, K., Makita, N., & George, A. L., Jr. Molecular mechanism for an inherited cardiac arrhythmia. Nature 376, 683-685 (1995).
18. Akopian, A. N. et al. The tetrodotoxin-resistant sodium channel SNS has a specialized function in pain pathways. Nat. Neurosci. 2, 541-548 (1999).
19. Lai, J. et al. Inhibition of neuropathic pain by decreased expression of the tetrodotoxin-resistant sodium channel, NaV1.8. Pain 95, 143-152 (2002).
20. Khasar, S. G., Gold, M. S., & Levine, J. D. A tetrodotoxin-resistant sodium current mediates inflammatory pain in the rat. Neurosci. Lett. 256, 17-20 (1998).
21. Laird, J. M., Souslova, V., Wood, J. N., & Cervero, F. Deficits in visceral pain and referred hyperalgesia in Nav1.8 (SNS/PN3)-null mice. J. Neurosci. 22, 8352-8356 (2002).
22. Kerr, B. J., Souslova, V., McMahon, S. B., & Wood, J. N. A role for the TTX-resistant sodium channel Nav 1.8 in NGF-induced hyperalgesia, but not neuropathic pain. Neuroreport 12, 3077-3080 (2001).
23. Porreca, F. et al. A comparison of the potential role of the tetrodotoxin-insensitive sodium channels, PN3/SNS and NaN/SNS2, in rat models of chronic pain. Proc. Natl. Acad. Sci. U.S.A 96, 7640-7644 (1999).
24. Watanabe, E. et al. Nav2/NaG channel is involved in control of salt-intake behavior in the CNS. J. Neurosci. 20, 7743-7751 (2000).
25. Sugawara, T. et al. A missense mutation of the Na+ channel alpha II subunit gene Na(v)1.2 in a patient with febrile and afebrile seizures causes channel dysfunction. Proc. Natl. Acad. Sci. U.S.A 98, 6384-6389 (2001).
26. Akai, J. et al. A novel SCN5A mutation associated with idiopathic ventricular fibrillation without typical ECG findings of Brugada syndrome. FEBS Lett. 479, 29-34 (2000).

What is claimed is:

1. A method for reducing pain in a mammal afflicted therewith, comprising administering to said mammal an effective amount of an agent that selectively decreases SCN9A-mediated ion flux activity in said mammal.

2. The method of claim 1, wherein said agent is a voltage dependent blocker of SCN9A.

3. The method of claim 2, wherein said agent decreases the amount of SCN9A-mediated ion flux activity in said mammal.

4. The method of claim 2, wherein said agent decreases the rate of SCN9A-mediated ion flux activity in said mammal.

5. The method of claim 2, wherein said agent decreases the ion flux activity of SCN9A polypeptide in said mammal.

6. The method of claim 5, wherein said polypeptide comprises the amino acid sequence encoded by SEQ. ID NO. 1, 3, 5, 15, 17, or 19.

7. The method of claim 1, wherein said mammal is a human patient.

8. The method of claim 1, wherein said pain is chronic pain.

9. The method of claim 8, wherein said chronic pain is due to a cancerous condition.

10. The method of claim 8, wherein said chronic pain is neuropathic pain.

* * * * *

SEQUENCE LISTING

<160> NUMBER OF SEQ ID NOS: 122

<210> SEQ ID NO 1
<211> LENGTH: 6367
<212> TYPE: DNA
<213> ORGANISM: Homo sapiens

<400> SEQUENCE: 1

| | | | | | | |
|---|---|---|---|---|---|---|
| ctcttatgtg | aggagctgaa | gaggaattaa | aatatacagg | atgaaaagat | ggcaatgttg | 60 |
| cctcccccag | gacctcagag | ctttgtccat | ttcacaaaac | agtctcttgc | cctcattgaa | 120 |
| caacgcattg | ctgaaagaaa | atcaaaggaa | cccaagaag | aaaagaaaga | tgatgatgaa | 180 |
| gaagccccaa | agccaagcag | tgacttggaa | gctggcaaac | agctgccctt | catctatggg | 240 |
| gacattcctc | ccggcatggt | gtcagagccc | ctggaggact | tggacccta | ctatgcagac | 300 |
| aaaaagactt | tcatagtatt | gaacaaaggg | aaaacaatct | tccgtttcaa | tgccacacct | 360 |
| gctttatata | tgctttctcc | tttcagtcct | ctaagaagaa | tatctattaa | gattttagta | 420 |
| cactccttat | tcagcatgct | catcatgtgc | actattctga | caaactgcat | atttatgacc | 480 |
| atgaataacc | caccggactg | gaccaaaaat | gtcgagtaca | cttttactgg | aatatatact | 540 |
| tttgaatcac | ttgtaaaaat | ccttgcaaga | ggcttctgtg | taggagaatt | cacttttctt | 600 |
| cgtgacccgt | ggaactggct | ggattttgtc | gtcattgttt | ttgcgtattt | aacagaattt | 660 |
| gtaaacctag | gcaatgtttc | agctcttcga | actttcagag | tattgagagc | tttgaaaact | 720 |
| atttctgtaa | tcccaggcct | gaagacaatt | gtagggggctt | tgatccagtc | agtgaagaag | 780 |
| ctttctgatg | tcatgatcct | gactgtgttc | tgtctgagtg | tgtttgcact | aattggacta | 840 |
| cagctgttca | tgggaaacct | gaagcataaa | tgttttcgaa | attcacttga | aaataatgaa | 900 |
| acattagaaa | gcataatgaa | taccctagag | agtgaagaag | actttagaaa | atatttttat | 960 |
| tacttggaag | gatccaaaga | tgctctcctt | tgtggtttca | gcacagattc | aggtcagtgt | 1020 |
| ccagaggggt | acacctgtgt | gaaaattggc | agaaaccctg | attatggcta | cacgagcttt | 1080 |
| gacactttca | gctgggcctt | cttagccttg | tttaggctaa | tgacccaaga | ttactgggaa | 1140 |
| aaccttac | aacagacgct | gcgtgctgct | ggcaaaacct | acatgatctt | ctttgtcgta | 1200 |
| gtgatttttcc | tgggctcctt | ttatctaata | aacttgatcc | tggctgtggt | tgccatggca | 1260 |
| tatgaagaac | agaaccaggc | aaacattgaa | gaagctaaac | agaaagaatt | agaatttcaa | 1320 |
| cagatgttag | accgtcttaa | aaaagagcaa | gaagaagctg | aggcaattgc | agcggcagcg | 1380 |
| gctgaatata | caagtattag | gagaagcaga | attatgggcc | tctcagagag | ttcttctgaa | 1440 |
| acatccaaac | tgagctctaa | aagtgctaaa | gaaagaagaa | acagaagaaa | gaaaaagaat | 1500 |
| caaaagaagc | tctccagtgg | agaggaaaag | ggagatgctg | agaaattgtc | gaaatcagaa | 1560 |
| tcagaggaca | gcatcagaag | aaaaagtttc | caccttggtg | tcgaagggca | taggcgagca | 1620 |
| catgaaaaga | ggttgtctac | ccccaatcag | tcaccactca | gcattcgtgg | ctccttgttt | 1680 |
| tctgcaaggc | gaagcagcag | aacaagtctt | tttagtttca | aggcagagg | aagagatata | 1740 |
| ggatctgaga | ctgaatttgc | cgatgatgag | cacagcattt | ttggagacaa | tgagagcaga | 1800 |
| aggggctcac | tgtttgtgcc | ccacagaccc | caggagcgac | gcagcagtaa | catcagccaa | 1860 |
| gccagtaggt | ccccaccaat | gctgccggtg | aacgggaaaa | tgcacagtgc | tgtggactgc | 1920 |
| aacggtgtgg | tctccctggt | tgatggacgc | tcagccctca | tgctccccaa | tggacagctt | 1980 |
| ctgccagagg | gcacgaccaa | tcaaatacac | aagaaaaggc | gttgtagttc | ctatctcctt | 2040 |

-continued

```
tcagaggata tgctgaatga tcccaacctc agacagagag caatgagtag agcaagcata    2100
ttaacaaaca ctgtggaaga acttgaagag tccagacaaa aatgtccacc ttggtggtac    2160
agatttgcac acaaattctt gatctggaat tgctctccat attggataaa attcaaaaag    2220
tgtatctatt ttattgtaat ggatcctttt gtagatcttg caattaccat ttgcatagtt    2280
ttaaacacat tatttatggc tatggaacac cacccaatga ctgaggaatt caaaaatgta    2340
cttgctatag gaaatttggt ctttactgga atctttgcag ctgaaatggt attaaaactg    2400
attgccatgg atccatatga gtatttccaa gtaggctgga atattttga cagccttatt    2460 gtgactttaa gttagtggaa gctctttcta gcagatgtgg aaggattgtc agttctgcga    2520
tcattcagac tgctccgagt cttcaagttg gcaaaatcct ggccaacatt gaacatgctg    2580
attaagatca ttggtaactc agtagggct ctaggtaacc tcaccttagt gttggccatc    2640
atcgtcttca tttttgctgt ggtcggcatg cagctctttg gtaagagcta caaagaatgt    2700
gtctgcaaga tcaatgatga ctgtacgctc ccacggtggc acatgaacga cttcttccac    2760
tccttcctga ttgtgttccg cgtgctgtgt ggagagtgga tagagaccat gtgggactgt    2820
atggaggtcg ctggtcaagc tatgtgcctt attgtttaca tgatggtcat ggtcattgga    2880
aacctggtgg tcctaaacct atttctggcc ttattattga gctcatttag ttcagacaat    2940
cttacagcaa ttgaagaaga ccctgatgca aacaacctcc agattgcagt gactagaatt    3000
aaaaagggaa taaattatgt gaaacaaacc ttacgtgaat ttattctaaa agcatttttcc    3060 aaaaagccaa agatttccag ggagataaga caagcagaag atctgaatac taagaaggaa    3120
aactatattt ctaaccatac acttgctgaa atgagcaaag gtcacaattt cctcaaggaa    3180
aaagataaaa tcagtggttt tggaagcagc gtggacaaac acttgatgga agacagtgat    3240
ggtcaatcat ttattcacaa tcccagcctc acagtgacag tgccaattgc acctggggaa    3300
tccgatttgg aaaatatgaa tgctgaggaa cttagcagtg attcggatag tgaatacagc    3360
aaagtgagat taaaccggtc aagctcctca gagtgcagca cagttgataa cccttttgcct    3420 ggagaaggag aagaagcaga ggctgaacct atgaattccg atgagccaga ggcctgtttc    3480
acagatggtt gtgtatggag gttctcatgc tgccaagtta acatagagtc agggaaagga    3540
aaaatctggt ggaacatcag gaaaacctgc tacaagattg ttgaacacag ttggtttgaa    3600
agcttcattg tcctcatgat cctgctcagc agtggtgccc tggcttttga agatatttat    3660
attgaaagga aaagaccat taagattatc ctggagtatg cagacaagat cttcacttac    3720
atcttcattc tggaaatgct tctaaaatgg atagcatatg gttataaaac atatttcacc    3780
aatgcctggt gttggctgga tttcctaatt gttgatgttt ctttggttac tttagtggca    3840
aacactcttg gctactcaga tcttggcccc attaaatccc ttcggacact gagagcttta    3900
agacctctaa gagccttatc tagatttgaa ggaatgaggg tcgttgtgaa tgcactcata    3960
ggagcaattc cttccatcat gaatgtgcta cttgtgtgtc ttatattctg gctgatattc    4020
agcatcatgg gagtaaattt gtttgctggc aagttctatg agtgtattaa caccacagat    4080
gggtcacggt ttcctgcaag tcaagttcca atcgttccg aatgttttgc ccttatgaat    4140
gttagtcaaa atgtgcgatg gaaaaacctg aaagtgaact ttgataatgt cggacttggt    4200
tacctatctc tgcttcaagt tgcaactttt aagggatgga cgattattat gtatgcagca    4260
gtggattctg ttaatgtaga caagcagccc aaatatgaat atagcctcta catgtatatt    4320
tattttgtcg tctttatcat ctttgggtca ttcttcactt tgaacttgtt cattggtgtc    4380
atcatagata atttcaacca acagaaaaag aagcttggag gtcaagacat ctttatgaca    4440
```

```
gaagaacaga agaaatacta taatgcaatg aaaaagctgg ggtccaagaa gccacaaaag   4500
ccaattcctc gaccagggaa caaaatccaa ggatgtatat ttgacctagt gacaaatcaa   4560
gcctttgata ttagtatcat ggttcttatc tgtctcaaca tggtaaccat gatggtagaa   4620
aaggagggtc aaagtcaaca tatgactgaa gttttatatt ggataaatgt ggttttttata  4680
atccttttca ctggagaatg tgtgctaaaa ctgatctccc tcagacacta ctacttcact   4740
gtaggatgga atattttgat tttgtggtt gtgattatct ccattgtagg tatgtttcta    4800
gctgatttga ttgaaacgta ttttgtgtcc cctaccctgt tccgagtgat ccgtcttgcc   4860
aggattggcc gaatcctacg tctagtcaaa ggagcaaagg ggatccgcac gctgctcttt   4920
gctttgatga tgtccccttcc tgcgttgttt aacatcggcc tcctgctctt cctggtcatg   4980
ttcatctacg ccatctttgg aatgtccaac tttgcctatg ttaaaaagga agatggaatt   5040
aatgacatgt tcaattttga gacctttggc aacagtatga tttgcctgtt ccaaattaca   5100
acctctgctg gctgggatgg attgctagca cctattctta acagtaagcc acccgactgt   5160
gacccaaaaa aagttcatcc tggaagttca gttgaaggag actgtggtaa cccatctgtt   5220
ggaatattct actttgttag ttatatcatc atatccttcc tggttgtggt gaacatgtac   5280
attgcagtca tactggagaa tttagtgtt gccactgaag aaagtactga acctctgagt   5340
gaggatgact ttgagatgtt ctatgaggtt tgggagaagt ttgatcccga tgcgacccag   5400
tttatagagt tctctaaact ctctgatttt gcagctgccc tggatcctcc tcttctcata   5460
gcaaaaccca acaaagtcca gctcattgcc atggatctgc ccatggttag tggtgaccgg   5520
atccattgtc ttgacatctt atttgctttt acaaagcgtg ttttgggtga gagtggggag   5580
atggattctc ttcgttcaca gatggaagaa aggttcatgt ctgcaaatcc ttccaaagtg   5640
tcctatgaac ccatcacaac cacactaaaa cggaaacaag aggatgtgtc tgctactgtc   5700
attcagcgtg cttatagacg ttaccgctta aggcaaaatg tcaaaaatat atcaagtata   5760
tacataaaag atggagacag agatgatgat ttactcaata aaaaagatat ggcttttgat   5820
aatgttaatg agaactcaag tccagaaaaa acagatgcca cttcatccac cacctctcca   5880
ccttcatatg atagtgtaac aaagccagac aaagagaaat atgaacaaga cagaacagaa   5940
aaggaagaca agggaaaga cagcaaggaa agcaaaaaat agagcttcat ttttgatata   6000
ttgtttacag cctgtgaaag tgatttattt gtgttaataa aactcttttg aggaagtcta   6060
tgccaaaatc cttttttatca aaatattctc gaaggcagtg cagtcactaa ctctgatttc   6120
ctaagaaagg tgggcagcat tagcagatgg ttatttttgc actgatgatt ctttaagaat   6180
cgtaagagaa ctctgtagga attattgatt atagcataca aaagtgattc agttttttgg   6240
tttttaataa atcagaagac catgtagaaa actttacat ctgccttgtc atcttttcac    6300
aggattgtaa ttagtcttgt ttcccatgta aataaacaac acacgcatac agaaaaaaaa   6360
aaaaaaa                                                             6367
```

<210> SEQ ID NO 2
<211> LENGTH: 1977
<212> TYPE: PRT
<213> ORGANISM: Homo sapiens

<400> SEQUENCE: 2

```
Met Ala Met Leu Pro Pro Gly Pro Gln Ser Phe Val His Phe Thr
1               5                   10                  15

Lys Gln Ser Leu Ala Leu Ile Glu Gln Arg Ile Ala Glu Arg Lys Ser
            20                  25                  30
```

-continued

```
Lys Glu Pro Lys Glu Glu Lys Asp Asp Glu Ala Pro Lys
         35                  40                  45

Pro Ser Ser Asp Leu Glu Ala Gly Lys Gln Leu Pro Phe Ile Tyr Gly
     50                  55                  60

Asp Ile Pro Pro Gly Met Val Ser Glu Pro Leu Glu Asp Leu Asp Pro
 65                  70                  75                  80

Tyr Tyr Ala Asp Lys Lys Thr Phe Ile Val Leu Asn Lys Gly Lys Thr
                 85                  90                  95

Ile Phe Arg Phe Asn Ala Thr Pro Ala Leu Tyr Met Leu Ser Pro Phe
            100                 105                 110

Ser Pro Leu Arg Arg Ile Ser Ile Lys Ile Leu Val His Ser Leu Phe
        115                 120                 125

Ser Met Leu Ile Met Cys Thr Ile Leu Thr Asn Cys Ile Phe Met Thr
    130                 135                 140

Met Asn Asn Pro Pro Asp Trp Thr Lys Asn Val Glu Tyr Thr Phe Thr
145                 150                 155                 160

Gly Ile Tyr Thr Phe Glu Ser Leu Val Lys Ile Leu Ala Arg Gly Phe
                165                 170                 175

Cys Val Gly Glu Phe Thr Phe Leu Arg Asp Pro Trp Asn Trp Leu Asp
            180                 185                 190

Phe Val Val Ile Val Phe Ala Tyr Leu Thr Glu Phe Val Asn Leu Gly
        195                 200                 205

Asn Val Ser Ala Leu Arg Thr Phe Arg Val Leu Arg Ala Leu Lys Thr
    210                 215                 220

Ile Ser Val Ile Pro Gly Leu Lys Thr Ile Val Gly Ala Leu Ile Gln
225                 230                 235                 240

Ser Val Lys Lys Leu Ser Asp Val Met Ile Leu Thr Val Phe Cys Leu
                245                 250                 255

Ser Val Phe Ala Leu Ile Gly Leu Gln Leu Phe Met Gly Asn Leu Lys
            260                 265                 270

His Lys Cys Phe Arg Asn Ser Leu Glu Asn Asn Glu Thr Leu Glu Ser
        275                 280                 285

Ile Met Asn Thr Leu Glu Ser Glu Glu Asp Phe Arg Lys Tyr Phe Tyr
    290                 295                 300

Tyr Leu Glu Gly Ser Lys Asp Ala Leu Leu Cys Gly Phe Ser Thr Asp
305                 310                 315                 320

Ser Gly Gln Cys Pro Glu Gly Tyr Thr Cys Val Lys Ile Gly Arg Asn
                325                 330                 335

Pro Asp Tyr Gly Tyr Thr Ser Phe Asp Thr Phe Ser Trp Ala Phe Leu
            340                 345                 350

Ala Leu Phe Arg Leu Met Thr Gln Asp Tyr Trp Glu Asn Leu Tyr Gln
        355                 360                 365

Gln Thr Leu Arg Ala Ala Gly Lys Thr Tyr Met Ile Phe Phe Val Val
    370                 375                 380

Val Ile Phe Leu Gly Ser Phe Tyr Leu Ile Asn Leu Ile Leu Ala Val
385                 390                 395                 400

Val Ala Met Ala Tyr Glu Glu Gln Asn Gln Ala Asn Ile Glu Glu Ala
                405                 410                 415

Lys Gln Lys Glu Leu Glu Phe Gln Gln Met Leu Asp Arg Leu Lys Lys
            420                 425                 430

Glu Gln Glu Glu Ala Glu Ala Ile Ala Ala Ala Ala Glu Tyr Thr
        435                 440                 445

Ser Ile Arg Arg Ser Arg Ile Met Gly Leu Ser Glu Ser Ser Glu
    450                 455                 460
```

-continued

```
Thr Ser Lys Leu Ser Ser Lys Ser Ala Lys Glu Arg Arg Asn Arg Arg
465                 470                 475                 480

Lys Lys Lys Asn Gln Lys Lys Leu Ser Ser Gly Glu Glu Lys Gly Asp
                485                 490                 495

Ala Glu Lys Leu Ser Lys Ser Glu Ser Glu Asp Ser Ile Arg Arg Lys
            500                 505                 510

Ser Phe His Leu Gly Val Glu Gly His Arg Arg Ala His Glu Lys Arg
        515                 520                 525

Leu Ser Thr Pro Asn Gln Ser Pro Leu Ser Ile Arg Gly Ser Leu Phe
    530                 535                 540

Ser Ala Arg Arg Ser Ser Arg Thr Ser Leu Phe Ser Phe Lys Gly Arg
545                 550                 555                 560

Gly Arg Asp Ile Gly Ser Glu Thr Glu Phe Ala Asp Asp Glu His Ser
                565                 570                 575

Ile Phe Gly Asp Asn Glu Ser Arg Arg Gly Ser Leu Phe Val Pro His
                580                 585                 590

Arg Pro Gln Glu Arg Arg Ser Ser Asn Ile Ser Gln Ala Ser Arg Ser
            595                 600                 605

Pro Pro Met Leu Pro Val Asn Gly Lys Met His Ser Ala Val Asp Cys
        610                 615                 620

Asn Gly Val Val Ser Leu Val Asp Gly Arg Ser Ala Leu Met Leu Pro
625                 630                 635                 640

Asn Gly Gln Leu Leu Pro Glu Gly Thr Thr Asn Gln Ile His Lys Lys
                645                 650                 655

Arg Arg Cys Ser Ser Tyr Leu Leu Ser Glu Asp Met Leu Asn Asp Pro
                660                 665                 670

Asn Leu Arg Gln Arg Ala Met Ser Arg Ala Ser Ile Leu Thr Asn Thr
            675                 680                 685

Val Glu Glu Leu Glu Glu Ser Arg Gln Lys Cys Pro Pro Trp Trp Tyr
        690                 695                 700

Arg Phe Ala His Lys Phe Leu Ile Trp Asn Cys Ser Pro Tyr Trp Ile
705                 710                 715                 720

Lys Phe Lys Lys Cys Ile Tyr Phe Ile Val Met Asp Pro Phe Val Asp
                725                 730                 735

Leu Ala Ile Thr Ile Cys Ile Val Leu Asn Thr Leu Phe Met Ala Met
                740                 745                 750

Glu His His Pro Met Thr Glu Glu Phe Lys Asn Val Leu Ala Ile Gly
            755                 760                 765

Asn Leu Val Phe Thr Gly Ile Phe Ala Ala Glu Met Val Leu Lys Leu
    770                 775                 780

Ile Ala Met Asp Pro Tyr Glu Tyr Phe Gln Val Gly Trp Asn Ile Phe
785                 790                 795                 800

Asp Ser Leu Ile Val Thr Leu Ser Leu Val Glu Leu Phe Leu Ala Asp
                805                 810                 815

Val Glu Gly Leu Ser Val Leu Arg Ser Phe Arg Leu Leu Arg Val Phe
            820                 825                 830

Lys Leu Ala Lys Ser Trp Pro Thr Leu Asn Met Leu Ile Lys Ile Ile
        835                 840                 845

Gly Asn Ser Val Gly Ala Leu Gly Asn Leu Thr Leu Val Leu Ala Ile
    850                 855                 860

Ile Val Phe Ile Phe Ala Val Val Gly Met Gln Leu Phe Gly Lys Ser
865                 870                 875                 880

Tyr Lys Glu Cys Val Cys Lys Ile Asn Asp Asp Cys Thr Leu Pro Arg
```

```
                885              890              895
Trp His Met Asn Asp Phe Phe His Ser Phe Leu Ile Val Phe Arg Val
            900              905              910
Leu Cys Gly Glu Trp Ile Glu Thr Met Trp Asp Cys Met Glu Val Ala
            915              920              925
Gly Gln Ala Met Cys Leu Ile Val Tyr Met Met Val Met Val Ile Gly
            930              935              940
Asn Leu Val Val Leu Asn Leu Phe Leu Ala Leu Leu Leu Ser Ser Phe
945              950              955              960
Ser Ser Asp Asn Leu Thr Ala Ile Glu Glu Asp Pro Asp Ala Asn Asn
            965              970              975
Leu Gln Ile Ala Val Thr Arg Ile Lys Lys Gly Ile Asn Tyr Val Lys
            980              985              990
Gln Thr Leu Arg Glu Phe Ile Leu Lys Ala Phe Ser Lys Lys Pro Lys
            995              1000             1005
Ile Ser Arg Glu Ile Arg Gln Ala Glu Asp Leu Asn Thr Lys Lys
       1010             1015             1020
Glu Asn Tyr Ile Ser Asn His Thr Leu Ala Glu Met Ser Lys Gly
       1025             1030             1035
His Asn Phe Leu Lys Glu Lys Asp Lys Ile Ser Gly Phe Gly Ser
       1040             1045             1050
Ser Val Asp Lys His Leu Met Glu Asp Ser Asp Gly Gln Ser Phe
       1055             1060             1065
Ile His Asn Pro Ser Leu Thr Val Thr Val Pro Ile Ala Pro Gly
       1070             1075             1080
Glu Ser Asp Leu Glu Asn Met Asn Ala Glu Glu Leu Ser Ser Asp
       1085             1090             1095
Ser Asp Ser Glu Tyr Ser Lys Val Arg Leu Asn Arg Ser Ser Ser
       1100             1105             1110
Ser Glu Cys Ser Thr Val Asp Asn Pro Leu Pro Gly Glu Gly Glu
       1115             1120             1125
Glu Ala Glu Ala Glu Pro Met Asn Ser Asp Glu Pro Glu Ala Cys
       1130             1135             1140
Phe Thr Asp Gly Cys Val Trp Arg Phe Ser Cys Cys Gln Val Asn
       1145             1150             1155
Ile Glu Ser Gly Lys Gly Lys Ile Trp Trp Asn Ile Arg Lys Thr
       1160             1165             1170
Cys Tyr Lys Ile Val Glu His Ser Trp Phe Glu Ser Phe Ile Val
       1175             1180             1185
Leu Met Ile Leu Leu Ser Ser Gly Ala Leu Ala Phe Glu Asp Ile
       1190             1195             1200
Tyr Ile Glu Arg Lys Lys Thr Ile Lys Ile Ile Leu Glu Tyr Ala
       1205             1210             1215
Asp Lys Ile Phe Thr Tyr Ile Phe Ile Leu Glu Met Leu Leu Lys
       1220             1225             1230
Trp Ile Ala Tyr Gly Tyr Lys Thr Tyr Phe Thr Asn Ala Trp Cys
       1235             1240             1245
Trp Leu Asp Phe Leu Ile Val Asp Val Ser Leu Val Thr Leu Val
       1250             1255             1260
Ala Asn Thr Leu Gly Tyr Ser Asp Leu Gly Pro Ile Lys Ser Leu
       1265             1270             1275
Arg Thr Leu Arg Ala Leu Arg Pro Leu Arg Ala Leu Ser Arg Phe
       1280             1285             1290
```

```
Glu Gly Met Arg Val Val Asn Ala Leu Ile Gly Ala Ile Pro
1295                1300                1305

Ser Ile Met Asn Val Leu Leu Val Cys Leu Ile Phe Trp Leu Ile
1310                1315                1320

Phe Ser Ile Met Gly Val Asn Leu Phe Ala Gly Lys Phe Tyr Glu
1325                1330                1335

Cys Ile Asn Thr Thr Asp Gly Ser Arg Phe Pro Ala Ser Gln Val
1340                1345                1350

Pro Asn Arg Ser Glu Cys Phe Ala Leu Met Asn Val Ser Gln Asn
1355                1360                1365

Val Arg Trp Lys Asn Leu Lys Val Asn Phe Asp Asn Val Gly Leu
1370                1375                1380

Gly Tyr Leu Ser Leu Leu Gln Val Ala Thr Phe Lys Gly Trp Thr
1385                1390                1395

Ile Ile Met Tyr Ala Ala Val Asp Ser Val Asn Val Asp Lys Gln
1400                1405                1410

Pro Lys Tyr Glu Tyr Ser Leu Tyr Met Tyr Ile Tyr Phe Val Val
1415                1420                1425

Phe Ile Ile Phe Gly Ser Phe Phe Thr Leu Asn Leu Phe Ile Gly
1430                1435                1440

Val Ile Ile Asp Asn Phe Asn Gln Gln Lys Lys Lys Leu Gly Gly
1445                1450                1455

Gln Asp Ile Phe Met Thr Glu Glu Gln Lys Lys Tyr Tyr Asn Ala
1460                1465                1470

Met Lys Lys Leu Gly Ser Lys Lys Pro Gln Lys Pro Ile Pro Arg
1475                1480                1485

Pro Gly Asn Lys Ile Gln Gly Cys Ile Phe Asp Leu Val Thr Asn
1490                1495                1500

Gln Ala Phe Asp Ile Ser Ile Met Val Leu Ile Cys Leu Asn Met
1505                1510                1515

Val Thr Met Met Val Glu Lys Glu Gly Gln Ser Gln His Met Thr
1520                1525                1530

Glu Val Leu Tyr Trp Ile Asn Val Val Phe Ile Ile Leu Phe Thr
1535                1540                1545

Gly Glu Cys Val Leu Lys Leu Ile Ser Leu Arg His Tyr Tyr Phe
1550                1555                1560

Thr Val Gly Trp Asn Ile Phe Asp Phe Val Val Ile Ile Ser
1565                1570                1575

Ile Val Gly Met Phe Leu Ala Asp Leu Ile Glu Thr Tyr Phe Val
1580                1585                1590

Ser Pro Thr Leu Phe Arg Val Ile Arg Leu Ala Arg Ile Gly Arg
1595                1600                1605

Ile Leu Arg Leu Val Lys Gly Ala Lys Gly Ile Arg Thr Leu Leu
1610                1615                1620

Phe Ala Leu Met Met Ser Leu Pro Ala Leu Phe Asn Ile Gly Leu
1625                1630                1635

Leu Leu Phe Leu Val Met Phe Ile Tyr Ala Ile Phe Gly Met Ser
1640                1645                1650

Asn Phe Ala Tyr Val Lys Lys Glu Asp Gly Ile Asn Asp Met Phe
1655                1660                1665

Asn Phe Glu Thr Phe Gly Asn Ser Met Ile Cys Leu Phe Gln Ile
1670                1675                1680

Thr Thr Ser Ala Gly Trp Asp Gly Leu Leu Ala Pro Ile Leu Asn
1685                1690                1695
```

| | | | | | | | | | |
|---|---|---|---|---|---|---|---|---|---|
|Ser|Lys|Pro|Pro|Asp|Cys|Asp|Pro|Lys|Lys|Val|His|Pro|Gly|Ser|
| |1700| | | |1705| | | |1710| |
|Ser|Val|Glu|Gly|Asp|Cys|Gly|Asn|Pro|Ser|Val|Gly|Ile|Phe|Tyr|
| |1715| | | |1720| | | |1725| |
|Phe|Val|Ser|Tyr|Ile|Ile|Ile|Ser|Phe|Leu|Val|Val|Val|Asn|Met|
| |1730| | | |1735| | | |1740| |
|Tyr|Ile|Ala|Val|Ile|Leu|Glu|Asn|Phe|Ser|Val|Ala|Thr|Glu|Glu|
| |1745| | | |1750| | | |1755| |
|Ser|Thr|Glu|Pro|Leu|Ser|Glu|Asp|Asp|Phe|Glu|Met|Phe|Tyr|Glu|
| |1760| | | |1765| | | |1770| |
|Val|Trp|Glu|Lys|Phe|Asp|Pro|Asp|Ala|Thr|Gln|Phe|Ile|Glu|Phe|
| |1775| | | |1780| | | |1785| |
|Ser|Lys|Leu|Ser|Asp|Phe|Ala|Ala|Ala|Leu|Asp|Pro|Pro|Leu|Leu|
| |1790| | | |1795| | | |1800| |
|Ile|Ala|Lys|Pro|Asn|Lys|Val|Gln|Leu|Ile|Ala|Met|Asp|Leu|Pro|
| |1805| | | |1810| | | |1815| |
|Met|Val|Ser|Gly|Asp|Arg|Ile|His|Cys|Leu|Asp|Ile|Leu|Phe|Ala|
| |1820| | | |1825| | | |1830| |
|Phe|Thr|Lys|Arg|Val|Leu|Gly|Glu|Ser|Gly|Glu|Met|Asp|Ser|Leu|
| |1835| | | |1840| | | |1845| |
|Arg|Ser|Gln|Met|Glu|Glu|Arg|Phe|Met|Ser|Ala|Asn|Pro|Ser|Lys|
| |1850| | | |1855| | | |1860| |
|Val|Ser|Tyr|Glu|Pro|Ile|Thr|Thr|Thr|Leu|Lys|Arg|Lys|Gln|Glu|
| |1865| | | |1870| | | |1875| |
|Asp|Val|Ser|Ala|Thr|Val|Ile|Gln|Arg|Ala|Tyr|Arg|Arg|Tyr|Arg|
| |1880| | | |1885| | | |1890| |
|Leu|Arg|Gln|Asn|Val|Lys|Asn|Ile|Ser|Ser|Ile|Tyr|Ile|Lys|Asp|
| |1895| | | |1900| | | |1905| |
|Gly|Asp|Arg|Asp|Asp|Leu|Leu|Asn|Lys|Lys|Asp|Met|Ala|Phe|
| |1910| | | |1915| | | |1920| |
|Asp|Asn|Val|Asn|Glu|Asn|Ser|Ser|Pro|Glu|Lys|Thr|Asp|Ala|Thr|
| |1925| | | |1930| | | |1935| |
|Ser|Ser|Thr|Thr|Ser|Pro|Pro|Ser|Tyr|Asp|Ser|Val|Thr|Lys|Pro|
| |1940| | | |1945| | | |1950| |
|Asp|Lys|Glu|Lys|Tyr|Glu|Gln|Asp|Arg|Thr|Glu|Lys|Glu|Asp|Lys|
| |1955| | | |1960| | | |1965| |
|Gly|Lys|Asp|Ser|Lys|Glu|Ser|Lys|Lys|
| |1970| | | |1975|

<210> SEQ ID NO 3
<211> LENGTH: 6367
<212> TYPE: DNA
<213> ORGANISM: Homo sapiens

<400> SEQUENCE: 3

```
ctcttatgtg aggagctgaa gaggaattaa aatatacagg atgaaaagat ggcaatgttg      60
cctcccccag gacctcagag ctttgtccat ttcacaaaac agtctcttgc cctcattgaa     120
caacgcattg ctgaaagaaa atcaaaggaa cccaagaaag aaaagaaaga tgatgatgaa     180
gaagccccaa agccaagcag tgacttggaa gctggcaaac aactgccctt catctatggg     240
gacattcctc ccggcatggt gtcagagccc tggaggact tgaccccta ctatgcagac     300 aaaaagactt tcatagtatt gaacaaaggg aaaacaatct ccgtttcaa tgccacacct     360 gctttatata tgctttctcc tttcagtcct ctaagaagaa tatctattaa gattttagta     420
```

```
cactccttat tcagcatgct catcatgtgc actattctga caaactgcat atttatgacc    480
atgaataacc cgccggactg gaccaaaaat gtcgagtaca cttttactgg aatatatact    540
tttgaatcac ttgtaaaaat ccttgcaaga ggcttctgtg taggagaatt cacttttctt    600
cgtgacccgt ggaactggct ggattttgtc gtcattgttt ttgcatatgt gacagagttt    660
gtggacctgg gcaatgtctc agcattgaga acattcagag ttctccgagc attgaaaaca    720
atttcagtca ttccaggcct gaagacaatt gtaggggctt tgatccagtc agtgaagaag    780
ctttctgatg tcatgatcct gactgtgttc tgtctgagtg tgtttgcact aattggacta    840
cagctgttca tgggaaacct gaagcataaa tgttttcgaa attcacttga aaataatgaa    900
acattagaaa gcataatgaa taccctagag agtgaagaag actttagaaa atattttat    960 tacttggaag gatccaaaga tgctctcctt tgtggtttca gcacagattc aggtcagtgt    1020
ccagaggggt acacctgtgt gaaaattggc agaaaccctg attatggcta cacgagcttt    1080
gacactttca gctgggcctt cttagccttg tttaggctaa tgacccaaga ttactgggaa    1140
aacctttacc aacagacgct gcgtgccgct ggcaaaacct acatgatctt ctttgtcgta    1200
gtgattttcc tgggctcctt ttatctaata aacttgatcc tggctgtggt tgccatggca    1260
tatgaagaac agaaccaggc aaacattgaa gaagctaaac agaaagaatt agagtttcaa    1320
cagatgttag accgacttaa aaaagagcaa gaagaagctg aggcaattgc agcggcagcg    1380
gctgaatata caagtattag gagaagcaga attatgggcc tctcagagag ttcttctgaa    1440
acatccaaac tgagctctaa aagtgctaaa gaaagaagaa acagaagaaa gaaaagaat    1500 caaaagaagc tctccagtgg agaggaaaag ggagatgctg agaaattgtc gaaatcagaa    1560
tcagaggaca gcatcagaag aaaaagtttc caccttggtg tcgaagggca taggcgagca    1620
catgaaaaga ggttgtctac ccccaatcag tcaccactca gcattcgtgg ctccttgttt    1680
tctgcaaggc gaagcagcag aacaagtctt tttagtttca aaggcagagg aagagatata    1740
ggatctgaga ctgaatttgc cgatgatgag cacagcattt ttggagacaa tgagagcaga    1800
aggggctcac tgtttgtgcc ccacagaccc caggagcgac gcagcagtaa catcagccaa    1860
gccagtaggt ccccaccaat gctgccggtg aacgggaaaa tgcacagtgc tgtggactgc    1920
aacggtgtgg tctccctggt tgatggacgc tcagccctca tgctcccaa tggacagctt    1980 ctgccagagg gcacgaccaa tcaaatacac aagaaaaggc gttgtagttc ctatctcctt    2040
tcagaggata tgctgaatga tcccaacctc agacagagag caatgagtag agcaagcata    2100
ttaacaaaca ctgtggaaga acttgaagag tccagacaaa aatgtccacc ttggtggtac    2160
agatttgcac acaaattctt gatctggaat gctctccat attggataaa attcaaaaag    2220
tgtatctatt ttattgtaat ggatccttt gtagatcttg caattaccat ttgcatagtt    2280
ttaaacacat tatttatggc tatggaacac cacccaatga ctgaggaatt caaaaatgta    2340
cttgctatag aaatttggt cttttactgga atctttgcag ctgaaatggt attaaaactg    2400
attgccatgg atccatatga gtatttccaa gtaggctgga atattttttga cagccttatt    2460 gtgactttaa gttagtggaa gctctttcta gcagatgtgg aaggattgtc agttctgcga    2520
tcattcagac tgctccgagt cttcaagttg gcaaaatcct ggccaacatt gaacatgctg    2580
attaagatca ttggtaactc agtaggggct ctaggtaacc tcaccttagt gttggccatc    2640
atcgtcttca tttttgctgt ggtcggcatg cagctctttg gtaagagcta caaagaatgt    2700
gtctgcaaga tcaatgatga ctgtacgctc ccacggtggc acatgaacga cttcttccac    2760
tccttcctga ttgtgttccg cgtgctgtgt ggagagtgga tagagaccat gtgggactgt    2820
```

-continued

```
atggaggtcg ctggtcaagc tatgtgcctt attgtttaca tgatggtcat ggtcattgga      2880
aacctggtgg tcctaaacct atttctggcc ttattattga gctcatttag ttcagacaat      2940
cttacagcaa ttgaagaaga ccctgatgca acaacctcc  agattgcagt gactagaatt      3000
aaaaagggaa taaattatgt gaaacaaacc ttacgtgaat ttattctaaa agcatttttcc     3060
aaaaagccaa agatttccag ggagataaga caagcagaag atctgaatac taagaaggaa     3120
aactatattt ctaaccatac acttgctgaa atgagcaaag gtcacaattt cctcaaggaa     3180
aaagataaaa tcagtggttt tggaagcagc gtggacaaac acttgatgga agacagtgat     3240
ggtcaatcat ttattcacaa tcccagcctc acagtgacag tgccaattgc acctggggaa     3300
tccgatttgg aaaatatgaa tgctgaggaa cttagcagtg attcggatag tgaatacagc     3360
aaagtgagat aaaccggtc  aagctcctca gagtgcagca cagttgataa cccttttgcct    3420
ggagaaggag aagaagcaga ggctgaacct atgaattccg atgagccaga ggcctgtttc     3480
acagatggtt gtgtacggag gttctcatgc tgccaagtta acatagagtc agggaaagga     3540
aaaatctggt ggaacatcag gaaaacctgc tacaagattg ttgaacacag ttggtttgaa     3600
agcttcattg tcctcatgat cctgctcagc agtggtgccc tggcttttga agatatttat     3660
attgaaagga aaaagaccat taagattatc ctggagtatg cagacaagat cttcacttac     3720
atcttcattc tggaaatgct tctaaaatgg atagcatatg gttataaaac atatttcacc     3780
aatgcctggt gttggctgga tttcctaatt gttgatgttt ctttggttac tttagtggca     3840
aacactcttg gctactcaga tcttggcccc attaaatccc ttcggacact gagagcttta     3900
agacctctaa gagccttatc tagatttgaa ggaatgaggg tcgttgtgaa tgcactcata     3960
ggagcaattc cttccatcat gaatgtgcta cttgtgtgtc ttatattctg gctgatattc     4020
agcatcatgg gagtaaattt gtttgctggc aagttctatg agtgtattaa caccacagat     4080
gggtcacggt ttcctgcaag tcaagttcca atcgttccg  aatgttttgc ccttatgaat     4140
gttagtcaaa atgtgcgatg gaaaaacctg aaagtgaact ttgataatgt cggacttggt     4200
tacctatctc tgcttcaagt tgcaactttt aagggatgga cgattattat gtatgcagca     4260
gtggattctg ttaatgtaga caagcagccc aaatatgaat atagcctcta catgtatatt     4320
tattttgtcg tctttatcat ctttgggtca ttcttcactt tgaacttgtt cattggtgtc     4380
atcatagata atttcaacca acagaaaaag aagcttggag tcaagacat  ctttatgaca     4440
gaagaacaga agaaatacta taatgcaatg aaaaagctgg ggtccaagaa gccacaaaag     4500
ccaattcctc gaccagggaa caaaatccaa ggatgtatat tgacctagt  gacaaatcaa     4560
gcctttgata ttagtatcat ggttcttatc tgtctcaaca tggtaaccat gatggtagaa     4620
aaggagggtc aaagtcaaca tatgactgaa gtttttatatt ggataaatgt ggttttata    4680
atccttttca ctggagaatg tgtgctaaaa ctgatctccc tcagacacta ctacttcact     4740
gtaggatgga atattttga  ttttgtggtt gtgattatct ccattgtagg tatgtttcta     4800
gctgatttga ttgaaacgta ttttgtgtcc cctaccctgt tccgagtgat ccgtcttgcc     4860
aggattggcc gaatcctacg tctagtcaaa ggagcaaagg ggatccgcac gctgctcttt     4920
gctttgatga tgtcccttcc tgcgttgttt aacatcggcc tcctgctctt cctggtcatg     4980
ttcatctacg ccatctttgg aatgtccaac tttgcctatg ttaaaaagga agatggaatt     5040
aatgacatgt tcaattttga gacctttggc aacagtatga tttgcctgtt ccaaattaca     5100
acctctgctg gctgggatgg attgctagca cctattctta acagtaagcc acccgactgt     5160
gacccaaaaa aagttcatcc tggaagttca gttgaaggag actgtggtaa cccatctgtt     5220
```

```
ggaatattct actttgttag ttatatcatc atatccttcc tggttgtggt gaacatgtac    5280
attgcagtca tactggagaa ttttagtgtt gccactgaag aaagtactga acctctgagt    5340
gaggatgact ttgagatgtt ctatgaggtt tgggagaagt ttgatcccga tgcgacccag    5400
tttatagagt tctctaaact ctctgatttt gcagctgccc tggatcctcc tcttctcata    5460
gcaaaaccca acaaagtcca gctcattgcc atggatctgc ccatggttag tggtgaccgg    5520
atccattgtc ttgacatctt atttgctttt acaaagcgtg ttttgggtga gagtggggag    5580
atggattctc ttcgttcaca gatggaagaa aggttcatgt ctgcaaatcc ttccaaagtg    5640
tcctatgaac ccatcacaac cacactaaaa cggaaacaag aggatgtgtc tgctactgtc    5700
attcagcgtg cttatagacg ttaccgctta aggcaaaatg tcaaaatat atcaagtata     5760 tacataaaag atggagacag agatgatgat ttactcaata aaaagatat ggcttttgat     5820 aatgttaatg agaactcaag tccagaaaaa acagatgcca cttcatccac cacctctcca    5880
ccttcatatg atagtgtaac aaagccagac aaagagaaat atgaacaaga cagaacagaa    5940
aaggaagaca agggaaaga cagcaaggaa agcaaaaaat agagcttcat ttttgatata     6000
ttgtttacag cctgtgaaag tgatttattt gtgttaataa aactcttttg aggaagtcta    6060
tgccaaaatc ctttttatca aaatattctc gaaggcagtg cagtcactaa ctctgatttc    6120
ctaagaaagg tgggcagcat tagcagatgg ttatttttgc actgatgatt ctttaagaat    6180
cgtaagagaa ctctgtagga attattgatt atagcataca aaagtgattc agttttttgg    6240
tttttaataa atcagaagac catgtagaaa acttttacat ctgccttgtc atcttttcac    6300
aggattgtaa ttagtcttgt ttcccatgta aataaacaac acacgcatac agaaaaaaaa    6360
aaaaaaa                                                              6367
```

<210> SEQ ID NO 4
<211> LENGTH: 1977
<212> TYPE: PRT
<213> ORGANISM: Homo sapiens

<400> SEQUENCE: 4

```
Met Ala Met Leu Pro Pro Gly Pro Gln Ser Phe Val His Phe Thr
1               5                   10                  15

Lys Gln Ser Leu Ala Leu Ile Glu Gln Arg Ile Ala Glu Arg Lys Ser
            20                  25                  30

Lys Glu Pro Lys Glu Glu Lys Lys Asp Asp Asp Glu Glu Ala Pro Lys
        35                  40                  45

Pro Ser Ser Asp Leu Glu Ala Gly Lys Gln Leu Pro Phe Ile Tyr Gly
    50                  55                  60

Asp Ile Pro Pro Gly Met Val Ser Glu Pro Leu Glu Asp Leu Asp Pro
65                  70                  75                  80

Tyr Tyr Ala Asp Lys Lys Thr Phe Ile Val Leu Asn Lys Gly Lys Thr
                85                  90                  95

Ile Phe Arg Phe Asn Ala Thr Pro Ala Leu Tyr Met Leu Ser Pro Phe
            100                 105                 110

Ser Pro Leu Arg Arg Ile Ser Ile Lys Ile Leu Val His Ser Leu Phe
        115                 120                 125

Ser Met Leu Ile Met Cys Thr Ile Leu Thr Asn Cys Ile Phe Met Thr
    130                 135                 140

Met Asn Asn Pro Pro Asp Trp Thr Lys Asn Val Glu Tyr Thr Phe Thr
145                 150                 155                 160

Gly Ile Tyr Thr Phe Glu Ser Leu Val Lys Ile Leu Ala Arg Gly Phe
                165                 170                 175
```

```
Cys Val Gly Glu Phe Thr Phe Leu Arg Asp Pro Trp Asn Trp Leu Asp
            180                 185                 190

Phe Val Val Ile Val Phe Ala Tyr Val Thr Glu Phe Val Asp Leu Gly
            195                 200                 205

Asn Val Ser Ala Leu Arg Thr Phe Arg Val Leu Arg Ala Leu Lys Thr
210                 215                 220

Ile Ser Val Ile Pro Gly Leu Lys Thr Ile Val Gly Ala Leu Ile Gln
225                 230                 235                 240

Ser Val Lys Lys Leu Ser Asp Val Met Ile Leu Thr Val Phe Cys Leu
                245                 250                 255

Ser Val Phe Ala Leu Ile Gly Leu Gln Leu Phe Met Gly Asn Leu Lys
                260                 265                 270

His Lys Cys Phe Arg Asn Ser Leu Glu Asn Asn Glu Thr Leu Glu Ser
                275                 280                 285

Ile Met Asn Thr Leu Glu Ser Glu Glu Asp Phe Arg Lys Tyr Phe Tyr
        290                 295                 300

Tyr Leu Glu Gly Ser Lys Asp Ala Leu Leu Cys Gly Phe Ser Thr Asp
305                 310                 315                 320

Ser Gly Gln Cys Pro Glu Gly Tyr Thr Cys Val Lys Ile Gly Arg Asn
                325                 330                 335

Pro Asp Tyr Gly Tyr Thr Ser Phe Asp Thr Phe Ser Trp Ala Phe Leu
                340                 345                 350

Ala Leu Phe Arg Leu Met Thr Gln Asp Tyr Trp Glu Asn Leu Tyr Gln
                355                 360                 365

Gln Thr Leu Arg Ala Ala Gly Lys Thr Tyr Met Ile Phe Phe Val Val
        370                 375                 380

Val Ile Phe Leu Gly Ser Phe Tyr Leu Ile Asn Leu Ile Leu Ala Val
385                 390                 395                 400

Val Ala Met Ala Tyr Glu Glu Gln Asn Gln Ala Asn Ile Glu Glu Ala
                405                 410                 415

Lys Gln Lys Glu Leu Glu Phe Gln Gln Met Leu Asp Arg Leu Lys Lys
                420                 425                 430

Glu Gln Glu Glu Ala Glu Ala Ile Ala Ala Ala Ala Ala Glu Tyr Thr
                435                 440                 445

Ser Ile Arg Arg Ser Arg Ile Met Gly Leu Ser Glu Ser Ser Ser Glu
        450                 455                 460

Thr Ser Lys Leu Ser Ser Lys Ser Ala Lys Glu Arg Arg Asn Arg Arg
465                 470                 475                 480

Lys Lys Lys Asn Gln Lys Lys Leu Ser Ser Gly Glu Glu Lys Gly Asp
                485                 490                 495

Ala Glu Lys Leu Ser Lys Ser Glu Ser Glu Asp Ser Ile Arg Arg Lys
                500                 505                 510

Ser Phe His Leu Gly Val Glu Gly His Arg Arg Ala His Glu Lys Arg
                515                 520                 525

Leu Ser Thr Pro Asn Gln Ser Pro Leu Ser Ile Arg Gly Ser Leu Phe
        530                 535                 540

Ser Ala Arg Arg Ser Ser Arg Thr Ser Leu Phe Ser Phe Lys Gly Arg
545                 550                 555                 560

Gly Arg Asp Ile Gly Ser Glu Thr Glu Phe Ala Asp Asp Glu His Ser
                565                 570                 575

Ile Phe Gly Asp Asn Glu Ser Arg Arg Gly Ser Leu Phe Val Pro His
        580                 585                 590

Arg Pro Gln Glu Arg Arg Ser Ser Asn Ile Ser Gln Ala Ser Arg Ser
```

-continued

```
                595                 600                 605
    Pro Pro Met Leu Pro Val Asn Gly Lys Met His Ser Ala Val Asp Cys
        610                 615                 620

Asn Gly Val Val Ser Leu Val Asp Gly Arg Ser Ala Leu Met Leu Pro
    625                 630                 635                 640

Asn Gly Gln Leu Leu Pro Glu Gly Thr Thr Asn Gln Ile His Lys Lys
                    645                 650                 655

Arg Arg Cys Ser Ser Tyr Leu Leu Ser Glu Asp Met Leu Asn Asp Pro
                660                 665                 670

Asn Leu Arg Gln Arg Ala Met Ser Arg Ala Ser Ile Leu Thr Asn Thr
                675                 680                 685

Val Glu Glu Leu Glu Glu Ser Arg Gln Lys Cys Pro Pro Trp Trp Tyr
    690                 695                 700

Arg Phe Ala His Lys Phe Leu Ile Trp Asn Cys Ser Pro Tyr Trp Ile
    705                 710                 715                 720

Lys Phe Lys Lys Cys Ile Tyr Phe Ile Val Met Asp Pro Phe Val Asp
                    725                 730                 735

Leu Ala Ile Thr Ile Cys Ile Val Leu Asn Thr Leu Phe Met Ala Met
                740                 745                 750

Glu His His Pro Met Thr Glu Glu Phe Lys Asn Val Leu Ala Ile Gly
                755                 760                 765

Asn Leu Val Phe Thr Gly Ile Phe Ala Ala Glu Met Val Leu Lys Leu
    770                 775                 780

Ile Ala Met Asp Pro Tyr Glu Tyr Phe Gln Val Gly Trp Asn Ile Phe
    785                 790                 795                 800

Asp Ser Leu Ile Val Thr Leu Ser Leu Val Glu Leu Phe Leu Ala Asp
                    805                 810                 815

Val Glu Gly Leu Ser Val Leu Arg Ser Phe Arg Leu Leu Arg Val Phe
                820                 825                 830

Lys Leu Ala Lys Ser Trp Pro Thr Leu Asn Met Leu Ile Lys Ile Ile
                835                 840                 845

Gly Asn Ser Val Gly Ala Leu Gly Asn Leu Thr Leu Val Leu Ala Ile
    850                 855                 860

Ile Val Phe Ile Phe Ala Val Val Gly Met Gln Leu Phe Gly Lys Ser
    865                 870                 875                 880

Tyr Lys Glu Cys Val Cys Lys Ile Asn Asp Asp Cys Thr Leu Pro Arg
                    885                 890                 895

Trp His Met Asn Asp Phe Phe His Ser Phe Leu Ile Val Phe Arg Val
                900                 905                 910

Leu Cys Gly Glu Trp Ile Glu Thr Met Trp Asp Cys Met Glu Val Ala
                915                 920                 925

Gly Gln Ala Met Cys Leu Ile Val Tyr Met Met Val Met Val Ile Gly
    930                 935                 940

Asn Leu Val Leu Asn Leu Phe Leu Ala Leu Leu Leu Ser Ser Phe
    945                 950                 955                 960

Ser Ser Asp Asn Leu Thr Ala Ile Glu Glu Asp Pro Asp Ala Asn Asn
                    965                 970                 975

Leu Gln Ile Ala Val Thr Arg Ile Lys Lys Gly Ile Asn Tyr Val Lys
                980                 985                 990

Gln Thr Leu Arg Glu Phe Ile Leu Lys Ala Phe Ser Lys Lys Pro Lys
                995                 1000                1005

Ile Ser Arg Glu Ile Arg Gln Ala Glu Asp Leu Asn Thr Lys Lys
        1010                1015                1020
```

-continued

```
Glu Asn Tyr Ile Ser Asn His Thr Leu Ala Glu Met Ser Lys Gly
1025                1030                1035

His Asn Phe Leu Lys Glu Lys Asp Lys Ile Ser Gly Phe Gly Ser
1040                1045                1050

Ser Val Asp Lys His Leu Met Glu Asp Ser Asp Gly Gln Ser Phe
1055                1060                1065

Ile His Asn Pro Ser Leu Thr Val Thr Val Pro Ile Ala Pro Gly
1070                1075                1080

Glu Ser Asp Leu Glu Asn Met Asn Ala Glu Glu Leu Ser Ser Asp
1085                1090                1095

Ser Asp Ser Glu Tyr Ser Lys Val Arg Leu Asn Arg Ser Ser Ser
1100                1105                1110

Ser Glu Cys Ser Thr Val Asp Asn Pro Leu Pro Gly Glu Gly Glu
1115                1120                1125

Glu Ala Glu Ala Glu Pro Met Asn Ser Asp Glu Pro Glu Ala Cys
1130                1135                1140

Phe Thr Asp Gly Cys Val Arg Arg Phe Ser Cys Cys Gln Val Asn
1145                1150                1155

Ile Glu Ser Gly Lys Gly Lys Ile Trp Trp Asn Ile Arg Lys Thr
1160                1165                1170

Cys Tyr Lys Ile Val Glu His Ser Trp Phe Glu Ser Phe Ile Val
1175                1180                1185

Leu Met Ile Leu Leu Ser Ser Gly Ala Leu Ala Phe Glu Asp Ile
1190                1195                1200

Tyr Ile Glu Arg Lys Lys Thr Ile Lys Ile Ile Leu Glu Tyr Ala
1205                1210                1215

Asp Lys Ile Phe Thr Tyr Ile Phe Ile Leu Glu Met Leu Leu Lys
1220                1225                1230

Trp Ile Ala Tyr Gly Tyr Lys Thr Tyr Phe Thr Asn Ala Trp Cys
1235                1240                1245

Trp Leu Asp Phe Leu Ile Val Asp Val Ser Leu Val Thr Leu Val
1250                1255                1260

Ala Asn Thr Leu Gly Tyr Ser Asp Leu Gly Pro Ile Lys Ser Leu
1265                1270                1275

Arg Thr Leu Arg Ala Leu Arg Pro Leu Arg Ala Leu Ser Arg Phe
1280                1285                1290

Glu Gly Met Arg Val Val Val Asn Ala Leu Ile Gly Ala Ile Pro
1295                1300                1305

Ser Ile Met Asn Val Leu Leu Val Cys Leu Ile Phe Trp Leu Ile
1310                1315                1320

Phe Ser Ile Met Gly Val Asn Leu Phe Ala Gly Lys Phe Tyr Glu
1325                1330                1335

Cys Ile Asn Thr Thr Asp Gly Ser Arg Phe Pro Ala Ser Gln Val
1340                1345                1350

Pro Asn Arg Ser Glu Cys Phe Ala Leu Met Asn Val Ser Gln Asn
1355                1360                1365

Val Arg Trp Lys Asn Leu Lys Val Asn Phe Asp Asn Val Gly Leu
1370                1375                1380

Gly Tyr Leu Ser Leu Leu Gln Val Ala Thr Phe Lys Gly Trp Thr
1385                1390                1395

Ile Ile Met Tyr Ala Ala Val Asp Ser Val Asn Val Asp Lys Gln
1400                1405                1410

Pro Lys Tyr Glu Tyr Ser Leu Tyr Met Tyr Ile Tyr Phe Val Val
1415                1420                1425
```

```
Phe Ile Ile Phe Gly Ser Phe Phe Thr Leu Asn Leu Phe Ile Gly
    1430            1435                1440

Val Ile Ile Asp Asn Phe Asn Gln Gln Lys Lys Lys Leu Gly Gly
    1445            1450                1455

Gln Asp Ile Phe Met Thr Glu Glu Gln Lys Lys Tyr Tyr Asn Ala
    1460            1465                1470

Met Lys Lys Leu Gly Ser Lys Lys Pro Gln Lys Pro Ile Pro Arg
    1475            1480                1485

Pro Gly Asn Lys Ile Gln Gly Cys Ile Phe Asp Leu Val Thr Asn
    1490            1495                1500

Gln Ala Phe Asp Ile Ser Ile Met Val Leu Ile Cys Leu Asn Met
    1505            1510                1515

Val Thr Met Met Val Glu Lys Glu Gly Gln Ser Gln His Met Thr
    1520            1525                1530

Glu Val Leu Tyr Trp Ile Asn Val Val Phe Ile Ile Leu Phe Thr
    1535            1540                1545

Gly Glu Cys Val Leu Lys Leu Ile Ser Leu Arg His Tyr Tyr Phe
    1550            1555                1560

Thr Val Gly Trp Asn Ile Phe Asp Phe Val Val Val Ile Ile Ser
    1565            1570                1575

Ile Val Gly Met Phe Leu Ala Asp Leu Ile Glu Thr Tyr Phe Val
    1580            1585                1590

Ser Pro Thr Leu Phe Arg Val Ile Arg Leu Ala Arg Ile Gly Arg
    1595            1600                1605

Ile Leu Arg Leu Val Lys Gly Ala Lys Gly Ile Arg Thr Leu Leu
    1610            1615                1620

Phe Ala Leu Met Met Ser Leu Pro Ala Leu Phe Asn Ile Gly Leu
    1625            1630                1635

Leu Leu Phe Leu Val Met Phe Ile Tyr Ala Ile Phe Gly Met Ser
    1640            1645                1650

Asn Phe Ala Tyr Val Lys Lys Glu Asp Gly Ile Asn Asp Met Phe
    1655            1660                1665

Asn Phe Glu Thr Phe Gly Asn Ser Met Ile Cys Leu Phe Gln Ile
    1670            1675                1680

Thr Thr Ser Ala Gly Trp Asp Gly Leu Leu Ala Pro Ile Leu Asn
    1685            1690                1695

Ser Lys Pro Pro Asp Cys Asp Pro Lys Lys Val His Pro Gly Ser
    1700            1705                1710

Ser Val Glu Gly Asp Cys Gly Asn Pro Ser Val Gly Ile Phe Tyr
    1715            1720                1725

Phe Val Ser Tyr Ile Ile Ile Ser Phe Leu Val Val Val Asn Met
    1730            1735                1740

Tyr Ile Ala Val Ile Leu Glu Asn Phe Ser Val Ala Thr Glu Glu
    1745            1750                1755

Ser Thr Glu Pro Leu Ser Glu Asp Asp Phe Glu Met Phe Tyr Glu
    1760            1765                1770

Val Trp Glu Lys Phe Asp Pro Asp Ala Thr Gln Phe Ile Glu Phe
    1775            1780                1785

Ser Lys Leu Ser Asp Phe Ala Ala Ala Leu Asp Pro Pro Leu Leu
    1790            1795                1800

Ile Ala Lys Pro Asn Lys Val Gln Leu Ile Ala Met Asp Leu Pro
    1805            1810                1815

Met Val Ser Gly Asp Arg Ile His Cys Leu Asp Ile Leu Phe Ala
```

-continued

| | 1820 | | | | 1825 | | | | 1830 | | |
|---|---|---|---|---|---|---|---|---|---|---|---|
| Phe | Thr | Lys | Arg | Val | Leu | Gly | Glu | Ser | Gly | Glu | Met | Asp | Ser | Leu |
| | | 1835 | | | | 1840 | | | | 1845 | |
| Arg | Ser | Gln | Met | Glu | Glu | Arg | Phe | Met | Ser | Ala | Asn | Pro | Ser | Lys |
| | | 1850 | | | | 1855 | | | | 1860 | |
| Val | Ser | Tyr | Glu | Pro | Ile | Thr | Thr | Thr | Leu | Lys | Arg | Lys | Gln | Glu |
| | | 1865 | | | | 1870 | | | | 1875 | |
| Asp | Val | Ser | Ala | Thr | Val | Ile | Gln | Arg | Ala | Tyr | Arg | Arg | Tyr | Arg |
| | | 1880 | | | | 1885 | | | | 1890 | |
| Leu | Arg | Gln | Asn | Val | Lys | Asn | Ile | Ser | Ser | Ile | Tyr | Ile | Lys | Asp |
| | | 1895 | | | | 1900 | | | | 1905 | |
| Gly | Asp | Arg | Asp | Asp | Asp | Leu | Leu | Asn | Lys | Lys | Asp | Met | Ala | Phe |
| | | 1910 | | | | 1915 | | | | 1920 | |
| Asp | Asn | Val | Asn | Glu | Asn | Ser | Ser | Pro | Glu | Lys | Thr | Asp | Ala | Thr |
| | | 1925 | | | | 1930 | | | | 1935 | |
| Ser | Ser | Thr | Thr | Ser | Pro | Pro | Ser | Tyr | Asp | Ser | Val | Thr | Lys | Pro |
| | | 1940 | | | | 1945 | | | | 1950 | |
| Asp | Lys | Glu | Lys | Tyr | Glu | Gln | Asp | Arg | Thr | Glu | Lys | Glu | Asp | Lys |
| | | 1955 | | | | 1960 | | | | 1965 | |
| Gly | Lys | Asp | Ser | Lys | Glu | Ser | Lys | Lys |
| | | 1970 | | | | 1975 | |

<210> SEQ ID NO 5
<211> LENGTH: 6397
<212> TYPE: DNA
<213> ORGANISM: Homo sapiens

<400> SEQUENCE: 5

```
ctcttatgtg aggagctgaa gaggaattaa aatatacagg atgaaaagat ggcaatgttg      60
cctcccccag gacctcagag ctttgtccat tcacaaaaac agtctcttgc cctcattgaa     120
caacgcattg ctgaaagaaa atcaaaggaa cccaaagaag aaaagaaaga tgatgatgaa     180
gaagccccaa agccaagcag tgacttggaa gctggcaaac aactgcccct catctatggg     240
gacattcctc ccggcatggt gtcagagccc tggaggact  tggaccccta ctatgcagac     300
aaaaagactt tcatagtatt gaacaaaggg aaaacaatct tccgtttcaa tgccacacct     360
gctttatata tgctttctcc tttcagtcct ctaagaagaa tatctattaa gattttagta     420
cactccttat tcagcatgct catcatgtgc actattctga caaactgcat atttatgacc     480
atgaataacc cgccggactg gaccaaaaat gtcgagtaca cttttactgg aatatatact     540
tttgaatcac ttgtaaaaat ccttgcaaga ggcttctgtg taggagaatt cacttttctt     600
cgtgacccgt ggaactggct ggattttgtc gtcattgttt ttgcgtattt aacagaattt     660
gtaaacctag gcaatgtttc agctcttcga actttcagag tattgagagc tttgaaaact     720
atttctgtaa tcccaggcct gaagacaatt gtagggcttt tgatccagtc agtgaagaag     780
cttttctgatg tcatgatcct gactgtgttc tgtctgagtg tgtttgcact aattggacta     840
cagctgttca tggaaaacct gaagcataaa tgttttcgaa attcacttga aaataatgaa     900
acattagaaa gcataatgaa taccctagag agtgaagaag actttagaaa atattttat      960
tacttggaag atccaagaga tgctctcctt tgtggtttca gcacagattc aggtcagtgt    1020
ccagaggggt acacctgtgt gaaaattggc agaaaccctg attatggcta cacgagcttt    1080
gacacttttc ctgggcctt  cttagccttg tttaggctaa tgacccaaga ttactgggaa    1140
aacctttacc aacagacgct gcgtgccgct ggcaaaacct acatgatctt ctttgtcgta    1200
```

```
gtgattttcc tgggctcctt ttatctaata aacttgatcc tggctgtggt tgccatggca   1260
tatgaagaac agaaccaggc aaacattgaa gaagctaaac agaaagaatt agagtttcaa   1320
cagatgttag accgacttaa aaaagagcaa gaagaagctg aggcaattgc agcggcagcg   1380
gctgaatata caagtattag gagaagcaga attatgggcc tctcagagag ttcttctgaa   1440
acatccaaac tgagctctaa aagtgctaaa gaagaagaa acagaagaaa gaaaagaat    1500 caaaagaagc tctccagtgg agaggaaaag ggagatgctg agaaattgtc gaaatcagaa   1560
tcagaggaca gcatcagaag aaaaagtttc caccttggtg tcgaagggca taggcgagca   1620
catgaaagaa ggttgtctac ccccaatcag tcaccactca gcattcgtgg ctccttgttt   1680
tctgcaaggc gaagcagcag aacaagtctt tttagtttca aaggcagagg aagagatata   1740
ggatctgaga ctgaatttgc cgatgatgag cacagcattt ttggagacaa tgagagcaga   1800
aggggctcac tgtttgtgcc ccacagaccc caggagcgac gcagcagtaa catcagccaa   1860
gccagtaggt ccccaccaat gctgccggtg aacgggaaaa tgcacagtgc tgtggactgc   1920
aacggtgtgg tctccctggt tgatggacgc tcagccctca tgctcccaa tggacagctt    1980 ctgccagagg tgataataga taaggcaact tctgatgaca gcggcacgac caatcaaata   2040
cacaagaaaa ggcgttgtag ttcctatctc ctttcagagg atatgctgaa tgatcccaac   2100
ctcagacaga gagcaatgag tagagcaagc atattaacaa acactgtgga agaacttgaa   2160
gagtccagac aaaaatgtcc accttggtgg tacagatttg cacacaaatt cttgatctgg   2220
aattgctctc catattggat aaaattcaaa aagtgtatct atttattgt aatggatcct    2280 tttgtagatc ttgcaattac catttgcata gttttaaaca cattatttat ggctatggaa   2340
caccacccaa tgactgagga attcaaaaat gtacttgcta taggaaattt ggtctttact   2400
ggaatctttg cagctgaaat ggtattaaaa ctgattgcca tggatccata tgagtatttc   2460
caagtaggct ggaatatttt tgacagcctt attgtgactt taagtttagt ggagctcttt   2520
ctagcagatg tggaaggatt gtcagttctg cgatcattca gactgctccg agtcttcaag   2580
ttggcaaaat cctggccaac attgaacatg ctgattaaga tcattggtaa ctcagtaggg   2640
gctctaggta acctccacctt agtgttggcc atcatcgtct tcatttttgc tgtggtcggc   2700
atgcagctct ttggtaagag ctacaaagaa tgtgtctgca agatcaatga tgactgtacg   2760
ctcccacggt ggcacatgaa cgacttcttc cactccttcc tgattgtgtt ccgcgtgctg   2820
tgtggagagt ggatagagac catgtgggac tgtatggagg tcgctggtca agctatgtgc   2880
cttattgttt acatgatggt catggtcatt ggaaacctgg tggtcctaaa cctatttctg   2940
gccttattat tgagctcatt tagttcagac aatcttacag caattgaaga agaccctgat   3000
gcaaacaacc tccagattgc agtgactaga attaaaaagg gaataaatta tgtgaaacaa   3060
accttacgtg aatttattct aaaagcattt tccaaaaagc caaagatttc cagggagata   3120
agacaagcag aagatctgaa tactaagaag gaaaactata tttctaacca tacacttgct   3180
gaaatgagca aaggtcacaa tttcctcaag gaaaagata aaatcagtgg ttttggaagc    3240
agcgtggaca aacacttgat ggaagacagt gatggtcaat catttattca caatcccagc   3300
ctcacagtga cagtgccaat tgcacctggg gaatccgatt tggaaaatat gaatgctgag   3360
gaacttagca gtgattcgga tagtgaatac agcaaagtga gattaaaccg gtcaagctcc   3420
tcagagtgca gcacagttga taaccctttg cctggagaag gagaagaagc agaggctgaa   3480
cctatgaatt ccgatgagcc agaggcctgt ttcacagatg ttgtgtacg gaggttctca   3540 tgctgccaag ttaacataga gtcagggaaa ggaaaaatct ggtggaacat caggaaaacc   3600
```

```
tgctacaaga ttgttgaaca cagttggttt gaaagcttca ttgtcctcat gatcctgctc    3660
agcagtggtg ccctggcttt tgaagatatt tatattgaaa ggaaaaagac cattaagatt    3720
atcctggagt atgcagacaa gatcttcact tacatcttca ttctggaaat gcttctaaaa    3780
tggatagcat atggttataa aacatatttc accaatgcct ggtgttggct ggatttccta    3840
attgttgatg tttctttggt tactttagtg gcaaacactc ttggctactc agatcttggc    3900
cccattaaat cccttcggac actgagagct ttaagacctc taagagcctt atctagattt    3960
gaaggaatga gggtcgttgt gaatgcactc ataggagcaa ttccttccat catgaatgtg    4020
ctacttgtgt gtcttatatt ctggctgata ttcagcatca tgggagtaaa tttgtttgct    4080
ggcaagttct atgagtgtat taacaccaca gatgggtcac ggtttcctgc aagtcaagtt    4140
ccaaatcgtt ccgaatgttt tgcccttatg aatgttagtc aaaatgtgcg atggaaaaac    4200
ctgaaagtga actttgataa tgtcggactt ggttacctat ctctgcttca agttgcaact    4260
tttaagggat ggacgattat tatgtatgca gcagtggatt ctgttaatgt agacaagcag    4320
cccaaatatg aatatagcct ctacatgtat atttattttg tcgtctttat catctttggg    4380
tcattcttca ctttgaactt gttcattggt gtcatcatag ataatttcaa ccaacagaaa    4440
aagaagcttg gaggtcaaga catctttatg acagaagaac agaagaaata ctataatgca    4500
atgaaaaagc tggggtccaa gaagccacaa aagccaattc ctcgaccagg gaacaaaatc    4560
caaggatgta tatttgacct agtgacaaat caagcctttg atattagtat catggttctt    4620
atctgtctca acatggtaac catgatggta gaaaaggagg gtcaaagtca acatatgact    4680
gaagttttat attggataaa tgtggttttt ataatccttt tcactggaga atgtgtgcta    4740
aaactgatct ccctcagaca ctactacttc actgtaggat ggaatatttt tgattttgtg    4800
gttgtgatta tctccattgt aggtatgttt ctagctgatt tgattgaaac gtattttgtg    4860 tccccctaccc tgttccgagt gatccgtctt gccaggattg gccgaatcct acgtctagtc    4920
aaaggagcaa aggggatccg cacgctgctc tttgctttga tgatgtccct tcctgcgttg    4980
tttaacatcg gcctcctgct cttcctggtc atgttcatct acgccatctt tggaatgtcc    5040
aactttgcct atgttaaaaa ggaagatgga attaatgaca tgttcaattt tgagaccttt    5100
ggcaacagta tgatttgcct gttccaaatt acaacctctg ctggctggga tggattgcta    5160
gcacctattc ttaacagtaa gccacccgac tgtgacccaa aaaagttca tcctggaagt    5220 tcagttgaag gagactgtgg taacccatct gttggaatat tctactttgt tagttatatc    5280
atcatatcct tcctggttgt ggtgaacatg tacattgcag tcatactgga gaattttagt    5340
gttgccactg aagaaagtac tgaacctctg agtgaggatg actttgagat gttctatgag    5400
gtttgggaga agtttgatcc cgatgcgacc cagtttatag agttctctaa actctctgat    5460
tttgcagctg ccctggatcc tcctcttctc atagcaaaac ccaacaaagt ccagctcatt    5520
gccatggatc tgcccatggt tagtggtgac cggatccatt gtcttgacat cttattgct    5580 tttacaaagc gtgttttggg tgagagtggg gagatggatt ctcttcgttc acagatggaa    5640
gaaaggttca tgtctgcaaa tccttccaaa gtgtcctatg aacccatcac aaccacacta    5700
aaacggaaac aagaggatgt gtctgctact gtcattcagc gtgcttatag acgttaccgc    5760
ttaaggcaaa atgtcaaaaa tatatcaagt atatacataa aagatggaga cagagatgat    5820
gatttactca ataaaaaaga tatggctttt gataatgtta atgagaactc aagtccagaa    5880
aaaacagatg ccacttcatc caccacctct ccacctcat atgatagtgt aacaaagcca    5940
gacaaagaga aatatgaaca agacagaaca gaaaaggaag acaaagggaa agacagcaag    6000
```

```
gaaagcaaaa aatagagctt catttttgat atattgttta cagcctgtga aagtgattta    6060
tttgtgttaa taaaactctt ttgaggaagt ctatgccaaa atcctttta tcaaaatatt     6120 ctcgaaggca gtgcagtcac taactctgat ttcctaagaa aggtgggcag cattagcaga    6180
tggttatttt tgcactgatg attctttaag aatcgtaaga gaactctgta ggaattattg    6240
attatagcat acaaaagtga ttcagttttt tggtttttaa taaatcagaa gaccatgtag    6300
aaaactttta catctgcctt gtcatctttt cacaggattg taattagtct tgtttcccat    6360
gtaaataaac aacacacgca tacagaaaaa aaaaaaa                              6397
```

<210> SEQ ID NO 6
<211> LENGTH: 1988
<212> TYPE: PRT
<213> ORGANISM: Homo sapiens

<400> SEQUENCE: 6

```
Met Ala Met Leu Pro Pro Gly Pro Gln Ser Phe Val His Phe Thr
1               5                   10                  15

Lys Gln Ser Leu Ala Leu Ile Glu Gln Arg Ile Ala Glu Arg Lys Ser
            20                  25                  30

Lys Glu Pro Lys Glu Glu Lys Asp Asp Asp Glu Glu Ala Pro Lys
        35                  40                  45

Pro Ser Ser Asp Leu Glu Ala Gly Lys Gln Leu Pro Phe Ile Tyr Gly
    50                  55                  60

Asp Ile Pro Pro Gly Met Val Ser Glu Pro Leu Glu Asp Leu Asp Pro
65                  70                  75                  80

Tyr Tyr Ala Asp Lys Lys Thr Phe Ile Val Leu Asn Lys Gly Lys Thr
                85                  90                  95

Ile Phe Arg Phe Asn Ala Thr Pro Ala Leu Tyr Met Leu Ser Pro Phe
            100                 105                 110

Ser Pro Leu Arg Arg Ile Ser Ile Lys Ile Leu Val His Ser Leu Phe
        115                 120                 125

Ser Met Leu Ile Met Cys Thr Ile Leu Thr Asn Cys Ile Phe Met Thr
    130                 135                 140

Met Asn Asn Pro Pro Asp Trp Thr Lys Asn Val Glu Tyr Thr Phe Thr
145                 150                 155                 160

Gly Ile Tyr Thr Phe Glu Ser Leu Val Lys Ile Leu Ala Arg Gly Phe
                165                 170                 175

Cys Val Gly Glu Phe Thr Phe Leu Arg Asp Pro Trp Asn Trp Leu Asp
            180                 185                 190

Phe Val Val Ile Val Phe Ala Tyr Leu Thr Glu Phe Val Asn Leu Gly
        195                 200                 205

Asn Val Ser Ala Leu Arg Thr Phe Arg Val Leu Arg Ala Leu Lys Thr
    210                 215                 220

Ile Ser Val Ile Pro Gly Leu Lys Thr Ile Val Gly Ala Leu Ile Gln
225                 230                 235                 240

Ser Val Lys Lys Leu Ser Asp Val Met Ile Leu Thr Val Phe Cys Leu
                245                 250                 255

Ser Val Phe Ala Leu Ile Gly Leu Gln Leu Phe Met Gly Asn Leu Lys
            260                 265                 270

His Lys Cys Phe Arg Asn Ser Leu Glu Asn Asn Glu Thr Leu Glu Ser
        275                 280                 285

Ile Met Asn Thr Leu Glu Ser Glu Glu Asp Phe Arg Lys Tyr Phe Tyr
    290                 295                 300

Tyr Leu Glu Gly Ser Lys Asp Ala Leu Leu Cys Gly Phe Ser Thr Asp
```

```
                  305                 310                 315                 320
        Ser Gly Gln Cys Pro Glu Gly Tyr Thr Cys Val Lys Ile Gly Arg Asn
                        325                 330                 335

Pro Asp Tyr Gly Tyr Thr Ser Phe Asp Thr Phe Ser Trp Ala Phe Leu
                        340                 345                 350

Ala Leu Phe Arg Leu Met Thr Gln Asp Tyr Trp Glu Asn Leu Tyr Gln
                        355                 360                 365

Gln Thr Leu Arg Ala Ala Gly Lys Thr Tyr Met Ile Phe Phe Val Val
                370                 375                 380

Val Ile Phe Leu Gly Ser Phe Tyr Leu Ile Asn Leu Ile Leu Ala Val
        385                 390                 395                 400

Val Ala Met Ala Tyr Glu Glu Gln Asn Gln Ala Asn Ile Glu Glu Ala
                        405                 410                 415

Lys Gln Lys Glu Leu Glu Phe Gln Gln Met Leu Asp Arg Leu Lys Lys
                        420                 425                 430

Glu Gln Glu Glu Ala Glu Ala Ile Ala Ala Ala Ala Ala Glu Tyr Thr
                        435                 440                 445

Ser Ile Arg Arg Ser Arg Ile Met Gly Leu Ser Glu Ser Ser Ser Glu
                450                 455                 460

Thr Ser Lys Leu Ser Ser Lys Ser Ala Lys Glu Arg Arg Asn Arg Arg
        465                 470                 475                 480

Lys Lys Lys Asn Gln Lys Lys Leu Ser Ser Gly Glu Glu Lys Gly Asp
                        485                 490                 495

Ala Glu Lys Leu Ser Lys Ser Glu Ser Glu Asp Ser Ile Arg Arg Lys
                        500                 505                 510

Ser Phe His Leu Gly Val Glu Gly His Arg Arg Ala His Glu Lys Arg
                        515                 520                 525

Leu Ser Thr Pro Asn Gln Ser Pro Leu Ser Ile Arg Gly Ser Leu Phe
                530                 535                 540

Ser Ala Arg Arg Ser Ser Arg Thr Ser Leu Phe Ser Phe Lys Gly Arg
        545                 550                 555                 560

Gly Arg Asp Ile Gly Ser Glu Thr Glu Phe Ala Asp Asp Glu His Ser
                        565                 570                 575

Ile Phe Gly Asp Asn Glu Ser Arg Arg Gly Ser Leu Phe Val Pro His
                        580                 585                 590

Arg Pro Gln Glu Arg Arg Ser Ser Asn Ile Ser Gln Ala Ser Arg Ser
                        595                 600                 605

Pro Pro Met Leu Pro Val Asn Gly Lys Met His Ser Ala Val Asp Cys
                610                 615                 620

Asn Gly Val Val Ser Leu Val Asp Gly Arg Ser Ala Leu Met Leu Pro
        625                 630                 635                 640

Asn Gly Gln Leu Leu Pro Glu Val Ile Ile Asp Lys Ala Thr Ser Asp
                        645                 650                 655

Asp Ser Gly Thr Thr Asn Gln Ile His Lys Lys Arg Arg Cys Ser Ser
                        660                 665                 670

Tyr Leu Leu Ser Glu Asp Met Leu Asn Asp Pro Asn Leu Arg Gln Arg
                        675                 680                 685

Ala Met Ser Arg Ala Ser Ile Leu Thr Asn Thr Val Glu Glu Leu Glu
                690                 695                 700

Glu Ser Arg Gln Lys Cys Pro Pro Trp Trp Tyr Arg Phe Ala His Lys
        705                 710                 715                 720

Phe Leu Ile Trp Asn Cys Ser Pro Tyr Trp Ile Lys Phe Lys Lys Cys
                        725                 730                 735
```

Ile Tyr Phe Ile Val Met Asp Pro Phe Val Asp Leu Ala Ile Thr Ile
              740                 745                 750

Cys Ile Val Leu Asn Thr Leu Phe Met Ala Met Glu His Pro Met
              755                 760                 765

Thr Glu Glu Phe Lys Asn Val Leu Ala Ile Gly Asn Leu Val Phe Thr
770                 775                 780

Gly Ile Phe Ala Ala Glu Met Val Leu Lys Leu Ile Ala Met Asp Pro
785                 790                 795                 800

Tyr Glu Tyr Phe Gln Val Gly Trp Asn Ile Phe Asp Ser Leu Ile Val
              805                 810                 815

Thr Leu Ser Leu Val Glu Leu Phe Leu Ala Asp Val Glu Gly Leu Ser
              820                 825                 830

Val Leu Arg Ser Phe Arg Leu Leu Arg Val Phe Lys Leu Ala Lys Ser
              835                 840                 845

Trp Pro Thr Leu Asn Met Leu Ile Lys Ile Ile Gly Asn Ser Val Gly
              850                 855                 860

Ala Leu Gly Asn Leu Thr Leu Val Leu Ala Ile Ile Val Phe Ile Phe
865                 870                 875                 880

Ala Val Val Gly Met Gln Leu Phe Gly Lys Ser Tyr Lys Glu Cys Val
              885                 890                 895

Cys Lys Ile Asn Asp Asp Cys Thr Leu Pro Arg Trp His Met Asn Asp
              900                 905                 910

Phe Phe His Ser Phe Leu Ile Val Phe Arg Val Leu Cys Gly Glu Trp
              915                 920                 925

Ile Glu Thr Met Trp Asp Cys Met Glu Val Ala Gly Gln Ala Met Cys
              930                 935                 940

Leu Ile Val Tyr Met Met Val Met Val Ile Gly Asn Leu Val Val Leu
945                 950                 955                 960

Asn Leu Phe Leu Ala Leu Leu Leu Ser Ser Phe Ser Ser Asp Asn Leu
              965                 970                 975

Thr Ala Ile Glu Glu Asp Pro Asp Ala Asn Asn Leu Gln Ile Ala Val
              980                 985                 990

Thr Arg Ile Lys Lys Gly Ile Asn Tyr Val Lys Gln Thr Leu Arg Glu
              995                1000                1005

Phe Ile Leu Lys Ala Phe Ser Lys Lys Pro Lys Ile Ser Arg Glu
              1010                1015                1020

Ile Arg Gln Ala Glu Asp Leu Asn Thr Lys Lys Glu Asn Tyr Ile
              1025                1030                1035

Ser Asn His Thr Leu Ala Glu Met Ser Lys Gly His Asn Phe Leu
              1040                1045                1050

Lys Glu Lys Asp Lys Ile Ser Gly Phe Gly Ser Ser Val Asp Lys
              1055                1060                1065

His Leu Met Glu Asp Ser Asp Gly Gln Ser Phe Ile His Asn Pro
              1070                1075                1080

Ser Leu Thr Val Thr Val Pro Ile Ala Pro Gly Glu Ser Asp Leu
              1085                1090                1095

Glu Asn Met Asn Ala Glu Glu Leu Ser Ser Asp Ser Asp Ser Glu
              1100                1105                1110

Tyr Ser Lys Val Arg Leu Asn Arg Ser Ser Ser Ser Glu Cys Ser
              1115                1120                1125

Thr Val Asp Asn Pro Leu Pro Gly Glu Gly Glu Ala Glu Ala
              1130                1135                1140

Glu Pro Met Asn Ser Asp Glu Pro Glu Ala Cys Phe Thr Asp Gly
              1145                1150                1155

```
Cys Val Arg Arg Phe Ser Cys Cys Gln Val Asn Ile Glu Ser Gly
1160                1165                1170

Lys Gly Lys Ile Trp Trp Asn Ile Arg Lys Thr Cys Tyr Lys Ile
1175                1180                1185

Val Glu His Ser Trp Phe Glu Ser Phe Ile Val Leu Met Ile Leu
1190                1195                1200

Leu Ser Ser Gly Ala Leu Ala Phe Glu Asp Ile Tyr Ile Glu Arg
1205                1210                1215

Lys Lys Thr Ile Lys Ile Ile Leu Glu Tyr Ala Asp Lys Ile Phe
1220                1225                1230

Thr Tyr Ile Phe Ile Leu Glu Met Leu Leu Lys Trp Ile Ala Tyr
1235                1240                1245

Gly Tyr Lys Thr Tyr Phe Thr Asn Ala Trp Cys Trp Leu Asp Phe
1250                1255                1260

Leu Ile Val Asp Val Ser Leu Val Thr Leu Val Ala Asn Thr Leu
1265                1270                1275

Gly Tyr Ser Asp Leu Gly Pro Ile Lys Ser Leu Arg Thr Leu Arg
1280                1285                1290

Ala Leu Arg Pro Leu Arg Ala Leu Ser Arg Phe Glu Gly Met Arg
1295                1300                1305

Val Val Val Asn Ala Leu Ile Gly Ala Ile Pro Ser Ile Met Asn
1310                1315                1320

Val Leu Leu Val Cys Leu Ile Phe Trp Leu Ile Phe Ser Ile Met
1325                1330                1335

Gly Val Asn Leu Phe Ala Gly Lys Phe Tyr Glu Cys Ile Asn Thr
1340                1345                1350

Thr Asp Gly Ser Arg Phe Pro Ala Ser Gln Val Pro Asn Arg Ser
1355                1360                1365

Glu Cys Phe Ala Leu Met Asn Val Ser Gln Asn Val Arg Trp Lys
1370                1375                1380

Asn Leu Lys Val Asn Phe Asp Asn Val Gly Leu Gly Tyr Leu Ser
1385                1390                1395

Leu Leu Gln Val Ala Thr Phe Lys Gly Trp Thr Ile Ile Met Tyr
1400                1405                1410

Ala Ala Val Asp Ser Val Asn Val Asp Lys Gln Pro Lys Tyr Glu
1415                1420                1425

Tyr Ser Leu Tyr Met Tyr Ile Tyr Phe Val Val Phe Ile Ile Phe
1430                1435                1440

Gly Ser Phe Phe Thr Leu Asn Leu Phe Ile Gly Val Ile Ile Asp
1445                1450                1455

Asn Phe Asn Gln Gln Lys Lys Lys Leu Gly Gly Gln Asp Ile Phe
1460                1465                1470

Met Thr Glu Glu Gln Lys Lys Tyr Tyr Asn Ala Met Lys Lys Leu
1475                1480                1485

Gly Ser Lys Lys Pro Gln Lys Pro Ile Pro Arg Pro Gly Asn Lys
1490                1495                1500

Ile Gln Gly Cys Ile Phe Asp Leu Val Thr Asn Gln Ala Phe Asp
1505                1510                1515

Ile Ser Ile Met Val Leu Ile Cys Leu Asn Met Val Thr Met Met
1520                1525                1530

Val Glu Lys Glu Gly Gln Ser Gln His Met Thr Glu Val Leu Tyr
1535                1540                1545

Trp Ile Asn Val Val Phe Ile Ile Leu Phe Thr Gly Glu Cys Val
```

-continued

```
            1550                1555                1560

Leu Lys Leu Ile Ser Leu Arg His Tyr Tyr Phe Thr Val Gly Trp
    1565                1570                1575

Asn Ile Phe Asp Phe Val Val Val Ile Ile Ser Ile Val Gly Met
    1580                1585                1590

Phe Leu Ala Asp Leu Ile Glu Thr Tyr Phe Val Ser Pro Thr Leu
    1595                1600                1605

Phe Arg Val Ile Arg Leu Ala Arg Ile Gly Arg Ile Leu Arg Leu
    1610                1615                1620

Val Lys Gly Ala Lys Gly Ile Arg Thr Leu Leu Phe Ala Leu Met
    1625                1630                1635

Met Ser Leu Pro Ala Leu Phe Asn Ile Gly Leu Leu Leu Phe Leu
    1640                1645                1650

Val Met Phe Ile Tyr Ala Ile Phe Gly Met Ser Asn Phe Ala Tyr
    1655                1660                1665

Val Lys Lys Glu Asp Gly Ile Asn Asp Met Phe Asn Phe Glu Thr
    1670                1675                1680

Phe Gly Asn Ser Met Ile Cys Leu Phe Gln Ile Thr Thr Ser Ala
    1685                1690                1695

Gly Trp Asp Gly Leu Leu Ala Pro Ile Leu Asn Ser Lys Pro Pro
    1700                1705                1710

Asp Cys Asp Pro Lys Lys Val His Pro Gly Ser Ser Val Glu Gly
    1715                1720                1725

Asp Cys Gly Asn Pro Ser Val Gly Ile Phe Tyr Phe Val Ser Tyr
    1730                1735                1740

Ile Ile Ile Ser Phe Leu Val Val Val Asn Met Tyr Ile Ala Val
    1745                1750                1755

Ile Leu Glu Asn Phe Ser Val Ala Thr Glu Glu Ser Thr Glu Pro
    1760                1765                1770

Leu Ser Glu Asp Asp Phe Glu Met Phe Tyr Glu Val Trp Glu Lys
    1775                1780                1785

Phe Asp Pro Asp Ala Thr Gln Phe Ile Glu Phe Ser Lys Leu Ser
    1790                1795                1800

Asp Phe Ala Ala Ala Leu Asp Pro Pro Leu Leu Ile Ala Lys Pro
    1805                1810                1815

Asn Lys Val Gln Leu Ile Ala Met Asp Leu Pro Met Val Ser Gly
    1820                1825                1830

Asp Arg Ile His Cys Leu Asp Ile Leu Phe Ala Phe Thr Lys Arg
    1835                1840                1845

Val Leu Gly Glu Ser Gly Glu Met Asp Ser Leu Arg Ser Gln Met
    1850                1855                1860

Glu Glu Arg Phe Met Ser Ala Asn Pro Ser Lys Val Ser Tyr Glu
    1865                1870                1875

Pro Ile Thr Thr Thr Leu Lys Arg Lys Gln Glu Asp Val Ser Ala
    1880                1885                1890

Thr Val Ile Gln Arg Ala Tyr Arg Arg Tyr Arg Leu Arg Gln Asn
    1895                1900                1905

Val Lys Asn Ile Ser Ser Ile Tyr Ile Lys Asp Gly Asp Arg Asp
    1910                1915                1920

Asp Asp Leu Leu Asn Lys Lys Asp Met Ala Phe Asp Asn Val Asn
    1925                1930                1935

Glu Asn Ser Ser Pro Glu Lys Thr Asp Ala Thr Ser Ser Thr Thr
    1940                1945                1950
```

| | | |
|---|---|---|
| Ser Pro Pro Ser Tyr Asp Ser Val Thr Lys Pro Asp Lys Glu Lys | | |
| 1955 1960 1965 | | |
| | | |
| Tyr Glu Gln Asp Arg Thr Glu Lys Glu Asp Lys Gly Lys Asp Ser | | |
| 1970 1975 1980 | | |
| | | |
| Lys Glu Ser Lys Lys | | |
| 1985 | | |

<210> SEQ ID NO 7
<211> LENGTH: 6367
<212> TYPE: DNA
<213> ORGANISM: Homo sapiens

<400> SEQUENCE: 7

| | |
|---|---|
| ctcttatgtg aggagctgaa gaggaattaa aatatacagg atgaaaagat ggcaatgttg | 60 |
| cctcccccag gacctcagag ctttgtccat ttcacaaaac agtctcttgc cctcattgaa | 120 |
| caacgcattg ctgaaagaaa atcaaaggaa cccaagaaag aaaagaaaga tgatgatgaa | 180 |
| gaagccccaa agccaagcag tgacttggaa gctggcaaac agctgccctt catctatggg | 240 |
| gacattcctc ccggcatggt gtcagagccc ctggaggact ggaccccta ctatgcagac | 300 |
| aaaaagactt tcatagtatt gaacaaaggg aaaacaatct tccgtttcaa tgccacacct | 360 |
| gctttatata tgctttctcc tttcagtcct ctaagaagaa tatctattaa gattttagta | 420 |
| cactccttat tcagcatgct catcatgtgc actattctga caaactgcat atttatgacc | 480 |
| atgaataacc caccggactg gaccaaaaat gtcgagtaca cttttactgg aatatatact | 540 |
| tttgaatcac ttgtaaaaat ccttgcaaga ggcttctgtg taggagaatt cacttttctt | 600 |
| cgtgacccgt ggaactggct ggattttgtc gtcattgttt ttgcgtattt aacagaattt | 660 |
| gtaaacctag gcaatgtttc agctcttcga actttcagag tattgagagc tttgaaaact | 720 |
| atttctgtaa tcccaggcct gaagacaatt gtagggctt tgatccagtc agtgaagaag | 780 |
| cttttctgatg tcatgatcct gactgtgttc tgtctgagtg tgtttgcact aattggacta | 840 |
| cagctgttca tgggaaacct gaagcataaa tgttttcgaa attcacttga aaataatgaa | 900 |
| acattagaaa gcataatgaa taccctagag agtgaagaag actttagaaa atattttat | 960 |
| tacttggaag gatccaaaga tgctctcctt tgtggtttca gcacagattc aggtcagtgt | 1020 |
| ccagaggggt acacctgtgt gaaaattggc agaaaccctg attatggcta cacgagcttt | 1080 |
| gacactttca gctgggcctt cttagccttg tttaggctaa tgacccaaga ttactgggaa | 1140 |
| aacctttacc aacagacgct gcgtgctgct ggcaaaacct acatgatctt ctttgtcgta | 1200 |
| gtgattttcc tgggctcctt ttatctaata aacttgatcc tggctgtggt tgccatggca | 1260 |
| tatgaagaac agaaccaggc aaacattgaa gaagctaaac agaaagaatt agaatttcaa | 1320 |
| cagatgttag accgtcttaa aaaagagcaa gaagaagctg aggcaattgc agcggcagcg | 1380 |
| gctgaatata taagtattag agaagcagaa attatgggcc tctcagagag ttcttctgaa | 1440 |
| acatccaaac tgagctctaa aagtgctaaa gaaagaagaa acagaagaaa gaaaagaat | 1500 |
| caaaagaagc tctccagtgg agaggaaaag ggagatgctg agaaattgtc gaaatcagaa | 1560 |
| tcagaggaca gcatcagaag aaaaagtttc caccttggtg tcgaagggca taggcgagca | 1620 |
| catgaaaaga ggttgtctac ccccaatcag tcaccactca gcattcgtgg ctccttgttt | 1680 |
| tctgcaaggc gaagcagcag aacaagtctt tttagtttca aggcagagg aagagatata | 1740 |
| ggatctgaga ctgaatttgc cgatgatgag cacagcattt ttggagacaa tgagagcaga | 1800 |
| aggggctcac tgtttgtgcc ccacagaccc caggagcgac gcagcagtaa catcagccaa | 1860 |
| gccagtaggt ccccaccaat gctgccggtg aacgggaaaa tgcacagtgc tgtggactgc | 1920 |

```
aacggtgtgg tctccctggt tgatggacgc tcagccctca tgctccccaa tggacagctt      1980
ctgccagagg gcacgaccaa tcaaatacac aagaaaaggc gttgtagttc ctatctcctt      2040
tcagaggata tgctgaatga tcccaacctc agacagagag caatgagtag agcaagcata      2100
ttaacaaaca ctgtggaaga acttgaagag tccagacaaa aatgtccacc ttggtggtac      2160
agatttgcac acaaattctt gatctggaat tgctctccat attggataaa attcaaaaag      2220
tgtatctatt ttattgtaat ggatcctttt gtagatcttg caattaccat ttgcatagtt      2280
ttaaacacat tatttatggc tatgaacac cacccaatga ctgaggaatt caaaaatgta      2340
cttgctatag gaaatttggt ctttactgga atctttgcag ctgaaatggt attaaaactg      2400
attgccatgg atccatatga gtatttccaa gtaggctgga atattttga cagccttatt      2460 gtgactttaa gtttagtgga gctctttcta gcagatgtgg aaggattgtc agttctgcga      2520
tcattcagac tgctccgagt cttcaagttg gcaaaatcct ggccaacatt gaacatgctg      2580
attaagatca ttggtaactc agtaggggct ctaggtaacc tcaccttagt gttggccatc      2640
atcgtcttca ttttgctgt ggtcggcatg cagctctttg gtaagagcta caaagaatgt      2700
gtctgcaaga tcaatgatga ctgtacgctc ccacggtggc acatgaacga cttcttccac      2760
tccttcctga ttgtgttccg cgtgctgtgt ggagagtgga tagagaccat gtgggactgt      2820
atggaggtcg ctggtcaagc tatgtgcctt attgtttaca tgatggtcat ggtcattgga      2880
aacctggtgg tcctaaaccct atttctggcc ttattattga gctcatttag ttcagacaat      2940
cttacagcaa ttgaagaaga ccctgatgca aacaacctcc agattgcagt gactagaatt      3000
aaaaagggaa taattatgt gaaacaaacc ttacgtgaat ttattctaaa agcattttcc      3060
aaaaagccaa agatttccag ggagataaga caagcagaag atctgaatac taagaaggaa      3120
aactatattt ctaaccatac acttgctgaa atgagcaaag gtcacaattt cctcaaggaa      3180
aaagataaaa tcagtggttt tggaagcagc gtggacaaac acttgatgga agacagtgat      3240
ggtcaatcat ttattcacaa tcccagcctc acagtgacag tgccaattgc acctggggaa      3300
tccgatttgg aaaatatgaa tgctgaggaa cttagcagtg attcggatag tgaatacagc      3360
aaagtgagat taaaccggtc aagctcctca gagtgcagca cagttgataa ccccttttgcct      3420 ggagaaggag aagaagcaga ggctgaacct atgaattccg atgagccaga ggcctgtttc      3480
acagatggtt gtgtatggag gttctcatgc tgccaagtta acatagagtc agggaaagga      3540
aaaatctggt ggaacatcag gaaaacctgc tacaagattg ttgaacacag ttggtttgaa      3600
agcttcattg tcctcatgat cctgctcagc agtggtgccc tggcttttga agatatttat      3660
attgaaagga aaagaccat taagattatc ctggagtatg cagacaagat cttcacttac      3720
atcttcattc tggaaatgct tctaaaatgg atagcatatg gttataaaac atatttcacc      3780
aatgcctggt gttggctgga tttcctaatt gttgatgttt cttgggttac tttagtggca      3840
aacactcttg gctactcaga tcttggcccc attaaatccc ttcggacact gagagcttta      3900
agacctctaa gagccttatc tagatttgaa ggaatgaggg tcgttgtgaa tgcactcata      3960
ggagcaattc cttccatcat gaatgtgcta cttgtgtgtc ttatattctg gctgatattc      4020
agcatcatgg gagtaaattt gtttgctggc aagttctatg agtgtattaa caccacagat      4080
gggtcacggt ttcctgcaag tcaagttcca atcgttccg aatgttttgc ccttatgaat      4140
gttagtcaaa atgtgcgatg gaaaaacctg aaagtgaact ttgataatgt cggacttggt      4200
tacctatctc tgcttcaagt tgcaacttt aagggatgga cgattattat gtatgcagca      4260
gtggattctg ttaatgtaga caagcagccc aaatatgaat atagcctcta catgtatatt      4320
```

| | | | | |
|---|---|---|---|---|
| tattttgtcg | tctttatcat | ctttgggtca | ttcttcactt | tgaacttgtt cattggtgtc | 4380 |
| atcatagata | atttcaacca | acagaaaaag | aagcttggag | gtcaagacat ctttatgaca | 4440 |
| gaagaacaga | agaaatacta | taatgcaatg | aaaaagctgg | ggtccaagaa gccacaaaag | 4500 |
| ccaattcctc | gaccagggaa | caaaatccaa | ggatgtatat | ttgacctagt gacaaatcaa | 4560 |
| gcctttgata | ttagtatcat | ggttcttatc | tgtctcaaca | tggtaaccat gatggtagaa | 4620 |
| aaggagggtc | aaagtcaaca | tatgactgaa | gttttatatt | ggataaatgt ggtttttata | 4680 |
| atccttttca | ctggagaatg | tgtgctaaaa | ctgatctccc | tcagacacta ctacttcact | 4740 |
| gtaggatgga | atattttga | ttttgtggtt | gtgattatct | ccattgtagg tatgtttcta | 4800 |
| gctgatttga | ttgaaacgta | ttttgtgtcc | cctaccctgt | tccgagtgat ccgtcttgcc | 4860 |
| aggattggcc | gaatcctacg | tctagtcaaa | ggagcaaagg | ggatccgcac gctgctcttt | 4920 |
| gctttgatga | tgtcccttcc | tgcgttgttt | aacatcggcc | tcctgctctt cctggtcatg | 4980 |
| ttcatctacg | ccatctttgg | aatgtccaac | tttgcctatg | ttaaaaagga agatggaatt | 5040 |
| aatgacatgt | tcaattttga | gacctttggc | aacagtatga | tttgcctgtt ccaaattaca | 5100 |
| acctctgctg | gctgagatgg | attgctagca | cctattctta | acagtaagcc acccgactgt | 5160 |
| gacccaaaaa | aagttcatcc | tggaagttca | gttgaaggag | actgtggtaa cccatctgtt | 5220 |
| ggaatattct | actttgttag | ttatatcatc | atatccttcc | tggttgtggt gaacatgtac | 5280 |
| attgcagtca | tactggagaa | ttttagtgtt | gccactgaag | aaagtactga acctctgagt | 5340 |
| gaggatgact | tgagatgtt | ctatgaggtt | tgggagaagt | tgatcccga tgcgacccag | 5400 |
| tttatagagt | tctctaaact | ctctgatttt | gcagctgccc | tggatcctcc tcttctcata | 5460 |
| gcaaaaccca | acaaagtcca | gctcattgcc | atggatctgc | ccatggttag tggtgaccgg | 5520 |
| atccattgtc | ttgacatctt | atttgctttt | acaaagcgtg | ttttgggtga gagtggggag | 5580 |
| atggattctc | ttcgttcaca | gatggaagaa | aggttcatgt | ctgcaaatcc ttccaaagtg | 5640 |
| tcctatgaac | ccatcacaac | cacactaaaa | cggaaacaag | aggatgtgtc tgctactgtc | 5700 |
| attcagcgtg | cttatagacg | ttaccgctta | aggcaaaatg | tcaaaaatat atcaagtata | 5760 |
| tacataaaag | atggagacag | agatgatgat | ttactcaata | aaaaagatat ggcttttgat | 5820 |
| aatgttaatg | agaactcaag | tccagaaaaa | acagatgcca | cttcatccac cacctctcca | 5880 |
| ccttcatatg | atagtgtaac | aaagccagac | aaagagaaat | atgaacaaga cagaacagaa | 5940 |
| aaggaagaca | aagggaaaga | cagcaaggaa | agcaaaaaat | agagcttcat ttttgatata | 6000 |
| ttgtttacag | cctgtgaaag | tgatttattt | gtgttaataa | aactcttttg aggaagtcta | 6060 |
| tgccaaaatc | cttttatca | aaatattctc | gaaggcagtg | cagtcactaa ctctgatttc | 6120 |
| ctaagaaagg | tgggcagcat | tagcagatgg | ttattttgc | actgatgatt ctttaagaat | 6180 |
| cgtaagagaa | ctctgtagga | attattgatt | atagcataca | aaagtgattc agttttttgg | 6240 |
| tttttaataa | atcagaagac | catgtagaaa | actttacat | ctgccttgtc atcttttcac | 6300 |
| aggattgtaa | ttagtcttgt | ttcccatgta | aataaacaac | acacgcatac agaaaaaaaa | 6360 |
| aaaaaaa | | | | | 6367 |

<210> SEQ ID NO 8
<211> LENGTH: 1688
<212> TYPE: PRT
<213> ORGANISM: Homo sapiens

<400> SEQUENCE: 8

Met Ala Met Leu Pro Pro Pro Gly Pro Gln Ser Phe Val His Phe Thr

```
                  5                   10                  15
1
Lys Gln Ser Leu Ala Leu Ile Glu Gln Arg Ile Ala Glu Arg Lys Ser
                    20                  25                  30

Lys Glu Pro Lys Glu Lys Lys Asp Asp Glu Glu Ala Pro Lys
            35                  40                  45

Pro Ser Ser Asp Leu Glu Ala Gly Lys Gln Leu Pro Phe Ile Tyr Gly
        50                  55                  60

Asp Ile Pro Pro Gly Met Val Ser Glu Pro Leu Glu Asp Leu Asp Pro
65                  70                  75                  80

Tyr Tyr Ala Asp Lys Lys Thr Phe Ile Val Leu Asn Lys Gly Lys Thr
                85                  90                  95

Ile Phe Arg Phe Asn Ala Thr Pro Ala Leu Tyr Met Leu Ser Pro Phe
            100                 105                 110

Ser Pro Leu Arg Arg Ile Ser Ile Lys Ile Leu Val His Ser Leu Phe
        115                 120                 125

Ser Met Leu Ile Met Cys Thr Ile Leu Thr Asn Cys Ile Phe Met Thr
    130                 135                 140

Met Asn Asn Pro Pro Asp Trp Thr Lys Asn Val Glu Tyr Thr Phe Thr
145                 150                 155                 160

Gly Ile Tyr Thr Phe Glu Ser Leu Val Lys Ile Leu Ala Arg Gly Phe
                165                 170                 175

Cys Val Gly Glu Phe Thr Phe Leu Arg Asp Pro Trp Asn Trp Leu Asp
            180                 185                 190

Phe Val Val Ile Val Phe Ala Tyr Leu Thr Glu Phe Val Asn Leu Gly
        195                 200                 205

Asn Val Ser Ala Leu Arg Thr Phe Arg Val Leu Arg Ala Leu Lys Thr
    210                 215                 220

Ile Ser Val Ile Pro Gly Leu Lys Thr Ile Val Gly Ala Leu Ile Gln
225                 230                 235                 240

Ser Val Lys Lys Leu Ser Asp Val Met Ile Leu Thr Val Phe Cys Leu
                245                 250                 255

Ser Val Phe Ala Leu Ile Gly Leu Gln Leu Phe Met Gly Asn Leu Lys
            260                 265                 270

His Lys Cys Phe Arg Asn Ser Leu Glu Asn Asn Glu Thr Leu Glu Ser
        275                 280                 285

Ile Met Asn Thr Leu Glu Ser Glu Glu Asp Phe Arg Lys Tyr Phe Tyr
    290                 295                 300

Tyr Leu Glu Gly Ser Lys Asp Ala Leu Leu Cys Gly Phe Ser Thr Asp
305                 310                 315                 320

Ser Gly Gln Cys Pro Glu Gly Tyr Thr Cys Val Lys Ile Gly Arg Asn
                325                 330                 335

Pro Asp Tyr Gly Tyr Thr Ser Phe Asp Thr Phe Ser Trp Ala Phe Leu
            340                 345                 350

Ala Leu Phe Arg Leu Met Thr Gln Asp Tyr Trp Glu Asn Leu Tyr Gln
        355                 360                 365

Gln Thr Leu Arg Ala Ala Gly Lys Thr Tyr Met Ile Phe Phe Val Val
    370                 375                 380

Val Ile Phe Leu Gly Ser Phe Tyr Leu Ile Asn Leu Ile Leu Ala Val
385                 390                 395                 400

Val Ala Met Ala Tyr Glu Glu Gln Asn Gln Ala Asn Ile Glu Glu Ala
                405                 410                 415

Lys Gln Lys Glu Leu Glu Phe Gln Gln Met Leu Asp Arg Leu Lys Lys
            420                 425                 430
```

```
Glu Gln Glu Glu Ala Glu Ala Ile Ala Ala Ala Ala Glu Tyr Thr
        435                 440                 445
Ser Ile Arg Arg Ser Arg Ile Met Gly Leu Ser Glu Ser Ser Glu
450                 455                 460
Thr Ser Lys Leu Ser Ser Lys Ser Ala Lys Glu Arg Arg Asn Arg Arg
465                 470                 475                 480
Lys Lys Lys Asn Gln Lys Lys Leu Ser Ser Gly Glu Glu Lys Gly Asp
                485                 490                 495
Ala Glu Lys Leu Ser Lys Ser Glu Ser Glu Asp Ser Ile Arg Arg Lys
                500                 505                 510
Ser Phe His Leu Gly Val Glu Gly His Arg Arg Ala His Glu Lys Arg
            515                 520                 525
Leu Ser Thr Pro Asn Gln Ser Pro Leu Ser Ile Arg Gly Ser Leu Phe
530                 535                 540
Ser Ala Arg Arg Ser Ser Arg Thr Ser Leu Phe Ser Phe Lys Gly Arg
545                 550                 555                 560
Gly Arg Asp Ile Gly Ser Glu Thr Glu Phe Ala Asp Asp Glu His Ser
                565                 570                 575
Ile Phe Gly Asp Asn Glu Ser Arg Arg Gly Ser Leu Phe Val Pro His
            580                 585                 590
Arg Pro Gln Glu Arg Arg Ser Ser Asn Ile Ser Gln Ala Ser Arg Ser
        595                 600                 605
Pro Pro Met Leu Pro Val Asn Gly Lys Met His Ser Ala Val Asp Cys
610                 615                 620
Asn Gly Val Val Ser Leu Val Asp Gly Arg Ser Ala Leu Met Leu Pro
625                 630                 635                 640
Asn Gly Gln Leu Leu Pro Glu Gly Thr Thr Asn Gln Ile His Lys Lys
                645                 650                 655
Arg Arg Cys Ser Ser Tyr Leu Leu Ser Glu Asp Met Leu Asn Asp Pro
            660                 665                 670
Asn Leu Arg Gln Arg Ala Met Ser Arg Ala Ser Ile Leu Thr Asn Thr
        675                 680                 685
Val Glu Glu Leu Glu Glu Ser Arg Gln Lys Cys Pro Pro Trp Trp Tyr
690                 695                 700
Arg Phe Ala His Lys Phe Leu Ile Trp Asn Cys Ser Pro Tyr Trp Ile
705                 710                 715                 720
Lys Phe Lys Lys Cys Ile Tyr Phe Ile Val Met Asp Pro Phe Val Asp
                725                 730                 735
Leu Ala Ile Thr Ile Cys Ile Val Leu Asn Thr Leu Phe Met Ala Met
            740                 745                 750
Glu His His Pro Met Thr Glu Glu Phe Lys Asn Val Leu Ala Ile Gly
        755                 760                 765
Asn Leu Val Phe Thr Gly Ile Phe Ala Ala Glu Met Val Leu Lys Leu
770                 775                 780
Ile Ala Met Asp Pro Tyr Glu Tyr Phe Gln Val Gly Trp Asn Ile Phe
785                 790                 795                 800
Asp Ser Leu Ile Val Thr Leu Ser Leu Val Glu Leu Phe Leu Ala Asp
                805                 810                 815
Val Glu Gly Leu Ser Val Leu Arg Ser Phe Arg Leu Leu Arg Val Phe
            820                 825                 830
Lys Leu Ala Lys Ser Trp Pro Thr Leu Asn Met Leu Ile Lys Ile Ile
        835                 840                 845
Gly Asn Ser Val Gly Ala Leu Gly Asn Leu Thr Leu Val Leu Ala Ile
850                 855                 860
```

```
Ile Val Phe Ile Phe Ala Val Val Gly Met Gln Leu Phe Gly Lys Ser
865                 870                 875                 880

Tyr Lys Glu Cys Val Cys Lys Ile Asn Asp Asp Cys Thr Leu Pro Arg
                885                 890                 895

Trp His Met Asn Asp Phe Phe His Ser Phe Leu Ile Val Phe Arg Val
            900                 905                 910

Leu Cys Gly Glu Trp Ile Glu Thr Met Trp Asp Cys Met Glu Val Ala
            915                 920                 925

Gly Gln Ala Met Cys Leu Ile Val Tyr Met Met Val Met Val Ile Gly
        930                 935                 940

Asn Leu Val Val Leu Asn Leu Phe Leu Ala Leu Leu Leu Ser Ser Phe
945                 950                 955                 960

Ser Ser Asp Asn Leu Thr Ala Ile Glu Glu Asp Pro Asp Ala Asn Asn
                965                 970                 975

Leu Gln Ile Ala Val Thr Arg Ile Lys Lys Gly Ile Asn Tyr Val Lys
            980                 985                 990

Gln Thr Leu Arg Glu Phe Ile Leu Lys Ala Phe Ser Lys Lys Pro Lys
        995                 1000                1005

Ile Ser Arg Glu Ile Arg Gln Ala Glu Asp Leu Asn Thr Lys Lys
1010                1015                1020

Glu Asn Tyr Ile Ser Asn His Thr Leu Ala Glu Met Ser Lys Gly
1025                1030                1035

His Asn Phe Leu Lys Glu Lys Asp Lys Ile Ser Gly Phe Gly Ser
1040                1045                1050

Ser Val Asp Lys His Leu Met Glu Asp Ser Asp Gly Gln Ser Phe
1055                1060                1065

Ile His Asn Pro Ser Leu Thr Val Thr Val Pro Ile Ala Pro Gly
1070                1075                1080

Glu Ser Asp Leu Glu Asn Met Asn Ala Glu Glu Leu Ser Ser Asp
1085                1090                1095

Ser Asp Ser Glu Tyr Ser Lys Val Arg Leu Asn Arg Ser Ser Ser
1100                1105                1110

Ser Glu Cys Ser Thr Val Asp Asn Pro Leu Pro Gly Glu Gly Glu
1115                1120                1125

Glu Ala Glu Ala Glu Pro Met Asn Ser Asp Glu Pro Glu Ala Cys
1130                1135                1140

Phe Thr Asp Gly Cys Val Trp Arg Phe Ser Cys Cys Gln Val Asn
1145                1150                1155

Ile Glu Ser Gly Lys Gly Lys Ile Trp Trp Asn Ile Arg Lys Thr
1160                1165                1170

Cys Tyr Lys Ile Val Glu His Ser Trp Phe Glu Ser Phe Ile Val
1175                1180                1185

Leu Met Ile Leu Leu Ser Ser Gly Ala Leu Ala Phe Glu Asp Ile
1190                1195                1200

Tyr Ile Glu Arg Lys Lys Thr Ile Lys Ile Ile Leu Glu Tyr Ala
1205                1210                1215

Asp Lys Ile Phe Thr Tyr Ile Phe Ile Leu Glu Met Leu Leu Lys
1220                1225                1230

Trp Ile Ala Tyr Gly Tyr Lys Thr Tyr Phe Thr Asn Ala Trp Cys
1235                1240                1245

Trp Leu Asp Phe Leu Ile Val Asp Val Ser Leu Val Thr Leu Val
1250                1255                1260

Ala Asn Thr Leu Gly Tyr Ser Asp Leu Gly Pro Ile Lys Ser Leu
```

```
                      1265                1270                1275

Arg Thr Leu Arg Ala Leu Arg Pro Leu Arg Ala Leu Ser Arg Phe
        1280                1285                1290

Glu Gly Met Arg Val Val Asn Ala Leu Ile Gly Ala Ile Pro
        1295                1300                1305

Ser Ile Met Asn Val Leu Leu Val Cys Leu Ile Phe Trp Leu Ile
        1310                1315                1320

Phe Ser Ile Met Gly Val Asn Leu Phe Ala Gly Lys Phe Tyr Glu
        1325                1330                1335

Cys Ile Asn Thr Thr Asp Gly Ser Arg Phe Pro Ala Ser Gln Val
        1340                1345                1350

Pro Asn Arg Ser Glu Cys Phe Ala Leu Met Asn Val Ser Gln Asn
        1355                1360                1365

Val Arg Trp Lys Asn Leu Lys Val Asn Phe Asp Asn Val Gly Leu
        1370                1375                1380

Gly Tyr Leu Ser Leu Leu Gln Val Ala Thr Phe Lys Gly Trp Thr
        1385                1390                1395

Ile Ile Met Tyr Ala Ala Val Asp Ser Val Asn Val Asp Lys Gln
        1400                1405                1410

Pro Lys Tyr Glu Tyr Ser Leu Tyr Met Tyr Ile Tyr Phe Val Val
        1415                1420                1425

Phe Ile Ile Phe Gly Ser Phe Phe Thr Leu Asn Leu Phe Ile Gly
        1430                1435                1440

Val Ile Ile Asp Asn Phe Asn Gln Gln Lys Lys Lys Leu Gly Gly
        1445                1450                1455

Gln Asp Ile Phe Met Thr Glu Glu Gln Lys Lys Tyr Tyr Asn Ala
        1460                1465                1470

Met Lys Lys Leu Gly Ser Lys Lys Pro Gln Lys Pro Ile Pro Arg
        1475                1480                1485

Pro Gly Asn Lys Ile Gln Gly Cys Ile Phe Asp Leu Val Thr Asn
        1490                1495                1500

Gln Ala Phe Asp Ile Ser Ile Met Val Leu Ile Cys Leu Asn Met
        1505                1510                1515

Val Thr Met Met Val Glu Lys Glu Gly Gln Ser Gln His Met Thr
        1520                1525                1530

Glu Val Leu Tyr Trp Ile Asn Val Val Phe Ile Ile Leu Phe Thr
        1535                1540                1545

Gly Glu Cys Val Leu Lys Leu Ile Ser Leu Arg His Tyr Tyr Phe
        1550                1555                1560

Thr Val Gly Trp Asn Ile Phe Asp Phe Val Val Val Ile Ile Ser
        1565                1570                1575

Ile Val Gly Met Phe Leu Ala Asp Leu Ile Glu Thr Tyr Phe Val
        1580                1585                1590

Ser Pro Thr Leu Phe Arg Val Ile Arg Leu Ala Arg Ile Gly Arg
        1595                1600                1605

Ile Leu Arg Leu Val Lys Gly Ala Lys Gly Ile Arg Thr Leu Leu
        1610                1615                1620

Phe Ala Leu Met Met Ser Leu Pro Ala Leu Phe Asn Ile Gly Leu
        1625                1630                1635

Leu Leu Phe Leu Val Met Phe Ile Tyr Ala Ile Phe Gly Met Ser
        1640                1645                1650

Asn Phe Ala Tyr Val Lys Lys Glu Asp Gly Ile Asn Asp Met Phe
        1655                1660                1665
```

```
Asn Phe Glu Thr Phe Gly Asn  Ser Met Ile Cys Leu  Phe Gln Ile
    1670             1675                 1680

Thr Thr  Ser Ala Gly
    1685

<210> SEQ ID NO 9
<211> LENGTH: 6367
<212> TYPE: DNA
<213> ORGANISM: Homo sapiens

<400> SEQUENCE: 9
ctcttatgtg aggagctgaa gaggaattaa aatatacagg atgaaaagat ggcaatgttg      60
cctcccccag gacctcagag ctttgtccat ttcacaaaac agtctcttgc cctcattgaa     120
caacgcattg ctgaaagaaa atcaaaggaa cccaaagaag aaaagaaaga tgatgatgaa     180
gaagccccaa agccaagcag tgacttggaa gctggcaaac agctgccctt catctatggg     240
gacattcctc ccggcatggt gtcagagccc ctggaggact ggaccccta ctatgcagac     300 aaaaagactt tcatagtatt gaacaaaggg aaaacaatct tccgtttcaa tgccacacct     360
gctttatata tgctttctcc tttcagtcct ctaagaagaa tatctattaa gattttagta     420
cactccttat tcagcatgct catcatgtgc actattctga caaactgcat atttatgacc     480
atgaataacc caccggactg gaccaaaaat gtcgagtaca cttttactgg aatatatact     540
tttgaatcac ttgtaaaaat ccttgcaaga ggcttctgtg taggagaatt cacttttctt     600
cgtgacccgt ggaactggct ggattttgtc gtcattgttt ttgcgtattt aacagaattt     660
gtaaacctag gcaatgtttc agctcttcga actttcagag tattgagagc tttgaaaact     720
atttctgtaa tcccaggcct gaagacaatt gtaggggctt tgatccagtc agtgaagaag     780
ctttctgatg tcatgatcct gactgtgttc tgtctgagtg tgtttgcact aattggacta     840
cagctgttca tgggaaacct gaagcataaa tgttttcgaa attcacttga aaataatgaa     900
acattagaaa gcataatgaa taccctagag agtgaagaag actttagaaa atatttttat     960
tacttggaag gatccaaaga tgctctcctt tgtggtttca gcacagattc aggtcagtgt    1020
ccagaggggt aaacctgtgt gaaaattggc agaaaccctg attatggcta cacgagcttt    1080
gacactttca gctgggcctt cttagccttg tttaggctaa tgacccaaga ttactgggaa    1140 aaccttacc aacagacgct gcgtgctgct ggcaaaacct acatgatctt ctttgtcgta    1200
gtgattttcc tgggctcctt ttatctaata aacttgatcc tggctgtggt tgccatggca    1260
tatgaagaac agaaccaggc aaacattgaa gaagctaaac agaaagaatt agaatttcaa    1320
cagatgttag accgtcttaa aaaagagcaa gaagaagctg aggcaattgc agcggcagcg    1380
gctgaatata caagtattag gagaagcaga attatgggcc tctcagagag ttcttctgaa    1440
acatccaaac tgagctctaa aagtgctaaa gaaagaagaa acagaagaaa gaaaaagaat    1500
caaaagaagc tctccagtgg agaggaaaag ggagatgctg agaaattgtc gaaatcagaa    1560
tcagaggaca gcatcagaag aaaaagtttc caccttggtg tcgaagggca taggcgagca    1620
catgaaaaga ggttgtctac ccccaatcag tcaccactca gcattcgtgg ctccttgttt    1680
tctgcaaggc gaagcagcag aacaagtctt tttagtttca aggcagagg aagagatata    1740 ggatctgaga ctgaatttgc cgatgatgag cacagcattt ttggagacaa tgagagcaga    1800
aggggctcac tgtttgtgcc ccacagaccc caggagcgac gcagcagtaa catcagccaa    1860
gccagtaggt ccccaccaat gctgccggtg aacgggaaaa tgcacagtgc tgtggactgc    1920
aacggtgtgg tctccctggt tgatggacgc tcagccctca tgctcccaa tggacagctt    1980
```

```
ctgccagagg gcacgaccaa tcaaatacac aagaaaaggc gttgtagttc ctatctcctt    2040
tcagaggata tgctgaatga tcccaacctc agacagagag caatgagtag agcaagcata    2100
ttaacaaaca ctgtggaaga acttgaagag tccagacaaa aatgtccacc ttggtggtac    2160
agatttgcac acaaattctt gatctggaat tgctctccat attggataaa attcaaaaag    2220
tgtatctatt ttattgtaat ggatcctttt gtagatcttg caattaccat ttgcatagtt    2280
ttaaacacat tatttatggc tatggaacac cacccaatga ctgaggaatt caaaaatgta    2340
cttgctatag gaaatttggt ctttactgga atctttgcag ctgaaatggt attaaaactg    2400
attgccatgg atccatatga gtatttccaa gtaggctgga atattttttga cagccttatt    2460 gtgactttaa gtttagtgga gctctttcta gcagatgtgg aaggattgtc agttctgcga    2520
tcattcagac tgctccgagt cttcaagttg gcaaaatcct ggccaacatt gaacatgctg    2580
attaagatca ttggtaactc agtaggggct ctaggtaacc tcaccttagt gttggccatc    2640
atcgtcttca ttttttgctgt ggtcggcatg cagctctttg gtaagagcta caaagaatgt    2700
gtctgcaaga tcaatgatga ctgtacgctc ccacggtggc acatgaacga cttcttccac    2760
tccttcctga ttgtgttccg cgtgctgtgt ggagagtgga tagagaccat gtgggactgt    2820
atggaggtcg ctggtcaagc tatgtgcctt attgtttaca tgatggtcat ggtcattgga    2880
aacctggtgg tcctaaacct atttctggcc ttattattga gctcatttag ttcagacaat    2940
cttacagcaa ttgaagaaga ccctgatgca aacaacctcc agattgcagt gactagaatt    3000
aaaaagggaa taaattatgt gaaacaaacc ttacgtgaat ttattctaaa agcatttttcc   3060 aaaaagccaa agatttccag ggagataaga caagcagaag atctgaatac taagaaggaa    3120 aactatatttt ctaaccatac acttgctgaa atgagcaaag gtcacaattt cctcaaggaa    3180
aaagataaaa tcagtggttt tggaagcagc gtggacaaac acttgatgga agacagtgat    3240
ggtcaatcat ttattcacaa tcccagcctc acagtgacag tgccaattgc acctggggaa    3300
tccgatttgg aaaatatgaa tgctgaggaa cttagcagtg attcggatag tgaatacagc    3360
aaagtgagat taaaccggtc aagctcctca gagtgcagca cagttgataa ccctttgcct    3420
ggagaaggag aagaagcaga ggctgaacct atgaattccg atgagccaga ggcctgtttc    3480
acagatggtt gtgtatggag gttctcatgc tgccaagtta acatagagtc agggaaagga    3540
aaaatctggt ggaacatcag gaaaacctgc tacaagattg ttgaacacag ttggtttgaa    3600
agcttcattg tcctcatgat cctgctcagc agtggtgccc tggcttttga agatatttat    3660
attgaaagga aaaagaccat taagattatc ctggagtatg cagacaagat cttcacttac    3720
atcttcattc tggaaatgct tctaaaatgg ataqcatatg gttataaaac atatttcacc    3780
aatgcctggt gttggctgga tttcctaatt gttgatgttt ctttggttac tttagtggca    3840
aacactcttg gctactcaga tcttggcccc attaaatccc ttcggacact gagagcttta    3900
agacctctaa gagccttatc tagatttgaa ggaatgaggg tcgttgtgaa tgcactcata    3960
ggagcaattc cttccatcat gaatgtgcta cttgtgtgtc ttatattctg gctgatattc    4020
agcatcatgg gagtaaattt gtttgctggc aagttctatg agtgtattaa caccacagat    4080
gggtcacggt tcctgcaag tcaagttcca atcgttccg aatgttttgc ccttatgaat    4140
gttagtcaaa atgtgcgatg gaaaaacctg aaagtgaact tgataatgt cggacttggt    4200 tacctatctc tgcttcaagt tgcaactttt aagggatgga tgattattat gtatgcagca    4260
gtggattctg ttaatgtaga caagcagccc aaatatgaat atagcctcta catgtatatt    4320
tattttgtcg tctttatcat ctttgggtca ttcttcactt tgaacttgtt cattggtgtc    4380
```

-continued

```
atcatagata atttcaacca acagaaaaag aagcttggag gtcaagacat ctttatgaca    4440
gaagaacaga agaaatacta taatgcaatg aaaaagctgg ggtccaagaa gccacaaaag    4500
ccaattcctc gaccagggaa caaaatccaa ggatgtatat ttgacctagt gacaaatcaa    4560
gcctttgata ttagtatcat ggttcttatc tgtctcaaca tggtaaccat gatggtagaa    4620
aaggagggtc aaagtcaaca tatgactgaa gttttatatt ggataaatgt ggttttata     4680 atccttttca ctggagaatg tgtgctaaaa ctgatctccc tcagacacta ctacttcact    4740
gtaggatgga atattttga ttttgtggtt gtgattatct ccattgtagg tatgtttcta     4800
gctgatttga ttgaaacgta ttttgtgtcc cctaccctgt tccgagtgat ccgtcttgcc    4860
aggattggcc gaatcctacg tctagtcaaa ggagcaaagg ggatccgcac gctgctcttt    4920
gctttgatga tgtcccttcc tgcgttgttt aacatcggcc tcctgctctt cctggtcatg    4980
ttcatctacg ccatctttgg aatgtccaac tttgcctatg ttaaaaagga agatggaatt    5040
aatgacatgt tcaattttga gacctttggc aacagtatga tttgcctgtt ccaaattaca    5100
acctctgctg gctgggatgg attgctagca cctattctta acagtaagcc acccgactgt    5160
gacccaaaaa aagttcatcc tggaagttca gttgaaggag actgtggtaa cccatctgtt    5220
ggaatattct actttgttag ttatatcatc atatccttcc tggttgtggt gaacatgtac    5280
attgcagtca tactgagaa ttttagtgtt gccactgaag aaagtactga acctctgagt    5340
gaggatgact ttgagatgtt ctatgaggtt tgggagaagt tgatcccga tgcgacccag    5400 tttatagagt tctctaaact ctctgatttt gcagctgccc tggatcctcc tcttctcata    5460 gcaaaccca acaaagtcca gctcattgcc atggatctgc ccatggttag tggtgaccgg    5520
atccattgtc ttgacatctt atttgctttt acaaagcgtg ttttgggtga gagtggggag    5580
atggattctc ttcgttcaca gatggaagaa aggttcatgt ctgcaaatcc ttccaaagtg    5640
tcctatgaac ccatcacaac cacactaaaa cggaaacaag aggatgtgtc tgctactgtc    5700
attcagcgtg cttatagacg ttaccgctta aggcaaaatg tcaaaaatat atcaagtata    5760
tacataaaag atggagacag agatgatgat ttactcaata aaaaagatat ggcttttgat    5820
aatgttaatg agaactcaag tccagaaaaa acagatgcca cttcatccac cacctctcca    5880
ccttcatatg atagtgtaac aaagccagac aaagagaaat atgaacaaga cagaacagaa    5940
aaggaagaca aagggaaaga cagcaaggaa agcaaaaaat agagcttcat ttttgatata    6000
ttgtttacag cctgtgaaag tgatttattt gtgttaataa aactcttttg aggaagtcta    6060
tgccaaaatc cttttatca aaatattctc gaaggcagtg cagtcactaa ctctgatttc     6120
ctaagaaagg tgggcagcat tagcagatgg ttattttgc actgatgatt ctttaagaat     6180
cgtaagagaa ctctgtagga attattgatt atagcataca aaagtgattc agttttttgg    6240
tttttaataa atcagaagac catgtagaaa acttttacat ctgccttgtc atcttttcac    6300
aggattgtaa ttagtcttgt ttcccatgta aataaacaac acacgcatac agaaaaaaaa    6360
aaaaaaa                                                               6367
```

<210> SEQ ID NO 10
<211> LENGTH: 327
<212> TYPE: PRT
<213> ORGANISM: Homo sapiens

<400> SEQUENCE: 10

Met Ala Met Leu Pro Pro Pro Gly Pro Gln Ser Phe Val His Phe Thr
1               5                   10                  15

Lys Gln Ser Leu Ala Leu Ile Glu Gln Arg Ile Ala Glu Arg Lys Ser

```
                        20                  25                  30
Lys Glu Pro Lys Glu Glu Lys Asp Asp Glu Glu Ala Pro Lys
            35                  40                  45
Pro Ser Ser Asp Leu Glu Ala Gly Lys Gln Leu Pro Phe Ile Tyr Gly
50                  55                  60
Asp Ile Pro Pro Gly Met Val Ser Glu Pro Leu Glu Asp Leu Asp Pro
65                  70                  75                  80
Tyr Tyr Ala Asp Lys Lys Thr Phe Ile Val Leu Asn Lys Gly Lys Thr
                85                  90                  95
Ile Phe Arg Phe Asn Ala Thr Pro Ala Leu Tyr Met Leu Ser Pro Phe
            100                 105                 110
Ser Pro Leu Arg Arg Ile Ser Ile Lys Ile Leu Val His Ser Leu Phe
            115                 120                 125
Ser Met Leu Ile Met Cys Thr Ile Leu Thr Asn Cys Ile Phe Met Thr
            130                 135                 140
Met Asn Asn Pro Pro Asp Trp Thr Lys Asn Val Glu Tyr Thr Phe Thr
145                 150                 155                 160
Gly Ile Tyr Thr Phe Glu Ser Leu Val Lys Ile Leu Ala Arg Gly Phe
                165                 170                 175
Cys Val Gly Glu Phe Thr Phe Leu Arg Asp Pro Trp Asn Trp Leu Asp
            180                 185                 190
Phe Val Val Ile Val Phe Ala Tyr Leu Thr Glu Phe Val Asn Leu Gly
            195                 200                 205
Asn Val Ser Ala Leu Arg Thr Phe Arg Val Leu Arg Ala Leu Lys Thr
            210                 215                 220
Ile Ser Val Ile Pro Gly Leu Lys Thr Ile Val Gly Ala Leu Ile Gln
225                 230                 235                 240
Ser Val Lys Lys Leu Ser Asp Val Met Ile Leu Thr Val Phe Cys Leu
                245                 250                 255
Ser Val Phe Ala Leu Ile Gly Leu Gln Leu Phe Met Gly Asn Leu Lys
            260                 265                 270
His Lys Cys Phe Arg Asn Ser Leu Glu Asn Asn Glu Thr Leu Glu Ser
            275                 280                 285
Ile Met Asn Thr Leu Glu Ser Glu Asp Phe Arg Lys Tyr Phe Tyr
            290                 295                 300
Tyr Leu Glu Gly Ser Lys Asp Ala Leu Leu Cys Gly Phe Ser Thr Asp
305                 310                 315                 320
Ser Gly Gln Cys Pro Glu Gly
                325

<210> SEQ ID NO 11
<211> LENGTH: 6367
<212> TYPE: DNA
<213> ORGANISM: Homo sapiens

<400> SEQUENCE: 11
ctcttatgtg aggagctgaa gaggaattaa aatatacagg atgaaagat ggcaatgttg      60 cctcccccag gacctcagag ctttgtccat ttcacaaaac agtctcttgc cctcattgaa    120
caacgcattg ctgaaagaaa atcaaaggaa cccaaagaag aaagaaaga tgatgatgaa      180 gaagccccaa agccaagcag tgacttggaa gctggcaaac aactgccctt catctatggg    240
gacattcctc ccggcatggt gtcagagccc tggaggact tggacccta ctatgcagac      300 aaaaagactt tcatagtatt gaacaaaggg aaaacaatct ccgtttcaa tgccacacct      360 gctttatata tgctttctcc tttcagtcct ctaagaagaa tatctattaa gatttagta     420
```

| | |
|---|---:|
| cactccttat tcagcatgct catcatgtgc actattctga caaactgcat atttatgacc | 480 |
| atgaataacc cgccggactg gaccaaaaat gtcgagtaca cttttactgg aatatatact | 540 |
| tttgaatcac ttgtaaaaat ccttgcaaga ggcttctgtg taggagaatt cacttttctt | 600 |
| cgtgacccgt ggaactggct ggattttgtc gtcattgttt ttgcgtattt aacagaattt | 660 |
| gtaaacctag gcaatgtttc agctcttcga actttcagag tattgagagc tttgaaaact | 720 |
| atttctgtaa tcccaggcct gaagacaatt gtagggcett tgatccagtc agtgaagaag | 780 |
| cttctgatg tcatgatcct gactgtgttc tgtctgagtg tgtttgcact aattggacta | 840 |
| cagctgttca tgggaaacct gaagcataaa tgttttcgaa attcacttga aaataatgaa | 900 |
| acattagaaa gcaatgaa taccctagag agtgaagaag actttagaaa atatttttat | 960 |
| tacttggaag gatccaaaga tgctctcctt tgtggtttca gcacagattc aggtcagtgt | 1020 |
| ccagagggt acacctgtgt gaaaattggc agaaaccctg attatggcta cacgagcttt | 1080 |
| gacactttca gctgggcctt cttagccttg tttaggctaa tgacccaaga ttactgggaa | 1140 |
| aaccttacc aacagacgct gcgtgccgct ggcaaaacct acatgatctt ctttgtcgta | 1200 |
| gtgattttcc tgggctcctt ttatctaata aacttgatcc tggctgtggt tgccatggca | 1260 |
| tatgaagaac agaaccaggc aaacattgaa gaagctaaac agaaagaatt agagtttcaa | 1320 |
| cagatgttag accgacttaa aaaagagcaa gaagaagctg aggcaattgc agcggcagcg | 1380 |
| gctgaatata caagtattag gagaagcaga attatgggcc tctcagagag ttcttctgaa | 1440 |
| acatccaaac tgagctctaa aagtgctaaa gaaagaagaa acagaagaaa gaaaagaat | 1500 |
| caaaagaagc tctccagtgg agaggaaaag ggagatgctg agaaattgtc gaaatcagaa | 1560 |
| tcagaggaca gcatcagaag aaaaagtttc caccttggtg tcgaagggca taggcgagca | 1620 |
| catgaaaaga ggttgtctac ccccaatcag tcaccactca gcattcgtgg ctccttgttt | 1680 |
| tctgcaaggc gaagcagcag aacaagtctt tttagtttca aaggcagagg aagagatata | 1740 |
| ggatctgaga ctgaatttgc cgatgatgag cacagcattt ttggagacaa tgagagcaga | 1800 |
| aggggctcac tgtttgtgcc ccacagaccc caggagcgac gcagcagtaa catcagccaa | 1860 |
| gccagtaggt ccccaccaat gctgccggtg aacgggaaaa tgcacagtgc tgtggactgc | 1920 |
| aacggtgtgg tctccctggt tgatggacgc tcagccctca tgctccccaa tggacagctt | 1980 |
| ctgccagagg gcacgaccaa tcaaatacac aagaaaaggc gttgtagttc ctatctcctt | 2040 |
| tcagaggata tgctgaatga tcccaacctc agacagagag caatgagtag agcaagcata | 2100 |
| ttaacaaaca ctgtggaaga acttgaagag tccagacaaa aatgtccacc ttggtggtac | 2160 |
| agatttgcac acaaattctt gatctggaat tgctctccat attggataaa attcaaaaag | 2220 |
| tgtatctatt ttattgtaat ggatccttt gtagatcttg caattaccat ttgcatagtt | 2280 |
| ttaaacacat tatttatggc tatgaacac cacccaatga ctgaggaatt caaaaatgta | 2340 |
| cttgctatag gaaatttggt cttactgga atctttgcag ctgaaatggt attaaaactg | 2400 |
| attgccatgg atccatatga gtatttccaa gtaggctgga atatttttga cagccttatt | 2460 |
| gtgactttaa gtttagtgga gctctttcta gcagatgtgg aaggattgtc agttctgcga | 2520 |
| tcattcagac tgctctgagt cttcaagttg gcaaaatcct ggccaacatt gaacatgctg | 2580 |
| attaagatca ttggtaactc agtaggggct ctaggtaacc tcaccttagt gttggccatc | 2640 |
| atcgtcttca tttttgctgt ggtcggcatg cagctctttg gtaagagcta caagaatgt | 2700 |
| gtctgcaaga tcaatgatga ctgtacgctc ccacggtggc acatgaacga cttcttccac | 2760 |
| tccttcctga ttgtgttccg cgtgctgtgt ggagagtgga tagagaccat gtgggactgt | 2820 |

```
atggaggtcg ctggtcaagc tatgtgcctt attgtttaca tgatggtcat ggtcattgga    2880
aacctggtgg tcctaaacct atttctggcc ttattattga gctcatttag ttcagacaat    2940
cttacagcaa ttgaagaaga ccctgatgca acaacctcc agattgcagt gactagaatt      3000
aaaaagggaa taaattatgt gaaacaaacc ttacgtgaat ttattctaaa agcatttcc      3060 aaaaagccaa agatttccag ggagataaga caagcagaag atctgaatac taagaaggaa    3120 aactatatt ctaaccatac acttgctgaa atgagcaaag gtcacaattt cctcaaggaa      3180
aaagataaaa tcagtggttt tggaagcagc gtggacaaac acttgatgga agacagtgat    3240
ggtcaatcat ttattcacaa tcccagcctc acagtgacag tgccaattgc acctggggaa    3300
tccgatttgg aaaatatgaa tgctgaggaa cttagcagtg attcggatag tgaatacagc    3360
aaagtgagat taaaccggtc aagctcctca gagtgcagca cagttgataa ccctttgcct    3420
ggagaaggag aagaagcaga ggctgaacct atgaattccg atgagccaga ggcctgtttc    3480
acagatggtt gtgtacggag gttctcatgc tgccaagtta acatagagtc agggaaagga    3540
aaaatctggt ggaacatcag gaaaacctgc tacaagattg ttgaacacag ttggtttgaa    3600
agcttcattg tcctcatgat cctgctcagc agtggtgccc tggcttttga agatatttat    3660
attgaaagga aaagaccat taagattatc ctggagtatg cagacaagat cttcacttac     3720
atcttcattc tggaaatgct tctaaaatgg atagcatatg ttataaaac atatttcacc     3780 aatgcctggt gttggctgga tttcctaatt gttgatgttt ctttggttac tttagtggca    3840
aacactcttg gctactcaga tcttggcccc attaaatccc ttcggacact gagagcttta    3900
agacctctaa gagccttatc tagatttgaa ggaatgaggg tcgttgtgaa tgcactcata    3960
ggagcaattc cttccatcat gaatgtgcta cttgtgtgtc ttatattctg gctgatattc    4020
agcatcatgg gagtaaattt gttgctggc aagttctatg agtgtattaa caccacagat    4080
gggtcacggt ttcctgcaag tcaagttcca atcgttccg aatgttttgc ccttatgaat    4140
gttagtcaaa atgtgcgatg gaaaaacctg aaagtgaact ttgataatgt cggacttggt    4200
tacctatctc tgcttcaagt tgcaactttt aagggatgga cgattattat gtatgcagca    4260
gtggattctg ttaatgtaga caagcagccc aaatatgaat atagcctcta catgtatatt    4320
tattttgtcg tctttatcat cttgggtca ttcttcactt tgaacttgtt cattggtgtc     4380
atcatagata atttcaacca acagaaaaag aagcttggag gtcaagacat ctttatgaca    4440
gaagaacaga gaaatacta taatgcaatg aaaaagctgg ggtccaagaa gccacaaaag    4500
ccaattcctc gaccagggaa caaaatccaa ggatgtatat ttgacctagt gacaaatcaa    4560
gcctttgata ttagtatcat ggttcttatc tgtctcaaca tggtaaccat gatggtagaa    4620
aaggagggtc aaagtcaaca tatgactgaa gtttatatat ggataaatgt ggttttata    4680 atcctttca ctggagaatg tgtgctaaaa ctgatctcc tcagacacta ctacttcact     4740
gtaggatgga atatttttga ttttgtggtt gtgattatct ccattgtagg tatgtttcta    4800
gctgatttga ttgaaacgta ttttgtgtcc cctaccctgt tccgagtgat ccgtcttgcc    4860
aggattggcc gaatcctacg tctagtcaaa ggagcaaagg ggatccgcac gctgctcttt    4920
gctttgatga tgtccttcc tgcgttgttt aacatcggcc tcctgctctt cctggtcatg    4980
ttcatctacg ccatctttgg aatgtccaac tttgcctatg ttaaaaagga agatggaatt    5040
aatgacatgt tcaattttga gacctttggc aacagtatga tttgcctgtt ccaaattaca    5100
acctctgctg gctgggatgg attgctagca cctattctta cagtaagcc acccgactgt    5160 gacccaaaaa aagttcatcc tggaagttca gttgaaggag actgtggtaa cccatctgtt    5220
```

```
ggaatattct actttgttag ttatatcatc atatccttcc tggttgtggt gaacatgtac    5280
attgcagtca tactggagaa ttttagtgtt gccactgaag aaagtactga acctctgagt    5340
gaggatgact ttgagatgtt ctatgaggtt tgggagaagt ttgatcccga tgcgacccag    5400
tttatagagt tctctaaact ctctgatttt gcagctgccc tggatcctcc tcttctcata    5460
gcaaaaccca acaaagtcca gctcattgcc atggatctgc ccatggttag tggtgaccgg    5520
atccattgtc ttgacatctt atttgctttt acaaagcgtg ttttgggtga gagtggggag    5580
atggattctc ttcgttcaca gatggaagaa aggttcatgt ctgcaaatcc ttccaaagtg    5640
tcctatgaac ccatcacaac cacactaaaa cggaaacaag aggatgtgtc tgctactgtc    5700
attcagcgtg cttatagacg ttaccgctta aggcaaaatg tcaaaaatat atcaagtata    5760
tacataaaag atggagacag agatgatgat ttactcaata aaaaagatat ggcttttgat    5820
aatgttaatg agaactcaag tccagaaaaa acagatgcca cttcatccac cacctctcca    5880
ccttcatatg atagtgtaac aaagccagac aaagagaaat atgaacaaga cagaacagaa    5940
aaggaagaca aagggaaaga cagcaaggaa agcaaaaaat agagcttcat ttttgatata    6000
ttgtttacag cctgtgaaag tgatttattt gtgttaataa aactcttttg aggaagtcta    6060
tgccaaaatc cttttttatca aaatattctc gaaggcagtg cagtcactaa ctctgatttc    6120
ctaagaaagg tgggcagcat tagcagatgg ttattttttgc actgatgatt ctttaagaat    6180
cgtaagagaa ctctgtagga attattgatt atagcataca aaagtgattc agttttttgg    6240 ttttttaataa atcagaagac catgtagaaa acttttacat ctgccttgtc atctttttcac   6300 aggattgtaa ttagtcttgt ttcccatgta aataaacaac acacgcatac agaaaaaaaa    6360
aaaaaaa                                                              6367
```

<210> SEQ ID NO 12
<211> LENGTH: 829
<212> TYPE: PRT
<213> ORGANISM: Homo sapiens

<400> SEQUENCE: 12

```
Met Ala Met Leu Pro Pro Gly Pro Gln Ser Phe Val His Phe Thr
1               5                   10                  15

Lys Gln Ser Leu Ala Leu Ile Glu Gln Arg Ile Ala Glu Arg Lys Ser
            20                  25                  30

Lys Glu Pro Lys Glu Glu Lys Lys Asp Asp Asp Glu Glu Ala Pro Lys
        35                  40                  45

Pro Ser Ser Asp Leu Glu Ala Gly Lys Gln Leu Pro Phe Ile Tyr Gly
    50                  55                  60

Asp Ile Pro Pro Gly Met Val Ser Glu Pro Leu Glu Asp Leu Asp Pro
65                  70                  75                  80

Tyr Tyr Ala Asp Lys Lys Thr Phe Ile Val Leu Asn Lys Gly Lys Thr
                85                  90                  95

Ile Phe Arg Phe Asn Ala Thr Pro Ala Leu Tyr Met Leu Ser Pro Phe
            100                 105                 110

Ser Pro Leu Arg Arg Ile Ser Ile Lys Ile Leu Val His Ser Leu Phe
        115                 120                 125

Ser Met Leu Ile Met Cys Thr Ile Leu Thr Asn Cys Ile Phe Met Thr
    130                 135                 140

Met Asn Asn Pro Pro Asp Trp Thr Lys Asn Val Glu Tyr Thr Phe Thr
145                 150                 155                 160

Gly Ile Tyr Thr Phe Glu Ser Leu Val Lys Ile Leu Ala Arg Gly Phe
```

-continued

```
                165                 170                 175
Cys Val Gly Glu Phe Thr Phe Leu Arg Asp Pro Trp Asn Trp Leu Asp
            180                 185                 190
Phe Val Val Ile Val Phe Ala Tyr Leu Thr Glu Phe Val Asn Leu Gly
            195                 200                 205
Asn Val Ser Ala Leu Arg Thr Phe Arg Val Leu Arg Ala Leu Lys Thr
            210                 215                 220
Ile Ser Val Ile Pro Gly Leu Lys Thr Ile Val Gly Ala Leu Ile Gln
225                 230                 235                 240
Ser Val Lys Lys Leu Ser Asp Val Met Ile Leu Thr Val Phe Cys Leu
                245                 250                 255
Ser Val Phe Ala Leu Ile Gly Leu Gln Leu Phe Met Gly Asn Leu Lys
            260                 265                 270
His Lys Cys Phe Arg Asn Ser Leu Glu Asn Asn Glu Thr Leu Glu Ser
            275                 280                 285
Ile Met Asn Thr Leu Glu Ser Glu Glu Asp Phe Arg Lys Tyr Phe Tyr
            290                 295                 300
Tyr Leu Glu Gly Ser Lys Asp Ala Leu Leu Cys Gly Phe Ser Thr Asp
305                 310                 315                 320
Ser Gly Gln Cys Pro Glu Gly Tyr Thr Cys Val Lys Ile Gly Arg Asn
                325                 330                 335
Pro Asp Tyr Gly Tyr Thr Ser Phe Asp Thr Phe Ser Trp Ala Phe Leu
            340                 345                 350
Ala Leu Phe Arg Leu Met Thr Gln Asp Tyr Trp Glu Asn Leu Tyr Gln
            355                 360                 365
Gln Thr Leu Arg Ala Ala Gly Lys Thr Tyr Met Ile Phe Phe Val Val
            370                 375                 380
Val Ile Phe Leu Gly Ser Phe Tyr Leu Ile Asn Leu Ile Leu Ala Val
385                 390                 395                 400
Val Ala Met Ala Tyr Glu Glu Gln Asn Gln Ala Asn Ile Glu Glu Ala
                405                 410                 415
Lys Gln Lys Glu Leu Glu Phe Gln Gln Met Leu Asp Arg Leu Lys Lys
            420                 425                 430
Glu Gln Glu Glu Ala Glu Ala Ile Ala Ala Ala Ala Glu Tyr Thr
            435                 440                 445
Ser Ile Arg Arg Ser Arg Ile Met Gly Leu Ser Glu Ser Ser Ser Glu
            450                 455                 460
Thr Ser Lys Leu Ser Ser Lys Ser Ala Lys Glu Arg Arg Asn Arg Arg
465                 470                 475                 480
Lys Lys Lys Asn Gln Lys Lys Leu Ser Ser Gly Glu Glu Lys Gly Asp
                485                 490                 495
Ala Glu Lys Leu Ser Lys Ser Glu Ser Glu Asp Ser Ile Arg Arg Lys
            500                 505                 510
Ser Phe His Leu Gly Val Glu Gly His Arg Arg Ala His Glu Lys Arg
            515                 520                 525
Leu Ser Thr Pro Asn Gln Ser Pro Leu Ser Ile Arg Gly Ser Leu Phe
            530                 535                 540
Ser Ala Arg Arg Ser Ser Arg Thr Ser Leu Phe Ser Phe Lys Gly Arg
545                 550                 555                 560
Gly Arg Asp Ile Gly Ser Glu Thr Glu Phe Ala Asp Asp Glu His Ser
                565                 570                 575
Ile Phe Gly Asp Asn Glu Ser Arg Arg Gly Ser Leu Phe Val Pro His
            580                 585                 590
```

```
Arg Pro Gln Glu Arg Arg Ser Ser Asn Ile Ser Gln Ala Ser Arg Ser
        595                 600                 605
Pro Pro Met Leu Pro Val Asn Gly Lys Met His Ser Ala Val Asp Cys
610                 615                 620
Asn Gly Val Val Ser Leu Val Asp Gly Arg Ser Ala Leu Met Leu Pro
625                 630                 635                 640
Asn Gly Gln Leu Leu Pro Glu Gly Thr Thr Asn Gln Ile His Lys Lys
                645                 650                 655
Arg Arg Cys Ser Ser Tyr Leu Leu Ser Glu Asp Met Leu Asn Asp Pro
            660                 665                 670
Asn Leu Arg Gln Arg Ala Met Ser Arg Ala Ser Ile Leu Thr Asn Thr
        675                 680                 685
Val Glu Glu Leu Glu Glu Ser Arg Gln Lys Cys Pro Pro Trp Trp Tyr
690                 695                 700
Arg Phe Ala His Lys Phe Leu Ile Trp Asn Cys Ser Pro Tyr Trp Ile
705                 710                 715                 720
Lys Phe Lys Lys Cys Ile Tyr Phe Ile Val Met Asp Pro Phe Val Asp
                725                 730                 735
Leu Ala Ile Thr Ile Cys Ile Val Leu Asn Thr Leu Phe Met Ala Met
            740                 745                 750
Glu His His Pro Met Thr Glu Glu Phe Lys Asn Val Leu Ala Ile Gly
        755                 760                 765
Asn Leu Val Phe Thr Gly Ile Phe Ala Ala Glu Met Val Leu Lys Leu
770                 775                 780
Ile Ala Met Asp Pro Tyr Glu Tyr Phe Gln Val Gly Trp Asn Ile Phe
785                 790                 795                 800
Asp Ser Leu Ile Val Thr Leu Ser Leu Val Glu Leu Phe Leu Ala Asp
                805                 810                 815
Val Glu Gly Leu Ser Val Leu Arg Ser Phe Arg Leu Leu
            820                 825

<210> SEQ ID NO 13
<211> LENGTH: 2521
<212> TYPE: DNA
<213> ORGANISM: Homo sapiens

<400> SEQUENCE: 13
tcgtcattgt ttttgcgtaa gtactttcag cttttttgaaa cggcaaattt atgaaaatct     60
caggcagcac agtgttccaa taacagcaaa cctctggggt ctgatttttc cagcatggaa    120
tgtctgtatt taaggaaaaa tggaagctat atgaaagcta gtcattgata ggcaaatact    180 aaattttttca aaaagactat ctcccactca gaggtatgtg acatcattga gattgatcat    240
cttcctccat gctcagcact tggatggata gtctatgcag tgccaattag gtttacactt    300
tttccaagtt cttgtttaaa aatgaataaa acctataaga agcacacaaa aaactcaggc    360
ctttaaatac aagtacagtg ctctttatat taccctgtat tattcaatta ttttatattt    420
ttgtattaaa atataaaagt atatatttgt aaaagagctg tcactgctta ctaagcctaa    480
gattaatgca ttgtatacac attatatata cactcagttt attttcaagg aaaatattac    540
attacagtat aatttttaatt tattcataat tgttactctt ttcccaaatg tatttatcag    600
aaaaatggat ttttacaatc tcatatctag atattctatt ttccgttaat gactttgaat    660
tatcaaagta atccaggttc actggagcca cctagacaat acagaagggt cttaagattc    720
ctaatatccg attccttcat ccctgcctaa cctcttttcc atcaggctcc ctcctttga    780 ggtcacatat gatggggcag ttccatctgc tacctgctgc taagaaaaca ttgtgcaaag    840
```

```
aagactgcct cttctcatag gtctccttttt tttcctattg gtacaattca aatactacaa      900
aattcacaat tttaaagtat acaattcagt gtttttcagt atattgacaa acttgcgcaa      960
catcaccact acctaattag agaagtttaa caaccccaaa tagaaactct gtactcatta     1020
gcagtcactt caatttcctt ctctccctgg ccccttggaa accactcatc tatgttttat     1080
ctctatggat tgtctatttt ggatttttt atgaatggaa atatcaaaca gtatgcagcc      1140
ttttgtgtct gacacttagc atactatttt caatgtttta taaaaaatta aaagtctaaa     1200
ttaccataat gttaagggtc caacaattga aacatttagt tgtttacgca tttaagtgta     1260
tgaatccaat ttaataatat ataatatctg tattttgttt gcatcaaatg agtcaaatca     1320
atgctaatta aattaagtta gttatgatag caaaaaagac ttgcagaact atacatttaa     1380
aatagaagcc ccaaacgtag aaaataccct gactaaaggc tcaggtaagt atcatagact     1440
ctatctaaat tctgaataat tctgatttaa ttctacaggt atttaacaga atttgtaaac     1500
ctaggcaatg tttcagctct tcgaacttc agagtattga gagctttgaa aactatttct     1560
gtaatcccag gtaagaagta attggtgtga agcattaggc cactcataac tccaactatt     1620
tgggagttgt tctttgttcg tttgtgtgtg tgtcgtcact gtgtgtataa actcccctat     1680
tacagatatg tgacagagtt tgtggacctg ggcaatgtct cagcattgag aacattcaga     1740
gttctccgag cattgaaaac aatttcagtc attccaggtg agagtggggt taaacaccag     1800
ggctgacttt gatcttttga aagaaagaca taaaaaaaac cttctcttat gcaattttaa     1860
ttaaatttga tttcttctgt tttccacaat cattatcaaa agtcaaccct tgagtttaat     1920
caattgcatg ggtctttagg atgaggatga ctacttggct cacatctcaa cttgaaatct     1980
tccctcctgt ctgagggttt gttttttccat ttgcttatac aggaaggaaa atttcaatcc    2040
attttaattg atttaaaat acttaggaaa gagatcataa atatcagcat ggggatattg      2100
catgacattg ttttttattt tttctcagca aaccatttct ttattgaaaa ttattacaag     2160
gtgtcactat atgctgtaat tgttttggt gccatttata gagaagtggt tgtttgaca       2220
aacattagaa cttacaaaaa ttattttaa agtggtttga atagccaaat tgttcatttt      2280
gacaacctag gtattctttg agaatatgtt cctattttta accatttgct gtaatatata     2340
aaaacaaagt atatataaaa tagcaaaccc agaaggcttt ttttgaatta ggttacttaa     2400
ggtcattgat ttgatataat gcatgacttt ctaggaaagc ttgtgttttt tgtttcgatt     2460
cagaggcttt atgtcattac aaacacttt ttctcccatt ttcaggcctg aagacaattg      2520
t                                                                    2521

<210> SEQ ID NO 14
<211> LENGTH: 9963
<212> TYPE: DNA
<213> ORGANISM: Homo sapiens

<400> SEQUENCE: 14
aaatattaaa acattgaaaa acttttttt accctttttg gtttatcatc ttccttctct       60
ccttcaactt ccatttttt cattcagttt ttccctcat tccaactctt ctttctttaa      120
ttaacataa tagagactcg gagttcaaaa tatgtgttgt ttctattgaa ttgatagatt      180
ttttttttt ttttgagaca gggtctctgt ctgtcatcca agctggaccg cagtggtgtg      240
atcatggctc actgcagact caacctcccc aggctcaggt gatcctccca ccttagctac     300
tctcaagcag ctgagactac aggtgcacag ctccatgcct ggctaatttt tgtacttttc     360
ctagagacag ggtgtcactg tgttgcccat gctgttcttg aactcctgcc ctcaagtgat     420
```

```
tcacccgcct tggcctccga aaatgttgga attacaggca cgagccactg tgcctggtct    480
attgaatgga atttatgttt atcctttcca attttaaaat agttaacttt aaagttgtgt    540
attttacatt cattgtcttc aaaccaaaca aaatccaaaa acttttctac tttttgaatt    600
gaattttttc tctcctttttg aataataaaa cctggtcatt gatgtatgtg tactcatctg   660 atattttga tttaacaaaa tcaaatggag ggttcacgtt agtattttat gcttttttaaa   720 agtagacatg cttatgctct tccctaaaac ttttatttca gcattactta gataagccct    780
ggcatctgta ttttttttagg ttacacagat gattttttttg tataccctgg tcaatagcca  840
cagtggagta tacctgcatt ctgatatata cactcttgac aaccatagag acaaatgata    900
cttagctgca tttttaacat tacctaacat aagtgaaagg gatttttaaaa cagtagtatt   960 ttggaaaaca gcagataata aaacattaat tttgtgttgt gggttattgg tattaagtat   1020
catgtaatgc ccacatctca aagctcacta tggaagaatt ggtgtcagat aataggaaga   1080
ttgatattgt tgaaaaccat gcattcagca agccagccat tggtagcacc caatgaagtg   1140
ttcagtattc atctaagcag agaaagtaga agacacaatc tttactgtaa ctttgagtgt   1200
ttgcagtgtg tcagatggtc ccttgaagaa gaaatattaa taaaaatgaa ttgcaaattg   1260
tctccaattt acctgaaaga gatcaaaata atgtatctaa atatatggtg tttgaaaggt   1320
gtagagtcag tccatattttt tcaagcccag tgaaggtaac agaacagttt ctacttaagc   1380
agctgtttgt tggtttctttt ggctcaagag agaggtataa tatcttcttt tattttacag   1440
ctttttaatc ataataataa ctattataaa attaacaaat gcacatggta actaattcaa   1500 acaattttttg ctttatcccct ttaaagccat tatctaggga ataatcactt cccgcttttt  1560
taaaaaaaag tttttctgat attttccttt ttatctctaa ataatatgct tatgtctcat   1620
ttttatttca tcaacttatg taatgttttc taactttcta atttgaaaat gaggaattta   1680 ttttattttat gtaaacttttt ctcttttctgc cccattctca aattccaagc agttatgttt  1740
tcatttctaa gtaattctat gggttggatt tataccttta aatggaatat acctgaacct   1800
ctatttcttg ttacttaaac tttagccagg atgcactaac tgccttcaat gtaagataag   1860
gggtcagctc tccaactttt ccctcaccac taatccccct ctacctctca attttttgtaa 1920 gctattccat tacttttaca ctgataatat ttaacacata tatgtgtata tcttgtcttt   1980
gtgtaaataa agttctataa ttgtacttac attttatata tgctttggta attggcacat   2040
ttgtgagatg attaactgat acaatttaac aatattataa ttatgtatgt atttttcatt   2100
ttaaaacaag taacatggtt tgatctagag gaggaattta aacctctcat tcaaactctg   2160
ctacttgaag aacacatcaa actcaagtgg atcctctctg cttcaattct accagttgtt   2220
caagttcatg cctcattttg aattgattcc tatttggaca atatggctat ttacacgttc   2280
taaagaaaca aattcccttt gcttttattc acactatttg tgaaacatct tgtattctat   2340
gtgttttaga agtacttttt ttttttttgct ctaccttaat ccaaagtaac ttaaaaaaaa  2400
aagataaaaa ggagttaaat tttgaatttt cttataccta gaaatatatt ttgtttgcca   2460
tcacacttga taataggttg tctgataata gaatttgatt caaatatttt tctctcatca   2520
cactgaaagc attgattgtg ttctagtgtc aattatggct aaggaaattt taatggcaat   2580
ctaattttca ttctttttag ttagttatct tattttttgga agattataaa atcttgtttc   2640
tattgttaat gctctaaaact ttcacaagaa tggaactttt aaattgatct tcttttgtac   2700
ttttagcttg atgactcttg gtgaattttc tgccattact ttgtttatta tttcctatct   2760
actatttgct gctctcttga gactaatgtc gaacaacatg gattattctg tatcttctaa   2820
```

```
gttttatttt gtacttttt  aatttttaaa attctcctaa aatatataga aaaatctaag    2880
atatagaact ccatgcattt ttacatatac atattttccc atgtaaccat cacatagatc    2940
aaggtataga acgtttctag cacctgagaa tgctcactgg tgccccattc tggtaaagtg    3000
cccctttggg gtaaagtaaa aggtaactac aattatgact tctccttttc agcaagcatt    3060
ctactgaaat ttttgtttc  acaaagcatg acctttaccc agaattgatg ttgttgtttt    3120
tggtagccta ttttttttt  ttaataaaag atactctgtc tcctcaaatt tctctaggaa    3180
tactaacttt aacttctcaa tatcccacaa tgtttgcttt tttttttcta aagttaaaag    3240
tttggtctgt tcatcttagt cttcaatttt tatgtttggt agatcttcat taccaattta    3300
ttcttgataa tctattaata tttatggaag aaaggccagg ttggtgttgg ccaggtttgc    3360
atctgtcttt atacaggtct gtttcccaga caaatcctct cttgaaagag agggatgact    3420
gaaaggtctg tgtatataca tgtatggtgt actgacaggc aggctacatt ttaggatgta    3480
tggatgagga gtagataagg gagtcaccct tccctcgact ccaccctggt tctagctaaa    3540
atggacatgg ataccctagg agtcctacct taattaatgc agatattatc cttttggtga    3600
tagcttggag ataaaccact ctgctacata tttaacatag agagggaagt gggacaatgt    3660
tttctgcaac attattgaat aaataatcca tggattaatc aacttgtttt ctgatctaca    3720
tcacatattt gccatagaaa tctgtgactt ctctgctaga aagaaattct aacattctca    3780
gatgagtgtt ctagactgta gcttctgctt tgatctcctc actagggtaa tcttatgatt    3840
tatgataact ttttttgtct tcctctggtt tttagtgata ttatctaaca tttcgccact    3900
gtacatcttt gttttactg  caatggaaat ttgaaggcca gagagtgtga taaacacatg    3960
ggataagacc attttcatga actgggagct gacattgctt tgactggaaa gatgtgtgaa    4020
gaaaaataga tgctagatag acaaatacat gatatgatat ttggacagac atagatccat    4080
agatggataa gcatagataa aacatatcta tatatatgtg tgtgtctgca tacatagaaa    4140
ataagaaaga gttcagaata aatatttcca tattgatttt aactataggt aatcttagat    4200
acaagaataa cacattcatt ttttaatttt agtagttgcc taagtattct ctaatatgag    4260
attaatggtg agtgggtaag atagtaatga gaaaacaaaa gtactgcctt tatatgcaac    4320 attgggatt  cattctaaag aagatacaat catagtaatg ttaataaaag tggaaatgta    4380
gcaatatatt tttcaaaatt gtaaattaaa catgacaaga ataaatattg attgatttca    4440
ttgactatat aaaattaggt caaataattt taaatgattt ttttcaaagt atattttctt    4500
tcttctggat agaaaaacat gacattttcg ttgtacaaat ttgaaaagta aagtataaag    4560
acataaaaat aatccataat ctcttaacta gggctaaact ttgttaaatg cattgtgtat    4620
ttaaattaaa tatcatttta aaaattatta ttaatttaca tctatctgtg tgtataacct    4680
ggattccact tattatgcat tatatttta  taattcattt aattcattaa atagtctttg    4740
aacgctctct ttcaaagctg ctcattattt cattatacat tcattacttc atttagtgta    4800
acccttactg ttaggatttt ggattgatta taattttca  atattataaa aatattgtag    4860
taaatatatt tatacatgtt agaggacacc tgagattact gtctttgaat aaaattcctag   4920 aaggaaaatt atttggcaat ataaacgaat tcacgtgttt aaggcttttg atagatatta    4980
caaaattacc ctcaaaaagt ttgtacactt tatttattta tttgagacgg agtctcgctc    5040
tattgcccag gctggagtgc agtggcacga tcttggctca ctgcaagctc cgcctcctgg    5100
gttcacgcca ttctctgcct cagcctcccg agcagctggg actataggcg cctgccaaca    5160
tgcctggcta atttttttgt acttttagta gagacagggt ttcacagtgt tcgccaggtt    5220
```

```
ggtctcgatc tcctgacctc atgatctgcc tgcctgggcc tcccaaagtt ctgggattat    5280
aggcgtgagc caccgcaccc agacagtaca cattatttat tactttcatc cagacaggca    5340
acactgattt cccctataac ctctctaata tcactattac ttttgttaaa atctttgcta    5400
atgattaata ggccaaattt ggttccccat gtttatttta atatttgttt ctttgattac    5460
tagtgaggtt tgacatggtt acaagtgttt attaaccatt tgtatttta gataattatg     5520 ttttttacta aattttatga gatatattaa tatctttatt cattaaagga aaagcacttc    5580
atctgtcatt tgtattgtac ttttttttatt ttgtggatgc cttccacttt taaaaacctt   5640
cattgttatg agattaaatc tagcattctt tatcttttc gattttgcct ttggtgtaat     5700
gctttacaag tcctctctac tctcacatta ataagtatt cattttcact tttattagaa     5760
tgtttgagct ttatttttcc atttaaatat ttactccacc agaaatctca aatcttaaac    5820
taaatgcctg actaatgaaa actcctgtgg cctgtttatc cagaagacta agggaagagg    5880
aaagaagttg tagtcacaca taggtcctgc cccatcattg catcttcttt gtgtgtgttg    5940
gtgaagtgtg aggctccatt tttacttatg ttgccctctg taaccctgtc agcctatcat    6000
cttgccaccc cactggcctg gtacaataac ttccaagcaa actcagatgc caactaaagc    6060
tgctcttctt caaagctata aaattagtaa aatgaaagga gtttcaccct ctccaaacta    6120
gaggatgatg atgaaatctg atcaaggtct cttcaacttc catttcacag atcatgatgt    6180
taagcaggtg cttagtgtct tccttttaatt tagcttgatc agggaaatat tgcccatgca   6240
tggtaccact agcattgacc acccctttgcc tctgcttttt tcatatactt tagtcattct   6300
ggagctgtgt tgagcatgtg catggggggtt gggggagaca gagacagagg agaataggaa   6360
tattggaaga atcaaactgg taatggacat ctgagttcac aacatctttg tacctagatt    6420
tctgtcaaat aattcttgaa agagatggta ccctccagtt gaatgtagaa tctacaaaaa    6480
caccagttat tcaagccaac tttcttcaa gagccacagt atgtctacac tgaaagtcta    6540
gtgaggcaag ttatcccgtc ttctcacctt tatgatttcc aaaagtgttg aggaatctcc    6600
aaagcacaag tggcaactgc tttgatttga ttcattgatt tgtttccttt ttactaaatc    6660
tcttcctatt ctgaggacaa ttttcacata ttttaggatt caaaattctt aatgcatatt    6720
catagtagtt ttattaagat ataatttaca caccataaaa aatcaccatt ttaaagtgta    6780
tcactcagtg gttttagta tgttcacaaa ggtatgcaac aatcatcatt atgtagtttt     6840
agaatatttt tatcaccccca aaagaagccc catactcttt aaccattaac cacataacca   6900
tcaataatca cttcctatta cacccagcct ctgacaaaaa atactctaca ttttgtttct    6960
ggggatttgc ctattctgga catttcataa gatggaatca tatcgtatgt ggccttttgg    7020
ctctgtgttc tttcacgggg ttttcatcac atccatgttg taacatgtac ctatacttca    7080
tttgttttta ttgctaaata ctaattcagt gtttgaatat cccacattcc tttatccatt    7140
tattcattgg tgagtaatga ggttgtgttt acttttggc tagtatgaat aatgctgctg     7200
aacattcatg taaacgttct tgtgtggaca tatgttttaa attcccttga gtctgtacca    7260
agtagtggaa ttgccgagtc ataacttact ctttaccttt cagaatcatc ctacttttga    7320
atgtgtatat gaaatatccc ttattttca ctacattctt taaaaacctt tatcctaact     7380 ttggttcca tcaaaataca ggcatacttc atttatggg gctttacttt attgcacttc      7440
aagatactgc attctttaca agttgaaggt ttgtggcaac cctgcattaa gcaagtctgt    7500
cagcgtaatt ttttcaacag catgtgctca cttcatgcat ctgtgtcaca ctttggcaat    7560
tctcacaata tttcaacttt gtaattgcca ttatttaatt attactgtat gtgttatggt    7620
```

```
gatctatgat cagtgatctt tgttgttact gtggtaattg ttttggggtg ctatgaacca   7680
catccacata agacagcaaa caatcattaa atgtgacgtg ttctgtttca gcatccctat   7740
ctctctccct ttcctcaggc ttccctgttc cctgacacac aacgatgtta aaattaggcc   7800
aattagtaac ccattcccac ccctaatgtt caagtaaagg aagaattgcg catttctcac   7860
tttaaatcag aagctagaaa tgattaagct tagtgaggaa ggcatgttga agccaagat   7920 aggccaaaat ctaggcctct tgcactaagt acttagccaa gttgtgaatg caaaggaaac   7980
attcttgaag gaaatcaaat gtgctactcc agtgaacaca tgaatgataa gaaaacaaaa   8040
cagccttatt gcaaatatag agaaagtttt agtgatctag atagaagatc aaccagccac   8100
aacatttcct taagccaaag cctaatccac agcaaggcca taactccaat tgtatgaagg   8160
ctgagaggtg aagaagctgg aaaaaaaagg tttgaagctg gcagacggta ccccatgaga   8220
ttgaaggaaa gaagtcactg ccataacata aaaatgcaag gtgaaacagc aagtgccaat   8280
ggagaagatg cagcaagtta ttcagaagat ctagctaaga tcattgataa gagtggttac   8340
attaaacaac agatttgcaa tgaaggtcta acagccttct actagaagaa tatattatag   8400
ctagaaagga gaagtcaatg tctggcttca aagcttcaac gaacaggctg actctcttgt   8460
taggggataa tgcagctggt gactttaaat tgaagcaaat gctaatttat cgttcagaaa   8520
atcttagaat tatattattt aattattcag aatattaata attatttact attcagaaaa   8580
ttacataata attatattat ttactattca gaaaattaca taataattat attatttact   8640
attcagaaaa ttaaataatt atattcttta ctatccagaa aattaaataa taactatatt   8700
atttaattat tcagaaaatt aaataataat tatattattt aatcattcag aaaatctctt   8760
aagaattata ctaaatctac tctgcctgtg ctctataaat agaacaacaa agcctggatg   8820
acagcacgtc tgtttacagc atggttcact aaatatttta ggcccagtgt tgatacttat   8880
agctcaggaa aaaaaaaaaa gatttctttc aaaatatcac tgcctattga caatgtgcct   8940
ggtcactcaa gagctctaac ggagaggtac aagggcatta atgttatttt catgcctgct   9000
aacgctatcc attctgtagc ctatgggcca aagagtaatt tcaacttta agtcttattt   9060 tttaataaat acattttata agactatagc tgccatagat agtgattcct ctgatgggtc   9120
tgggaaaagt aaattgaaaa tcttctggaa aggattcacc attctagatg ttattagaac   9180
attaatgatt tgtgggagga gggcaatata caaacattaa taggaaattg gaatgagttg   9240
attccaactc tcatggatga ctatgagagg tttaagactt cagtgatgga agaactgca   9300 gatgtggtgg aaatagcaag agaattagaa ttaagagatg gagcctaaaa ttgtgactga   9360
attgctgcca tctcgcggta acttgaatgg atgaggagtt gcttctgatt gataagcaaa   9420
gaaagtggtt tcgtgagatg gaatcttctc ctggtcaaga tgttatgaac attgttgaag   9480
tgacagcaga ggatttagaa tattacataa gtttagttgg taaaacagca tcaggctgga   9540
gagtggtgct accaaaggca ttatcataaa gactttttaaa agaggaaagt tgagttgaat   9600
tgcaccaaag gtaaatatag acgaaaagaa ggggaattta ggaaaattta ctcagaaaat   9660
tgtcattttt tactttaaag ctatgaagcg taaacttcaa atttctgagt ataaagatgg   9720
ttagaaggca cgaaagataa gtcccgccca ttgcctgaca catagtaatc ccttaacaag   9780
ctgataattc tagaacatgt tacctttttgt agttgaaact aaaaatctgt ttatgttgtt   9840
attattagtt tttaatgggc ctttcttggc aggcaaatag ttaagtcttt atttctttgt   9900
ttccatccag gcctcttatg tgaggagctg aagaggaatt aaaatataca ggatgaaaag   9960
atg                                                                 9963
```

<210> SEQ ID NO 15
<211> LENGTH: 9298
<212> TYPE: DNA
<213> ORGANISM: Mus musculus

<400> SEQUENCE: 15

| | | | | | |
|---|---|---|---|---|---|
| tacaggatga | gaagatggcg | atgttgcctc | cgccaggacc | tcagagcttc | gttcacttca | 60 |
| caaaacagtc | ccttgccctc | attgaacaac | gcatttctga | agaaaaagcc | aagggacaca | 120 |
| aagatgaaaa | gaaagatgat | gaggaagaag | gtcccaagcc | cagtagtgac | ttggaagcag | 180 |
| gtaaacagct | accttcatc | tacggagaca | ttcccccggg | aatggtgtca | gagcccctgg | 240 |
| aggacctgga | cccatactat | gcagacaaaa | aaactttat | agtattgaac | aaagggaaag | 300 |
| caatcttccg | tttcaacgcc | accctgctt | tgtacatgct | gtctcccttc | agtcctctca | 360 |
| gaagaatatc | tattaagatt | ttagtgcact | ccttattcag | catgctaatc | atgtgcacaa | 420 |
| ttctgacaaa | ctgcatattc | atgaccatga | gcaaccctcc | agattggacc | aaaaacgtag | 480 |
| agtacacttt | tactgggata | tatacttttg | aatcactcat | aaaaatcctt | gcaagaggct | 540 |
| tttgcgtggg | cgaattcacc | ttcctccgtg | acccttggaa | ctggctggac | tttgttgtca | 600 |
| ttgttttgc | gtatttaaca | gaatttgtaa | acctaggcaa | tgtttcagct | cttcgaactt | 660 |
| tcagagtctt | gagagctttg | aaaactattt | ctgtaattcc | aggactaaaa | accatcgtgg | 720 |
| gggccctgat | ccaatcagtg | aagaagctct | ctgacgtcat | gatcctcact | gtgttctgtc | 780 |
| tcagtgtgtt | cgcactaatt | ggactacaac | tgttatggg | caacttgaag | cataaatgtt | 840 |
| tccggaagga | ccttgagcag | aatgaaacat | agaaagcat | catgagtact | gctgagagtg | 900 |
| aagaagaatt | gaaagatat | ttttattact | tggagggatc | caaagatgct | cttctttgcg | 960 |
| gtttcagcac | agattcaggg | cagtgtcctg | aagggtacga | gtgtgtgaca | gctggcagaa | 1020 |
| acccagatta | tggctacaca | agctttgaca | cgttcggctg | ggccttcttg | gccttgtttc | 1080 |
| ggctaatgac | tcaggactac | tgggagaacc | tttatcaaca | gacactgcgt | gctgctggca | 1140 |
| aaacctacat | gattttcttt | gtcgtggtga | tatttctggg | atccttttac | ctgataaact | 1200 |
| tgatcctggc | tgtggtagcc | atggcgtacg | aggaacagaa | ccaggccaac | atcgaagaag | 1260 |
| ctaaacagaa | agagttagaa | tttcagcaga | tgttagaccg | actcaaaaaa | gagcaggaag | 1320 |
| aagccgaggc | gatcgctgca | gccgctgctg | agtacacgag | tttagggcgg | agcaggatta | 1380 |
| tgggactctc | tgagagctct | tcagaaacct | ccaggctgag | ctcaaagagt | gccaaggaga | 1440 |
| gaagaaaccg | aagaaagaaa | aaaaacaga | agctgtccag | tggcgaggaa | aagggtgatg | 1500 |
| atgagaagct | gtccaagtca | gggtcagagg | aaagcatccg | aaagaaaagc | ttccatctcg | 1560 |
| gcgtggaagg | gcaccaccgg | gccagggaaa | agaggctgtc | caccccaac | cagtcaccac | 1620 |
| tcagcattcg | tgggtccttg | ttttctgcca | ggcgcagcag | cagaacaagt | ctcttcagtt | 1680 |
| ttaaggggcg | aggaagagat | ctgggatctg | aaacggaatt | tgctgatgat | gagcatagca | 1740 |
| tttttggaga | caacgagagc | agaagggtt | cactatttgt | accccataga | ccccgggagc | 1800 |
| ggcgcagcag | taacatcagc | caggccagta | ggtcccacc | agtgctgccg | gtgaacggga | 1860 |
| agatgcacag | tgcagtggac | tgcaatggcg | tggtgtcgct | tgttgatgga | ccctcagccc | 1920 |
| tcatgctccc | caatggacag | cttcttccag | aggtgataat | agataaggca | acttccgacg | 1980 |
| acagcggcac | aactaatcag | atgcgtaaaa | aaggctctc | tagttcttac | tttttgtctg | 2040 |
| aggacatgct | gaatgaccca | catctcaggc | aaagggccat | gagcagagca | agcattctaa | 2100 |
| ccaacacagt | agaagaactt | gaagaatcta | gacaaaaatg | tccaccatgg | tggtacagat | 2160 |

```
ttgctcacac attttaatc tggaattgtt ctccatattg gataaaattc aaaaagttca   2220 tctatttat tgtaatggat cctttgtag atcttgcaat taccatttgc atagttttaa   2280
acaccttgtt tatggctatg gagcaccatc caatgacgga tgaattcaaa atgtacttg   2340 cagtcgggaa cctggtcttc acagggatct tcgcagctga aatggtactg aagttaatag   2400
ccatggatcc ctatgaatat ttccaagtag ggtggaatat ttttgacagc ctgattgtga   2460
cgttgagttt ggtggagctt ttcctagcag atgtggaagg attatcagtc ctgcggtcct   2520
ttagattgct gcgagtcttc aagttggcaa atcctggcc cacactgaat atgctcatta   2580
agatcatcgg caactcggtg ggcgcactgg gcaacctgac cctggtgctg gccatcatcg   2640
tcttcatttt tgccgtggtc ggcatgcagc tgtttggaaa gagctacaag gagtgtgttt   2700
gcaagatcaa cgagaactgc aagctcccac gctggcacat gaacgacttc ttccactcct   2760
tcctgatcgt gttccgtgtg ctgtgtgggg agtggataga gaccatgtgg gactgcatgg   2820
aggttgcggg ccagaccatg tgccttattg tttacatgat ggtcatggtg attgggaacc   2880
ttgtggtcct gaacctgttt ctggctttat tactgagttc ctttagttct gacaatctta   2940
cagcaattga agaagacacc gacgcaaaca acctccagat tgcagtggcc agaattaaaa   3000
gagggatcaa ttatgtgaaa cagaccctgc gtgaattcat tctaaagtca ttttccaaaa   3060
agccaaaggg ctccaaggac acaaaacgaa cagcggatcc caacaacaaa agagaaaact   3120
atatctcaaa ccgtaccctt gcggagataa gcaaagatca caatttcctc aaagaaaagg   3180
ataagatcag tggttttagc agcagtcag acaaaagctt tatggatgaa aacgattacc   3240
agtcctttat tcataatccc agcctcacag tgacagtgcc cattgcacct ggggagtctg   3300
atttggagaa tatgaacaca gaagagctta gcagtgactc agatagtgac tacagcaaag   3360
agagacggaa ccgatcaagt tcttcagagt gcagcacagt tgataaccct ctgccaggag   3420
aagaggaggc agaagctgag cctatcaatg cagatgagcc cgaagcctgt tttacagatg   3480
gctgtgtgag gagatttcca tgctgccaag ttaacataga ctccgggaaa gggaaagttt   3540
ggtggaccat ccggaagacc tgctacagga tagtggagca cagctggttt gaaagcttca   3600
ttgttctcat gatcctgctc agcagtggag ctctggcttt tgaggatata tatattgaaa   3660 agaaaagac cattaagatt atcctggagt atgctgacaa gatattcacc tacatcttca   3720
ttctggaaat gcttctaaaa tgggtggcat acgggtataa aacatatttc actaatgcct   3780
ggtgttggct ggacttctta attgttgatg tgtctctagt tactttagta gccaacactc   3840
ttggctactc agaccttggc cccattaaat ctctacggac actgagggcc ctaagacccc   3900
taagagcttt gtctagattt gaaggaatga gggtagtggt caacgcactc ataggagcaa   3960
tcccttccat catgaatgtg cttcttgtgt gccttatatt ctggctaata tttagcatca   4020
tgggagtcaa tctgtttgct ggcaagttct atgagtgtgt taacaccaca gatggctcac   4080
gattttctgt atctcaagtt gcaaaccgtt ctgagtgttt tgccctgatg aatgttagtg   4140
gaaatgtgcg atggaaaaac ctgaaagtaa acttcgataa cgttggactt ggttacctgt   4200
cgctgcttca agttgcaacg ttcaagggct ggatggatat tatgtatgca gcagttgact   4260
ctgttaatgt aaatgcacaa ccaatatatg aatacaacct ctacatgtac atttattttg   4320
tcatcttcat catcttggc tcattcttca cttttgaactt gttcattggt gtcatcatcg   4380
ataatttcaa ccaacagaag aagaagcttg gaggtcaaga tatctttatg acagaagaac   4440
agaagaaata ctataatgca atgaagaagc tggggtccaa gaaaccacaa aaaccaattc   4500
cgaggccagg gaacaaattc caaggatgca tatttgactt agtgacaaac caagcttttg   4560
```

```
atatcaccat catggttctt atctgcctca atatggtaac catgatggta gaaaaagagg   4620
ggcaaactga ctacatgagt tttgtgctat actggatcaa cgtggtcttc atcatcctgt   4680
tcactgggga gtgtgtgctg aagctgatct ctctcaggca ttactacttc actgtgggat   4740
ggaacatttt tgattttgtg gtagtgatcc tctccattgt aggaatgttt ctcgctgaga   4800
tgatagagaa gtatttcgtg tctcctaccc tgttccgagt cattcgcctg gccaggattg   4860
gacgaatcct acgcctgatc aaaggcgcca aggggatccg cacgctgctc tttgctctga   4920
tgatgtccct tcctgcgctg ttcaacatcg gcctcctgct tttcctcgtc atgttcatct   4980
acgccatctt tgggatgtcc aactttgcct acgttaaaaa ggaagctgga attaatgaca   5040
tgttcaactt tgagaccttc ggcaacagca tgatctgcct gttccaaatc accacctctg   5100
cgggctggga tggactgctg gcccccatcc tcaacagtgc acctcctgac tgtgacccaa   5160
aaaaggttca cccaggaagt tcagtggaag gggactgtgg aaatccatct gtgggaattt   5220
tctactttgt cagctacatc atcatatcct tcctggttgt ggtgaacatg tacattgctg   5280
tcatcctgga gaacttcagc gttgccacag aagaaagtac tgagcccctg agtgaggacg   5340
actttgagat gttctacgaa gtctgggaga gttcgaccc tgacgccacc cagttcatag   5400
agttctgcaa gctctctgac tttgcagcag ccctggatcc tccctcctc atcgcaaagc   5460 caaacaaagt ccagctcatt gccatggacc tgcccatggt gagtggagac cgcatcccact   5520 gcctggacat cttatttgct tttacaaagc gggtcctggg cgagagcgga gagatggatt   5580
cccttcgttc acagatggaa gaaaggttta tgtcagccaa tccttctaaa gtgtcctatg   5640
agcccatcac aaccacactg aagcgaaaac aagaggatgt atctgcgact atcattcagc   5700
gtgcttacag acgtaccgc cttaggcaaa acgtcaagaa tatatcaagt atatatataa   5760
aagatggaga cagagatgac gatttgccca ataaagaaga tatagttttt gataatgtta   5820
acgagaactc aagtccagaa aagacagatg caacagcctc taccatctct ccaccttcct   5880
atgacagtgt cacaaagcca gatcaagaga aatatgaaac agacaaaacg gagaaggaag   5940
acaaagagaa agacgaaagc aggaaataga gcttcggttt tgatacactg tttacagcct   6000
gcgaaggtga ctcactcgtg ttaataagac tcttttacgg aggtctatgc caaactcttt   6060
ttatcaaata ttctcaaagg cagcacagcc actagctctg atccagtgaa acaagagaga   6120
agcatttaca catggctact ttttgcgttg gtcaatgatt ctttaagaat tgtgcatgta   6180
actctacagg gaataatcat tattgcaatc aagggtgact taatgatttt aaatatcaga   6240
aaaccacata gaacattttc tcttttgcct ccatttcttt ccctagattc taagtagatg   6300
tgtacccatg tgaatataga aattcaggcg cacatgctca cagtcacaaa cacaaacagg   6360
attagctgtg atttggaatt cgatgtaaat atttcacctg tgatttgcaa tgaaattcct   6420
tgtaaaagaa atgcgaatta gtgatgaagg ttttgtgaaa acatcttatc attagggagt   6480
cagaatttct gtccataaag aattcagttt atattttgag gtgctgaaac ttatcctaca   6540
ttgcatcaaa atcaatttat aggtatctgt aaaatgtcat gggactgaaa acatatata   6600 ggctacttgt ttaagaaatg ctttcattc atatagatag gcattcacct tgatttatgg   6660
acatctttgg cattttgtga tcacatgatt cttccacaaa attgcttagc tggaacttca   6720
ggcacacatc acagagaaca gctacccagt cttatgcccc tctctgtttg tacaataatc   6780
acagagcttg aaacattatt tgaactataa atatcaggtt tctccacata gacatatgaa   6840
tattgttaac agaaaaaaat tttatttaca gcgtttatt tactaatatt tatccaatct   6900
agtttgccca atgagacagc tcatgactca catctgaaag ccagttgcca catttatctt   6960
```

```
cttatgtaac tttggtttgt catactttat gtctaagcaa attgaatgtc tcctttctaa    7020
tgagatgtac cctgaaatgc agttaggtac ttgatacttt agcgcttgtt tgagcagatg    7080
actggagcac agtgtggact gcatctctta aatacaatcc ttaatgtgtt tggcagcttc    7140
tcaggttaca aggaacaccc ggcttttagt gtctatctgt tcaccaggtg tttagtatga    7200
atgaaacggc attcaaagag tgagtctcac tggcttgctt tattactgat gccttccta    7260
tggagaatta atcctctgaa gccccattat gtcccctgt aaataatgta gatgtcactt    7320
ccttcttaat attctaatcc atactgtgaa atcgattttg catttatcgg tcaaatagag    7380
cattttgaga tagttggagt taccctgcca aggattagaa atctacttca tgtttttaaa    7440
gtacttgtta aaaatgaacg accctggcac attctctcat aattttattc cagccatgtg    7500
aaatctttct tctaaacact ttatccttgc ggaggaaaaa aaaatgagc tgatgagcca    7560
tttaagcaca aaggggcttt atttagaaga ttccaagggg gaactttgaa gtaaatatat    7620
aaaacatact tcatcaattt gcctataaaa ctaaagagg aacacaggaa tattgataaa    7680
ataagtcatt aaaacacatt ctttatttct tgcccagttt aaaagaaaga actaaacatc    7740
cctagagaga ggaagagaca tagagagaga gtgactaata aaagaggga gagaagaaac    7800
aaggcaccaa ggacaaaaag agataattag acagaacttg tccaggtttt cacactatgt    7860
gctctgtcca gtaccgtaca caagaacctc tttccaaata tttgtcctaa ggctctaaga    7920
agttaagtac gaggctgaag gttgaataca actgtcttta atcattaaca gtttggggag    7980
ctacttttaa acgtctatgg aagatgccaa gcagtggtaa gccagacaat acagagcact    8040
gcatatctgt caagcagctg aaatatgttt gggcaactta atggtgagcc acacaaaaca    8100
tccatttgta acaattttaa tacattcaat taagaaacca ggattttat tattttgcac    8160
ccataaaaat ataactatat tgttcatttt tattgataga gtatgtgtga atcttattga    8220
ttatctgtaa tttactatta atgttttac agtgactgtt tttttgtgt gtgtaaactt    8280
aatatatgtc agcaactggt tcctcaacac aattttttt agcattacaa aaaatgaac    8340
aggtataaag gttctctttt ttctacatca tgttgaacat attttgttct gaattacata    8400
gttttaaatg taatattaag ttttatattc atatatgttt aacatcaaaa tcactactta    8460
tgacattgtt atcaatttaa aaaatagtat ttgacactag gatagcattt aattaaagct    8520
aaaaagctta caccccattt catgttgatt agtgtttgga ctaactctaa aatgtcatca    8580
atggaagcta gtcactgaaa ttattttatc tattgtcata gaatggtgac tacccaaaaa    8640
atataagtta gcattaaata gaagaaagcg tacgtgacca caaatccatg cacagggttg    8700
tgtgaagaca ggagaacctc atttttctgt tttgtctctt tccactgtgt aaaaagtcta    8760
catctgtggg ctatttctaa attcaaattg tcacaatttg caatcataaa tgtttagcat    8820
actttgtaga attttgatag ttttgtaaaa gagtgaaaaa caaatgcata tgtaaataaa    8880
gcagcccata ctagcagatt cctcaaatgt taatatgtaa ataaagcagc ccttactagc    8940
agattcatca aatgttaata tgtaaataaa gcagtcctta ttagcagatt tgtcatatgt    9000
taaggggagt aatgataagg aggcaactaa atcaggatgg tcagtaactg atctgggttt    9060
agaactgtgt ttggagccat caatttttaa atatatgttc tcactatgtt attagttgtc    9120
tgaagaagca atcaagaatt gctcccagaa aatgagtaag tagccatgaa tatatgaatg    9180
ctgtttacag aacccataga cctatgaatg ctcaaaatgt ttgggtttgt caaaaaatta    9240
cattgtagtt atacttgata cttaaaaact gttaatagag tctaaaataa aagtcgct    9298
```

-continued

```
<210> SEQ ID NO 16
<211> LENGTH: 1984
<212> TYPE: PRT
<213> ORGANISM: Mus musculus

<400> SEQUENCE: 16

Met Ala Met Leu Pro Pro Gly Pro Gln Ser Phe Val His Phe Thr
1               5                   10                  15

Lys Gln Ser Leu Ala Leu Ile Glu Gln Arg Ile Ser Glu Glu Lys Ala
            20                  25                  30

Lys Gly His Lys Asp Glu Lys Lys Asp Asp Glu Glu Glu Gly Pro Lys
        35                  40                  45

Pro Ser Ser Asp Leu Glu Ala Gly Lys Gln Leu Pro Phe Ile Tyr Gly
    50                  55                  60

Asp Ile Pro Pro Gly Met Val Ser Glu Pro Leu Glu Asp Leu Asp Pro
65                  70                  75                  80

Tyr Tyr Ala Asp Lys Lys Thr Phe Ile Val Leu Asn Lys Gly Lys Ala
                85                  90                  95

Ile Phe Arg Phe Asn Ala Thr Pro Ala Leu Tyr Met Leu Ser Pro Phe
            100                 105                 110

Ser Pro Leu Arg Arg Ile Ser Ile Lys Ile Leu Val His Ser Leu Phe
        115                 120                 125

Ser Met Leu Ile Met Cys Thr Ile Leu Thr Asn Cys Ile Phe Met Thr
    130                 135                 140

Met Ser Asn Pro Pro Asp Trp Thr Lys Asn Val Glu Tyr Thr Phe Thr
145                 150                 155                 160

Gly Ile Tyr Thr Phe Glu Ser Leu Ile Lys Ile Leu Ala Arg Gly Phe
                165                 170                 175

Cys Val Gly Glu Phe Thr Phe Leu Arg Asp Pro Trp Asn Trp Leu Asp
            180                 185                 190

Phe Val Val Ile Val Phe Ala Tyr Leu Thr Glu Phe Val Asn Leu Gly
        195                 200                 205

Asn Val Ser Ala Leu Arg Thr Phe Arg Val Leu Arg Ala Leu Lys Thr
    210                 215                 220

Ile Ser Val Ile Pro Gly Leu Lys Thr Ile Val Gly Ala Leu Ile Gln
225                 230                 235                 240

Ser Val Lys Lys Leu Ser Asp Val Met Ile Leu Thr Val Phe Cys Leu
                245                 250                 255

Ser Val Phe Ala Leu Ile Gly Leu Gln Leu Phe Met Gly Asn Leu Lys
            260                 265                 270

His Lys Cys Phe Arg Lys Asp Leu Glu Gln Asn Glu Thr Leu Glu Ser
        275                 280                 285

Ile Met Ser Thr Ala Glu Ser Glu Glu Glu Leu Lys Arg Tyr Phe Tyr
    290                 295                 300

Tyr Leu Glu Gly Ser Lys Asp Ala Leu Leu Cys Gly Phe Ser Thr Asp
305                 310                 315                 320

Ser Gly Gln Cys Pro Glu Gly Tyr Glu Cys Val Thr Ala Gly Arg Asn
                325                 330                 335

Pro Asp Tyr Gly Tyr Thr Ser Phe Asp Thr Phe Gly Trp Ala Phe Leu
            340                 345                 350

Ala Leu Phe Arg Leu Met Thr Gln Asp Tyr Trp Glu Asn Leu Tyr Gln
        355                 360                 365

Gln Thr Leu Arg Ala Ala Gly Lys Thr Tyr Met Ile Phe Phe Val Val
    370                 375                 380

Val Ile Phe Leu Gly Ser Phe Tyr Leu Ile Asn Leu Ile Leu Ala Val
```

```
              385                 390                 395                 400
Val Ala Met Ala Tyr Glu Glu Gln Asn Gln Ala Asn Ile Glu Glu Ala
                405                 410                 415

Lys Gln Lys Glu Leu Glu Phe Gln Gln Met Leu Asp Arg Leu Lys Lys
            420                 425                 430

Glu Gln Glu Glu Ala Glu Ala Ile Ala Ala Ala Ala Glu Tyr Thr
        435                 440                 445

Ser Leu Gly Arg Ser Arg Ile Met Gly Leu Ser Glu Ser Ser Ser Glu
    450                 455                 460

Thr Ser Arg Leu Ser Ser Lys Ser Ala Lys Glu Arg Arg Asn Arg Arg
465                 470                 475                 480

Lys Lys Lys Lys Gln Lys Leu Ser Ser Gly Glu Glu Lys Gly Asp Asp
                485                 490                 495

Glu Lys Leu Ser Lys Ser Gly Ser Glu Glu Ser Ile Arg Lys Lys Ser
            500                 505                 510

Phe His Leu Gly Val Glu Gly His His Arg Ala Arg Glu Lys Arg Leu
        515                 520                 525

Ser Thr Pro Asn Gln Ser Pro Leu Ser Ile Arg Gly Ser Leu Phe Ser
    530                 535                 540

Ala Arg Arg Ser Ser Arg Thr Ser Leu Phe Ser Phe Lys Gly Arg Gly
545                 550                 555                 560

Arg Asp Leu Gly Ser Glu Thr Glu Phe Ala Asp Glu His Ser Ile
                565                 570                 575

Phe Gly Asp Asn Glu Ser Arg Arg Gly Ser Leu Phe Val Pro His Arg
            580                 585                 590

Pro Arg Glu Arg Arg Ser Ser Asn Ile Ser Gln Ala Ser Arg Ser Pro
        595                 600                 605

Pro Val Leu Pro Val Asn Gly Lys Met His Ser Ala Val Asp Cys Asn
    610                 615                 620

Gly Val Val Ser Leu Val Asp Gly Pro Ser Ala Leu Met Leu Pro Asn
625                 630                 635                 640

Gly Gln Leu Leu Pro Glu Val Ile Ile Asp Lys Ala Thr Ser Asp Asp
                645                 650                 655

Ser Gly Thr Thr Asn Gln Met Arg Lys Lys Arg Leu Ser Ser Ser Tyr
            660                 665                 670

Phe Leu Ser Glu Asp Met Leu Asn Asp Pro His Leu Arg Gln Arg Ala
        675                 680                 685

Met Ser Arg Ala Ser Ile Leu Thr Asn Thr Val Glu Glu Leu Glu Glu
    690                 695                 700

Ser Arg Gln Lys Cys Pro Pro Trp Trp Tyr Arg Phe Ala His Thr Phe
705                 710                 715                 720

Leu Ile Trp Asn Cys Ser Pro Tyr Trp Ile Lys Phe Lys Lys Phe Ile
                725                 730                 735

Tyr Phe Ile Val Met Asp Pro Phe Val Asp Leu Ala Ile Thr Ile Cys
            740                 745                 750

Ile Val Leu Asn Thr Leu Phe Met Ala Met Glu His His Pro Met Thr
        755                 760                 765

Asp Glu Phe Lys Asn Val Leu Ala Val Gly Asn Leu Val Phe Thr Gly
    770                 775                 780

Ile Phe Ala Ala Glu Met Val Leu Lys Leu Ile Ala Met Asp Pro Tyr
785                 790                 795                 800

Glu Tyr Phe Gln Val Gly Trp Asn Ile Phe Asp Ser Leu Ile Val Thr
                805                 810                 815
```

-continued

Leu Ser Leu Val Glu Leu Phe Leu Ala Asp Val Glu Gly Leu Ser Val
            820                 825                 830

Leu Arg Ser Phe Arg Leu Leu Arg Val Phe Lys Leu Ala Lys Ser Trp
            835                 840                 845

Pro Thr Leu Asn Met Leu Ile Lys Ile Ile Gly Asn Ser Val Gly Ala
    850                 855                 860

Leu Gly Asn Leu Thr Leu Val Leu Ala Ile Ile Val Phe Ile Phe Ala
865                 870                 875                 880

Val Val Gly Met Gln Leu Phe Gly Lys Ser Tyr Lys Glu Cys Val Cys
                885                 890                 895

Lys Ile Asn Glu Asn Cys Lys Leu Pro Arg Trp His Met Asn Asp Phe
            900                 905                 910

Phe His Ser Phe Leu Ile Val Phe Arg Val Leu Cys Gly Glu Trp Ile
            915                 920                 925

Glu Thr Met Trp Asp Cys Met Glu Val Ala Gly Gln Thr Met Cys Leu
            930                 935                 940

Ile Val Tyr Met Met Val Met Val Ile Gly Asn Leu Val Val Leu Asn
945                 950                 955                 960

Leu Phe Leu Ala Leu Leu Leu Ser Ser Phe Ser Ser Asp Asn Leu Thr
            965                 970                 975

Ala Ile Glu Glu Asp Thr Asp Ala Asn Asn Leu Gln Ile Ala Val Ala
            980                 985                 990

Arg Ile Lys Arg Gly Ile Asn Tyr Val Lys Gln Thr Leu Arg Glu Phe
            995                 1000                1005

Ile Leu Lys Ser Phe Ser Lys Lys Pro Lys Gly Ser Lys Asp Thr
    1010                1015                1020

Lys Arg Thr Ala Asp Pro Asn Asn Lys Arg Glu Asn Tyr Ile Ser
    1025                1030                1035

Asn Arg Thr Leu Ala Glu Ile Ser Lys Asp His Asn Phe Leu Lys
    1040                1045                1050

Glu Lys Asp Lys Ile Ser Gly Phe Ser Ser Leu Asp Lys Ser
    1055                1060                1065

Phe Met Asp Glu Asn Asp Tyr Gln Ser Phe Ile His Asn Pro Ser
    1070                1075                1080

Leu Thr Val Thr Val Pro Ile Ala Pro Gly Glu Ser Asp Leu Glu
    1085                1090                1095

Asn Met Asn Thr Glu Glu Leu Ser Ser Asp Ser Asp Ser Asp Tyr
    1100                1105                1110

Ser Lys Glu Arg Arg Asn Arg Ser Ser Ser Ser Glu Cys Ser Thr
    1115                1120                1125

Val Asp Asn Pro Leu Pro Gly Glu Glu Glu Ala Glu Ala Glu Pro
    1130                1135                1140

Ile Asn Ala Asp Glu Pro Glu Ala Cys Phe Thr Asp Gly Cys Val
    1145                1150                1155

Arg Arg Phe Pro Cys Cys Gln Val Asn Ile Asp Ser Gly Lys Gly
    1160                1165                1170

Lys Val Trp Trp Thr Ile Arg Lys Thr Cys Tyr Arg Ile Val Glu
    1175                1180                1185

His Ser Trp Phe Glu Ser Phe Ile Val Leu Met Ile Leu Leu Ser
    1190                1195                1200

Ser Gly Ala Leu Ala Phe Glu Asp Ile Tyr Ile Glu Lys Lys Lys
    1205                1210                1215

Thr Ile Lys Ile Ile Leu Glu Tyr Ala Asp Lys Ile Phe Thr Tyr
    1220                1225                1230

```
Ile Phe Ile Leu Glu Met Leu Leu Lys Trp Val Ala Tyr Gly Tyr
    1235                1240                1245

Lys Thr Tyr Phe Thr Asn Ala Trp Cys Trp Leu Asp Phe Leu Ile
    1250                1255                1260

Val Asp Val Ser Leu Val Thr Leu Val Ala Asn Thr Leu Gly Tyr
    1265                1270                1275

Ser Asp Leu Gly Pro Ile Lys Ser Leu Arg Thr Leu Arg Ala Leu
    1280                1285                1290

Arg Pro Leu Arg Ala Leu Ser Arg Phe Glu Gly Met Arg Val Val
    1295                1300                1305

Val Asn Ala Leu Ile Gly Ala Ile Pro Ser Ile Met Asn Val Leu
    1310                1315                1320

Leu Val Cys Leu Ile Phe Trp Leu Ile Phe Ser Ile Met Gly Val
    1325                1330                1335

Asn Leu Phe Ala Gly Lys Phe Tyr Glu Cys Val Asn Thr Thr Asp
    1340                1345                1350

Gly Ser Arg Phe Ser Val Ser Gln Val Ala Asn Arg Ser Glu Cys
    1355                1360                1365

Phe Ala Leu Met Asn Val Ser Gly Asn Val Arg Trp Lys Asn Leu
    1370                1375                1380

Lys Val Asn Phe Asp Asn Val Gly Leu Gly Tyr Leu Ser Leu Leu
    1385                1390                1395

Gln Val Ala Thr Phe Lys Gly Trp Met Asp Ile Met Tyr Ala Ala
    1400                1405                1410

Val Asp Ser Val Asn Val Asn Ala Gln Pro Ile Tyr Glu Tyr Asn
    1415                1420                1425

Leu Tyr Met Tyr Ile Tyr Phe Val Ile Phe Ile Ile Phe Gly Ser
    1430                1435                1440

Phe Phe Thr Leu Asn Leu Phe Ile Gly Val Ile Ile Asp Asn Phe
    1445                1450                1455

Asn Gln Gln Lys Lys Lys Leu Gly Gly Gln Asp Ile Phe Met Thr
    1460                1465                1470

Glu Glu Gln Lys Lys Tyr Tyr Asn Ala Met Lys Lys Leu Gly Ser
    1475                1480                1485

Lys Lys Pro Gln Lys Pro Ile Pro Arg Pro Gly Asn Lys Phe Gln
    1490                1495                1500

Gly Cys Ile Phe Asp Leu Val Thr Asn Gln Ala Phe Asp Ile Thr
    1505                1510                1515

Ile Met Val Leu Ile Cys Leu Asn Met Val Thr Met Met Val Glu
    1520                1525                1530

Lys Glu Gly Gln Thr Asp Tyr Met Ser Phe Val Leu Tyr Trp Ile
    1535                1540                1545

Asn Val Val Phe Ile Ile Leu Phe Thr Gly Glu Cys Val Leu Lys
    1550                1555                1560

Leu Ile Ser Leu Arg His Tyr Tyr Phe Thr Val Gly Trp Asn Ile
    1565                1570                1575

Phe Asp Phe Val Val Val Ile Leu Ser Ile Val Gly Met Phe Leu
    1580                1585                1590

Ala Glu Met Ile Glu Lys Tyr Phe Val Ser Pro Thr Leu Phe Arg
    1595                1600                1605

Val Ile Arg Leu Ala Arg Ile Gly Arg Ile Leu Arg Leu Ile Lys
    1610                1615                1620

Gly Ala Lys Gly Ile Arg Thr Leu Leu Phe Ala Leu Met Met Ser
```

```
                    1625                1630                1635

Leu Pro Ala Leu Phe Asn Ile Gly Leu Leu Phe Leu Val Met
    1640                1645                1650

Phe Ile Tyr Ala Ile Phe Gly Met Ser Asn Phe Ala Tyr Val Lys
    1655                1660                1665

Lys Glu Ala Gly Ile Asn Asp Met Phe Asn Phe Glu Thr Phe Gly
    1670                1675                1680

Asn Ser Met Ile Cys Leu Phe Gln Ile Thr Thr Ser Ala Gly Trp
    1685                1690                1695

Asp Gly Leu Leu Ala Pro Ile Leu Asn Ser Ala Pro Pro Asp Cys
    1700                1705                1710

Asp Pro Lys Lys Val His Pro Gly Ser Ser Val Glu Gly Asp Cys
    1715                1720                1725

Gly Asn Pro Ser Val Gly Ile Phe Tyr Phe Val Ser Tyr Ile Ile
    1730                1735                1740

Ile Ser Phe Leu Val Val Val Asn Met Tyr Ile Ala Val Ile Leu
    1745                1750                1755

Glu Asn Phe Ser Val Ala Thr Glu Glu Ser Thr Glu Pro Leu Ser
    1760                1765                1770

Glu Asp Asp Phe Glu Met Phe Tyr Glu Val Trp Glu Lys Phe Asp
    1775                1780                1785

Pro Asp Ala Thr Gln Phe Ile Glu Phe Cys Lys Leu Ser Asp Phe
    1790                1795                1800

Ala Ala Ala Leu Asp Pro Pro Leu Leu Ile Ala Lys Pro Asn Lys
    1805                1810                1815

Val Gln Leu Ile Ala Met Asp Leu Pro Met Val Ser Gly Asp Arg
    1820                1825                1830

Ile His Cys Leu Asp Ile Leu Phe Ala Phe Thr Lys Arg Val Leu
    1835                1840                1845

Gly Glu Ser Gly Glu Met Asp Ser Leu Arg Ser Gln Met Glu Glu
    1850                1855                1860

Arg Phe Met Ser Ala Asn Pro Ser Lys Val Ser Tyr Glu Pro Ile
    1865                1870                1875

Thr Thr Thr Leu Lys Arg Lys Gln Glu Asp Val Ser Ala Thr Ile
    1880                1885                1890

Ile Gln Arg Ala Tyr Arg Arg Tyr Arg Leu Arg Gln Asn Val Lys
    1895                1900                1905

Asn Ile Ser Ser Ile Tyr Ile Lys Asp Gly Asp Arg Asp Asp Asp
    1910                1915                1920

Leu Pro Asn Lys Glu Asp Ile Val Phe Asp Asn Val Asn Glu Asn
    1925                1930                1935

Ser Ser Pro Glu Lys Thr Asp Ala Thr Ala Ser Thr Ile Ser Pro
    1940                1945                1950

Pro Ser Tyr Asp Ser Val Thr Lys Pro Asp Gln Glu Lys Tyr Glu
    1955                1960                1965

Thr Asp Lys Thr Glu Lys Glu Asp Lys Glu Lys Asp Glu Ser Arg
    1970                1975                1980

Lys

<210> SEQ ID NO 17
<211> LENGTH: 9265
<212> TYPE: DNA
<213> ORGANISM: Mus musculus

<400> SEQUENCE: 17
```

```
tacaggatga aagatggcg atgttgcctc cgccaggacc tcagagcttc gttcacttca      60
caaaacagtc ccttgccctc attgaacaac gcatttctga agaaaaagcc aagggacaca    120
aagatgaaaa gaaagatgat gaggaagaag gtcccaagcc cagtagtgac ttggaagcag    180
gtaaacagct acccttcatc tacggagaca ttccccgggg aatggtgtca gagcccctgg    240
aggacctgga cccatactat gcagacaaaa aaacttttat agtattgaac aaagggaaag    300
caatcttccg tttcaacgcc acccctgctt tgtacatgct gtctcccttc agtcctctca    360
gaagaatatc tattaagatt ttagtgcact ccttattcag catgctaatc atgtgcacaa    420
ttctgacaaa ctgcatattc atgaccatga gcaaccctcc agattggacc aaaaacgtag    480
agtacacttt tactgggata tacttttg aatcactcat aaaaatcctt gcaagaggct       540
tttgcgtggg cgaattcacc ttcctccgtg acccttggaa ctggctggac tttgttgtca    600
ttgttttgc atatgtgaca gagttttgtg acctgggcaa tgtctcagcg ttgagaacat      660
tcagagttct ccgagcattg aaaacaatat cagtcattcc aggactaaaa accatcgtgg    720
gggccctgat ccaatcagtg aagaagctct ctgacgtcat gatcctcact gtgttctgtc    780
tcagtgtgtt cgcactaatt ggactacaac tgtttatggg caacttgaag cataaatgtt    840
tccggaagga ccttgagcag aatgaaacat tagaaagcat catgagtact gctgagagtg    900
aagaagaatt gaaagatat ttttattact tggagggatc caaagatgct cttctttgcg     960
gtttcagcac agattcaggg cagtgtcctg aagggtacga gtgtgtgaca gctggcagaa   1020
acccagatta tggctacaca agctttgaca cgttcggctg ggccttcttg gccttgtttc   1080
ggctaatgac tcaggactac tgggagaacc tttatcaaca gacactgcgt gctgctggca   1140
aaacctacat gattttcttt gtcgtggtga tatttctggg atccttttac ctgataaact   1200
tgatcctggc tgtggtagcc atggcgtacg aggaacagaa ccaggccaac atcgaagaag   1260
ctaaacagaa agagttagaa tttcagcaga tgttagaccg actcaaaaaa gagcaggaag   1320
aagccgaggc gatcgctgca gccgctgctg agtacacgag tttagggcgg agcaggatta   1380
tgggactctc tgagagctct tcagaaacct ccaggctgag ctcaaagagt gccaaggaga   1440
gaagaaaccg aagaaagaaa aaaaacaga agctgtccag tggcgaggaa aagggtgatg   1500
atgagaagct gtccaagtca gggtcagagg aaagcatccg aaagaaaagc ttccatctcg   1560
gcgtggaagg gcaccaccgg gccagggaaa agaggctgtc caccccaac cagtcaccac     1620
tcagcattcg tgggtccttg ttttctgcca ggcgcagcag cagaacaagt ctcttcagtt   1680
ttaaggggcg aggaagagat ctgggatctg aaacggaatt tgctgatgat gagcatagca   1740
tttttggaga caacgagagc agaagggggtt cactatttgt accccataga ccccgggagc   1800
ggcgcagcag taacatcagc caggccagta ggtccccacc agtgctgccg gtgaacggga   1860
agatgcacag tgcagtggac tgcaatggcg tggtgtcgct tgttgatgga ccctcagccc   1920
tcatgctccc caatggacag cttcttccag agggcacaac taatcagatg cgtaaaaaa     1980
ggctctctag ttcttacttt ttgtctgagg acatgctgaa tgaccacat ctcaggcaaa     2040
gggccatgag cagagcaagc attctaacca acacagtaga agaacttgaa gaatctagac   2100
aaaatgtcc accatggtgg tacagatttg ctcacacatt tttaatctgg aattgttctc     2160
catattggat aaaattcaaa aagttcatct atttattgt aatggatcct tttgtagatc      2220
ttgcaattac catttgcata gttttaaaca ccttgtttat ggctatggag caccatccaa    2280
tgacggatga attcaaaaat gtacttgcag tcggaacct ggtcttcaca gggatcttcg     2340
cagctgaaat ggtactgaag ttaatagcca tggatcccta tgaatatttc caagtagggt   2400
```

```
ggaatatttt tgacagcctg attgtgacgt tgagtttggt ggagcttttc ctagcagatg   2460
tggaaggatt atcagtcctg cggtccttta gattgctgcg agtcttcaag ttggcaaaat   2520
cctggcccac actgaatatg ctcattaaga tcatcggcaa ctcggtgggc gcactgggca   2580
acctgaccct ggtgctggcc atcatcgtct tcattttgc cgtggtcggc atgcagctgt    2640
ttggaaagag ctacaaggag tgtgtttgca agatcaacga gaactgcaag ctcccacgct   2700
ggcacatgaa cgacttcttc cactccttcc tgatcgtgtt ccgtgtgctg tgtggggagt   2760
ggatagagac catgtgggac tgcatggagg ttgcgggcca gaccatgtgc cttattgttt   2820
acatgatggt catggtgatt gggaaccttg tggtcctgaa cctgtttctg gctttattac   2880
tgagttcctt tagttctgac aatcttacag caattgaaga agacaccgac gcaaacaacc   2940
tccagattgc agtggccaga attaaagag ggatcaatta tgtgaaacag accctgcgtg    3000
aattcattct aaagtcattt tccaaaaagc caagggctc caaggacaca aaacgaacag    3060
cggatcccaa caacaaaaga gaaaactata tctcaaaccg tacccttgcg gagataagca   3120
aagatcacaa tttcctcaaa gaaaaggata agatcagtgg ttttagcagc agtctagaca   3180
aaagctttat ggatgaaaac gattaccagt cctttattca taatcccagc ctcacagtga   3240
cagtgcccat tgcacctggg gagtctgatt tggagaatat gaacacagaa gagcttagca   3300
gtgactcaga tagtgactac agcaaagaga gacggaaccg atcaagttct tcagagtgca   3360
gcacagttga taaccctctg ccaggagaag aggaggcaga agctgagcct atcaatgcag   3420
atgagcccga agcctgtttt acagatggct gtgtgaggag atttccatgc tgccaagtta   3480
acatagactc cgggaaaggg aaagtttggt ggaccatccg gaagacctgc tacaggatag   3540
tggagcacag ctggtttgaa agcttcattg ttctcatgat cctgctcagc agtggagctc   3600
tggcttttga ggatatatat attgaaaaga aaaagaccat taagattatc ctggagtatg   3660
ctgacaagat attcacctac atcttcattc tggaaatgct tctaaaatgg gtggcatacg   3720
ggtataaaac atatttcact aatgcctggt gttggctgga cttcttaatt gttgatgtgt   3780
ctctagttac tttagtagcc aacactcttg gctactcaga ccttggcccc attaaatctc   3840
tacggacact gagggcccta agacccctaa gagctttgtc tagatttgaa ggaatgaggg   3900
tagtggtcaa cgcactcata ggagcaatcc cttccatcat gaatgtgctt cttgtgtgcc   3960
ttatattctg gctaatattt agcatcatgg gagtcaatct gtttgctggc aagttctatg   4020
agtgtgttaa caccacagat ggctcacgat tttctgtatc tcaagttgca aaccgttctg   4080
agtgttttgc cctgatgaat gttagtggaa atgtgcgatg gaaaaacctg aaagtaaact   4140
tcgataacgt tggacttggt tacctgtcgc tgcttcaagt tgcaacgttc aagggctgga   4200
tggatattat gtatgcagca gttgactctg ttaatgtaaa tgcacaacca atatatgaat   4260
acaacctcta catgtacatt tattttgtca tcttcatcat ctttggctca ttcttcactt   4320
tgaacttgtt cattggtgtc atcatcgata atttcaacca acagaagaag aagcttggag   4380
gtcaagatat ctttatgaca gaagaacaga gaaatactaa taatgcaatg aagaagctgg   4440
ggtccaagaa accacaaaaa ccaattccga ggccagggaa caaattccaa ggatgcatat   4500
ttgacttagt gacaaaccaa gcttttgata tcaccatcat ggttcttatc tgcctcaata   4560
tggtaaccat gatggtagaa aaagaggggc aaactgacta catgagtttt gtgctatact   4620
ggatcaacgt ggtcttcatc atcctgttca ctggggagtg tgtgctgaag ctgatctctc   4680
tcaggcatta ctacttcact gtgggatgga acatttttga ttttgtggta gtgatcctct   4740
ccattgtagg aatgtttctc gctgagatga tagagaagta tttcgtgtct cctaccctgt   4800
```

```
tccgagtcat tcgcctggcc aggattggac gaatcctacg cctgatcaaa ggcgccaagg    4860
ggatccgcac gctgctcttt gctctgatga tgtcccttcc tgcgctgttc aacatcggcc    4920
tcctgctttt cctcgtcatg ttcatctacg ccatctttgg gatgtccaac tttgcctacg    4980
ttaaaaagga agctggaatt aatgacatgt tcaactttga gaccttcggc aacagcatga    5040
tctgcctgtt ccaaatcacc acctctgcgg gctgggatgg actgctggcc ccatcctca    5100 acagtgcacc tcctgactgt gacccaaaaa aggttcaccc aggaagttca gtggaagggg    5160
actgtggaaa tccatctgtg ggaattttct actttgtcag ctacatcatc atatccttcc    5220
tggttgtggt gaacatgtac attgctgtca tcctggagaa cttcagcgtt gccacagaag    5280
aaagtactga gcccctgagt gaggacgact ttgagatgtt ctacgaagtc tgggagaagt    5340
tcgaccctga cgccacccag ttcatagagt tctgcaagct ctctgacttt gcagcagccc    5400
tggatcctcc cctcctcatc gcaaagccaa acaaagtcca gctcattgcc atggacctgc    5460
ccatggtgag tggagaccgc atccactgcc tggacatctt atttgctttt acaaagcggg    5520
tcctgggcga gagcggagag atggattccc ttcgttcaca gatggaagaa aggtttatgt    5580
cagccaatcc ttctaaagtg tcctatgagc ccatcacaac cacactgaag cgaaaacaag    5640
aggatgtatc tgcgactatc attcagcgtg cttacagacg gtaccgcctt aggcaaaacg    5700
tcaagaatat atcaagtata tatataaaag atggagacag agatgacgat ttgcccaata    5760
aagaagatat agtttttgat aatgttaacg agaactcaag tccagaaaag acagatgcaa    5820
cagcctctac catctctcca ccttcctatg acagtgtcac aaagccagat caagagaaat    5880
atgaaacaga caaaacggag aaggaagaca agagaaaga cgaaagcagg aaatagagct    5940
tcggttttga tacactgttt acagcctgcg aaggtgactc actcgtgtta ataagactct    6000
tttacggagg tctatgccaa actcttttta tcaaatattc tcaaaggcag cacagccact    6060
agctctgatc cagtgaaaca agagagaagc atttacacat ggctactttt tgcgttggtc    6120
aatgattctt taagaattgt gcatgtaact ctacagggaa taatcattat tgcaatcaag    6180
ggtgacttaa tgattttaaa tatcagaaaa ccacatagaa cattttctct tttgcctcca    6240
tttctttccc tagattctaa gtagatgtgt acccatgtga atatagaaat tcaggcgcac    6300
atgctcacag tcacaaacac aaacaggatt agctgtgatt tggaattcga tgtaaatatt    6360
tcacctgtga tttgcaatga aattccttgt aaaagaaatg cgaattagtg atgaaggttt    6420
tgtgaaaaca tcttatcatt agggagtcag aatttctgtc cataaagaat tcagtttata    6480
ttttgaggtg ctgaaactta tcctacattg catcaaaatc aatttatagg tatctgtaaa    6540
atgtcatggg actgaaaaac atatataggc tacttgttta agaaatggct ttcattcata    6600
tagataggca ttcaccttga tttatggaca tctttggcat tttgtgatca catgattctt    6660
ccacaaaatt gcttagctgg aacttcaggc acacatcaca gagaacagct acccagtctt    6720
atgcccctct ctgtttgtac aataatcaca gagcttgaaa cattatttga actataaata    6780
tcaggtttct ccacatagac atatgaatat tgttaacaga aaaaaatttt atttacagcg    6840
ttttatttac taatatttat ccaatctagt ttgcccaatg agacagctca tgactcacat    6900
ctgaaagcca gttgccacat ttatcttctt atgtaacttt ggtttgtcat actttatgtc    6960
taagcaaatt gaatgtctcc tttctaatga gatgtaccct gaaatgcagt taggtacttg    7020
atactttagc gcttgtttga gcagatgact ggagcacagt gtggactgca tctcttaaat    7080
acaatcctta atgtgtttgg cagcttctca ggttacaagg aacacccggc ttttagtgtc    7140
tatctgttca ccaggtgttt agtatgaatg aaacggcatt caaagagtga gtctcactgg    7200
```

```
cttgctttat tactgatgcc ttccctatgg agaattaatc ctctgaagcc ccattatgtc    7260
cccctgtaaa taatgtagat gtcacttcct tcttaatatt ctaatccata ctgtgaaatc    7320
gattttgcat ttatcggtca aatagagcat tttgagatag ttggagttac cctgccaagg    7380
attagaaatc tacttcatgt ttttaaagta cttgttaaaa atgaacgacc ctggcacatt    7440
ctctcataat tttattccag ccatgtgaaa tctttcttct aaacacttta tccttgcgga    7500
ggaaaaaaaa aatgagctga tgagccattt aagcacaaag gggctttatt tagaagattc    7560 caaggggaa ctttgaagta aatatataaa acatacttca tcaatttgcc tataaaacta    7620
aaagaggaac acaggaatat tgataaaata agtcattaaa acacattctt tatttcttgc    7680
ccagtttaaa agaaagaact aaacatccct agagagagga agagacatag agagagagtg    7740
actaatagaa agagggagag aagaaacaag gcaccaagga caaaaagaga taattagaca    7800
gaacttgtcc aggttttcac actatgtgct ctgtccagta ccgtacacaa gaacctcttt    7860
ccaaatattt gtcctaaggc tctaagaagt taagtacgag gctgaaggtt gaatacaact    7920
gtctttaatc attaacagtt tggggagcta cttttaaacg tctatggaag atgccaagca    7980
gtggtaagcc agacaataca gagcactgca tatctgtcaa gcagctgaaa tatgtttggg    8040
caacttaatg gtgagccaca caaacatcc atttgtaaca attttaatac attcaattaa    8100
gaaaccagga ttttattat tttgcaccca taaaaatata actatattgt tcattttat    8160 tgatagagta tgtgtgaatc ttattgatta tctgtaattt actattaatg tttttacagt    8220
gactgttttt tttgtgtgtg taaacttaat atatgtcagc aactggttcc tcaacacaat    8280 ttttttagc attacaaaaa aatgaacagg tataaaggtt ctctttttc tacatcatgt    8340 tgaacatatt ttgttctgaa ttacatagtt ttaaatgtaa tattaagttt tatattcata    8400
tatgtttaac atcaaaatca ctacttatga cattgttatc aatttaaaaa atagtatttg    8460
acactaggat agcatttaat taaagctaaa aagcttacac cccatttcat gttgattagt    8520
gtttggacta actctaaaat gtcatcaatg gaagctagtc actgaaatta ttttatctat    8580
tgtcatagaa tggtgactac ccaaaaaata taagttagca ttaaatagaa gaaagcgtac    8640
gtgaccacaa atccatgcac agggttgtgt gaagacagga gaacctcatt tttctgtttt    8700
gtctctttcc actgtgtaaa aagtctacat ctgtgggcta tttctaaatt caaattgtca    8760
caatttgcaa tcataaatgt ttagcatact ttgtagaatt ttgatagttt tgtaaaagag    8820
tgaaaaacaa atgcatatgt aaataaagca gcccatacta gcagattcct caaatgttaa    8880
tatgtaaata aagcagccct tactagcaga ttcatcaaat gttaatatgt aaataaagca    8940
gtccttatta gcagatttgt catatgttaa ggggagtaat gataaggagg caactaaatc    9000
aggatggtca gtaactgatc tgggtttaga actgtgtttg gagccatcaa ttttaaata    9060 tatgttctca ctatgttatt agttgtctga agaagcaatc aagaattgct cccagaaaat    9120
gagtaagtag ccatgaatat atgaatgctg tttacagaac ccatagacct atgaatgctc    9180
aaaatgtttg ggtttgtcaa aaaattacat tgtagttata cttgatactt aaaaactgtt    9240
aatagagtct aaaataaaag tcgct                                         9265
```

<210> SEQ ID NO 18
<211> LENGTH: 1973
<212> TYPE: PRT
<213> ORGANISM: Mus musculus

<400> SEQUENCE: 18

Met Ala Met Leu Pro Pro Pro Gly Pro Gln Ser Phe Val His Phe Thr

-continued

```
1               5                   10                  15
Lys Gln Ser Leu Ala Leu Ile Glu Gln Arg Ile Ser Glu Glu Lys Ala
                20                  25                  30

Lys Gly His Lys Asp Glu Lys Asp Asp Glu Glu Glu Gly Pro Lys
                35                  40                  45

Pro Ser Ser Asp Leu Glu Ala Gly Lys Gln Leu Pro Phe Ile Tyr Gly
                50                  55                  60

Asp Ile Pro Pro Gly Met Val Ser Glu Pro Leu Glu Asp Leu Asp Pro
65                  70                  75                  80

Tyr Tyr Ala Asp Lys Lys Thr Phe Ile Val Leu Asn Lys Gly Lys Ala
                85                  90                  95

Ile Phe Arg Phe Asn Ala Thr Pro Ala Leu Tyr Met Leu Ser Pro Phe
                100                 105                 110

Ser Pro Leu Arg Arg Ile Ser Ile Lys Ile Leu Val His Ser Leu Phe
                115                 120                 125

Ser Met Leu Ile Met Cys Thr Ile Leu Thr Asn Cys Ile Phe Met Thr
                130                 135                 140

Met Ser Asn Pro Pro Asp Trp Thr Lys Asn Val Glu Tyr Thr Phe Thr
145                 150                 155                 160

Gly Ile Tyr Thr Phe Glu Ser Leu Ile Lys Ile Leu Ala Arg Gly Phe
                165                 170                 175

Cys Val Gly Glu Phe Thr Phe Leu Arg Asp Pro Trp Asn Trp Leu Asp
                180                 185                 190

Phe Val Val Ile Val Phe Ala Tyr Val Thr Glu Phe Val Asp Leu Gly
                195                 200                 205

Asn Val Ser Ala Leu Arg Thr Phe Arg Val Leu Arg Ala Leu Lys Thr
                210                 215                 220

Ile Ser Val Ile Pro Gly Leu Lys Thr Ile Val Gly Ala Leu Ile Gln
225                 230                 235                 240

Ser Val Lys Lys Leu Ser Asp Val Met Ile Leu Thr Val Phe Cys Leu
                245                 250                 255

Ser Val Phe Ala Leu Ile Gly Leu Gln Leu Phe Met Gly Asn Leu Lys
                260                 265                 270

His Lys Cys Phe Arg Lys Asp Leu Glu Gln Asn Glu Thr Leu Glu Ser
                275                 280                 285

Ile Met Ser Thr Ala Glu Ser Glu Glu Leu Lys Arg Tyr Phe Tyr
                290                 295                 300

Tyr Leu Glu Gly Ser Lys Asp Ala Leu Leu Cys Gly Phe Ser Thr Asp
305                 310                 315                 320

Ser Gly Gln Cys Pro Glu Gly Tyr Glu Cys Val Thr Ala Gly Arg Asn
                325                 330                 335

Pro Asp Tyr Gly Tyr Thr Ser Phe Asp Thr Phe Gly Trp Ala Phe Leu
                340                 345                 350

Ala Leu Phe Arg Leu Met Thr Gln Asp Tyr Trp Glu Asn Leu Tyr Gln
                355                 360                 365

Gln Thr Leu Arg Ala Ala Gly Lys Thr Tyr Met Ile Phe Phe Val Val
                370                 375                 380

Val Ile Phe Leu Gly Ser Phe Tyr Leu Ile Asn Leu Ile Leu Ala Val
385                 390                 395                 400

Val Ala Met Ala Tyr Glu Glu Gln Asn Gln Ala Asn Ile Glu Glu Ala
                405                 410                 415

Lys Gln Lys Glu Leu Glu Phe Gln Gln Met Leu Asp Arg Leu Lys Lys
                420                 425                 430
```

```
Glu Gln Glu Glu Ala Glu Ala Ile Ala Ala Ala Ala Glu Tyr Thr
        435                 440                 445
Ser Leu Gly Arg Ser Arg Ile Met Gly Leu Ser Glu Ser Ser Glu
    450                 455                 460
Thr Ser Arg Leu Ser Ser Lys Ser Ala Lys Glu Arg Arg Asn Arg Arg
465                 470                 475                 480
Lys Lys Lys Lys Gln Lys Leu Ser Ser Gly Glu Lys Gly Asp Asp
                485                 490                 495
Glu Lys Leu Ser Lys Ser Gly Ser Glu Glu Ser Ile Arg Lys Lys Ser
                500                 505                 510
Phe His Leu Gly Val Glu Gly His His Arg Ala Arg Glu Lys Arg Leu
                515                 520                 525
Ser Thr Pro Asn Gln Ser Pro Leu Ser Ile Arg Gly Ser Leu Phe Ser
    530                 535                 540
Ala Arg Arg Ser Ser Arg Thr Ser Leu Phe Ser Phe Lys Gly Arg Gly
545                 550                 555                 560
Arg Asp Leu Gly Ser Glu Thr Glu Phe Ala Asp Asp Glu His Ser Ile
                565                 570                 575
Phe Gly Asp Asn Glu Ser Arg Arg Gly Ser Leu Phe Val Pro His Arg
                580                 585                 590
Pro Arg Glu Arg Arg Ser Ser Asn Ile Ser Gln Ala Ser Arg Ser Pro
    595                 600                 605
Pro Val Leu Pro Val Asn Gly Lys Met His Ser Ala Val Asp Cys Asn
    610                 615                 620
Gly Val Val Ser Leu Val Asp Gly Pro Ser Ala Leu Met Leu Pro Asn
625                 630                 635                 640
Gly Gln Leu Leu Pro Glu Gly Thr Thr Asn Gln Met Arg Lys Lys Arg
                645                 650                 655
Leu Ser Ser Ser Tyr Phe Leu Ser Glu Asp Met Leu Asn Asp Pro His
                660                 665                 670
Leu Arg Gln Arg Ala Met Ser Arg Ala Ser Ile Leu Thr Asn Thr Val
    675                 680                 685
Glu Glu Leu Glu Glu Ser Arg Gln Lys Cys Pro Pro Trp Trp Tyr Arg
    690                 695                 700
Phe Ala His Thr Phe Leu Ile Trp Asn Cys Ser Pro Tyr Trp Ile Lys
705                 710                 715                 720
Phe Lys Lys Phe Ile Tyr Phe Ile Val Met Asp Pro Phe Val Asp Leu
                725                 730                 735
Ala Ile Thr Ile Cys Ile Val Leu Asn Thr Leu Phe Met Ala Met Glu
                740                 745                 750
His His Pro Met Thr Asp Glu Phe Lys Asn Val Leu Ala Val Gly Asn
                755                 760                 765
Leu Val Phe Thr Gly Ile Phe Ala Ala Glu Met Val Leu Lys Leu Ile
    770                 775                 780
Ala Met Asp Pro Tyr Glu Tyr Phe Gln Val Gly Trp Asn Ile Phe Asp
785                 790                 795                 800
Ser Leu Ile Val Thr Leu Ser Leu Val Glu Leu Phe Leu Ala Asp Val
                805                 810                 815
Glu Gly Leu Ser Val Leu Arg Ser Phe Arg Leu Leu Arg Val Phe Lys
                820                 825                 830
Leu Ala Lys Ser Trp Pro Thr Leu Asn Met Leu Ile Lys Ile Ile Gly
                835                 840                 845
Asn Ser Val Gly Ala Leu Gly Asn Leu Thr Leu Val Leu Ala Ile Ile
    850                 855                 860
```

```
Val Phe Ile Phe Ala Val Val Gly Met Gln Leu Phe Gly Lys Ser Tyr
865                 870                 875                 880

Lys Glu Cys Val Cys Lys Ile Asn Glu Asn Cys Lys Leu Pro Arg Trp
            885                 890                 895

His Met Asn Asp Phe Phe His Ser Phe Leu Ile Val Phe Arg Val Leu
        900                 905                 910

Cys Gly Glu Trp Ile Glu Thr Met Trp Asp Cys Met Glu Val Ala Gly
            915                 920                 925

Gln Thr Met Cys Leu Ile Val Tyr Met Met Val Met Val Ile Gly Asn
        930                 935                 940

Leu Val Val Leu Asn Leu Phe Leu Ala Leu Leu Leu Ser Ser Phe Ser
945                 950                 955                 960

Ser Asp Asn Leu Thr Ala Ile Glu Glu Asp Thr Asp Ala Asn Asn Leu
                965                 970                 975

Gln Ile Ala Val Ala Arg Ile Lys Arg Gly Ile Asn Tyr Val Lys Gln
                980                 985                 990

Thr Leu Arg Glu Phe Ile Leu Lys Ser Phe Ser Lys Lys Pro Lys Gly
            995                 1000                1005

Ser Lys Asp Thr Lys Arg Thr Ala Asp Pro Asn Asn Lys Arg Glu
    1010                1015                1020

Asn Tyr Ile Ser Asn Arg Thr Leu Ala Glu Ile Ser Lys Asp His
    1025                1030                1035

Asn Phe Leu Lys Glu Lys Asp Lys Ile Ser Gly Phe Ser Ser Ser
    1040                1045                1050

Leu Asp Lys Ser Phe Met Asp Glu Asn Asp Tyr Gln Ser Phe Ile
    1055                1060                1065

His Asn Pro Ser Leu Thr Val Thr Val Pro Ile Ala Pro Gly Glu
    1070                1075                1080

Ser Asp Leu Glu Asn Met Asn Thr Glu Glu Leu Ser Ser Asp Ser
    1085                1090                1095

Asp Ser Asp Tyr Ser Lys Glu Arg Arg Asn Arg Ser Ser Ser Ser
    1100                1105                1110

Glu Cys Ser Thr Val Asp Asn Pro Leu Pro Gly Glu Glu Glu Ala
    1115                1120                1125

Glu Ala Glu Pro Ile Asn Ala Asp Glu Pro Glu Ala Cys Phe Thr
    1130                1135                1140

Asp Gly Cys Val Arg Arg Phe Pro Cys Cys Gln Val Asn Ile Asp
    1145                1150                1155

Ser Gly Lys Gly Lys Val Trp Trp Thr Ile Arg Lys Thr Cys Tyr
    1160                1165                1170

Arg Ile Val Glu His Ser Trp Phe Glu Ser Phe Ile Val Leu Met
    1175                1180                1185

Ile Leu Leu Ser Ser Gly Ala Leu Ala Phe Glu Asp Ile Tyr Ile
    1190                1195                1200

Glu Lys Lys Lys Thr Ile Lys Ile Ile Leu Glu Tyr Ala Asp Lys
    1205                1210                1215

Ile Phe Thr Tyr Ile Phe Ile Leu Glu Met Leu Leu Lys Trp Val
    1220                1225                1230

Ala Tyr Gly Tyr Lys Thr Tyr Phe Thr Asn Ala Trp Cys Trp Leu
    1235                1240                1245

Asp Phe Leu Ile Val Asp Val Ser Leu Val Thr Leu Val Ala Asn
    1250                1255                1260

Thr Leu Gly Tyr Ser Asp Leu Gly Pro Ile Lys Ser Leu Arg Thr
```

```
                 1265                1270                1275

Leu Arg  Ala Leu Arg Pro  Leu Arg Ala Leu  Ser Arg Phe Glu Gly
         1280                1285                1290

Met Arg  Val Val Val Asn  Ala Leu Ile Gly  Ala Ile Pro Ser Ile
         1295                1300                1305

Met Asn  Val Leu Leu Val  Cys Leu Ile Phe  Trp Leu Ile Phe Ser
         1310                1315                1320

Ile Met  Gly Val Asn Leu  Phe Ala Gly Lys  Phe Tyr Glu Cys Val
         1325                1330                1335

Asn Thr  Thr Asp Gly Ser  Arg Phe Ser Val  Ser Gln Val Ala Asn
         1340                1345                1350

Arg Ser  Glu Cys Phe Ala  Leu Met Asn Val  Ser Gly Asn Val Arg
         1355                1360                1365

Trp Lys  Asn Leu Lys Val  Asn Phe Asp Asn  Val Gly Leu Gly Tyr
         1370                1375                1380

Leu Ser  Leu Leu Gln Val  Ala Thr Phe Lys  Gly Trp Met Asp Ile
         1385                1390                1395

Met Tyr  Ala Ala Val Asp  Ser Val Asn Val  Asn Ala Gln Pro Ile
         1400                1405                1410

Tyr Glu  Tyr Asn Leu Tyr  Met Tyr Ile Tyr  Phe Val Ile Phe Ile
         1415                1420                1425

Ile Phe  Gly Ser Phe Phe  Thr Leu Asn Leu  Phe Ile Gly Val Ile
         1430                1435                1440

Ile Asp  Asn Phe Asn Gln  Gln Lys Lys Lys  Leu Gly Gly Gln Asp
         1445                1450                1455

Ile Phe  Met Thr Glu Glu  Gln Lys Lys Tyr  Tyr Asn Ala Met Lys
         1460                1465                1470

Lys Leu  Gly Ser Lys Lys  Pro Gln Lys Pro  Ile Pro Arg Pro Gly
         1475                1480                1485

Asn Lys  Phe Gln Gly Cys  Ile Phe Asp Leu  Val Thr Asn Gln Ala
         1490                1495                1500

Phe Asp  Ile Thr Ile Met  Val Leu Ile Cys  Leu Asn Met Val Thr
         1505                1510                1515

Met Met  Val Glu Lys Glu  Gly Gln Thr Asp  Tyr Met Ser Phe Val
         1520                1525                1530

Leu Tyr  Trp Ile Asn Val  Val Phe Ile Ile  Leu Phe Thr Gly Glu
         1535                1540                1545

Cys Val  Leu Lys Leu Ile  Ser Leu Arg His  Tyr Tyr Phe Thr Val
         1550                1555                1560

Gly Trp  Asn Ile Phe Asp  Phe Val Val Val  Ile Leu Ser Ile Val
         1565                1570                1575

Gly Met  Phe Leu Ala Glu  Met Ile Glu Lys  Tyr Phe Val Ser Pro
         1580                1585                1590

Thr Leu  Phe Arg Val Ile  Arg Leu Ala Arg  Ile Gly Arg Ile Leu
         1595                1600                1605

Arg Leu  Ile Lys Gly Ala  Lys Gly Ile Arg  Thr Leu Leu Phe Ala
         1610                1615                1620

Leu Met  Met Ser Leu Pro  Ala Leu Phe Asn  Ile Gly Leu Leu Leu
         1625                1630                1635

Phe Leu  Val Met Phe Ile  Tyr Ala Ile Phe  Gly Met Ser Asn Phe
         1640                1645                1650

Ala Tyr  Val Lys Lys Glu  Ala Gly Ile Asn  Asp Met Phe Asn Phe
         1655                1660                1665
```

| Glu | Thr | Phe | Gly | Asn | Ser | Met | Ile | Cys | Leu | Phe | Gln | Ile | Thr | Thr |
|-----|-----|-----|-----|-----|-----|-----|-----|-----|-----|-----|-----|-----|-----|-----|
| | 1670 | | | | 1675 | | | | | 1680 | | | | |
| Ser | Ala | Gly | Trp | Asp | Gly | Leu | Leu | Ala | Pro | Ile | Leu | Asn | Ser | Ala |
| 1685 | | | | | 1690 | | | | | 1695 | | | | |
| Pro | Pro | Asp | Cys | Asp | Pro | Lys | Lys | Val | His | Pro | Gly | Ser | Ser | Val |
| 1700 | | | | | 1705 | | | | | 1710 | | | | |
| Glu | Gly | Asp | Cys | Gly | Asn | Pro | Ser | Val | Gly | Ile | Phe | Tyr | Phe | Val |
| 1715 | | | | | 1720 | | | | | 1725 | | | | |
| Ser | Tyr | Ile | Ile | Ile | Ser | Phe | Leu | Val | Val | Val | Asn | Met | Tyr | Ile |
| 1730 | | | | | 1735 | | | | | 1740 | | | | |
| Ala | Val | Ile | Leu | Glu | Asn | Phe | Ser | Val | Ala | Thr | Glu | Glu | Ser | Thr |
| 1745 | | | | | 1750 | | | | | 1755 | | | | |
| Glu | Pro | Leu | Ser | Glu | Asp | Asp | Phe | Glu | Met | Phe | Tyr | Glu | Val | Trp |
| 1760 | | | | | 1765 | | | | | 1770 | | | | |
| Glu | Lys | Phe | Asp | Pro | Asp | Ala | Thr | Gln | Phe | Ile | Glu | Phe | Cys | Lys |
| 1775 | | | | | 1780 | | | | | 1785 | | | | |
| Leu | Ser | Asp | Phe | Ala | Ala | Ala | Leu | Asp | Pro | Pro | Leu | Leu | Ile | Ala |
| 1790 | | | | | 1795 | | | | | 1800 | | | | |
| Lys | Pro | Asn | Lys | Val | Gln | Leu | Ile | Ala | Met | Asp | Leu | Pro | Met | Val |
| 1805 | | | | | 1810 | | | | | 1815 | | | | |
| Ser | Gly | Asp | Arg | Ile | His | Cys | Leu | Asp | Ile | Leu | Phe | Ala | Phe | Thr |
| 1820 | | | | | 1825 | | | | | 1830 | | | | |
| Lys | Arg | Val | Leu | Gly | Glu | Ser | Gly | Glu | Met | Asp | Ser | Leu | Arg | Ser |
| 1835 | | | | | 1840 | | | | | 1845 | | | | |
| Gln | Met | Glu | Glu | Arg | Phe | Met | Ser | Ala | Asn | Pro | Ser | Lys | Val | Ser |
| 1850 | | | | | 1855 | | | | | 1860 | | | | |
| Tyr | Glu | Pro | Ile | Thr | Thr | Thr | Leu | Lys | Arg | Lys | Gln | Glu | Asp | Val |
| 1865 | | | | | 1870 | | | | | 1875 | | | | |
| Ser | Ala | Thr | Ile | Ile | Gln | Arg | Ala | Tyr | Arg | Arg | Tyr | Arg | Leu | Arg |
| 1880 | | | | | 1885 | | | | | 1890 | | | | |
| Gln | Asn | Val | Lys | Asn | Ile | Ser | Ser | Ile | Tyr | Ile | Lys | Asp | Gly | Asp |
| 1895 | | | | | 1900 | | | | | 1905 | | | | |
| Arg | Asp | Asp | Asp | Leu | Pro | Asn | Lys | Glu | Asp | Ile | Val | Phe | Asp | Asn |
| 1910 | | | | | 1915 | | | | | 1920 | | | | |
| Val | Asn | Glu | Asn | Ser | Ser | Pro | Glu | Lys | Thr | Asp | Ala | Thr | Ala | Ser |
| 1925 | | | | | 1930 | | | | | 1935 | | | | |
| Thr | Ile | Ser | Pro | Pro | Ser | Tyr | Asp | Ser | Val | Thr | Lys | Pro | Asp | Gln |
| 1940 | | | | | 1945 | | | | | 1950 | | | | |
| Glu | Lys | Tyr | Glu | Thr | Asp | Lys | Thr | Glu | Lys | Glu | Asp | Lys | Glu | Lys |
| 1955 | | | | | 1960 | | | | | 1965 | | | | |
| Asp | Glu | Ser | Arg | Lys | | | | | | | | | | |
| 1970 | | | | | | | | | | | | | | |

<210> SEQ ID NO 19
<211> LENGTH: 9265
<212> TYPE: DNA
<213> ORGANISM: Mus musculus

<400> SEQUENCE: 19

```
tacaggatga gaagatggcg atgttgcctc cgccaggacc tcagagcttc gttcacttca      60
caaaacagtc ccttgccctc attgaacaac gcatttctga agaaaaagcc aagggacaca     120
aagatgaaaa gaaagatgat gaggaagaag gtcccaagcc cagtagtgac ttggaagcag     180
gtaaacagct acccttcatc tacggagaca ttccccgggg aatggtgtca gagcccctgg     240
aggacctgga cccatactat gcagacaaaa aaactttat agtattgaac aaagggaaag     300
```

```
caatcttccg tttcaacgcc acccctgctt tgtacatgct gtctcccttc agtcctctca    360
gaagaatatc tattaagatt ttagtgcact ccttattcag catgctaatc atgtgcacaa    420
ttctgacaaa ctgcatattc atgaccatga gcaaccctcc agattggacc aaaaacgtag    480
agtacacttt tactgggata tatacttttg aatcactcat aaaaatcctt gcaagaggct    540
tttgcgtggg cgaattcacc ttcctccgtg acccttggaa ctggctggac tttgttgtca    600 ttgttttgc gtatttaaca gaatttgtaa acctaggcaa tgtttcagct cttcgaactt     660
tcagagtctt gagagctttg aaaactattt ctgtaattcc aggactaaaa accatcgtgg    720
gggccctgat ccaatcagtg aagaagctct ctgacgtcat gatcctcact gtgttctgtc    780
tcagtgtgtt cgcactaatt ggactacaac tgtttatggg caacttgaag cataaatgtt    840
tccggaagga ccttgagcag aatgaaacat agaaagcat catgagtact gctgagagtg     900
aagaagaatt gaaagatat ttttattact tggagggatc caaagatgct cttctttgcg     960
gtttcagcac agattcaggg cagtgtcctg aagggtacga gtgtgtgaca gctggcagaa   1020
acccagatta tggctacaca agctttgaca cgttcggctg ggccttcttg gccttgtttc   1080
ggctaatgac tcaggactac tgggagaacc tttatcaaca gacactgcgt gctgctggca   1140
aaacctacat gattttcttt gtcgtggtga tatttctggg atccttttac ctgataaact   1200
tgatcctggc tgtggtagcc atggcgtacg aggaacagaa ccaggccaac atcgaagaag   1260
ctaaacagaa agagttagaa tttcagcaga tgttagaccg actcaaaaaa gagcaggaag   1320
aagccgaggc gatcgctgca gccgctgctg agtacacgag tttagggcgg agcaggatta   1380
tgggactctc tgagagctct tcagaaacct ccaggctgag ctcaaagagt gccaaggaga   1440
gaagaaaccg aagaaagaaa aaaaacaga agctgtccag tggcgaggaa aagggtgatg   1500
atgagaagct gtccaagtca gggtcagagg aaagcatccg aaagaaaagc ttccatctcg   1560
gcgtggaagg gcaccaccgg gccagggaaa agaggctgtc cacccccaac cagtcaccac   1620
tcagcattcg tgggtccttg ttttctgcca ggcgcagcag cagaacaagt ctcttcagtt   1680
ttaaggggcg aggaagagat ctgggatctg aaacggaatt tgctgatgat gagcatagca   1740
tttttggaga caacgagagc agaagggggtt cactatttgt accccataga ccccgggagc   1800
ggcgcagcag taacatcagc caggccagta ggtccccacc agtgctgccg gtgaacggga   1860
agatgcacag tgcagtggac tgcaatggcg tggtgtcgct tgttgatgga ccctcagccc   1920
tcatgctccc caatggacag cttcttccag agggcacaac taatcagatg cgtaaaaaaa   1980
ggctctctag ttcttacttt ttgtctgagg acatgctgaa tgacccacat ctcaggcaaa   2040
gggccatgag cagagcaagc attctaacca acacagtaga agaacttgaa gaatctagac   2100
aaaaatgtcc accatggtgg tacagatttg ctcacacatt tttaatctgg aattgttctc   2160
catattggat aaaattcaaa aagttcatct attttattgt aatggatcct tttgtagatc   2220
ttgcaattac catttgcata gttttaaaca ccttgtttat ggctatggag caccatccaa   2280
tgacggatga attcaaaaat gtacttcgca gtcgggaacct ggtcttcaca gggatcttcg   2340
cagctgaaat ggtactgaag ttaatagcca tggatcccta tgaatatttc caagtagggt   2400
ggaatatttt tgacagcctg attgtgacgt tgagtttggt ggagcttttc ctagcagatg   2460
tggaaggatt atcagtcctg cggtcccttta gattgctgcg agtcttcaag ttggcaaaat   2520
cctggcccac actgaatatg ctcattaaga tcatcggcaa ctcggtgggc gcactgggca   2580
acctgaccct ggtgctggcc atcatcgtct tcattttgc cgtggtcggc atgcagctgt   2640
ttggaaagag ctacaaggag tgtgtttgca agatcaacga gaactgcaag ctcccacgct   2700
```

```
ggcacatgaa cgacttcttc cactccttcc tgatcgtgtt ccgtgtgctg tgtggggagt    2760
ggatagagac catgtgggac tgcatggagg ttgcgggcca gaccatgtgc cttattgttt    2820
acatgatggt catggtgatt gggaaccttg tggtcctgaa cctgtttctg ctttattac     2880 tgagttcctt tagttctgac aatcttacag caattgaaga agacaccgac gcaaacaacc    2940
tccagattgc agtggccaga attaaaagag ggatcaatta tgtgaaacag accctgcgtg    3000
aattcattct aaagtcattt tccaaaaagc caagggctc caaggacaca aaacgaacag      3060
cggatcccaa caacaaaaga gaaaactata tctcaaaccg tacccttgcg gagataagca    3120
aagatcacaa tttcctcaaa gaaaaggata agatcagtgg ttttagcagc agtctagaca    3180
aaagctttat ggatgaaaac gattaccagt cctttattca taatcccagc ctcacagtga    3240
cagtgcccat tgcacctggg gagtctgatt tggagaatat gaacacagaa gagcttagca    3300
gtgactcaga tagtgactac agcaaagaga gacggaaccg atcaagttct tcagagtgca    3360
gcacagttga taaccctctg ccaggagaag aggaggcaga agctgagcct atcaatgcag    3420
atgagcccga agcctgtttt acagatggct gtgtgaggag atttccatgc tgccaagtta    3480
acatagactc cgggaaaggg aaagtttggt ggaccatccg gaagacctgc tacaggatag    3540
tggagcacag ctggtttgaa agcttcattg ttctcatgat cctgctcagc agtggagctc    3600
tggcttttga ggatatatat attgaaaaga aaaagaccat taagattatc ctggagtatg    3660
ctgacaagat attcacctac atcttcattc tggaaatgct tctaaaatgg gtggcatacg    3720
ggtataaaac atatttcact aatgcctggt gttggctgga cttcttaatt gttgatgtgt    3780
ctctagttac tttagtagcc aacactcttg gctactcaga ccttggcccc attaaatctc    3840
tacggacact gagggcccta agaccccta gagctttgtc tagatttgaa ggaatgaggg     3900
tagtggtcaa cgcactcata ggagcaatcc cttccatcat gaatgtgctt cttgtgtgcc    3960
ttatattctg gctaatattt agcatcatgg gagtcaatct gtttgctggc aagttctatg    4020
agtgtgttaa caccacagat ggctcacgat tttctgtatc tcaagttgca aaccgttctg    4080
agtgttttgc cctgatgaat gttagtggaa atgtgcgatg gaaaaacctg aaagtaaact    4140
tcgataacgt tggacttggt tacctgtcgc tgcttcaagt tgcaacgttc aagggctgga    4200
tggatattat gtatgcagca gttgactctg ttaatgtaaa tgcacaacca atatatgaat    4260
acaacctcta catgtacatt tattttgtca tcttcatcat ctttggctca ttcttcactt    4320
tgaacttgtt cattggtgtc atcatcgata atttcaacca acagaagaag aagcttggag    4380
gtcaagatat ctttatgaca gaagaacaga gaaatactaa atgcaatgaagaagctgg      4440 ggtccaagaa accacaaaaa ccaattccga ggccagggaa caaattccaa ggatgcatat    4500
ttgacttagt gacaaaccaa gcttttgata tcaccatcat ggttcttatc tgcctcaata    4560
tggtaaccat gatggtagaa aaagaggggc aaactgacta catgagtttt gtgctatact    4620
ggatcaacgt ggtcttcatc atcctgttca ctggggagtg tgtgctgaag ctgatctctc    4680
tcaggcatta ctacttcact gtgggatgga catttttga ttttgtggta gtgatcctct     4740
ccattgtagg aatgttctc gctgagatga tagagaagta tttcgtgtct cctaccctgt     4800
tccgagtcat tcgcctggcc aggattggac gaatcctacg cctgatcaaa ggcgccaagg    4860
ggatccgcac gctgctcttt gctctgatga tgtcccttcc tgcgctgttc aacatcggcc    4920
tcctgctttt cctcgtcatg ttcatctacg ccatctttgg gatgtccaac tttgcctacg    4980
ttaaaaagga agctggaatt aatgacatgt tcaactttga gaccttcggc aacagcatga    5040
tctgcctgtt ccaaatcacc acctctgcgg gctgggatgg actgctggcc cccatcctca    5100
```

```
acagtgcacc tcctgactgt gacccaaaaa aggttcaccc aggaagttca gtggaagggg    5160
actgtggaaa tccatctgtg ggaattttct actttgtcag ctacatcatc atatccttcc    5220
tggttgtggt gaacatgtac attgctgtca tcctggagaa cttcagcgtt gccacagaag    5280
aaagtactga gccctgagt gaggacgact ttgagatgtt ctacgaagtc tgggagaagt     5340
tcgaccctga cgccacccag ttcatagagt tctgcaagct ctctgacttt gcagcagccc    5400
tggatcctcc cctcctcatc gcaaagccaa acaaagtcca gctcattgcc atggacctgc    5460
ccatggtgag tggagaccgc atccactgcc tggacatctt atttgctttt acaaagcggg    5520
tcctgggcga gagcggagag atggattccc ttcgttcaca gatggaagaa aggtttatgt    5580
cagccaatcc ttctaaagtg tcctatgagc ccatcacaac cacactgaag cgaaaacaag    5640
aggatgtatc tgcgactatc attcagcgtg cttacagacg gtaccgcctt aggcaaaacg    5700
tcaagaatat atcaagtata tatataaaag atggagacag agatgacgat ttgcccaata    5760
aagaagatat agttttttgat aatgttaacg agaactcaag tccagaaaag acagatgcaa    5820
cagcctctac catctctcca ccttcctatg acagtgtcac aaagccagat caagagaaat    5880
atgaaacaga caaaacggag aaggaagaca agagaaaga cgaaagcagg aaatagagct    5940
tcggttttga tacactgttt acagcctgcg aaggtgactc actcgtgtta ataagactct    6000
tttacggagg tctatgccaa actctttta tcaaatattc tcaaaggcag cacagccact    6060
agctctgatc cagtgaaaca agagagaagc atttacacat ggctactttt tgcgttggtc    6120
aatgattctt taagaattgt gcatgtaact ctacagggaa taatcattat tgcaatcaag    6180
ggtgacttaa tgattttaaa tatcagaaaa ccacatagaa catttctct tttgcctcca     6240 tttctttccc tagattctaa gtagatgtgt acccatgtga atatagaaat tcaggcgcac    6300
atgctcacag tcacaaacac aaacaggatt agctgtgatt tggaattcga tgtaaatatt    6360
tcacctgtga tttgcaatga aattccttgt aaaagaaatg cgaattagtg atgaaggttt    6420
tgtgaaaaca tcttatcatt agggagtcag aatttctgtc cataaagaat tcagtttata    6480
ttttgaggtg ctgaaactta tcctacattg catcaaaatc aatttatagg tatctgtaaa    6540
atgtcatggg actgaaaaac atatataggc tacttgttta agaaatggct ttcattcata    6600
tagataggca ttcaccttga tttatggaca tcttttggcat tttgtgatca catgattctt    6660
ccacaaaatt gcttagctgg aacttcaggc acacatcaca gagaacagct acccagtctt    6720
atgcccctct ctgtttgtac aataatcaca gagcttgaaa cattatttga actataaata    6780
tcaggtttct ccacatagac atatgaatat tgttaacaga aaaaaatttt atttacagcg    6840
ttttatttac taatatttat ccaatctagt ttgcccaatg agacagctca tgactcacat    6900
ctgaaagcca gttgccacat ttatcttctt atgtaacttt ggtttgtcat actttatgtc    6960
taagcaaatt gaatgtctcc tttctaatga gatgtaccct gaaatgcagt taggtacttg    7020
atactttagc gcttgtttga gcagatgact ggagcacagt gtggactgca tctcttaaat    7080
acaatcctta atgtgtttgg cagcttctca ggttacaagg aacacccggc ttttagtgtc    7140
tatctgttca ccaggtgttt agtatgaatg aaacggcatt caaagagtga gtctcactgg    7200
cttgctttat tactgatgcc ttccctatgg agaattaatc ctctgaagcc ccattatgtc    7260
cccctgtaaa taatgtagat gtcacttcct tcttaatatt ctaatccata ctgtgaaatc    7320
gattttgcat ttatcggtca aatagagcat tttgagatag ttggagttac cctgccaagg    7380
attagaaatc tacttcatgt ttttaaagta cttgttaaaa atgaacgacc ctggcacatt    7440
ctctcataat tttattccag ccatgtgaaa tctttcttct aaacacttta tccttgcgga    7500
```

```
ggaaaaaaaa aatgagctga tgagccattt aagcacaaag gggctttatt tagaagattc    7560
caaggtggaa ctttgaagta aatatataaa acatacttca tcaatttgcc tataaaacta    7620
aaagaggaac acaggaatat tgataaaata agtcattaaa acacattctt tatttcttgc    7680
ccagtttaaa agaaagaact aaacatccct agagagagga agagacatag agagagagtg    7740
actaatagaa agaggagag aagaaacaag gcaccaagga caaaaagaga taattagaca    7800
gaacttgtcc aggttttcac actatgtgct ctgtccagta ccgtacacaa gaacctcttt    7860
ccaaatattt gtcctaaggc tctaagaagt taagtacgag gctgaaggtt gaatacaact    7920
gtctttaatc attaacagtt tggggagcta cttttaaacg tctatggaag atgccaagca    7980
gtggtaagcc agacaataca gagcactgca tatctgtcaa gcagctgaaa tatgtttggg    8040
caacttaatg gtgagccaca caaacatcc atttgtaaca atttaatac attcaattaa     8100 gaaaccagga ttttattat tttgcaccca taaaaatata actatattgt tcatttttat     8160
tgatagagta tgtgtgaatc ttattgatta tctgtaattt actattaatg tttttacagt    8220
gactgttttt tttgtgtgtg taaacttaat atatgtcagc aactggttcc tcaacacaat    8280 ttttttagc attacaaaaa aatgaacagg tataaaggtt ctcttttttc tacatcatgt     8340
tgaacatatt ttgttctgaa ttacatagtt ttaaatgtaa tattaagttt tatattcata    8400 tatgttaac atcaaaatca ctacttatga cattgttatc aattaaaaa atagtatttg     8460 acactaggat agcatttaat taaagctaaa aagcttacac cccatttcat gttgattagt    8520
gtttggacta actctaaaat gtcatcaatg gaagctagtc actgaaatta ttttatctat    8580
tgtcatagaa tggtgactac ccaaaaaata taagttagca ttaaatagaa gaaagcgtac    8640
gtgaccacaa atccatgcac agggttgtgt gaagacagga gaacctcatt tttctgtttt    8700
gtctctttcc actgtgtaaa aagtctacat ctgtgggcta tttctaaatt caaattgtca    8760
caatttgcaa tcataaatgt ttagcatact ttgtagaatt ttgatagttt tgtaaaagag    8820
tgaaaaacaa atgcatatgt aaataaagca gcccatacta gcagattcct caaatgttaa    8880
tatgtaaata aagcagccct tactagcaga ttcatcaaat gttaatatgt aaataaagca    8940
gtccttatta gcagatttgt catatgttaa ggggagtaat gataaggagg caactaaatc    9000
aggatggtca gtaactgatc tgggtttaga actgtgtttg gagccatcaa ttttaaata     9060 tatgttctca ctatgttatt agttgtctga agaagcaatc aagaattgct cccagaaaat    9120
gagtaagtag ccatgaatat atgaatgctg tttacagaac ccatagacct atgaatgctc    9180
aaaatgtttg ggtttgtcaa aaaattacat tgtagttata cttgatactt aaaaactgtt    9240
aatagagtct aaaataaaag tcgct                                          9265
```

<210> SEQ ID NO 20
<211> LENGTH: 1973
<212> TYPE: PRT
<213> ORGANISM: Mus musculus

<400> SEQUENCE: 20

Met Ala Met Leu Pro Pro Gly Pro Gln Ser Phe Val His Phe Thr
1               5                   10                  15

Lys Gln Ser Leu Ala Leu Ile Glu Gln Arg Ile Ser Glu Glu Lys Ala
            20                  25                  30

Lys Gly His Lys Asp Glu Lys Lys Asp Asp Glu Glu Glu Gly Pro Lys
        35                  40                  45

Pro Ser Ser Asp Leu Glu Ala Gly Lys Gln Leu Pro Phe Ile Tyr Gly
    50                  55                  60

```
Asp Ile Pro Pro Gly Met Val Ser Glu Pro Leu Glu Asp Leu Asp Pro
 65                  70                  75                  80

Tyr Tyr Ala Asp Lys Lys Thr Phe Ile Val Leu Asn Lys Gly Lys Ala
                 85                  90                  95

Ile Phe Arg Phe Asn Ala Thr Pro Ala Leu Tyr Met Leu Ser Pro Phe
            100                 105                 110

Ser Pro Leu Arg Arg Ile Ser Ile Lys Ile Leu Val His Ser Leu Phe
            115                 120                 125

Ser Met Leu Ile Met Cys Thr Ile Leu Thr Asn Cys Ile Phe Met Thr
            130                 135                 140

Met Ser Asn Pro Pro Asp Trp Thr Lys Asn Val Glu Tyr Thr Phe Thr
145                 150                 155                 160

Gly Ile Tyr Thr Phe Glu Ser Leu Ile Lys Ile Leu Ala Arg Gly Phe
                165                 170                 175

Cys Val Gly Glu Phe Thr Phe Leu Arg Asp Pro Trp Asn Trp Leu Asp
            180                 185                 190

Phe Val Val Ile Val Phe Ala Tyr Leu Thr Glu Phe Val Asn Leu Gly
            195                 200                 205

Asn Val Ser Ala Leu Arg Thr Phe Arg Val Leu Arg Ala Leu Lys Thr
            210                 215                 220

Ile Ser Val Ile Pro Gly Leu Lys Thr Ile Val Gly Ala Leu Ile Gln
225                 230                 235                 240

Ser Val Lys Lys Leu Ser Asp Val Met Ile Leu Thr Val Phe Cys Leu
                245                 250                 255

Ser Val Phe Ala Leu Ile Gly Leu Gln Leu Phe Met Gly Asn Leu Lys
            260                 265                 270

His Lys Cys Phe Arg Lys Asp Leu Glu Gln Asn Glu Thr Leu Glu Ser
            275                 280                 285

Ile Met Ser Thr Ala Glu Ser Glu Glu Leu Lys Arg Tyr Phe Tyr
            290                 295                 300

Tyr Leu Glu Gly Ser Lys Asp Ala Leu Leu Cys Gly Phe Ser Thr Asp
305                 310                 315                 320

Ser Gly Gln Cys Pro Glu Gly Tyr Glu Cys Val Thr Ala Gly Arg Asn
                325                 330                 335

Pro Asp Tyr Gly Tyr Thr Ser Phe Asp Thr Phe Gly Trp Ala Phe Leu
            340                 345                 350

Ala Leu Phe Arg Leu Met Thr Gln Asp Tyr Trp Glu Asn Leu Tyr Gln
            355                 360                 365

Gln Thr Leu Arg Ala Ala Gly Lys Thr Tyr Met Ile Phe Phe Val Val
370                 375                 380

Val Ile Phe Leu Gly Ser Phe Tyr Leu Ile Asn Leu Ile Leu Ala Val
385                 390                 395                 400

Val Ala Met Ala Tyr Glu Glu Gln Asn Gln Ala Asn Ile Glu Glu Ala
                405                 410                 415

Lys Gln Lys Glu Leu Glu Phe Gln Gln Met Leu Asp Arg Leu Lys Lys
            420                 425                 430

Glu Gln Glu Glu Ala Glu Ala Ile Ala Ala Ala Ala Glu Tyr Thr
            435                 440                 445

Ser Leu Gly Arg Ser Arg Ile Met Gly Leu Ser Glu Ser Ser Ser Glu
            450                 455                 460

Thr Ser Arg Leu Ser Ser Lys Ser Ala Lys Glu Arg Arg Asn Arg Arg
465                 470                 475                 480

Lys Lys Lys Lys Gln Lys Leu Ser Ser Gly Glu Glu Lys Gly Asp Asp
```

```
                    485                 490                 495
Glu Lys Leu Ser Lys Ser Gly Ser Glu Ser Ile Arg Lys Ser
                500                 505                 510

Phe His Leu Gly Val Glu Gly His His Arg Ala Arg Glu Lys Arg Leu
                515                 520                 525

Ser Thr Pro Asn Gln Ser Pro Leu Ser Ile Arg Gly Ser Leu Phe Ser
                530                 535                 540

Ala Arg Arg Ser Ser Arg Thr Ser Leu Phe Ser Phe Lys Gly Arg Gly
545                 550                 555                 560

Arg Asp Leu Gly Ser Glu Thr Glu Phe Ala Asp Asp Glu His Ser Ile
                565                 570                 575

Phe Gly Asp Asn Glu Ser Arg Arg Gly Ser Leu Phe Val Pro His Arg
                580                 585                 590

Pro Arg Glu Arg Arg Ser Ser Asn Ile Ser Gln Ala Ser Arg Ser Pro
                595                 600                 605

Pro Val Leu Pro Val Asn Gly Lys Met His Ser Ala Val Asp Cys Asn
                610                 615                 620

Gly Val Val Ser Leu Val Asp Gly Pro Ser Ala Leu Met Leu Pro Asn
625                 630                 635                 640

Gly Gln Leu Leu Pro Glu Gly Thr Thr Asn Gln Met Arg Lys Lys Arg
                645                 650                 655

Leu Ser Ser Ser Tyr Phe Leu Ser Glu Asp Met Leu Asn Asp Pro His
                660                 665                 670

Leu Arg Gln Arg Ala Met Ser Arg Ala Ser Ile Leu Thr Asn Thr Val
                675                 680                 685

Glu Glu Leu Glu Glu Ser Arg Gln Lys Cys Pro Pro Trp Trp Tyr Arg
690                 695                 700

Phe Ala His Thr Phe Leu Ile Trp Asn Cys Ser Pro Tyr Trp Ile Lys
705                 710                 715                 720

Phe Lys Lys Phe Ile Tyr Phe Ile Val Met Asp Pro Phe Val Asp Leu
                725                 730                 735

Ala Ile Thr Ile Cys Ile Val Leu Asn Thr Leu Phe Met Ala Met Glu
                740                 745                 750

His His Pro Met Thr Asp Glu Phe Lys Asn Val Leu Ala Val Gly Asn
                755                 760                 765

Leu Val Phe Thr Gly Ile Phe Ala Ala Glu Met Val Leu Lys Leu Ile
                770                 775                 780

Ala Met Asp Pro Tyr Glu Tyr Phe Gln Val Gly Trp Asn Ile Phe Asp
785                 790                 795                 800

Ser Leu Ile Val Thr Leu Ser Leu Val Glu Leu Phe Leu Ala Asp Val
                805                 810                 815

Glu Gly Leu Ser Val Leu Arg Ser Phe Arg Leu Leu Arg Val Phe Lys
                820                 825                 830

Leu Ala Lys Ser Trp Pro Thr Leu Asn Met Leu Ile Lys Ile Ile Gly
                835                 840                 845

Asn Ser Val Gly Ala Leu Gly Asn Leu Thr Leu Val Leu Ala Ile Ile
850                 855                 860

Val Phe Ile Phe Ala Val Val Gly Met Gln Leu Phe Gly Lys Ser Tyr
865                 870                 875                 880

Lys Glu Cys Val Cys Lys Ile Asn Glu Asn Cys Lys Leu Pro Arg Trp
                885                 890                 895

His Met Asn Asp Phe Phe His Ser Phe Leu Ile Val Phe Arg Val Leu
                900                 905                 910
```

-continued

```
Cys Gly Glu Trp Ile Glu Thr Met Trp Asp Cys Met Glu Val Ala Gly
            915                 920                 925
Gln Thr Met Cys Leu Ile Val Tyr Met Met Val Met Val Ile Gly Asn
            930                 935                 940
Leu Val Val Leu Asn Leu Phe Leu Ala Leu Leu Leu Ser Ser Phe Ser
945                 950                 955                 960
Ser Asp Asn Leu Thr Ala Ile Glu Glu Asp Thr Asp Ala Asn Asn Leu
            965                 970                 975
Gln Ile Ala Val Ala Arg Ile Lys Arg Gly Ile Asn Tyr Val Lys Gln
            980                 985                 990
Thr Leu Arg Glu Phe Ile Leu Lys Ser Phe Ser Lys Lys Pro Lys Gly
            995                 1000                1005
Ser Lys Asp Thr Lys Arg Thr Ala Asp Pro Asn Asn Lys Arg Glu
        1010                1015                1020
Asn Tyr Ile Ser Asn Arg Thr Leu Ala Glu Ile Ser Lys Asp His
        1025                1030                1035
Asn Phe Leu Lys Glu Lys Asp Lys Ile Ser Gly Phe Ser Ser Ser
        1040                1045                1050
Leu Asp Lys Ser Phe Met Asp Glu Asn Asp Tyr Gln Ser Phe Ile
        1055                1060                1065
His Asn Pro Ser Leu Thr Val Thr Val Pro Ile Ala Pro Gly Glu
        1070                1075                1080
Ser Asp Leu Glu Asn Met Asn Thr Glu Glu Leu Ser Ser Asp Ser
        1085                1090                1095
Asp Ser Asp Tyr Ser Lys Glu Arg Arg Asn Arg Ser Ser Ser Ser
        1100                1105                1110
Glu Cys Ser Thr Val Asp Asn Pro Leu Pro Gly Glu Glu Glu Ala
        1115                1120                1125
Glu Ala Glu Pro Ile Asn Ala Asp Glu Pro Glu Ala Cys Phe Thr
        1130                1135                1140
Asp Gly Cys Val Arg Arg Phe Pro Cys Cys Gln Val Asn Ile Asp
        1145                1150                1155
Ser Gly Lys Gly Lys Val Trp Trp Thr Ile Arg Lys Thr Cys Tyr
        1160                1165                1170
Arg Ile Val Glu His Ser Trp Phe Glu Ser Phe Ile Val Leu Met
        1175                1180                1185
Ile Leu Leu Ser Ser Gly Ala Leu Ala Phe Glu Asp Ile Tyr Ile
        1190                1195                1200
Glu Lys Lys Lys Thr Ile Lys Ile Ile Leu Glu Tyr Ala Asp Lys
        1205                1210                1215
Ile Phe Thr Tyr Ile Phe Ile Leu Glu Met Leu Leu Lys Trp Val
        1220                1225                1230
Ala Tyr Gly Tyr Lys Thr Tyr Phe Thr Asn Ala Trp Cys Trp Leu
        1235                1240                1245
Asp Phe Leu Ile Val Asp Val Ser Leu Val Thr Leu Val Ala Asn
        1250                1255                1260
Thr Leu Gly Tyr Ser Asp Leu Gly Pro Ile Lys Ser Leu Arg Thr
        1265                1270                1275
Leu Arg Ala Leu Arg Pro Leu Arg Ala Leu Ser Arg Phe Glu Gly
        1280                1285                1290
Met Arg Val Val Val Asn Ala Leu Ile Gly Ala Ile Pro Ser Ile
        1295                1300                1305
Met Asn Val Leu Leu Val Cys Leu Ile Phe Trp Leu Ile Phe Ser
        1310                1315                1320
```

```
Ile Met Gly Val Asn Leu Phe Ala Gly Lys Phe Tyr Glu Cys Val
    1325                1330                1335

Asn Thr Thr Asp Gly Ser Arg Phe Ser Val Ser Gln Val Ala Asn
    1340                1345                1350

Arg Ser Glu Cys Phe Ala Leu Met Asn Val Ser Gly Asn Val Arg
    1355                1360                1365

Trp Lys Asn Leu Lys Val Asn Phe Asp Asn Val Gly Leu Gly Tyr
    1370                1375                1380

Leu Ser Leu Leu Gln Val Ala Thr Phe Lys Gly Trp Met Asp Ile
    1385                1390                1395

Met Tyr Ala Ala Val Asp Ser Val Asn Val Asn Ala Gln Pro Ile
    1400                1405                1410

Tyr Glu Tyr Asn Leu Tyr Met Tyr Ile Tyr Phe Val Ile Phe Ile
    1415                1420                1425

Ile Phe Gly Ser Phe Phe Thr Leu Asn Leu Phe Ile Gly Val Ile
    1430                1435                1440

Ile Asp Asn Phe Asn Gln Gln Lys Lys Lys Leu Gly Gly Gln Asp
    1445                1450                1455

Ile Phe Met Thr Glu Glu Gln Lys Lys Tyr Tyr Asn Ala Met Lys
    1460                1465                1470

Lys Leu Gly Ser Lys Lys Pro Gln Lys Pro Ile Pro Arg Pro Gly
    1475                1480                1485

Asn Lys Phe Gln Gly Cys Ile Phe Asp Leu Val Thr Asn Gln Ala
    1490                1495                1500

Phe Asp Ile Thr Ile Met Val Leu Ile Cys Leu Asn Met Val Thr
    1505                1510                1515

Met Met Val Glu Lys Glu Gly Gln Thr Asp Tyr Met Ser Phe Val
    1520                1525                1530

Leu Tyr Trp Ile Asn Val Val Phe Ile Ile Leu Phe Thr Gly Glu
    1535                1540                1545

Cys Val Leu Lys Leu Ile Ser Leu Arg His Tyr Tyr Phe Thr Val
    1550                1555                1560

Gly Trp Asn Ile Phe Asp Phe Val Val Val Ile Leu Ser Ile Val
    1565                1570                1575

Gly Met Phe Leu Ala Glu Met Ile Glu Lys Tyr Phe Val Ser Pro
    1580                1585                1590

Thr Leu Phe Arg Val Ile Arg Leu Ala Arg Ile Gly Arg Ile Leu
    1595                1600                1605

Arg Leu Ile Lys Gly Ala Lys Gly Ile Arg Thr Leu Leu Phe Ala
    1610                1615                1620

Leu Met Met Ser Leu Pro Ala Leu Phe Asn Ile Gly Leu Leu Leu
    1625                1630                1635

Phe Leu Val Met Phe Ile Tyr Ala Ile Phe Gly Met Ser Asn Phe
    1640                1645                1650

Ala Tyr Val Lys Lys Glu Ala Gly Ile Asn Asp Met Phe Asn Phe
    1655                1660                1665

Glu Thr Phe Gly Asn Ser Met Ile Cys Leu Phe Gln Ile Thr Thr
    1670                1675                1680

Ser Ala Gly Trp Asp Gly Leu Leu Ala Pro Ile Leu Asn Ser Ala
    1685                1690                1695

Pro Pro Asp Cys Asp Pro Lys Lys Val His Pro Gly Ser Ser Val
    1700                1705                1710

Glu Gly Asp Cys Gly Asn Pro Ser Val Gly Ile Phe Tyr Phe Val
```

```
                       1715                1720                1725

Ser Tyr Ile Ile Ile Ser Phe Leu Val Val Asn Met Tyr Ile
            1730                1735                1740

Ala Val Ile Leu Glu Asn Phe Ser Val Ala Thr Glu Glu Ser Thr
            1745                1750                1755

Glu Pro Leu Ser Glu Asp Asp Phe Glu Met Phe Tyr Glu Val Trp
            1760                1765                1770

Glu Lys Phe Asp Pro Asp Ala Thr Gln Phe Ile Glu Phe Cys Lys
            1775                1780                1785

Leu Ser Asp Phe Ala Ala Ala Leu Asp Pro Pro Leu Leu Ile Ala
            1790                1795                1800

Lys Pro Asn Lys Val Gln Leu Ile Ala Met Asp Leu Pro Met Val
            1805                1810                1815

Ser Gly Asp Arg Ile His Cys Leu Asp Ile Leu Phe Ala Phe Thr
            1820                1825                1830

Lys Arg Val Leu Gly Glu Ser Gly Glu Met Asp Ser Leu Arg Ser
            1835                1840                1845

Gln Met Glu Glu Arg Phe Met Ser Ala Asn Pro Ser Lys Val Ser
            1850                1855                1860

Tyr Glu Pro Ile Thr Thr Thr Leu Lys Arg Lys Gln Glu Asp Val
            1865                1870                1875

Ser Ala Thr Ile Ile Gln Arg Ala Tyr Arg Arg Tyr Arg Leu Arg
            1880                1885                1890

Gln Asn Val Lys Asn Ile Ser Ser Ile Tyr Ile Lys Asp Gly Asp
            1895                1900                1905

Arg Asp Asp Asp Leu Pro Asn Lys Glu Asp Ile Val Phe Asp Asn
            1910                1915                1920

Val Asn Glu Asn Ser Ser Pro Glu Lys Thr Asp Ala Thr Ala Ser
            1925                1930                1935

Thr Ile Ser Pro Pro Ser Tyr Asp Ser Val Thr Lys Pro Asp Gln
            1940                1945                1950

Glu Lys Tyr Glu Thr Asp Lys Thr Glu Lys Glu Asp Lys Glu Lys
            1955                1960                1965

Asp Glu Ser Arg Lys
            1970

<210> SEQ ID NO 21
<211> LENGTH: 60
<212> TYPE: DNA
<213> ORGANISM: Homo sapiens

<400> SEQUENCE: 21
ttccaaatta caacctctgc tggctgggat ggattgctag cacctattct taacagtaag    60

<210> SEQ ID NO 22
<211> LENGTH: 20
<212> TYPE: PRT
<213> ORGANISM: Homo sapiens

<400> SEQUENCE: 22

Phe Gln Ile Thr Thr Ser Ala Gly Trp Asp Gly Leu Leu Ala Pro Ile
1               5                   10                  15

Leu Asn Ser Lys
            20

<210> SEQ ID NO 23
<211> LENGTH: 60
```

```
<212> TYPE: DNA
<213> ORGANISM: Homo sapiens

<400> SEQUENCE: 23
ttccaaatta caacctctgc tggctgagat ggattgctag cacctattct taacagtaag    60

<210> SEQ ID NO 24
<211> LENGTH: 8
<212> TYPE: PRT
<213> ORGANISM: Homo sapiens

<400> SEQUENCE: 24

Phe Gln Ile Thr Thr Ser Ala Gly
1               5

<210> SEQ ID NO 25
<211> LENGTH: 60
<212> TYPE: DNA
<213> ORGANISM: Homo sapiens

<400> SEQUENCE: 25
tcaggtcagt gtccagaggg gtacacctgt gtgaaaattg cagaaaccc tgattatggc    60

<210> SEQ ID NO 26
<211> LENGTH: 20
<212> TYPE: PRT
<213> ORGANISM: Homo sapiens

<400> SEQUENCE: 26

Ser Gly Gln Cys Pro Glu Gly Tyr Thr Cys Val Lys Ile Gly Arg Asn
1               5                   10                  15

Pro Asp Tyr Gly
            20

<210> SEQ ID NO 27
<211> LENGTH: 60
<212> TYPE: DNA
<213> ORGANISM: Homo sapiens

<400> SEQUENCE: 27
tcaggtcagt gtccagaggg gtaaacctgt gtgaaaattg cagaaaccc tgattatggc    60

<210> SEQ ID NO 28
<211> LENGTH: 7
<212> TYPE: PRT
<213> ORGANISM: Homo sapiens

<400> SEQUENCE: 28

Ser Gly Gln Cys Pro Glu Gly
1               5

<210> SEQ ID NO 29
<211> LENGTH: 60
<212> TYPE: DNA
<213> ORGANISM: Homo sapiens

<400> SEQUENCE: 29
tcagttctgc gatcattcag actgctccga gtcttcaagt tggcaaaatc ctggccaaca    60

<210> SEQ ID NO 30
<211> LENGTH: 20
<212> TYPE: PRT
<213> ORGANISM: Homo sapiens

<400> SEQUENCE: 30
```

Ser Val Leu Arg Ser Phe Arg Leu Leu Arg Val Phe Lys Leu Ala Lys
1               5                   10                  15

Ser Trp Pro Thr
            20

<210> SEQ ID NO 31
<211> LENGTH: 60
<212> TYPE: DNA
<213> ORGANISM: Homo sapiens

<400> SEQUENCE: 31
tcagttctgc gatcattcag actgctctga gtcttcaagt tggcaaaatc ctggccaaca      60

<210> SEQ ID NO 32
<211> LENGTH: 9
<212> TYPE: PRT
<213> ORGANISM: Homo sapiens

<400> SEQUENCE: 32

Ser Val Leu Arg Ser Phe Arg Leu Leu
1               5

<210> SEQ ID NO 33
<211> LENGTH: 92
<212> TYPE: DNA
<213> ORGANISM: Homo sapiens

<400> SEQUENCE: 33
atatgtgaca gagtttgtgg acctgggcaa tgtctcagca ttgagaacat tcagagttct      60
ccgagcattg aaaacaattt cagtcattcc ag                                    92

<210> SEQ ID NO 34
<211> LENGTH: 31
<212> TYPE: PRT
<213> ORGANISM: Homo sapiens

<400> SEQUENCE: 34

Tyr Val Thr Glu Phe Val Asp Leu Gly Asn Val Ser Ala Leu Arg Thr
1               5                   10                  15

Phe Arg Val Leu Arg Ala Leu Lys Thr Ile Ser Val Ile Pro Gly
            20                  25                  30

<210> SEQ ID NO 35
<211> LENGTH: 92
<212> TYPE: DNA
<213> ORGANISM: Homo sapiens

<400> SEQUENCE: 35
gtatttaaca gaatttgtaa acctaggcaa tgtttcagct cttcgaactt tcagagtatt      60
gagagctttg aaaactattt ctgtaatccc ag                                    92

<210> SEQ ID NO 36
<211> LENGTH: 92
<212> TYPE: DNA
<213> ORGANISM: Lepus americanus

<400> SEQUENCE: 36
atatgtgacg gagtttgtgg acctgggcaa tgtctcagcg ttgagaacat tcagagttct      60
ccgagctttg aaaacaattt cagtcattcc ag                                    92

<210> SEQ ID NO 37

```
<211> LENGTH: 92
<212> TYPE: DNA
<213> ORGANISM: Lepus americanus

<400> SEQUENCE: 37
gtatttaaca gaatttgtaa acctaggcaa tgtttcagct cttcgaactt tcagagtctt    60
gagagctttg aaaactattt ctgtaatccc ag                                  92

<210> SEQ ID NO 38
<211> LENGTH: 92
<212> TYPE: DNA
<213> ORGANISM: Homo sapiens

<400> SEQUENCE: 38
atatgtgaca gagtttgtgg acctgggcaa tgtctcagcg ttgagaacat tcagagttct    60
ccgagcattg aaacaatttt cagtcattcc ag                                  92

<210> SEQ ID NO 39
<211> LENGTH: 92
<212> TYPE: DNA
<213> ORGANISM: Homo sapiens

<400> SEQUENCE: 39
gtatgtaaca gaatttgtaa acctaggcaa tgtttcagct cttcgaactt tcagagtctt    60
gagagctttg aaaactattt ctgtaattcc ag                                  92

<210> SEQ ID NO 40
<211> LENGTH: 92
<212> TYPE: DNA
<213> ORGANISM: Rattus norvegicus

<400> SEQUENCE: 40
atatgtgaca gagtttgtgg acctgggcaa tgtctcagcg ctgagaacgt tcagagttct    60
ccgagcattg aaacaatat cagtcattcc ag                                   92

<210> SEQ ID NO 41
<211> LENGTH: 92
<212> TYPE: DNA
<213> ORGANISM: Rattus norvegicus

<400> SEQUENCE: 41
gtatgtaaca gaatttgtaa acctaggcaa tgtttcagct cttcgaactt tcagagtctt    60
gagagctttg aaaactattt ctgtaattcc ag                                  92

<210> SEQ ID NO 42
<211> LENGTH: 92
<212> TYPE: DNA
<213> ORGANISM: Homo sapiens

<400> SEQUENCE: 42
atatgtgaca gagtttgtgg acctgggcaa tgtctcagcg ttgagaacat tcagagttct    60
ccgagcactg aaacaatttt cagtcattcc ag                                  92

<210> SEQ ID NO 43
<211> LENGTH: 92
<212> TYPE: DNA
<213> ORGANISM: Homo sapiens

<400> SEQUENCE: 43
gtatgtaaca gaatttgtaa gcctaggcaa tgtttcagcc cttcgaactt tcagagtctt    60
```

```
gagagctctg aaaactattt ctgtaattcc ag                                         92

<210> SEQ ID NO 44
<211> LENGTH: 92
<212> TYPE: DNA
<213> ORGANISM: Rattus norvegicus

<400> SEQUENCE: 44
atatgtgaca gagtttgtgg acctgggcaa tgtctcagcg ctgagaacgt tcagagttct          60
ccgagcattg aaaacaatat cagtcattcc ag                                         92

<210> SEQ ID NO 45
<211> LENGTH: 92
<212> TYPE: DNA
<213> ORGANISM: Rattus norvegicus

<400> SEQUENCE: 45
gtatgtaaca gaatttgtaa gcctaggcaa tgtttcagcc cttcgaactt tcagagtctt          60
gcgagctctg aaaactattt ctgtaattcc ag                                         92

<210> SEQ ID NO 46
<211> LENGTH: 24
<212> TYPE: DNA
<213> ORGANISM: Homo sapiens

<400> SEQUENCE: 46
aaaagtgatt gattcagttt tttg                                                  24

<210> SEQ ID NO 47
<211> LENGTH: 20
<212> TYPE: DNA
<213> ORGANISM: Homo sapiens

<400> SEQUENCE: 47
aaaagtgatt cagttttttg                                                       20

<210> SEQ ID NO 48
<211> LENGTH: 21
<212> TYPE: DNA
<213> ORGANISM: Homo sapiens

<400> SEQUENCE: 48 cagagggta cacctgtgtg a                                                      21

<210> SEQ ID NO 49
<211> LENGTH: 21
<212> TYPE: DNA
<213> ORGANISM: Homo sapiens

<400> SEQUENCE: 49 cagagggta aacctgtgtg a                                                      21

<210> SEQ ID NO 50
<211> LENGTH: 21
<212> TYPE: DNA
<213> ORGANISM: Homo sapiens

<400> SEQUENCE: 50
cttttagctc cgagtcttca a                                                     21

<210> SEQ ID NO 51
<211> LENGTH: 21
<212> TYPE: DNA
```

<213> ORGANISM: Homo sapiens

<400> SEQUENCE: 51
cttttagctc tgagtcttca a                                               21

<210> SEQ ID NO 52
<211> LENGTH: 22
<212> TYPE: DNA
<213> ORGANISM: Homo sapiens

<400> SEQUENCE: 52
ctgctggctg ggatggattt gc                                              22

<210> SEQ ID NO 53
<211> LENGTH: 22
<212> TYPE: DNA
<213> ORGANISM: Homo sapiens

<400> SEQUENCE: 53
ctgctggctg agatggattt gc                                              22

<210> SEQ ID NO 54
<211> LENGTH: 21
<212> TYPE: DNA
<213> ORGANISM: Homo sapiens

<400> SEQUENCE: 54
ctggcaaaca actgcccttc a                                               21

<210> SEQ ID NO 55
<211> LENGTH: 21
<212> TYPE: DNA
<213> ORGANISM: Homo sapiens

<400> SEQUENCE: 55
ctggcaaaca gctgcccttc a                                               21

<210> SEQ ID NO 56
<211> LENGTH: 21
<212> TYPE: DNA
<213> ORGANISM: Homo sapiens

<400> SEQUENCE: 56
tgaataaccc gccggactgg a                                               21

<210> SEQ ID NO 57
<211> LENGTH: 21
<212> TYPE: DNA
<213> ORGANISM: Homo sapiens

<400> SEQUENCE: 57
tgaataaccc accggactgg a                                               21

<210> SEQ ID NO 58
<211> LENGTH: 21
<212> TYPE: DNA
<213> ORGANISM: Homo sapiens

<400> SEQUENCE: 58
cgctgcgtgc cgctggcaaa a                                               21

<210> SEQ ID NO 59
<211> LENGTH: 21
<212> TYPE: DNA

<213> ORGANISM: Homo sapiens

<400> SEQUENCE: 59
cgctgcgtgc tgctggcaaa a        21

<210> SEQ ID NO 60
<211> LENGTH: 21
<212> TYPE: DNA
<213> ORGANISM: Homo sapiens

<400> SEQUENCE: 60
aagaattaga gtttcaacag a        21

<210> SEQ ID NO 61
<211> LENGTH: 21
<212> TYPE: DNA
<213> ORGANISM: Homo sapiens

<400> SEQUENCE: 61
aagaattaga atttcaacag a        21

<210> SEQ ID NO 62
<211> LENGTH: 21
<212> TYPE: DNA
<213> ORGANISM: Homo sapiens

<400> SEQUENCE: 62
tgttagaccg acttaaaaaa g        21

<210> SEQ ID NO 63
<211> LENGTH: 21
<212> TYPE: DNA
<213> ORGANISM: Homo sapiens

<400> SEQUENCE: 63
tgttagaccg tcttaaaaaa g        21

<210> SEQ ID NO 64
<211> LENGTH: 19
<212> TYPE: DNA
<213> ORGANISM: Homo sapiens

<400> SEQUENCE: 64
gttgtgtacg gaggttctc        19

<210> SEQ ID NO 65
<211> LENGTH: 19
<212> TYPE: DNA
<213> ORGANISM: Homo sapiens

<400> SEQUENCE: 65
gttgtgtatg gaggttctc        19

<210> SEQ ID NO 66
<211> LENGTH: 21
<212> TYPE: DNA
<213> ORGANISM: Homo sapiens

<400> SEQUENCE: 66
cgtattttgt gtcccctacc c        21

<210> SEQ ID NO 67
<211> LENGTH: 21
<212> TYPE: DNA

```
<213> ORGANISM: Homo sapiens

<400> SEQUENCE: 67
cgtattttgt ttcccctacc c                                          21

<210> SEQ ID NO 68
<211> LENGTH: 22
<212> TYPE: DNA
<213> ORGANISM: Homo sapiens

<400> SEQUENCE: 68
tttgcacctt tgaagactct gg                                         22

<210> SEQ ID NO 69
<211> LENGTH: 22
<212> TYPE: DNA
<213> ORGANISM: Homo sapiens

<400> SEQUENCE: 69
tttgcacctt gaaagactct gg                                         22

<210> SEQ ID NO 70
<211> LENGTH: 21
<212> TYPE: DNA
<213> ORGANISM: Homo sapiens

<400> SEQUENCE: 70 attttttct aaggaaaagt t                                           21

<210> SEQ ID NO 71
<211> LENGTH: 21
<212> TYPE: DNA
<213> ORGANISM: Homo sapiens

<400> SEQUENCE: 71 attttttct taggaaaagt t                                           21

<210> SEQ ID NO 72
<211> LENGTH: 21
<212> TYPE: DNA
<213> ORGANISM: Homo sapiens

<400> SEQUENCE: 72
atattcttag ttatttcaag t                                          21

<210> SEQ ID NO 73
<211> LENGTH: 21
<212> TYPE: DNA
<213> ORGANISM: Homo sapiens

<400> SEQUENCE: 73
atattcttag ctatttcaag t                                          21

<210> SEQ ID NO 74
<211> LENGTH: 21
<212> TYPE: DNA
<213> ORGANISM: Homo sapiens

<400> SEQUENCE: 74 cttttttgaaa tggcaaattt a                                         21

<210> SEQ ID NO 75
<211> LENGTH: 21
<212> TYPE: DNA
```

<213> ORGANISM: Homo sapiens

<400> SEQUENCE: 75 cttttttgaaa cggcaaattt a                                          21

<210> SEQ ID NO 76
<211> LENGTH: 21
<212> TYPE: DNA
<213> ORGANISM: Homo sapiens

<400> SEQUENCE: 76
tcagaaaaat tgatttttac a                                           21

<210> SEQ ID NO 77
<211> LENGTH: 21
<212> TYPE: DNA
<213> ORGANISM: Homo sapiens

<400> SEQUENCE: 77
tcagaaaaat ggatttttac a                                           21

<210> SEQ ID NO 78
<211> LENGTH: 21
<212> TYPE: DNA
<213> ORGANISM: Homo sapiens

<400> SEQUENCE: 78
ggatgcatat tgcctgggac c                                           21

<210> SEQ ID NO 79
<211> LENGTH: 21
<212> TYPE: DNA
<213> ORGANISM: Homo sapiens

<400> SEQUENCE: 79
ggatgcatat cgcctgggac c                                           21

<210> SEQ ID NO 80
<211> LENGTH: 21
<212> TYPE: DNA
<213> ORGANISM: Homo sapiens

<400> SEQUENCE: 80
tttgaatggc atatgtacct g                                           21

<210> SEQ ID NO 81
<211> LENGTH: 21
<212> TYPE: DNA
<213> ORGANISM: Homo sapiens

<400> SEQUENCE: 81
tttgaatggc gtatgtacct g                                           21

<210> SEQ ID NO 82
<211> LENGTH: 21
<212> TYPE: DNA
<213> ORGANISM: Homo sapiens

<400> SEQUENCE: 82
ggcatatgta tctggtgtat g                                           21

<210> SEQ ID NO 83
<211> LENGTH: 21
<212> TYPE: DNA

```
<213> ORGANISM: Homo sapiens

<400> SEQUENCE: 83
ggcatatgta cctggtgtat g                                              21

<210> SEQ ID NO 84
<211> LENGTH: 21
<212> TYPE: DNA
<213> ORGANISM: Homo sapiens

<400> SEQUENCE: 84
gcggtatatg cttggccttc t                                              21

<210> SEQ ID NO 85
<211> LENGTH: 21
<212> TYPE: DNA
<213> ORGANISM: Homo sapiens

<400> SEQUENCE: 85
gcggtatatg tttggccttc t                                              21

<210> SEQ ID NO 86
<211> LENGTH: 21
<212> TYPE: DNA
<213> ORGANISM: Homo sapiens

<400> SEQUENCE: 86
cccataatca cctcactgca t                                              21

<210> SEQ ID NO 87
<211> LENGTH: 21
<212> TYPE: DNA
<213> ORGANISM: Homo sapiens

<400> SEQUENCE: 87
cccataatca tctcactgca t                                              21

<210> SEQ ID NO 88
<211> LENGTH: 21
<212> TYPE: DNA
<213> ORGANISM: Homo sapiens

<400> SEQUENCE: 88
tttgtgaagc ttggggattg a                                              21

<210> SEQ ID NO 89
<211> LENGTH: 21
<212> TYPE: DNA
<213> ORGANISM: Homo sapiens

<400> SEQUENCE: 89
tttgtgaagc ctggggattg a                                              21

<210> SEQ ID NO 90
<211> LENGTH: 22
<212> TYPE: DNA
<213> ORGANISM: Homo sapiens

<400> SEQUENCE: 90 atttttttt tagggcacga cc                                              22

<210> SEQ ID NO 91
<211> LENGTH: 23
<212> TYPE: DNA
```

```
<213> ORGANISM: Homo sapiens

<400> SEQUENCE: 91 atttttttttt ttagggcacg acc                                      23

<210> SEQ ID NO 92
<211> LENGTH: 21
<212> TYPE: DNA
<213> ORGANISM: Homo sapiens

<400> SEQUENCE: 92
atgttctctg ttttttctc c                                          21

<210> SEQ ID NO 93
<211> LENGTH: 21
<212> TYPE: DNA
<213> ORGANISM: Homo sapiens

<400> SEQUENCE: 93
atgttctctg cttttttctc c                                         21

<210> SEQ ID NO 94
<211> LENGTH: 21
<212> TYPE: DNA
<213> ORGANISM: Homo sapiens

<400> SEQUENCE: 94
tagtgagttt tagaattgac t                                         21

<210> SEQ ID NO 95
<211> LENGTH: 21
<212> TYPE: DNA
<213> ORGANISM: Homo sapiens

<400> SEQUENCE: 95
tagtgagttt cagaattgac t                                         21

<210> SEQ ID NO 96
<211> LENGTH: 21
<212> TYPE: DNA
<213> ORGANISM: Homo sapiens

<400> SEQUENCE: 96
tgttattttt ataggtttct t                                         21

<210> SEQ ID NO 97
<211> LENGTH: 21
<212> TYPE: DNA
<213> ORGANISM: Homo sapiens

<400> SEQUENCE: 97
tgttattttt gtaggtttct t                                         21

<210> SEQ ID NO 98
<211> LENGTH: 22
<212> TYPE: DNA
<213> ORGANISM: Homo sapiens

<400> SEQUENCE: 98
cgaaggatat aagttattct tt                                        22

<210> SEQ ID NO 99
<211> LENGTH: 20
<212> TYPE: DNA
```

<213> ORGANISM: Homo sapiens

<400> SEQUENCE: 99
cgaaggatat gttattcttt                    20

<210> SEQ ID NO 100
<211> LENGTH: 21
<212> TYPE: DNA
<213> ORGANISM: Homo sapiens

<400> SEQUENCE: 100
tttaaatagt ctattaatta t                   21

<210> SEQ ID NO 101
<211> LENGTH: 21
<212> TYPE: DNA
<213> ORGANISM: Homo sapiens

<400> SEQUENCE: 101
tttaaatagt atattaatta t                   21

<210> SEQ ID NO 102
<211> LENGTH: 20
<212> TYPE: DNA
<213> ORGANISM: Homo sapiens

<400> SEQUENCE: 102
tttaaaaaaa tctttacatt                    20

<210> SEQ ID NO 103
<211> LENGTH: 21
<212> TYPE: DNA
<213> ORGANISM: Homo sapiens

<400> SEQUENCE: 103
tttaaaaaaa atctttacat t                   21

<210> SEQ ID NO 104
<211> LENGTH: 21
<212> TYPE: DNA
<213> ORGANISM: Homo sapiens

<400> SEQUENCE: 104
ataattaact aggactaaga t                   21

<210> SEQ ID NO 105
<211> LENGTH: 21
<212> TYPE: DNA
<213> ORGANISM: Homo sapiens

<400> SEQUENCE: 105
ataattaact gggactaaga t                   21

<210> SEQ ID NO 106
<211> LENGTH: 21
<212> TYPE: DNA
<213> ORGANISM: Homo sapiens

<400> SEQUENCE: 106
ttcatgatta attttattag a                   21

<210> SEQ ID NO 107
<211> LENGTH: 21
<212> TYPE: DNA

```
<213> ORGANISM: Homo sapiens

<400> SEQUENCE: 107
ttcatgatta gttttattag a                                              21

<210> SEQ ID NO 108
<211> LENGTH: 20
<212> TYPE: DNA
<213> ORGANISM: Homo sapiens

<400> SEQUENCE: 108 tttttttgttt ctttaccttg                                                20

<210> SEQ ID NO 109
<211> LENGTH: 24
<212> TYPE: DNA
<213> ORGANISM: Homo sapiens

<400> SEQUENCE: 109 tttttttgttt gtttctttac cttg                                           24

<210> SEQ ID NO 110
<211> LENGTH: 21
<212> TYPE: DNA
<213> ORGANISM: Homo sapiens

<400> SEQUENCE: 110
aatatttatt attcagattt t                                              21

<210> SEQ ID NO 111
<211> LENGTH: 21
<212> TYPE: DNA
<213> ORGANISM: Homo sapiens

<400> SEQUENCE: 111
aatatttatt tttcagattt t                                              21

<210> SEQ ID NO 112
<211> LENGTH: 51
<212> TYPE: DNA
<213> ORGANISM: Homo sapiens

<400> SEQUENCE: 112
ctgccagagg tgataataga taaggcaact tctgatgaca gcgtaaggac g              51

<210> SEQ ID NO 113
<211> LENGTH: 14
<212> TYPE: PRT
<213> ORGANISM: Homo sapiens

<400> SEQUENCE: 113

Leu Pro Glu Val Ile Ile Asp Lys Ala Thr Ser Asp Asp Ser
1               5                   10

<210> SEQ ID NO 114
<211> LENGTH: 11
<212> TYPE: PRT
<213> ORGANISM: Homo sapiens

<400> SEQUENCE: 114

Val Ile Ile Asp Lys Ala Thr Ser Asp Asp Ser
1               5                   10

<210> SEQ ID NO 115
```

```
<211> LENGTH: 11
<212> TYPE: PRT
<213> ORGANISM: Rattus rattus

<400> SEQUENCE: 115

Val Ile Ile Asp Lys Ala Thr Ser Asp Asp Ser
1               5                   10

<210> SEQ ID NO 116
<211> LENGTH: 11
<212> TYPE: PRT
<213> ORGANISM: Mus musculus

<400> SEQUENCE: 116

Val Ile Ile Asp Lys Ala Thr Ser Asp Asp Ser
1               5                   10

<210> SEQ ID NO 117
<211> LENGTH: 11
<212> TYPE: PRT
<213> ORGANISM: Rabbit

<400> SEQUENCE: 117

Val Ile Ile Asp Lys Ala Thr Ser Asp Asp Ser
1               5                   10

<210> SEQ ID NO 118
<211> LENGTH: 11
<212> TYPE: PRT
<213> ORGANISM: Homo sapiens

<400> SEQUENCE: 118

Val Ile Ile Asp Lys Pro Ala Thr Asp Asp Asn
1               5                   10

<210> SEQ ID NO 119
<211> LENGTH: 11
<212> TYPE: PRT
<213> ORGANISM: Rattus rattus

<400> SEQUENCE: 119

Val Ile Ile Asp Lys Pro Ala Thr Asp Asp Asn
1               5                   10

<210> SEQ ID NO 120
<211> LENGTH: 11
<212> TYPE: PRT
<213> ORGANISM: Homo sapiens

<400> SEQUENCE: 120

Val Lys Ile Asp Lys Ala Ala Thr Asp Asp Ser
1               5                   10

<210> SEQ ID NO 121
<211> LENGTH: 10
<212> TYPE: PRT
<213> ORGANISM: Rattus rattus

<400> SEQUENCE: 121

Val Lys Ile Asp Lys Ala Ala Thr Asp Ser
1               5                   10

<210> SEQ ID NO 122
<211> LENGTH: 10
<212> TYPE: PRT
<213> ORGANISM: Mus musculus
```

```
<400> SEQUENCE: 122

Val Lys Ile Asp Lys Ala Ala Thr Asp Ser
1               5                   10
```